(12) United States Patent
Dandu et al.

(10) Patent No.: US 9,029,538 B2
(45) Date of Patent: May 12, 2015

(54) URACIL DERIVATIVES AS AXL AND C-MET KINASE INHIBITORS

(71) Applicant: Ignyta, Inc., San Diego, CA (US)

(72) Inventors: Reddeppa Reddy Dandu, Downingtown, PA (US); Robert L. Hudkins, Chester Springs, PA (US); Kurt A. Josef, Radnor, PA (US); Catherine P. Prouty, Doylestown, PA (US); Rabindranath Tripathy, Churchville, PA (US)

(73) Assignee: Ignyta, Inc., San Diego, CA (US)

( * ) Notice: Subject to any disclaimer, the term of this patent is extended or adjusted under 35 U.S.C. 154(b) by 0 days.

(21) Appl. No.: 14/276,138

(22) Filed: May 13, 2014

(65) Prior Publication Data

US 2014/0275077 A1    Sep. 18, 2014

Related U.S. Application Data

(63) Continuation of application No. PCT/US2012/065019, filed on Nov. 14, 2012.

(60) Provisional application No. 61/559,312, filed on Nov. 14, 2011.

(51) Int. Cl.

| C07D 239/54 | (2006.01) |
|---|---|
| C07D 239/72 | (2006.01) |
| C07D 401/14 | (2006.01) |
| C07D 403/12 | (2006.01) |
| C07D 403/14 | (2006.01) |
| A61K 31/506 | (2006.01) |
| A61K 31/517 | (2006.01) |
| A61P 35/00 | (2006.01) |
| C07D 491/056 | (2006.01) |
| A61K 45/06 | (2006.01) |
| C07D 401/12 | (2006.01) |
| C07D 491/04 | (2006.01) |
| C07D 405/14 | (2006.01) |
| C07D 413/14 | (2006.01) |
| C07D 417/14 | (2006.01) |

(52) U.S. Cl.
CPC .......... *C07D 491/056* (2013.01); *C07D 403/12* (2013.01); *A61K 31/506* (2013.01); *A61K 31/517* (2013.01); *A61K 45/06* (2013.01); *C07D 403/14* (2013.01); *C07D 401/12* (2013.01); *C07D 491/04* (2013.01); *C07D 401/14* (2013.01); *C07D 405/14* (2013.01); *C07D 413/14* (2013.01); *C07D 417/14* (2013.01)

(58) Field of Classification Search
CPC .. C07D 487/04; C07D 401/14; C07D 403/12; C07D 403/14; A61K 31/506; A61K 31/517; A61K 31/4427; A61K 31/4725; A61K 45/06
USPC ......... 544/310.296, 310, 296; 514/269, 266.1
See application file for complete search history.

(56) References Cited

U.S. PATENT DOCUMENTS

2008/0004273 A1    1/2008    Raeppel et al.

FOREIGN PATENT DOCUMENTS

| EP | 1 153 920 | 10/2003 |
|---|---|---|
| WO | WO 98/13350 | 4/1998 |
| WO | WO 2009/127417 | 10/2009 |
| WO | WO 2011/045084 | 4/2011 |
| WO | WO 2012/028332 | 3/2012 |

OTHER PUBLICATIONS

Pyne et al. Cancer Res 2011 ;71:6576-6582.*
Jain et al., Nature Clinical Practice Oncology, 3(1), 24-40, 2006.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661,2000.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*

(Continued)

*Primary Examiner* — Venkataraman Balasubramanian
(74) *Attorney, Agent, or Firm* — Knobbe Martens Olson & Bear LLP

(57) ABSTRACT

The present application provides compounds of Formula I or salt forms thereof, wherein $R_a$, $R_b$, $R_c$, $R_d$, D, W, $R_{1a}$, $R_{1b}$, $R_{1c}$, Y, $R_3$, X, E and G are as defined herein, compositions, methods of treatment and uses thereof.

19 Claims, No Drawings

(56) References Cited

OTHER PUBLICATIONS

Agarwel et al., "Association of constitutively activated hepatocyte growth factor receptor (Met) with resistance to a dual EGFR/Her2 inhibitor in non-small-cell lung cancer cells," *Br. J. Cancer* (2009) 100, pp. 941-949.

Alvarez et al., "The Axl receptor tyrosine kinase is an adverse prognostic factor and a therapeutic target in esophageal adenocarcinoma," *Cancer Biology & Therapy* (2010) 10, pp. 1009-1018.

Avilla et al., "Activation of TYRO3/AXL Tyrosine Kinase Receptors in Thyroid Cancer," *Cancer Res.* (2011) 71, pp. 1792-1804.

Bachleitner-Hofmann et al., "HER kinase activation confers resistance to MET tyrosine kinase inhibition in MET oncogene-addicted gastric cancer cells," *Cancer Ther.* (2008) 7, pp. 3499-3508.

Bean et al., "MET amplification occurs with or without T790M mutations in EGFR mutant lung tumors with acquired resistance to gefitinib or erlotinib," *Proc. Natl Acad Sci.* (2007) 104, pp. 20932-20937.

Berge et al., "Pharmaceutical Salts," *J. Pharm. Sci.* (1977), 66, pp. 1-19.

Challier et al., "Differential expression of the ufo/axl oncogene in human leukemia-lymphoma cell lines," *Leukemia* (1996) 10, pp. 781-787.

Chun et al., "Synthesis and Biological Activities of Truncated Acridone: Structure-Activity Relationship Studies of Cytotoxic 5-Hydroxy-4-Quinolone," *Bioorganic & Medicinal Chem. Letters* (1997), vol. 7, pp. 789-792.

Chung et al., "Expression of the Proto-Oncogene Axl in Renal Cell Carcinoma," *DNA and Cell Biology* (2003) 22, pp. 533-540.

Comoglio et al., "Invasive growth: from development to metastasis," *J. Clin. Invest.* (2002), 109, pp. 857-862.

Crosier et al., "Identification of a Novel Receptor Tyrosine Kinase Expressed in Acute Myeloid Leukemic Blasts," *Leukemia and Lymphoma* (1994) 18, pp. 443-449.

Engelman et al., "MET Amplification Leads to Gefitinib Resistance in Lung Cancer by Activating ERBB3 Signaling," *Science* (2007) 316, pp. 1039-1043.

Fan et al., "The Multisubstrate Adapter Gab1 Regulates Hepatocyte Growth Factor (Scatter Factor)-c-Met Signaling for Cell Survival and DNA Repair," *Mol. Cell. Biol.* (2001) 21, pp. 4968-4984.

Furuta et al., "Identification of Potent and Selective Inhibitors of PDGF Receptor Autophosphorylation," *J. Med Chem.* (2006), 49, pp. 2186-2192.

Garofalo et al., "Design, Synthesis and DNA-Binding of N-Alkyl(aniline)quinazoline Derivatives," *J. Med. Chem.* (2010) 53, pp. 8089-8103.

Gjerdrum et al., "Axl is essential epithelial-to-mesenchymal transition-induced regulator of breast cancer metastasis and patient survival," *Proc. Natl Acad Sci.* (2010) 107, pp. 1124-1129.

Gorden et al., "EGFR inhibitors as first-line therapy in EGFR mutation-positive patients with NSCLC," *J. Oncol. Pharmacy Practice* (2012) 18, pp. 245-249.

Grande et al., "Targeting Oncogenic ALK: A Promising Strategy for Cancer Treatment," *Mol. Cancer Ther.* (2011) 10, pp. 569-579.

Green et al., "Overexpression of the Axl tyrosine kinase receptor in cutaneous SCC-derived cell lines and tumours," *Br. J. Cancer* (2006) 94, pp. 1446-1451.

Gustafsson et al., "Differential Expression of Axl and Gas6 in Renal Cell Carcinoma Reflecting Tumor Advancement and Survival," *Clin. Cancer Res.* (2009) 15, pp. 4742-4749.

Hafizi et al., "Signalling and functional diversity within the Axl subfamily of receptor tyrosine kinases," *Cytokine & Growth Factor Rev.* (2006) 17, pp. 295-304.

He et al., "Differential Expression of Axl in Hepatocellular Carcinoma and Correlation with Tumor Lymphatic Metastasis," *Mol. Carinogenesis* (2010) 49, pp. 882-891.

Hiscox et al., "Chronic exposure to fulvestrant promotes overexpression of the c-Met receptor in breast cancer cells: implications for tumour-stroma interactions," *Endocrine-Related Cancer* (2006) 13, pp. 1085-1099.

Holland et al., "Multiple Roles for the Receptor Tyrosine Kinase Axl in Tumor Formation," *Cancer Res.* (2005) 65, pp. 9294-9303.

Hong et al., "Receptor tyrosine kinase AXL is induced by chemotherapy drugs and overexpression of AXL confers drug resistance in acute myeloid leukemia," *Cancer Lett.* (2008) 268, pp. 314-324.

Hutterer et al., "Axl and Growth Arrest—Specific Gene 6 Are Frequently Overexpressed in Human Gliomas and Predict Poor Prognosis in Patients with Glioblastoma Multiforme," *Clin. Cancer Res.* (2008) 14, pp. 130-138.

Ito et al., "Expression of the Axl Receptor Tyrosine Kinase in Human Thyroid Carcinoma," *Thyroid* (1999) 9, pp. 563-567.

Jiang et al., "Hepatocyte growth factor, its receptor, and their potential value in cancer therapies," *Critical Rev. Oncology/Hematology* (2005) 53, pp. 35-69.

Janssen et al., "A novel putative tyrosine kinase receptor with oncogenic potential," *Oncogene* (1991) 6, pp. 2113-2120.

Keating et al., "Inhibition of Mer and Axl Receptor Tyrosine Kinases in Astrocytoma Cells Leads to Increased Apoptosis and Improved Chemosensitivity," *Mol. Cancer Ther.* (2010) 9, pp. 1298-1307.

Koorstra et al., "The Axl receptor tyrosine kinase confers an adverse prognostic influence in pancreatic cancer and represents a new therapeutic target," *Cancer Biology & Therapy* (2009 8, pp. 1-9.

Korshunov et al., "Axl, A Receptor Tyrosine Kinase, Mediates Flow-Induced Vascular Remodeling," *Circ. Res.* (2006) 98, pp. 1446-1452.

Kubo et al., "MET gene amplification or EGFR mutation activate MET in lung cancers untreated with EGFR tyrosine kinase inhibitors," *Int. J. Cancer* (2009) 124, pp. 1778-1784.

Kubo et al., Novel Potent Orally Active Selective VEGFR-2 Tyrosine Kinase Inhibitors: Synthesis, Structure-Activity Relationships, and Antitumor Activities of N-Phenyl-N'-{4-(4-quinolyloxy)phenyl}ureas, *J. Med. Chem.* (2005) 48, pp. 1359-1366.

Li et al., "Axl as a potential therapeutic target in cancer: role of Axl in tumor growth, metastasis and angiogenesis," *Oncogene* (2009) 28, pp. 3442-3455.

Linger et al., "TAM Receptor Tyrosine Kinases: Biologic Functions, Signaling, and Potential Therapeutic Targeting in Human Cancer," *Adv. Cancer Res.* (2008) 100, pp. 35-83.

Linger et al., "Taking aim at Mer and Axl receptor tyrosine kinases as novel therapeutic targets in solid tumors," *Expert Opin. Ther. Targets* (2010) 14; pp. 1073-1090.

Liu et al., "Induction, regulation, and biologic function of Axl receptor tyrosine kinase in Kaposi sarcoma," *Blood* (2010) 116, pp. 297-305.

Liu et al., "Novel Mechanism of Lapatinib Resistance in HER2-Positive Breast Tumor Cells: Activation of AXL," *Cancer Res.* (2009) 69, pp. 6871-6878.

Lu et al., "Tyro-3 family receptors are essential regulators of mammalian spermatogenesis," *Nature* (1999) 398; pp. 723-728.

Lu et al., "Homeostatic Regulation of the Immune System by Receptor Tyrosine Kinases of the Tyro 3 Family," *Science* (2001) 293, pp. 306-311.

Mahadevan et al., "A novel tyrosine kinase switch is a mechanism of imatinib resistance in gastrointestinal stromal tumors," *Oncogene* (2007) 26, pp. 3909-3919.

Mudduluru et al., "Myeloid Zinc Finger 1 Induces Migration, Invasion, and in Vivo Metastasis through Axl Gene Expression in Solid Cancer," *Mol. Cancer Res.* (2010) 8, pp. 159-169.

Mudduluru et al., "Regulation of Axl receptor tyrosine kinase expression by miR-34a and miR-199a/b in solid cancer," *Oncogene* (2011) 30, pp. 2888-2899.

O'Bryan et al., "The Transforming Receptor Tyrosine Kinase, Axl, Is Post-Translationally Regulated by Proteolytic Cleavage," *J. Biological Chem.* (1995) 270, pp. 551-557.

O'Bryan et al., "axl, a Transforming Gene Isolated from Primary Human Myeloid Leukemia Cells, Encodes a Novel Receptor Tyrosine Kinase," *Mol. Cell. Biol.* (1991), vol. 11, pp. 5016-5031.

Park et al., "The Axl/Gas6 pathway is required for optimal cytokine signaling during human natural killer cell development," *Blood* (2009) 113, pp. 2470-2477.

Prasad et al., "TAM receptor function in the retinal pigment epithelium," *Mol. Cell Neurosci.* (2006) 33, pp. 96-108.

Rankin et al., "AXL is an Essential Factor and Therapeutic Target for Metastatic Ovarian Cancer," *Cancer Res.* (2010) 70, pp. 7570-7579.

(56) References Cited

OTHER PUBLICATIONS

Rochlitz et al., "Axl expression is associated with adverse prognosis and with expression of Bcl-2 and CD34 in de novo acute myeloid leukemia (AML): results from a multicenter trial of the Swiss Group for Clinical Cancer Research (SAKK)," *Leukemia* (1999) 13, pp. 1352-1358.

Rosti et al., "Second-generation BCR-ABL inhibitors for frontline treatment of chronic myeloid leukemia in chronic phase," *Crtical Reviews in Oncology/Hematology* (2012) 82, pp. 159-170.

Rothlin et al., "TAM Receptors are Pleiotropic Inhibitors of the Innate Immune Response," *Cell* (2007) 131, pp. 1124-1136.

Sattler et al., "c-Met and Hepatocyte Growth Factor: Potential as Novel Targets in Cancer Therapy," *Curr. Oncol. Rept.* (2007) 9, pp. 102-108.

Sattler et al., "The MET axis as a therapeutic target," *Update on Cancer Therapeutics* (2009) 3, pp. 109-118.

Sawabu et al., "Growth Arrest-Specific Gene 6 and Axl Signaling Enhances Gastric Cancer Cell Survival via Akt Pathway," *Mol. Carcinogenesis* (2007) 46, pp. 155-164.

Shankar et al., "The Growth Arrest-Specific Gene Product Gas6 Promotes the Survival of Human Oligodendrocytes via a Phosphatidylinositol 3-Kinase-Dependent Pathway," *J. Neurosci.* (2003) 23, pp. 4208-4218.

Sharif et al., "Twist mediates suppression of inflammation by type I IFNs and Axl," *J. Exp. Med.* (2006) 203, pp. 1891-1901.

Shattuck et al., "Met Receptor Contributes to Trastuzumab Resistance of Her2-Overexpressing Breast Cancer Cells," *Cancer Res.* (2008) 68, pp. 1471-1477.

Shieh et al., "Expression of Axl in Lung Adenocarcinoma and Correlation with Tumor Progression," *Neoplasia* (2005) 7, pp. 1058-1064.

Shiozawa et al., "GAS6/AXL Axis Regulates Prostate Cancer Invasion, Proliferation, and Survival in the Bone Marrow Niche[1,2]," *Neoplasia* (2010) 12, pp. 116-127.

Smolen et al., "Amplification of MET may identify a subset of cancers with extreme sensitivity to the selective tyrosine kinase inhibitor PHA-665752," *Proc. Natl Acad Sci.* (2006) 103, pp. 2316-2321.

Song et al., "Overexpression of Receptor Tyrosine Kinase Axl Promotes Tumor Cell Invasion and Survival in Pancreatic Ductal Adenocarcinoma," *Cancer* (2011) 117, pp. 734-743.

Sun et al., "Coexpression of Gas6/Axl in Human Ovarian Cancer," *Oncology* (2004) 66, pp. 450-457.

Tai et al. "Axl promotes cell invasion by inducing MMP-9 activity through activation of $NF_{\kappa}B$ and Brg-1," *Oncogene* (2008) 27, pp. 4044-4055.

Tang et al., "Dual MET-EGFR combinatorial inhibition against T790M-EGFR-mediated erlotinib-resistant lung cancer," *Br. J. Cancer* (2008) 99, pp. 911-922.

Vajkoczy et al., "Dominant-negative inhibition of the Axl receptor tyrosine kinase suppresses brain tumor cell growth and invasion and prolongs survival," *Proc. Natl Acad Sci.* (2006) 103, pp. 5799-5804.

Vuoriluoto et al., Vimentin regulates EMT induction vy Slug and oncogenic H-Ras and migration by governing Axl expression in breast cancer, *Oncogene* (2011) 30, pp. 1436-1448.

Wu et al., "Clinical Significance of AXL Kinase Family in Gastric Cancer," *Anticancer Res.* (2002) 22, pp. 1071-1078.

Zee-Cheng et al., "Pyrimidines, VI. N-Methyl-as-triazine Analogs of the Natural Pyrimidines," *J. Org. Chem.* (1962) 77, pp. 976-981.

Zhang et al., "AXL is a Potential Target for Therapeutic Intervention in Breast Cancer Progression," *Cancer Res.* (2008) 68, pp. 1905-1915.

\* cited by examiner

URACIL DERIVATIVES AS AXL AND C-MET KINASE INHIBITORS

BACKGROUND

The present invention relates to novel compounds that are inhibitors of the receptor tyrosine kinases AXL and c-MET. The compounds are suitable for treatment of AXL or c-MET-mediated disorders such as cancer, and the development of resistance to cancer therapies.

Receptor tyrosine kinases (RTKs) are transmembrane proteins that transduce signals from the extracellular environment to the cytoplasm and nucleus to regulate normal cellular processes, including survival, growth, differentiation, adhesion, and mobility. Abnormal expression or activation of RTKs has been implicated in the pathogenesis of various human cancers, linked with cell transformation, tumor formation and metastasis. These observations have led to intense interest in the development of tyrosine kinase inhibitors as cancer therapeutics (Rosti et al, Crit. Rev. Oncol. Hematol. 2011. [Epub ahead of print]; Gorden et al, J. Oncol. Pharm. Pract. 2011. [Epub ahead of print]; Grande et al, Mol. Cancer Ther. 2011, 10, 569).

AXL is a member of the TAM (TYRO3, AXL, MER) receptor tyrosine kinase (RTK) family originally identified as a transforming gene expressed in cells from patients with chronic myelogenous leukemia (O'Bryan et. al Mol. Cell Biol. 1991, 11, 5016) or chronic myeloproliferative disorder (Janssen et. al Oncogene, 1991, 6, 2113). AXL activation occurs by binding of its cognate protein ligand, growth arrest specific 6 (Gash), homotypic dimerization through its extracellular domain or cross-talk via the interleukin (IL)-15 receptor or HER2. AXL signaling stimulates cellular responses, including activation of phosphoinositide 3-kinase-Akt, extracellular signal-regulated kinase (ERK) and p38 mitogen-activated protein kinase cascades, the NF-κB pathway, and signal transducer and activator of transcription (STAT) signaling (Hafizi et. al Cytokine Growth Factor Rev., 2006, 17, 295). Numerous biological consequences of AXL signaling, including invasion, migration, survival signaling, angiogenesis, resistance to chemotherapeutic and targeted drugs, cell transformation, and proliferation, represent undesirable traits associated with cancer (Linger et al. Adv. Cancer Res., 2008, 100, 35; Hafizi et. al Cytokine Growth Factor Rev., 2006, 17, 295; Holland et al, Cancer Res. 2005, 65, 9294).

AXL receptors regulate vascular smooth muscle homeostasis (Korshunov et al, Circ. Res. 2006, 98, 1446) and are implicated in the control of oligodendrocyte cell survival (Shankar et al, J. Neurosci. 2003, 23, 4208). Studies in knockout mice have revealed that TAM receptors play pivotal roles in innate immunity by inhibiting inflammation in macrophages and dendritic cells (Sharif et al, J. Exp. Med. 2006, 203, 1891; Rothlin et al, Cell. 2007, 131, 1124), promoting the phagocytosis of apoptotic cells (Lu et al, Nature. 1999, 398, 723; Lu & Lemke, Science. 2001, 293, 306; Prasad et al, Mol. Cell Neurosci. 2006, 3, 96) and stimulating the differentiation of natural killer cells (Park et al, Blood 2009, 113, 2470).

AXL has been found to be constitutively activated due to gene amplification and/or altered protein expression (O'Bryan et al, J. Biol. Chem. 1995, 270, 551; Linger et al, Expert Opin. Ther. Targets. 2010, 14, 1073; Mudduluru et al, Oncogene, 2011, 30, 2888). Altered expression of AXL has been reported in a variety of human cancers (Crosier et al, Leuk. Lymphoma. 1995, 18, 443; Challier et al, Leukemia. 1996, 10, 781; Ito et al, Thyroid. 1999, 9, 563; Sun et al, Oncology. 2004, 66, 450; Green et al, Br. J. Cancer. 2006, 94, 1446; Liu et al, Blood. 2010, 116, 297) and is associated with invasiveness and metastasis in lung cancer (Shieh et al, Neoplasia. 2005, 7, 1058), prostate cancer (Shiozawa et al, Neoplasia. 2010, 12, 116), breast cancer (Zhang et al, Cancer Res. 2008, 68, 1905), esophageal cancer (Hector et al, Cancer Biol. Ther. 2010, 10, 1009), ovarian cancer (Rankin et al, Cancer Res. 2010, 70, 7570), pancreatic cancer (Koorstra et al, Cancer Biol. Ther. 2009, 8, 618; Song et al, Cancer, 2011, 117, 734), liver cancer (He et al, Mol. Carcinog. 2010, 49, 882), gastric cancer (Wu et al, Anticancer Res. 2002, 22, 1071; Sawabu et al, Mol Carcinog. 2007, 46, 155), thyroid cancer (Avilla et al, Cancer Res. 2011, 71, 1792), renal cell carcinoma (Chung et al, DNA Cell Biol. 2003, 22, 533; Gustafsson et al, Clin. Cancer Res. 2009, 15, 4742) and glioblastoma (Hutterer et al, Clin. Cancer Res. 2008, 14, 130).

Indeed, AXL overexpression is associated with late stage and poor overall survival in many of those human cancers (Rochlitz et al, Leukemia, 1999, 13, 1352; Vajkoczy et al, Proc Natl. Acad. Sci. 2006, 103, 5799). AXL contributes to at least three of the six fundamental mechanisms of malignancy in human, by promoting cancer cell migration and invasion, involving in tumor angiogenesis, and facilitating cancer cell survival and tumor growth (Holland et al, Cancer Res. 2005, 65, 9294; Tai et al, Oncogene. 2008, 27, 4044; Li et al, Oncogene, 2009, 28, 3442; Mudduluru et al, Mol. Cancer Res. 2010, 8, 159). AXL is strongly induced by epithelial-to-mesenchymal transitions (EMT) in immortalized mammary epithelial cells and AXL knockdown completely prevented the spread of highly metastatic breast carcinoma cells from the mammary gland to lymph nodes and several major organs and increases overall survival (Gjerdrum et al, Proc. Natl. Acad. Sci. USA. 2010, 107, 1124; Vuoriluoto et al, Oncogene. 2011, 30, 1436), indicating AXL represents a critical downstream effector of tumor cell EMT requiring for cancer metastasis.

AXL is also induced during progression of resistance to therapies including imatinib in gastrointestinal stromal tumors (Mahadevan et al, Oncogene. 2007, 26, 3909) and Herceptin and EGFR inhibitor therapy (e.g. lapatinib) in breast cancer (Liu et al, Cancer Res. 2009, 69, 6871) via a "tyrosine kinase switch", and after chemotherapy in acute myeloid leukemia (Hong et al, Cancer Lett. 2008, 268, 314). AXL knockdown was also reported to lead to a significant increase in chemosensitivity of astrocytoma cells in response to chemotherapy treatment (Keating et al, Mol. Cancer Ther. 2010, 9, 1298). These data indicate AXL as an important mediator for tumor resistance to conventional chemotherapy and molecular-based cancer therapeutics.

The c-MET receptor was initially identified as the TPR-MET oncogene in an osteosarcoma cell line treated with a chemical carcinogen. The TPR-Met protein is able to transform and confer invasive and metastatic properties to non-tumorigenic cells (Sattler et. al, Current Oncology Rep., 2007, 9, 102). The oncogenic potential is a result of spontaneous dimerization and constitutive activation of TPR-MET. Aberrant expression of HGF and c-MET is associated with the development and poor prognosis of a wide range of solid tumors, including breast, prostate, thyroid, lung, stomach, colorectal, pancreatic, kidney, ovarian, and uterine carcinoma, malignant glioma, uveal melanoma, and osteo and soft-tissue sarcoma (Jaing et. al Critical Rev. Oncol/Hematol., 2005, 53, 35). Gastric tumors with an amplification of the wt-c-MET gene are more susceptible to MET inhibition, thereby making c-MET an attractive target (Smolen et. al Proc. Natl. Acad. Sci. USA, 2006, 103, 2316).

In vitro and in vivo studies have shown that increased and dysregulated c-MET activation leads to a wide range of biological responses associated with the malignant phenotype. These responses include increased motility/invasion, increased tumorigenicity, enhanced angiogenesis, protection of carcinoma cells from apoptosis induced by DNA-damaging agents such as adriamycin, ultraviolet light, and ionizing radiation, and enhanced rate of repair of DNA strand breaks [Comoglio et. al J. Clin. Invest., 2002, 109, 857, Sattler et. al Current Oncology Rep., 2007, 9, 102; Fan et. al, Mol. Cell Biol., 2001, 21, 4968). Based upon these data, HGF may enhance mutagenicity following DNA damage, allowing tumor cells with genetic damage to survive, and thus leading to resistance to chemo- and radiotherapeutic treatment regimens (Fan et. al, Mol. Cell Biol., 2001, 21, 4968; Hiscox et. al Endocrine-Related Cancer, 2004, 13, 1085).

MET amplification plays a unique critical role in mediating resistance of non-small cell lung cancer to EGFR inhibitors (e.g. Tarceva™, Iressa™, Tykerb™) the resistance of HER2 positive breast cancer to trastuzumab (Sattler et. al, Update Cancer Ther., 2009, 3, 109; Engleman et. al, Science, 2007, 316, 1039, Shattuck et. al Cancer Res., 2008, 68, 1471, Agarwal et. al, Br. J. Cancer, 2009, 100, 941; Kubo et. al, Int. J. Cancer 2009, 124, 1778) Inhibition of c-MET in Tarceva™ or Iressa™ resistant cells using shRNA or small molecules alone or in combination with an EGFR inhibitor overcame MET-mediated resistance to EGFR inhibitors [Agarwal et. al, Br. J. Cancer, 2009, 100, 941; Bachleitner-Hoffman et. al, Mol. Cancer Ther., 2008, 7, 3499, Tang et. al, Br. J. Cancer, 2008, 99, 911; Bean et. al, Proc. Natl. Acad. Sci. USA, 2007, 104, 20932). Due to the pleiotropic, pro-tumorigenic activities of the HGF-c-MET axis, inhibiting this pathway would be predicted to have potent anti-tumor effects in many common cancers through multiple complimentary mechanisms.

A need exists for AXL and c-MET inhibitors for use as pharmaceutical agents.

SUMMARY

The present invention provides a compound of Formula I

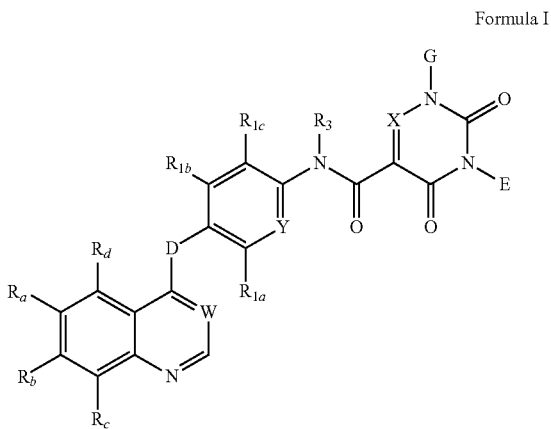

Formula I or a pharmaceutically acceptable salt form thereof, wherein $R_a$, $R_b$, $R_c$, $R_d$, D, W, Y, $R_{1a}$, $R_{1b}$, $R_{1c}$, $R_3$, X, G and E are as defined herein.

The compound of Formula I has AXL and c-MET inhibitory activity, and may be used to treat AXL-, or c-MET-mediated disorders or conditions.

The present invention further provides a pharmaceutical composition comprising at least one compound of the present invention together with at least one pharmaceutically acceptable carrier, diluent, or excipient therefor.

In another aspect, the present invention provides a method of treating a subject suffering from an AXL- or c-MET-mediated disorder or condition comprising administering to the subject a therapeutically effective amount the pharmaceutical composition of the present invention.

The present invention further provides a method of treating a proliferative disorder in a subject, comprising administering to the subject a therapeutically effective amount of a compound of the present invention.

DETAILED DESCRIPTION

I. Definitions

As used herein, the following terms have the meanings ascribed to them unless specified otherwise.

"Alkylamino" or an "alkylamino group" refers to an —NH-alkyl group.

"Alkoxy" or "alkoxy group" refers to an —O-alkyl group.

"Alkoxycarbonyl" refers to an alkyl-O—C(=O)— group.

"Alkyl" or "alkyl group" refers to a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc. Alkyl groups typically contain 1-10 carbon atoms, such as 1-6 carbon atoms.

"Substituted alkyl" indicates that one or more hydrogen atoms on an alkyl group has been replaced with a different atom or group of atoms and the atom or group of atoms replacing the hydrogen atom is a "substituent". Representative substituents include, but are not limited to, halogen, ($C_1$-$C_8$)alkyl, ($C_1$-$C_8$)alkoxy, ($C_1$-$C_8$)alkoxy($C_1$-$C_4$)alkyl, carboxyl, formyl, ($C_1$-$C_6$)acyl, halo($C_1$-$C_4$)alkyl, halo($C_1$-$C_4$)alkoxy, hydroxyl, nitro, cyano, amino, trifluoromethyl, mono- or di-($C_1$-$C_6$)alkylamino, oxo, ($C_6$-$C_{10}$)aryl, ($C_5$-$C_9$)heteroaryl, ($C_1$-$C_6$)alkoxycarbonyl, ($C_3$-$C_{10}$)cycloalkyl, ($C_3$-$C_{10}$)cycloalkyloxy, ($C_3$-$C_{10}$)cycloalkyl($C_1$-$C_6$)alkoxy, ($C_2$-$C_9$)heterocyclyl, ($C_2$-$C_9$)heterocyclyloxy, ($C_2$-$C_9$)heterocyclyl($C_1$-$C_4$)alkoxy, ($C_1$-$C_6$)alkoxycarbonyl($C_1$-$C_4$) alkyl, ($C_1$-$C_6$)alkoxycarbonyl, ($C_1$-$C_6$)alkylsulfinyl, ($C_1$-$C_6$) alkylsulfonyl, mono- and di-($C_1$-$C_6$)alkylaminocarbonyl, ($C_1$-$C_6$)acylthio, and ($C_1$-$C_6$)acyloxy.

"Alkenyl" refers to an alkyl group containing the requisite number of carbon atoms as described herein for "alkyl", and which contains at least one double bond. Representative examples of alkenyl groups include, but are not limited to ethenyl, allyl, isopropenyl, and 2-methyl-1-propenyl.

"Substituted alkenyl" indicates that one or more hydrogen atoms on an alkenyl group has been replaced with a different atom or group of atoms and the and the atom or group of atoms replacing the hydrogen atom is a "substituent". Representative substituents include, but are not limited to, halogen, ($C_1$-$C_8$)alkyl, ($C_1$-$C_8$)alkoxy, ($C_1$-$C_8$)alkoxy($C_1$-$C_4$) alkyl, carboxyl, formyl, ($C_1$-$C_6$)acyl, halo($C_1$-$C_4$)alkyl, halo ($C_1$-$C_4$)alkoxy, hydroxyl, nitro, cyano, amino, trifluoromethyl, mono- or di-($C_1$-$C_6$)alkylamino, oxo, ($C_6$-$C_{10}$)aryl, ($C_5$-$C_9$)heteroaryl, ($C_1$-$C_6$)alkoxycarbonyl, ($C_3$-$C_{10}$)cycloalkyl, ($C_3$-$C_{10}$)cycloalkyloxy, ($C_3$-$C_{10}$)cycloalkyl ($C_1$-$C_6$)alkoxy, ($C_2$-$C_9$)heterocyclyl, ($C_2$-$C_9$)heterocyclyloxy, ($C_2$-$C_9$)heterocyclyl($C_1$-$C_4$)alkoxy, ($C_1$-$C_6$)alkoxycarbonyl($C_1$-$C_4$)alkyl, ($C_1$-$C_6$)alkoxycarbonyl, ($C_1$-$C_6$)alkylsulfinyl, ($C_1$-$C_6$)alkylsulfonyl, mono- and di-($C_1$-$C_6$)alkylaminocarbonyl, ($C_1$-$C_6$)acylthio, and ($C_1$-$C_6$) acyloxy.

"Alkynyl" refers to an alkyl group containing the requisite number of carbon atoms as described herein for "alkyl", and which contains at least one triple bond. Representative examples of alkenyl groups include, but are not limited to ethynyl, propargyl, and 1- and 2-butynyl.

"Substituted alkynyl" indicates that one or more hydrogen atoms on an alkynyl group has been replaced with a different atom or group of atoms and the and the atom or group of atoms replacing the hydrogen atom is a "substituent". Representative substituents include, but are not limited to, halogen, ($C_1$-$C_8$)alkyl, ($C_1$-$C_8$)alkoxy, ($C_1$-$C_8$)alkoxy($C_1$-$C_4$)alkyl, carboxyl, formyl, ($C_1$-$C_6$)acyl, halo($C_1$-$C_4$)alkyl, halo($C_1$-$C_4$)alkoxy, hydroxyl, nitro, cyano, amino, trifluoromethyl, mono- or di-($C_1$-$C_6$)alkylamino, oxo, ($C_6$-$C_{10}$)aryl, ($C_5$-$C_9$)heteroaryl, ($C_1$-$C_6$)alkoxycarbonyl, ($C_3$-$C_{10}$)cycloalkyl, ($C_3$-$C_{10}$)cycloalkyloxy, ($C_3$-$C_{10}$)cycloalkyl($C_1$-$C_6$)alkoxy, ($C_2$-$C_9$)heterocyclyl, ($C_2$-$C_9$)heterocyclyloxy, ($C_2$-$C_9$)heterocyclyl($C_1$-$C_4$)alkoxy, ($C_1$-$C_6$)alkoxycarbonyl($C_1$-$C_4$)alkyl, ($C_1$-$C_6$)alkoxycarbonyl, ($C_1$-$C_6$)alkylsulfinyl, ($C_1$-$C_6$)alkylsulfonyl, mono- and di-($C_1$-$C_6$)alkylaminocarbonyl, ($C_1$-$C_6$)acylthio, and ($C_1$-$C_6$)acyloxy.

"Alkanoyl" refers to an alkyl-C(=O)— group.

The term "$C_{x-y}$" indicates the number of carbon atoms in a group. For example, a "$C_{1-6}$-alkyl" is an alkyl group having from one (1) to six (6) carbon atoms.

The term "cyano" refers to a CN group.

"Cycloalkyl" refers to a non-aromatic, saturated carbocyclic ring system, and may be monocyclic, bicyclic or tricyclic, and may be bridged, spiro and/or fused. Preferably the cycloalkyl group contains from 3 to 10 ring atoms. Examples include, but are not limited to cyclopropyl, cyclobutyl, cyclopentyl, cyclohexyl, cycloheptyl, and norbornyl.

"Cycloalkoxyalkyl" refers to a cycloalkyl-O-alkyl- group.

"Cycloalkylalkyl" refers to a cycloalkyl-alkyl- group.

"Carbamoyl" refers to a $NH_2C$(=O)— group.

"N-alkylcarbamoyl" or "alkyl carbamoyl" refers to an alkyl-NH—C(=O)— group.

"N,N-dialkylcarbamoyl" or "dialkylcarbamoyl" refers to an (alkyl)(alkyl)N—C(=O)— group. On such a group the alkyl groups may be the same or different.

"Aryl" or "aryl group" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, phenyl, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Preferably, the aryl group contains 6 (i.e., phenyl) or 9 to 15 ring atoms. More preferably, the aryl group contains 6 (i.e., phenyl), 9 or 10 ring atoms.

"Substituted aryl" indicates that one or more hydrogen atoms on an aryl group has been replaced with a different atom or group of atoms and the and the atom or group of atoms replacing the hydrogen atom is a "substituent". Representative substituents include, but are not limited to, halogen, ($C_1$-$C_8$)alkyl, ($C_1$-$C_8$)alkoxy, ($C_1$-$C_8$)alkoxy($C_1$-$C_4$)alkyl, carboxyl, formyl, ($C_1$-$C_6$)acyl, halo($C_1$-$C_4$)alkyl, halo($C_1$-$C_4$)alkoxy, hydroxyl, nitro, cyano, amino, trifluoromethyl, mono- or di-($C_1$-$C_6$)alkylamino, oxo, ($C_6$-$C_{10}$)aryl, ($C_5$-$C_9$)heteroaryl, ($C_1$-$C_6$)alkoxycarbonyl, ($C_3$-$C_{10}$)cycloalkyl, ($C_3$-$C_{10}$)cycloalkyloxy, ($C_3$-$C_{10}$)cycloalkyl($C_1$-$C_6$)alkoxy, ($C_2$-$C_9$)heterocyclyl, ($C_2$-$C_9$)heterocyclyloxy, ($C_2$-$C_9$)heterocyclyl($C_1$-$C_4$)alkoxy, ($C_1$-$C_6$)alkoxycarbonyl, ($C_1$-$C_6$)alkylsulfinyl, ($C_1$-$C_6$)alkylsulfonyl, mono- and di-($C_1$-$C_6$)alkylaminocarbonyl, ($C_1$-$C_6$)acylthio, and ($C_1$-$C_6$)acyloxy.

"Arylalkyl" refers to an aryl-alkyl- group.

"Arylalkoxy" refers to an aryl-alkyl-O— group.

"Arylalkoxyalkyl" refers to an aryl-alkyl-O-alkyl- group.

"Aryloxy" refers to an aryl-O— group.

"Heterocyclyl" or "heterocyclyl group" refers to 3-15 membered monocyclic, bicyclic, and tricyclic non-aromatic rings, which may be saturated or unsaturated, can be substituted or unsubstituted, may be bridged, spiro, and/or fused, and which contain, in addition to carbon atom(s), at least one heteroatom, such as nitrogen, oxygen or sulfur. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl, tetrahydropyranyl, piperidinyl, tetrahydrothienyl, homopiperidinyl, oxazolidinonyl, dihydropyrazolyl, dihydropyrrolyl, dihydropyrazinyl, dihydropyridinyl, dihydropyrimidinyl, dihydrofuryl, dihydropyranyl, quinuclidinyl, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane. Preferably, the heterocyclyl group contains from 3 to 10 ring atoms. More preferably, the heterocycyl group contains from 3 to 7 ring atoms. More preferably, the heterocyclyl group contains from 5 to 7 ring atoms, such as 5 ring atoms, 6 ring atoms, or 7 ring atoms. Unless otherwise indicated, the foregoing heterocyclyl groups can be C-attached or N-attached where such is possible and results in the creation of a stable structure. For example, piperidinyl can be piperidin-1-yl (N-attached) or piperidin-4-yl (C-attached). A heterocyclyl group can also include ring systems substituted on ring carbons with one or more —OH functional groups (which may further tautomerize to give a ring C=O group) and/or substituted on a ring sulfur atom by one (1) or two (2) oxygen atoms to give S=O or $SO_2$ groups, respectively.

"Substituted heterocyclyl" indicates that one or more hydrogen atoms on a heterocyclyl group has been replaced with a different atom or group of atoms and the and the atom or group of atoms replacing the hydrogen atom is a "substituent". Representative substituents include, but are not limited to, halogen, ($C_1$-$C_8$)alkyl, ($C_1$-$C_8$)alkoxy, ($C_1$-$C_8$)alkoxy($C_1$-$C_4$)alkyl, carboxyl, formyl, ($C_1$-$C_6$)acyl, halo($C_1$-$C_4$)alkyl, halo($C_1$-$C_4$)alkoxy, hydroxyl, nitro, cyano, amino, trifluoromethyl, mono- or di-($C_1$-$C_6$)alkylamino, oxo, ($C_6$-$C_{10}$)aryl, ($C_5$-$C_9$)heteroaryl, ($C_1$-$C_6$)alkoxycarbonyl, ($C_3$-$C_{10}$)cycloalkyl, ($C_3$-$C_{10}$)cycloalkyloxy, ($C_3$-$C_{10}$)cycloalkyl($C_1$-$C_6$)alkoxy, ($C_2$-$C_9$)heterocyclyl, ($C_2$-$C_9$)heterocyclyloxy, ($C_2$-$C_9$)heterocyclyl($C_1$-$C_4$)alkoxy, ($C_1$-$C_6$)alkoxycarbonyl($C_1$-$C_4$)alkyl, ($C_1$-$C_6$)alkoxycarbonyl, ($C_1$-$C_6$)alkylsulfinyl, ($C_1$-$C_6$)alkylsulfonyl, mono- and di-($C_1$-$C_6$)alkylaminocarbonyl, ($C_1$-$C_6$)acylthio, and ($C_1$-$C_6$)acyloxy.

"Heterocyclylalkoxyalkyl" refers to a heterocylylalkyl-O-alkyl- group.

"Heterocyclylcarbonyl" refers to a heterocyclyl-(C=O)— group.

"Heteroaryl" or "heteroaryl group" refers to (a) 5 and 6 membered monocyclic aromatic rings, which contain, in addition to carbon atom(s), at least one heteroatom, such as nitrogen, oxygen or sulfur, and (b) 7-15 membered bicyclic and tricyclic rings, which contain, in addition to carbon atom(s), at least one heteroatom, such as nitrogen, oxygen or sulfur, and in which at least one of the rings is aromatic.

Heteroaryl groups can be substituted or unsubstituted, and may be bridged, spiro, and/or fused. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0*2,7*]dodeca-2(7),3,5-trienyl, 12-oxa-10-aza-tricyclo[6.3.1.0*2,7*]dodeca-2(7),3,5-trienyl, 12-aza-tricyclo[7.2.1.0*2,7*]dodeca-2(7),3,5-trienyl, 10-aza-tricyclo[6.3.2.0*2,7*]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Preferably, the heteroaryl group contains 5, 6, or 8-15 ring atoms. More preferably, the heteroaryl group contains 5 to 10 ring atoms, such as 5, 6, 9, or 10 ring atoms. A heteroaryl group can also include ring systems substituted on ring carbons with one or more —OH or C=O functional groups and/or substituted on a ring sulfur atom by one (1) or two (2) oxygen atoms to give S=O or $SO_2$ groups, respectively.

"Substituted heteroaryl" indicates that one or more hydrogen atoms on a heteroaryl group has been replaced with a different atom or group of atoms and the and the atom or group of atoms replacing the hydrogen atom is a "substituent". Representative substituents include, but are not limited to, halogen, $(C_1-C_8)$alkyl, $(C_1-C_8)$alkoxy, $(C_1-C_8)$alkoxy($C_1$-$C_4$)alkyl, carboxyl, formyl, $(C_1-C_6)$acyl, halo($C_1-C_4$)alkyl, halo($C_1-C_4$)alkoxy, hydroxyl, nitro, cyano, amino, trifluoromethyl, mono- or di-$(C_1-C_6)$alkylamino, oxo, $(C_6-C_{10})$aryl, $(C_5-C_9)$heteroaryl, $(C_1-C_6)$alkoxycarbonyl, $(C_3-C_{10})$cycloalkyl, $(C_3-C_{10})$cycloalkyloxy, $(C_3-C_{10})$cycloalkyl($C_1-C_6$)alkoxy, $(C_2-C_9)$heterocyclyl, $(C_2-C_9)$heterocyclyloxy, $(C_2-C_9)$heterocyclyl($C_1-C_4$)alkoxy, $(C_1-C_6)$alkoxycarbonyl($C_1-C_4$)alkyl, $(C_1-C_6)$alkoxycarbonyl, $(C_1-C_6)$alkylsulfinyl, $(C_1-C_6)$alkylsulfonyl, mono- and di-$(C_1-C_6)$alkylaminocarbonyl, $(C_1-C_6)$acylthio, and $(C_1-C_6)$acyloxy.

"Heteroarylalkyl" refers to a heteroaryl-alkyl- group.

"Halo" and "halogen" include fluoro, chloro, bromo and iodo, and fluorine, chlorine, bromine and iodine atoms.

"Trihalomethyl" refers to a —$CH_3$ group, the hydrogens of which have been substituted with halogen atoms, which may be the same or different. Representative trihalomethyl groups include $CF_3$, $CCl_3$, $CBr_3$ or $CI_3$. A preferred trihalomethyl group is $CF_3$.

"Trihaloalkyl" refers to an alkyl group substituted by three halogen atoms, which may be the same or different.

"Alkoxyalkyl" or "alkoxyalkyl group" refers to an alkyl group containing an alkoxy group substituent.

"Hydroxyl", "hydroxy", "hydroxyl group" or "hydroxyl group" refers to an —OH group.

"Amino" or "amino group" refers to an —$NH_2$ group.

"Alkylamino" or "alkylamino group" refers to an alkyl-N(H)— group.

"Dialkylamino" or "dialkylamino" group refers to an (alkyl)(alkyl)N— group. In such a group the alkyl groups substituting the nitrogen may be the same or different.

"Carboxy", "carboxyl", "carboxy group" or "carboxyl group" refers to a —COOH group.

"Oxo" refers to a =O group.

"Pseudohalogen" refers to —OCN, —SCN, —$CF_3$, and —CN.

"Chemically stable" or "stable" refers to a compound that is sufficiently robust to be isolated to a useful degree of purity from a reaction mixture. The present invention is directed only to chemically stable compounds.

"Pharmaceutical composition" refers to a composition suitable for administration in medical or veterinary use.

When lists of alternative substituents include members which, owing to valency requirements, chemical stability, or other reasons, cannot be used to substitute a particular group, the list is intended to be read in context to include those members of the list that are suitable for substituting the particular group.

"Pharmaceutically acceptable" refers to physiologically tolerable materials, which do not typically produce an allergic or other untoward reaction, such as gastric upset, dizziness and the like, when administered to a mammal.

"Therapeutically effective amount" refers to an amount of a compound, or a pharmaceutically acceptable salt thereof, sufficient to inhibit, halt, or cause an improvement in a disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

"Subject" refers to a member of the class Mammalia. Examples of mammals include, without limitation, humans, primates, chimpanzees, rodents, mice, rats, rabbits, horses, livestock, dogs, cats, sheep, and cows.

"Treatment" refers to the acute or prophylactic diminishment or alleviation of at least one symptom or characteristic associated or caused by a disorder being treated. For example, treatment can include diminishment of several symptoms of a disorder or complete eradication of a disorder.

"Administering" refers to the method of contacting a compound with a subject. Modes of "administering" include, but are not limited to, methods that involve contacting the compound intravenously, intraperitoneally, intranasally, transdermally, topically, via implantation, subcutaneously, parentally, intramuscularly, orally, systemically, and via adsorption.

II. Compounds

The present invention provides a compound of Formula I or a salt form thereof,

Formula I

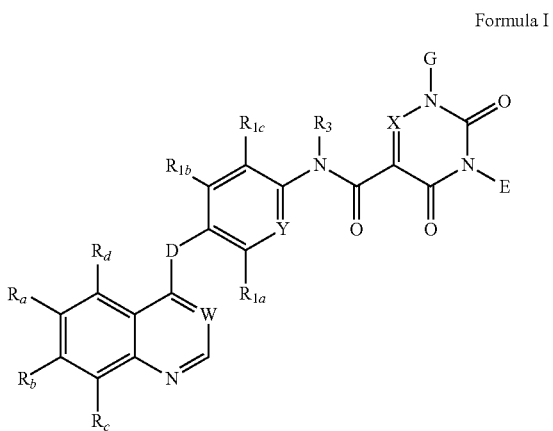

wherein:

E and G are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{3-11}$cycloalkyl optionally substituted by 1-6 $R^{19}$, 3-15 membered heterocyclyl optionally substituted by 1-6 $R^{19}$, 5-15 membered heteroaryl optionally substituted by 1-6 $R^{19}$, —C(=O)$R^{20}$, —C(=O)O$R^{20}$, —C(=O)N$R^{22}R^{23}$, —S(=O)$_2R^{20}$, and —S(=O)$_2$N$R^{22}R^{23}$;

X is N or C—$R_4$;

Y is N or C—$R_{1d}$;

$R_3$ is H or $C_{1-6}$alkyl;

D is —O—, —S—, —SO—, —SO$_2$—, —C(=O)—, —CHOH—, —CH$_2$—, —NH— or —N$C_{1-6}$alkyl-;

W is CH or N;

$R_a$, $R_b$, $R_c$, $R_d$, $R_{1a}$, $R_{1b}$, $R_{1c}$, $R_{1d}$, and $R_4$ are independently chosen from H, $C_{1-6}$alkyl optionally substituted by 1-6 $R^{119}$, $C_{2-6}$alkenyl optionally substituted by 1-6 $R^{119}$, $C_{2-6}$alkynyl optionally substituted by 1-6 $R^{119}$, $C_{6-11}$aryl optionally substituted by 1-6 $R^{119}$, $C_{3-11}$cycloalkyl optionally substituted by 1-6 $R^{119}$, 3-15 membered heterocyclyl optionally substituted by 1-6 $R^{119}$, 5-15 membered heteroaryl optionally substituted by 1-6 $R^{119}$, halogen, —CN, —C(=O)$R^{110}$, —C(=O)O$R^{110}$, —C(=O)N$R^{112}R^{113}$, —NC, —NO$_2$, —N$R^{112}R^{113}$, N$R^{114}$C(=O)$R^{110}$, —N$R^{114}$C(=O)O$R^{111}$, —N$R^{114}$C(=O)N$R^{112}R^{113}$, —N$R^{114}$S(=O)$_2R^{111}$, —N$R^{114}$S(=O)$_2$N$R^{112}R^{113}$, —O$R^{110}$, —OCN, —OC(=O)$R^{110}$, —OC(=O)N$R^{112}R^{113}$, —OC(=O)O$R^{110}$, —S(=O)$_nR^{110}$, and —S(=O)$_2$N$R^{112}R^{113}$;

or any of $R_a$ and $R_b$, $R_a$ and $R_d$, and $R_b$ and $R_c$ can, together with the atoms linking them, form a $C_{6-11}$aryl optionally substituted by 1-6 $R^{119}$, $C_{3-11}$cycloalkyl optionally substituted by 1-6 $R^{119}$, 3-15 membered heterocyclyl optionally substituted by 1-6 $R^{119}$ or a 5-15 membered heteroaryl optionally substituted by 1-6 $R^{119}$;

$R^{19}$ at each occurrence is independently chosen from $C_{1-6}$alkyl optionally substituted by 1-6 $R^{39}$, $C_{2-6}$alkenyl optionally substituted by 1-6 $R^{39}$, $C_{2-6}$alkynyl optionally substituted by 1-6 $R^{39}$, $C_{6-11}$aryl optionally substituted by 1-6 $R^{39}$, $C_{3-11}$cycloalkyl optionally substituted by 1-6 $R^{39}$, 3-15 membered heterocyclyl optionally substituted by 1-6 $R^{39}$, 5-15 membered heteroaryl optionally substituted by 1-6 $R^{39}$, halogen, —CN, —C(=O)$R^{30}$, —C(=O)O$R^{30}$, —C(=O)N$R^{32}R^{33}$, —NO$_2$, —N$R^{32}R^{33}$, —N$R^{34}$C(=O)$R^{30}$, —N$R^{34}$C(=O)O$R^{31}$, —N$R^{34}$C(=O)N$R^{32}R^{33}$, N$R^{34}$S(=O)$_2R^{31}$, N$R^{34}$S(=O)$_2$N$R^{32}R^{33}$, —O$R^{30}$, =O, —OC(=O)$R^{30}$, —OC(=O)N$R^{32}R^{33}$, —OC(=O)O$R^{30}$, —S(=O)$_nR^{30}$, and —S(=O)$_2$N$R^{32}R^{33}$;

$R^{20}$, $R^{30}$, $R^{31}$, and $R^{34}$ at each occurrence is independently chosen from H, $C_{1-6}$alkyl optionally substituted by 1-6 $R^{49}$, $C_{2-6}$alkenyl optionally substituted by 1-6 $R^{49}$, $C_{2-6}$alkynyl optionally substituted by 1-6 $R^{49}$, $C_{6-11}$aryl optionally substituted by 1-6 $R^{49}$, $C_{3-11}$cycloalkyl optionally substituted by 1-6 $R^{49}$, 3-15 membered heterocyclyl optionally substituted by 1-6 $R^{49}$, and 5-15 membered heteroaryl optionally substituted by 1-6 $R^{49}$;

$R^{22}$, $R^{23}$, $R^{32}$ and $R^{33}$ at each occurrence is independently chosen from H, $C_{1-6}$alkyl optionally substituted by 1-6 $R^{59}$, $C_{2-6}$alkenyl optionally substituted by 1-6 $R^{59}$, $C_{2-6}$alkynyl optionally substituted by 1-6 $R^{59}$, $C_{6-11}$aryl optionally substituted by 1-6 $R^{59}$, $C_{3-11}$cycloalkyl optionally substituted by 1-6 $R^{59}$, 3-15 membered heterocyclyl optionally substituted by 1-6 $R^{59}$, and 5-15 membered heteroaryl optionally substituted by 1-6 $R^{59}$;

or any $R^{22}$ and $R^{23}$ and/or $R^{32}$ and $R^{33}$ may form, together with the nitrogen atom to which they are attached, a 3-15 membered heterocyclyl optionally substituted by 1-6 $R^{69}$ or a 5-15 membered heteroaryl optionally substituted by 1-6 $R^{69}$;

$R^{39}$, $R^{49}$, $R^{59}$ and $R^{69}$ at each occurrence is independently chosen from $C_{1-6}$alkyl optionally substituted by 1-6 $R^{79}$, $C_{2-6}$alkenyl optionally substituted by 1-6 $R^{79}$, $C_{2-6}$alkynyl optionally substituted by 1-6 $R^{79}$, $C_{6-11}$aryl optionally substituted by 1-6 $R^{79}$, $C_{3-11}$cycloalkyl optionally substituted by 1-6 $R^{79}$, 3-15 membered heterocyclyl optionally substituted by 1-6 $R^{79}$, 5-15 membered heteroaryl optionally substituted by 1-6 $R^{79}$, halogen, —CN, —C(=O)$R^{70}$, —C(=O)O$R^{70}$, —C(=O)N$R^{72}R^{73}$, —NO$_2$, —N$R^{72}R^{73}$, —N$R^{74}$C(=O)$R^{70}$, —N$R^{74}$C(=O)O$R^{71}$, —N$R^{74}$C(=O)N$R^{72}R^{73}$, —N$R^{74}$S(=O)$_2R^{71}$, —N$R^{74}$S(=O)$_2$N$R^{72}R^{73}$, —O$R^{70}$, =O, —OC(=O)$R^{70}$, —OC(=O)N$R^{72}R^{73}$, —S(=O)$_nR^{70}$, and —S(=O)$_2$N$R^{72}R^{73}$;

$R^{70}$, $R^{71}$, $R^{72}$, $R^{73}$, and $R^{74}$ at each occurrence is independently chosen from H, $C_{1-6}$alkyl and $C_{1-6}$-haloalkyl;

$R^{79}$ at each occurrence is independently chosen from $C_{1-6}$alkyl, $C_{1-6}$-haloalkyl, benzyl, halogen, —CN, —C(=O)($C_{1-6}$alkyl), —C(=O)O($C_{1-6}$alkyl), —C(=O)N($C_{1-6}$alkyl)$_2$, —C(=O)OH, —C(=O)NH$_2$, —C(=O)NH$C_{1-6}$alkyl, —NO$_2$, —NH$_2$, —NH$C_{1-6}$alkyl, —N($C_{1-6}$alkyl)$_2$, —NHC(=O)$C_{1-6}$alkyl, —NHS(=O)$_2C_{1-6}$alkyl, —OH, —O$C_{1-6}$alkyl, =O, —OC(=O)$C_{1-6}$alkyl, —OS(=O)$_2C_{1-6}$alkyl, —S(=O)$_2C_{1-6}$alkyl, and —S(=O)$_2$N($C_{1-6}$alkyl)$_2$;

$R^{110}$, $R^{111}$, and $R^{114}$ at each occurrence is independently chosen from H, $C_{1-6}$alkyl optionally substituted by 1-6 $R^{129}$, $C_{2-6}$alkenyl optionally substituted by 1-6 $R^{129}$, $C_{2-6}$alkynyl optionally substituted by 1-6 $R^{129}$, $C_{6-11}$aryl optionally substituted by 1-6 $R^{129}$, $C_{3-11}$cycloalkyl optionally substituted by 1-6 $R^{129}$, 3-15 membered heterocyclyl optionally substituted by 1-6 $R^{129}$, and 5-15 membered heteroaryl optionally substituted by 1-6 $R^{129}$;

$R^{112}$ and $R^{113}$ at each occurrence is independently chosen from H, $C_{1-6}$ alkyl optionally substituted by 1-6 $R^{139}$, $C_{2-6}$alkenyl optionally substituted by 1-6 $R^{139}$, $C_{2-6}$alkynyl optionally substituted by 1-6 $R^{139}$, $C_{6-11}$aryl optionally substituted by 1-6 $R^{139}$, $C_{3-11}$ cycloalkyl optionally substituted by 1-6 $R^{139}$, 3-15 membered heterocyclyl optionally substituted by 1-6 $R^{139}$, and 5-15 membered heteroaryl optionally substituted by 1-6 $R^{139}$;

or any $R^{112}$ and $R^{113}$ may form, together with the nitrogen atom to which they are attached, a 3-15 membered heterocyclyl optionally substituted by 1-6 $R^{149}$ or a 5-15 membered heteroaryl optionally substituted by 1-6 $R^{149}$;

$R^{119}$ at each occurrence is independently chosen from $C_{1-6}$alkyl optionally substituted by 1-6 $R^{159}$, $C_{2-6}$alkenyl optionally substituted by 1-6 $R^{159}$, $C_{2-6}$alkynyl optionally substituted by 1-6 $R^{159}$, $C_{6-11}$aryl optionally substituted by 1-6 $R^{159}$, $C_{3-11}$cycloalkyl optionally substituted by 1-6 $R^{159}$, 3-15 membered heterocyclyl optionally substituted by 1-6 $R^{159}$, 5-15 membered heteroaryl optionally substituted by 1-6 $R^{159}$, halogen, —CN, —C(=O)$R^{150}$, —C(=O)O$R^{150}$, —C(=O)N$R^{152}R^{153}$, —NC, —NO$_2$, —N$R^{152}R^{153}$, —N$R^{154}$C(=O)$R^{150}$, —N$R^{154}$C(=O)O$R^{151}$, —N$R^{154}$C(=O)N$R^{152}R^{153}$, —N$R^{154}$S(=O)$_2R^{151}$, —N$R^{154}$S(=O)$_2$N$R^{152}R^{153}$, —O$R^{150}$, =O, —OC(=O)$R^{150}$, —OC(=O)N$R^{152}R^{153}$, —S(=O)$_n R^{150}$, and —S(=O)$_2$N$R^{152}R^{153}$;

$R^{150}$, $R^{151}$, $R^{152}$, $R^{153}$ and $R^{154}$ at each occurrence is independently chosen from H, $C_{1-6}$alkyl, benzyl, and $C_{1-6}$-haloalkyl;

$R^{129}$, $R^{139}$, $R^{149}$, and $R^{159}$ at each occurrence is independently chosen from $C_{1-6}$alkyl, $C_{1-6}$-haloalkyl, benzyl, halogen, —CN, —C(=O)($C_{1-6}$alkyl), —C(=O)O($C_{1-6}$alkyl), —C(=O)N($C_{1-6}$alkyl)$_2$, —C(=O)OH, —C(=O)NH$_2$, —C(=O)NHC$_{1-6}$alkyl, —NO$_2$, —NH$_2$, —NHC$_{1-6}$alkyl, —N($C_{1-6}$alkyl)$_2$, —NHC(=O)$C_{1-6}$alkyl, —NHS(=O)$_2C_{1-6}$alkyl, —OH, —O$C_{1-6}$alkyl, =O, —OC(=O)$C_{1-6}$alkyl, —OS(=O)$_2C_{1-6}$alkyl, —S(=O)$_2C_{1-6}$alkyl, and —S(=O)$_2$N($C_{1-6}$alkyl)$_2$; and n at each occurrence is independently chosen from 0, 1, and 2.

In one embodiment, E and G are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, phenyl optionally substituted by 1-5 $R^{19}$, $C_{3-6}$cycloalkyl optionally substituted by 1-6 $R^{19}$, 3-6 membered heterocyclyl optionally substituted by 1-5 $R^{19}$, 5-6 membered heteroaryl optionally substituted by 1-3 $R^{19}$, —C(=O)$R^{20}$, —C(=O)O$R^{20}$, —C(=O)N$R^{22}R^{23}$, —S(=O)$_2R^{20}$, and —S(=O)$_2$N$R^{22}R^{23}$.

In one embodiment, E is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$ aryl optionally substituted by 1-6 $R^{19}$, and $C_{3-11}$ cycloalkyl optionally substituted by 1-6 $R^{19}$.

In one embodiment, E is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, phenyl optionally substituted by 1-6 $R^{19}$, and $C_{3-6}$cycloalkyl optionally substituted by 1-6 $R^{19}$.

In one embodiment, E is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, and $C_{3-6}$cycloalkyl optionally substituted by 1-3 $R^{19}$.

In one embodiment, E is chosen from H, $C_{1-6}$alkyl optionally substituted by 1-3 $R^{19}$, $C_{2-6}$alkenyl, $C_{2-6}$alkynyl optionally substituted by —OH, phenyl optionally substituted by halogen, and $C_{3-6}$cycloalkyl.

In one embodiment, E is chosen from H, $C_{1-6}$alkyl optionally substituted by 1-3 $R^{19}$, $C_{2-6}$alkenyl, $C_{2-6}$alkynyl optionally substituted by —OH, phenyl optionally substituted by halogen, and cyclohexyl.

In one embodiment, E is chosen from H, $C_{1-6}$alkyl optionally substituted by 1-3 $R^{19}$, $C_{2-6}$alkenyl, $C_{2-6}$alkynyl optionally substituted by —OH, phenyl optionally substituted by fluoro, and cyclohexyl.

In one embodiment, E is chosen from $C_{1-6}$alkyl optionally substituted by $R^{19}$, phenyl, and p-fluorophenyl.

In one embodiment, E is phenyl optionally substituted by 1-5 halogen.

In one embodiment, E is $C_{1-6}$alkyl optionally substituted by $R^{19}$.

In one embodiment, E is p-fluorophenyl.

In one embodiment, G is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$ aryl optionally substituted by 1-6 $R^{19}$, $C_{3-11}$ cycloalkyl optionally substituted by 1-6 $R^{19}$, and 3-15 membered heterocyclyl optionally substituted by 1-6 $R^{19}$.

In one embodiment, G is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, phenyl optionally substituted by 1-3 $R^{19}$, $C_{3-6}$cycloalkyl optionally substituted by 1-3 $R^{19}$, and 3-6 membered heterocyclyl optionally substituted by 1-3 $R^{19}$.

In one embodiment, G is chosen from H, $C_{1-6}$alkyl optionally substituted by 1-3 $R^{19}$, $C_{2-6}$alkenyl optionally substituted by 1-3 halogen, $C_{2-6}$alkynyl, phenyl optionally substituted by 1-3 halogen, $C_{3-6}$cycloalkyl, and 3-6 membered heterocyclyl.

In one embodiment, G is chosen from H, $C_{1-6}$alkyl optionally substituted by 1-3 $R^{19}$, $C_{2-6}$alkenyl optionally substituted by 1-3 halogen, $C_{2-6}$alkynyl, phenyl optionally substituted by 1-3 halogen, $C_{3-6}$cycloalkyl, and 6 membered heterocyclyl.

In one embodiment, G is chosen from H, $C_{1-6}$alkyl optionally substituted by 1-3 $R^{19}$, $C_{3-6}$alkenyl optionally substituted by 1-3 fluoro, $C_{3-6}$alkynyl, phenyl optionally substituted by 1-3 fluoro, $C_{3-6}$cycloalkyl, and 6 membered heterocyclyl.

In one embodiment, G is chosen from H, $C_{1-6}$alkyl optionally substituted by 1-3 $R^{19}$, $C_{3-6}$alkenyl optionally substituted by 1-3 fluoro, $C_{3-6}$alkynyl, phenyl optionally substituted by 1-3 fluoro, $C_{3-6}$cycloalkyl, and 6 membered heterocyclyl.

In one embodiment, G is chosen from H, $C_{1-6}$alkyl optionally substituted by $R^{19}$ $C_{3-6}$alkenyl optionally substituted by 2 fluoro, $C_{3-6}$alkynyl, phenyl optionally substituted by fluoro, $C_{3-6}$cycloalkyl, and tetrahydropyranyl.

In one embodiment, G is H.

In one embodiment, G is $C_{1-6}$alkyl optionally substituted by $R^{19}$.

In one embodiment, G is $C_{1-6}$alkyl.

In one embodiment, G is $C_{3-6}$alkenyl optionally substituted by 2 fluoro.

In one embodiment, G is $C_{3-6}$alkynyl.

In one embodiment, G is phenyl optionally substituted by fluoro.

In one embodiment, G is p-fluorophenyl.

In one embodiment, G is $C_{3-6}$cycloalkyl.

In one embodiment, G is tetrahydropyranyl.

In one embodiment, X is N.

In one embodiment, X is C—$R_4$.

In one embodiment, Y is N.
In one embodiment, Y is CH.
In one embodiment, Y is C—$R_{1d}$.
In one embodiment, $R_3$ is H.
In one embodiment, $R_3$ is $C_{1-6}$alkyl.
In one embodiment, D is —O—, —S—, —C(=O)—, —CHOH—, —CH$_2$—, —NH— or —NC$_{1-6}$alkyl-.
In one embodiment, D is —O—, —S—, —C(=O)—, —CHOH—, —CH$_2$—, or —NH—.
In one embodiment, D is —O—, —S—, —C(=O)—, —CHOH—, or —CH$_2$—.
In one embodiment, D is —O—, —C(=O)—, —CHOH—, or —CH$_2$—.
In one embodiment, D is —O—, —C(=O)—, —CHOH—, or —CH$_2$—.
In one embodiment, D is —O—.
In one embodiment, D is —C(=O)—.
In one embodiment, D is —CHOH—.
In one embodiment, D is —CH$_2$—.
In one embodiment, W is CH.
In one embodiment, W is N.
In one embodiment, $R_a$, $R_b$, $R_c$, and $R_d$ are independently chosen from H, $C_{1-6}$alkyl optionally substituted by 1-6 $R^{119}$, $C_{2-6}$alkenyl optionally substituted by 1-6 $R^{119}$, $C_{2-6}$alkynyl optionally substituted by 1-6 $R^{119}$, $C_{6-11}$aryl optionally substituted by 1-6 $R^{119}$, $C_{3-11}$cycloalkyl optionally substituted by 1-6 $R^{119}$, 3-15 membered heterocyclyl optionally substituted by 1-6 $R^{119}$, 5-15 membered heteroaryl optionally substituted by 1-6 $R^{119}$, halogen, —CN, —C(=O)$R^{110}$, —C(=O)$NR^{112}R^{113}$, —NO$_2$, —$NR^{112}R^{113}$, —$NR^{114}$C(=O)$R^{110}$, —$NR^{114}$C(=O)$OR^{11}$, —$NR^{114}$C(=O)$NR^{112}R^{113}$, —$NR^{114}$S(=O)$_2R^{111}$, —$OR^{110}$, —S(=O)$_2R^{110}$, and —S(=O)$_2NR^{112}R^{113}$; or any of $R_a$ and $R_b$, $R_a$ and $R_d$, and $R_b$ and $R_c$ can, together with the atoms linking them, form a $C_{6-11}$aryl optionally substituted by 1-6 $R^{119}$, $C_{3-11}$cycloalkyl optionally substituted by 1-6 $R^{119}$, 3-15 membered heterocyclyl optionally substituted by 1-6 $R^{119}$ or a 5-15 membered heteroaryl optionally substituted by 1-6 $R^{119}$.

In one embodiment, $R_a$, $R_b$, $R_c$, and $R_d$ are independently chosen from H, $C_{1-6}$alkyl optionally substituted by 1-6 $R^{119}$, —CN, and —$OR^{110}$; or $R_a$ and $R_b$ can, together with the atoms linking them, form a 3-6 membered heterocyclyl optionally substituted by 1-6 $R^{119}$.

In one embodiment, $R_a$, $R_b$, $R_c$, and $R_d$ are independently chosen from H, $C_{1-6}$alkyl optionally substituted by 1-6 $R^{119}$, —CN, and —$OR^{110}$; or $R_a$ and $R_b$ can, together with the atoms linking them, form a 5-6 membered heterocyclyl optionally substituted by 1-6 $R^{119}$.

In one embodiment, $R_a$, $R_b$, $R_c$, and $R_d$ are independently chosen from H, $C_{1-6}$alkyl optionally substituted by 1-6 $R^{119}$, —CN, and —$OR^{110}$; or $R_a$ and $R_b$ can, together with the atoms linking them, form a 5-6 membered heterocyclyl.

In one embodiment, $R_a$ is chosen from H, —CN, and —$OC_{1-6}$alkyl; $R_b$ is chosen from H, $C_{1-6}$alkyl optionally substituted by 1-6 $R^{119}$, and —$OR^{110}$; $R_c$ is chosen from H and —$OC_{1-6}$alkyl; and $R_d$ is chosen from H and —$OC_{1-6}$alkyl; or $R_a$ and $R_b$ can, together with the atoms linking them, form a 5-6 membered heterocyclyl.

In one embodiment, $R_a$ is chosen from H, —CN, and —$OC_{1-6}$alkyl; $R_b$ is chosen from H, $C_{1-6}$alkyl optionally substituted by 6-membered heterocyclyl, and —$OR^{110}$; $R_c$ is chosen from H and —$OC_{1-6}$alkyl; and $R_d$ is chosen from H and —$OC_{1-6}$alkyl; or $R_a$ and $R_b$ can, together with the atoms linking them, form a 5-6 membered heterocyclyl.

In one embodiment, $R_a$ is chosen from H, —CN, and —$OC_{1-6}$alkyl; $R_b$ is chosen from H, $C_{1-6}$alkyl optionally sub-stituted by 6-membered heterocyclyl, —OH, —$OC_{1-6}$alkyl, —$OCH_2$phenyl, —$OC_{1-6}$alkyl-O—$C_{1-6}$alkyl; $R_c$ is chosen from H and —$OC_{1-6}$alkyl; and $R_d$ is chosen from H and —$OC_{1-6}$alkyl; or $R_a$ and $R_b$ can, together with the atoms linking them, form a 5-6 membered heterocyclyl.

In one embodiment, $R_a$ is chosen from H, —CN, and —$OC_{1-6}$alkyl; $R_b$ is chosen from H, $C_{1-6}$alkyl optionally substituted by morpholinyl, —OH, —$OC_{1-6}$alkyl, —$OCH_2$phenyl, —$OC_{1-6}$alkyl-O—$C_{1-6}$alkyl; $R_c$ is chosen from H and —$OC_{1-6}$alkyl; and $R_d$ is chosen from H and —$OC_{1-6}$alkyl; or $R_a$ and $R_b$ together form

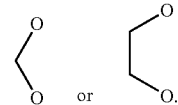

In one embodiment, $R_a$ is chosen from H and —$OC_{1-6}$alkyl; $R_b$ is chosen from H, $C_{1-6}$alkyl optionally substituted by morpholinyl, —OH, —$OC_{1-6}$alkyl, —$OCH_2$phenyl, —$OC_{1-6}$alkyl-O—$C_{1-6}$alkyl; $R_c$ is H; and $R_d$ is chosen from H and —$OC_{1-6}$alkyl; or $R_a$ and $R_b$ together form

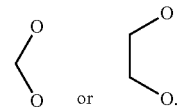

In one embodiment, $R_a$ is chosen from H and —$OC_{1-6}$alkyl; $R_b$ is chosen from $C_{1-6}$alkyl optionally substituted by morpholinyl, —OH, —$OC_{1-6}$alkyl, —$OCH_2$phenyl, —$OC_{1-6}$alkyl-O—$C_{1-6}$alkyl; $R_c$ is H; and $R_d$ is chosen from H and —$OC_{1-6}$alkyl; or $R_a$ and $R_b$ together form

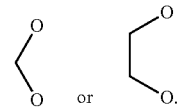

In one embodiment, $R_a$ is —$OC_{1-6}$alkyl; $R_b$ is chosen from H, $C_{1-6}$alkyl optionally substituted by morpholinyl, —OH, —$OC_{1-6}$alkyl, —$OCH_2$phenyl, —$OC_{1-6}$alkyl-O—$C_{1-6}$alkyl; $R_c$ is H; and $R_d$ is chosen from H and —$OC_{1-6}$alkyl; or $R_a$ and $R_b$ together form

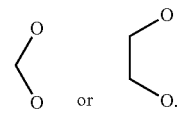

In one embodiment, $R_a$ is chosen from H and —$OC_{1-6}$alkyl; $R_b$ is chosen from H and —$OC_{1-6}$alkyl; $R_c$ is H; and $R_d$ is chosen from H and —$OC_{1-6}$alkyl; or $R_a$ and $R_b$ together form

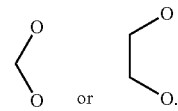

In one embodiment, $R_a$, $R_b$, $R_c$, and $R_d$ are independently chosen from H and —$OC_{1-6}$alkyl; or $R_a$ and $R_b$ together form

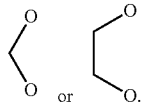

In one embodiment, $R_a$ is chosen from H and —$OC_{1-6}$alkyl; $R_b$ is chosen from H and —$OC_{1-6}$alkyl; $R_c$ is H; and $R_d$ is H; or $R_a$ and $R_b$ together form

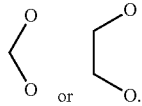

In one embodiment, $R_a$ is chosen from H and —$OC_{1-6}$alkyl; $R_b$ is chosen from H and —$OC_{1-6}$alkyl; $R_c$ is H; and $R_d$ is H.

In one embodiment, $R_a$ is chosen from H and —$OC_{1-3}$alkyl; $R_b$ is chosen from H and —$OC_{1-3}$alkyl; $R_c$ is H; and $R_d$ is H.

In one embodiment, $R_c$ is H; $R_d$ is H; and $R_a$ and $R_b$ together form

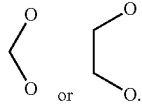

In one embodiment, $R_4$ is chosen from H, $C_{1-6}$alkyl, and $C_{1-6}$haloalkyl.

In one embodiment, $R_4$ is chosen from H and $C_{1-6}$alkyl.
In one embodiment, $R_4$ is chosen from H and $C_{1-3}$alkyl.
In one embodiment, $R_4$ is chosen from H and methyl.
In one embodiment, $R_4$ is H.
In one embodiment, $R_4$ is $C_{1-3}$ alkyl.
In one embodiment, $R_4$ is methyl.

In one embodiment, $R_{1a}$, $R_{1b}$, $R_{1c}$, and $R_{1d}$ are independently chosen from H, $C_{1-6}$alkyl optionally substituted by 1-6 $R^{119}$, $C_{3-6}$cycloalkyl optionally substituted by 1-6 $R^{119}$, 3-6 membered heterocyclyl optionally substituted by 1-6 $R^{119}$, halogen, —CN, —$NR^{112}R^{113}$, and —$OR^{110}$.

In one embodiment, $R_{1a}$, $R_{1b}$, $R_{1c}$, and $R_{1d}$ are independently chosen from H, $C_{1-6}$alkyl optionally substituted by 1-6 $R^{119}$, $C_{3-6}$cycloalkyl optionally substituted by 1-6 $R^{119}$ halogen, —$NR^{112}R^{113}$, and —$OR^{110}$.

In one embodiment, $R_{1a}$, $R_{1b}$, $R_{1c}$, and $R_{1d}$ are independently chosen from H, $C_{1-6}$alkyl, $C_{1-6}$haloalkyl, $C_{3-6}$cycloalkyl, halogen, —$NH_2$, —$NHC_{1-6}$alkyl$_2$, —$N(C_{1-6}$alkyl$)_2$, —OH, and —$OC_{1-6}$alkyl.

In one embodiment, $R_{1a}$, $R_{1b}$, $R_{1c}$, and $R_{1d}$ are independently chosen from H, $C_{1-6}$alkyl, $C_{1-6}$haloalkyl, $C_{3-6}$cycloalkyl, halogen, —$N(C_{1-6}$alkyl$)_2$, —$OC_{1-6}$alkyl.

In one embodiment, $R_{1a}$, $R_{1b}$, $R_{1c}$, and $R_{1d}$ are independently chosen from H, $C_{1-3}$alkyl, $C_{1-3}$ haloalkyl, $C_{3-6}$cycloalkyl, halogen, and —$OC_{1-3}$ alkyl.

In one embodiment, $R_{1a}$, $R_{1b}$, $R_{1c}$, and $R_{1d}$ are independently chosen from H, $C_{1-3}$alkyl, $C_{1-3}$ haloalkyl, cyclopropyl, halogen, and —$OC_{1-3}$ alkyl.

In one embodiment, $R_{1a}$, $R_{1b}$, $R_{1c}$, and $R_{1d}$ are independently chosen from H, halogen, and —$OC_{1-3}$alkyl.

In one embodiment, $R_{1a}$, $R_{1b}$, $R_{1c}$, and $R_{1d}$ are independently chosen from H, halogen, and methoxy.

In one embodiment, $R_{1a}$, $R_{1b}$, $R_{1c}$, and $R_{1d}$ are independently chosen from H and halogen.

In one embodiment, $R_{1a}$, $R_{1b}$, $R_{1c}$, and $R_{1d}$ are independently chosen from H and fluoro.

In one embodiment, $R_{1a}$ and $R_{1b}$ are independently chosen from H, $C_{1-6}$alkyl optionally substituted by 1-6 $R^{119}$, $C_{3-6}$cycloalkyl optionally substituted by 1-6 $R^{119}$ halogen, and —$OR^{110}$; and $R_{1c}$ and $R_{1d}$ are independently chosen from H, $C_{1-6}$alkyl optionally substituted by 1-6 $R^{119}$, halogen, —$NR^{112}R^{113}$, and —$OR^{110}$.

In one embodiment, $R_{1a}$ and $R_{1b}$ are independently chosen from H, $C_{1-6}$alkyl, $C_{1-6}$haloalkyl, $C_{3-6}$cycloalkyl, halogen, and —$OC_{1-6}$alkyl; and $R_{1c}$ and $R_{1d}$ are independently chosen from H, $C_{1-6}$alkyl, halogen, —$N(C_{1-6}$alkyl$)_2$, and —$OC_{1-6}$alkyl.

In one embodiment, $R_{1a}$ and $R_{1b}$ are independently chosen from H, $C_{1-3}$alkyl, $C_{1-3}$haloalkyl, $C_{3-6}$cycloalkyl, halogen, and —$OC_{1-3}$alkyl; and $R_{1c}$ and $R_{1d}$ are independently chosen from H, $C_{1-3}$alkyl, halogen, —$N(C_{1-3}$alkyl$)_2$, and —$OC_{1-3}$alkyl.

In one embodiment, $R_{1a}$ and $R_{1b}$ are independently chosen from H, $C_{1-3}$alkyl, $C_{1-3}$haloalkyl, cyclopropyl, halogen, and —$OC_{1-3}$alkyl; and $R_{1c}$ and $R_{1d}$ are independently chosen from H, $C_{1-3}$alkyl, halogen, —$N(C_{1-3}$alkyl$)_2$, and —$OC_{1-3}$alkyl.

In one embodiment, $R_{1a}$ and $R_{1b}$ are independently chosen from H, $C_{1-3}$alkyl, $C_{1-3}$haloalkyl, cyclopropyl, halogen, and —$OC_{1-3}$alkyl; and $R_{1c}$ and $R_{1d}$ are independently chosen from H, $C_{1-3}$alkyl, halogen, and —$OC_{1-3}$alkyl.

In one embodiment, $R_{1a}$, $R_{1c}$, and $R_{1d}$ are H and $R_{1b}$ is chosen from H, $C_{1-3}$alkyl, $C_{1-3}$haloalkyl, cyclopropyl, halogen, and —$OC_{1-3}$alkyl.

In one embodiment, $R_{1a}$, $R_{1c}$, and $R_{1d}$ are H and $R_{1b}$ is chosen from H, halogen, and —$OC_{1-3}$alkyl.

In one embodiment, $R_{1a}$, $R_{1c}$, and $R_{1d}$ are H and $R_{1b}$ is chosen from H and halogen.

In one embodiment, $R_{1a}$, $R_{1c}$, and $R_{1d}$ are H and $R_{1b}$ is chosen from H and fluoro.

In one embodiment, $R_{1a}$, $R_{1c}$, and $R_{1d}$ are H and $R_{1b}$ is halogen.

In one embodiment, $R_{1a}$, $R_{1c}$, and $R_{1d}$ are H and $R_{1b}$ is fluoro.

In one embodiment, $R^{19}$ at each occurrence is independently chosen from $C_{1-6}$alkyl optionally substituted by 1-6 $R^{39}$, $C_{6-11}$aryl optionally substituted by 1-6 $R^{39}$, $C_{3-11}$cycloalkyl optionally substituted by 1-6 $R^{39}$, 3-15 membered heterocyclyl optionally substituted by 1-6 $R^{39}$, 5-15 membered heteroaryl optionally substituted by 1-6 $R^{39}$, halogen, —CN, —C(=O)$OR^{30}$, —C(=O)$NR^{32}R^{33}$, —$NR^{32}R^{33}$, —$OR^{30}$, and =O.

In one embodiment, $R^{19}$ at each occurrence is independently chosen from $C_{1-6}$alkyl optionally substituted by 1-6 $R^{39}$, phenyl optionally substituted by 1-6 $R^{39}$, $C_{3-6}$cycloalkyl optionally substituted by 1-6 $R^{39}$, 3-6 membered heterocyclyl optionally substituted by 1-6 $R^{39}$, 5-6 membered heteroaryl optionally substituted by 1-6 $R^{39}$, halogen, —CN, —C(=O)$OR^{30}$, —C(=O)$NR^{32}R^{33}$, —$NR^{32}R^{33}$, —$OR^{30}$, and =O.

In one embodiment, $R^{19}$ at each occurrence is independently chosen from $C_{1-6}$alkyl, phenyl optionally substituted by 1-3 halogen, $C_{3-6}$cycloalkyl, 3-6 membered heterocyclyl, 5-6 membered heteroaryl optionally substituted by 1-3 $C_{1-6}$alkyl, halogen, —CN, —C(=O)OH, —C(=O)$OC_{1-6}$alkyl, —C(=O)$N(C_{1-6}$alkyl$)_2$, —$N(C_{1-6}$alkyl$)_2$, —OH, —$OC_{1-6}$alkyl, —Obenzyl, and =O.

In one embodiment, $R^{19}$ at each occurrence is independently chosen from $C_{1-6}$alkyl, phenyl optionally substituted by 1-3 halogen, $C_{3-6}$cycloalkyl, 5-6 membered heterocyclyl, 5-6 membered heteroaryl optionally substituted by 1-3 $C_{1-6}$alkyl, halogen, —CN, —C(=O)OH, —C(=O)OC$_{1-6}$alkyl, —C(=O)N(C$_1$-6alkyl)$_2$, —C(=O)pyrrolidinyl, —C(=O)morpholinyl, —N(C$_{1-6}$alkyl)$_2$, —OH, —OC$_{1-6}$alkyl, —Obenzyl, and =O.

In one embodiment, $R^{19}$ at each occurrence is independently chosen from $C_{3-6}$cycloalkyl and —OH.

In one embodiment, $R^{19}$ at each occurrence is independently chosen from cyclopropyl and —OH.

In one embodiment, $R^{20}$, $R^{30}$, $R^{31}$, $R^{34}$, $R^{22}$, $R^{23}$, $R^{32}$ and $R^{33}$ at each occurrence is independently chosen from H, $C_{1-6}$alkyl, $C_{1-6}$halolkyl, phenyl, benzyl, $C_{5-6}$cycloalkyl, 5-6 membered heterocyclyl, and 5-6 membered heteroaryl; or $R^{32}$ and $R^{33}$ may form, together with the nitrogen atom to which they are attached, a 5-6 membered heterocyclyl or a 5-6 membered heteroaryl.

In one embodiment, $R^{20}$, $R^{30}$, $R^{31}$, $R^{34}$, $R^{22}$, $R^{23}$, $R^{32}$ and $R^{33}$ at each occurrence is independently chosen from H, $C_{1-6}$alkyl, $C_{1-6}$halolkyl, phenyl, benzyl, $C_{5-6}$cycloalkyl, 5-6 membered heterocyclyl, and 5-6 membered heteroaryl.

In one embodiment, $R^{20}$, $R^{30}$, $R^{31}$, $R^{34}$, $R^{22}$, $R^{23}$, $R^{32}$ and $R^{33}$ at each occurrence is independently chosen from H and $C_{1-6}$alkyl.

In one embodiment, $R^{39}$, $R^{49}$, $R^{59}$ and $R^{69}$ at each occurrence is independently chosen from $C_{1-6}$alkyl, $C_{1-6}$haloalkyl, and benzyl.

In one embodiment, $R^{39}$, $R^{49}$, $R^{59}$ and $R^{69}$ at each occurrence is independently chosen from $C_{1-6}$alkyl and $C_{1-6}$haloalkyl.

In one embodiment, $R^{39}$, $R^{49}$, $R^{59}$ and $R^{69}$ at each occurrence is independently chosen from $C_{1-6}$alkyl.

In one embodiment, $R^{70}$, $R^{71}$, $R^{72}$, $R^{73}$, and $R^{74}$ at each occurrence is independently chosen from H and $C_{1-6}$alkyl.

In one embodiment, $R^{70}$, $R^{71}$, $R^{72}$, $R^{73}$, and $R^{74}$ at each occurrence is H.

In one embodiment, $R^{79}$ at each occurrence is independently chosen from $C_{1-6}$alkyl, $C_{1-6}$-haloalkyl, benzyl, and halogen.

In one embodiment, $R^{79}$ at each occurrence is independently chosen from $C_{1-6}$alkyl and $C_{1-6}$-haloalkyl.

In one embodiment, $R^{79}$ at each occurrence is independently chosen from $C_{1-6}$alkyl.

In one embodiment, $R^{110}$, $R^{111}$, $R^{112}$, $R^{113}$, and $R^{114}$ at each occurrence is independently chosen from H and $C_{1-6}$alkyl optionally substituted by 1-3 $R^{129}$.

In one embodiment, $R^{110}$, $R^{111}$, $R^{112}$, $R^{113}$, and $R^{114}$ at each occurrence is independently chosen from H and $C_{1-3}$alkyl optionally substituted by 1-3 $R^{129}$.

In one embodiment, $R^{110}$, $R^{111}$, $R^{112}$, $R^{113}$, and $R^{114}$ at each occurrence is independently chosen from H, benzyl, and $C_{1-6}$alkyl optionally substituted by —OC$_{1-3}$alkyl.

In one embodiment, $R^{110}$, $R^{111}$, $R^{112}$, $R^{113}$, and $R^{114}$ at each occurrence is independently chosen from H and $C_{1-3}$alkyl optionally substituted by —OC$_{1-3}$alkyl.

In one embodiment, $R^{110}$, $R^{111}$, $R^{112}$, $R^{113}$, and $R^{114}$ at each occurrence is independently chosen from H and $C_{1-3}$ alkyl.

In one embodiment, $R^{110}$, $R^{111}$, $R^{112}$, $R^{113}$, and $R^{114}$ at each occurrence is H.

In one embodiment, $R^{119}$ at each occurrence is independently chosen from $C_{1-6}$alkyl optionally substituted by 1-6 $R^{159}$, 3-15 membered heterocyclyl optionally substituted by 1-6 $R^{159}$, and halogen.

In one embodiment, $R^{119}$ at each occurrence is independently chosen from $C_{1-6}$alkyl optionally substituted by 1-3 $R^{159}$, 5-6 membered heterocyclyl optionally substituted by 1-3 $R^{159}$, and halogen.

In one embodiment, $R^{119}$ at each occurrence is independently chosen from $C_{1-6}$alkyl, $C_{1-6}$haloalkyl, 5-6 membered heterocyclyl, and halogen.

In one embodiment, $R^{119}$ at each occurrence is independently chosen from 5-6 membered heterocyclyl and halogen.

In one embodiment, $R^{119}$ at each occurrence is independently chosen from 6 membered heterocyclyl and halogen.

In one embodiment, $R^{119}$ at each occurrence is independently chosen from morpholinyl and halogen.

In one embodiment, $R^{119}$ at each occurrence is independently chosen from morpholinyl and fluoro.

In one embodiment, $R^{150}$, $R^{151}$, $R^{152}$, $R^{153}$ and $R^{154}$ at each occurrence is independently chosen from H and $C_{1-6}$alkyl.

In one embodiment, $R^{150}$, $R^{151}$, $R^{152}$, $R^{153}$ and $R^{154}$ at each occurrence is H.

In one embodiment, $R^{129}$, $R^{139}$, $R^{149}$, and $R^{159}$ at each occurrence is independently chosen from $C_{1-6}$alkyl, $C_{1-6}$-haloalkyl, benzyl, and halogen.

In one embodiment, $R^{129}$, $R^{139}$, $R^{149}$, and $R^{159}$ at each occurrence is independently chosen from $C_{1-6}$alkyl and halogen.

In one embodiment, $R^{129}$, $R^{139}$, $R^{149}$, and $R^{159}$ at each occurrence is halogen.

In one embodiment, $R^{129}$, $R^{139}$, $R^{149}$, and $R^{159}$ at each occurrence is $C_{1-6}$alkyl.

In one embodiment, n at each occurrence is 0 or 2.

In one embodiment, n at each occurrence is 0.

In one embodiment, n at each occurrence is 2.

The present invention also provides compounds of Formula II

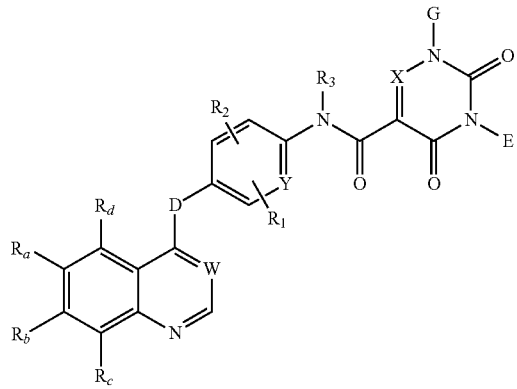

Formula II wherein:

$R_a$ is H, alkyl, halo, cyano, hydroxyl, amino, alkylamino, dialkylamino where the alkyl groups of dialkylamino may be the same or different, carbamoyl, N-alkylcarbamoyl, N,N-dialkylcarbamoyl, where the alkyl groups of dialkylcarbamoyl may be the same or different, trihalomethyl, or $R_a$ is OA;

$R_b$ is H, alkyl, halo, cyano, hydroxyl, amino, alkylamino, dialkylamino where the alkyl groups of dialkylamino may be the same or different, carbamoyl, N-alkylcarbamoyl, N,N-dialkylcarbamoyl, where the alkyl groups of dialkylcarbamoyl may be the same or different, trihalomethyl, or $R_b$ is OB;

$R_c$ is H, alkyl, halo, cyano, hydroxyl, amino, alkylamino, dialkylamino where the alkyl groups of dialkylamino may be the same or different, carbamoyl, N-alkylcarbamoyl, N,N-dialkylcarbamoyl, where the alkyl groups of dialkylcarbamoyl may be the same or different, trihalomethyl, or $R_c$ is OJ;

$R_d$ is H, alkyl, halo, cyano, hydroxyl, amino, alkylamino, dialkylamino where the alkyl groups of dialkylamino may be the same or different, carbamoyl, N-alkylcarbamoyl, N,N-dialkylcarbamoyl, where the alkyl groups of dialkylcarbamoyl may be the same or different, trihalomethyl, or $R_d$ is OL;

where A, B, J and L, are, independently, H, alkyl, alkoxyalkyl, cycloalkyl, cycloalkoxyalkyl, heterocyclylalkyl, heterocyclylalkoxyalkyl, arylalkyl or arylalkoxyalkyl, or A and B together with the oxygen atoms to which they are attached form

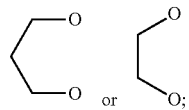

D is O, S, SO, $SO_2$, C=O, C(H)OH, $CH_2$, NH or N-alkyl;

E is H, alkyl, substituted alkyl, alkenyl, substituted alkenyl, alkynyl, substituted alkynyl, cycloalkyl, aryl, substituted aryl, heteroaryl, substituted heteroaryl, heterocyclyl, or heteroarylalkyl, where the heteroaryl group of heteroarylalkyl may be substituted or unsubstituted;

G is H, aryl, substituted aryl, heteroaryl, substituted heteroaryl, heterocyclyl, alkyl or cycloalkyl, cycloalkylalkyl, alkenyl or alkynyl, where alkyl, alkenyl or cycloalkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, carboxyl, oxo, carbamoyl, alkylcarbamoyl, dialkylcarbamoyl, where the alkyl groups of dialkylcarbamoyl may be the same or different, and heterocycyclylcarbonyl;

W is CH or N;

X is C—$R_4$ or N, where $R_4$ is H, OH or alkyl, where the alkyl group may be substituted by hydroxyl, alkoxy, alkylamino, or dialkyl amino, where the alkyl groups of dialkylamino may be the same or different;

Y is N, CH or C where C may be substituted with one of the groups $R_1$ or $R_2$; and $R_1$ and $R_2$ are, independently, H, alkyl, cycloalkyl, halo, alkoxy, trihaloalkyl, amino, alkylamino, dialkylamino, where the alkyl groups on dialkylamino may be the same or different, or heterocyclyl; and $R_3$ is H, or alkyl; or a pharmaceutically acceptable salt thereof.

A preferred embodiment of the present invention provides compounds of Formula II wherein W is CH.

Another preferred embodiment of the present invention provides compounds of Formula II wherein W is N.

Another preferred embodiment of the present invention provides compounds of Formula III.

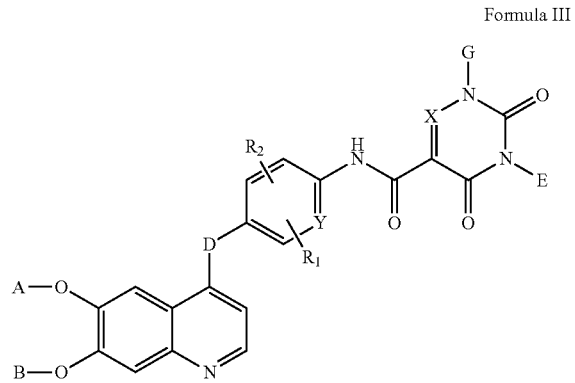

Formula III wherein:

A and B are, independently, H, alkyl, alkoxyalkyl, cycloalkyl, cycloalkoxyalkyl, heterocyclylalkyl, heterocyclylalkoxyalkyl, arylalkyl or arylalkoxyalkyl, or A and B together with the oxygen atoms to which they are attached form

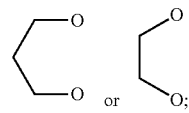

D is O, S, NH, or C=O;

E is H, alkyl, substituted alkyl, alkenyl, substituted alkenyl, alkynyl, substituted alkynyl, cycloalkyl, aryl, substituted aryl, heteroaryl, heterocyclyl, substituted heteroaryl, or heteroarylalkyl, where the heteroaryl group of heteroarylalkyl may be substituted or unsubstituted;

G is H, aryl, substituted aryl, heteroaryl, substituted heteroaryl, heterocyclyl, alkyl or cycloalkyl, cycloalkylalkyl, alkenyl or alkynyl, where alkyl, alkenyl or cycloalkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, carboxyl, oxo, carbamoyl, alkylcarbamoyl, dialkylcarbamoyl, where the alkyl groups of dialkylcarbamoyl may be the same or different, and heterocycyclylcarbonyl;

X is C—$R_4$ or N, where $R_4$ is H or alkyl;

Y is N, CH or C where C may be substituted with one of the groups $R_1$ or $R_2$; and $R_1$ and $R_2$ are, independently, H, alkyl, halo, alkoxy, trihaloalkyl, amino, alkylamino, dialkylamino, where the alkyl groups on dialkylamino may be the same or different; or a pharmaceutically acceptable salt thereof.

Another preferred embodiment of the present invention provides compounds of Formula III wherein A and B are, independently, alkyl, heterocyclylalkyl or heterocyclylalkoxyalkyl.

Another preferred embodiment of the present invention provides compounds of Formula III wherein A and B are, independently, alkyl.

Another preferred embodiment of the present invention provides compounds of Formula III wherein D is O, S or NH.

Another preferred embodiment of the present invention provides compounds of Formula III wherein D is O.

Another preferred embodiment of the present invention provides compounds of Formula III wherein $R_1$ and $R_2$ are, independently, halo, alkoxy, alkyl or H.

Another preferred embodiment of the present invention provides compounds of Formula III wherein $R_1$ and $R_2$ are, independently, halo or alkoxy.

Another preferred embodiment of the present invention provides compounds of Formula III wherein $R_1$ and $R_2$ are, independently, methoxy or fluoro.

Another preferred embodiment of the present invention provides compounds of Formula III wherein X is N or CH.

Another preferred embodiment of the present invention provides compounds of Formula III wherein X is CH.

Another preferred embodiment of the present invention provides compounds of Formula III wherein G is alkyl where alkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, carboxyl, oxo, carbamoyl, alkylcarbamoyl, dialkylcarbamoyl, where the alkyl groups of dialkylcarbamoyl may be the same or different, and heterocycyclylcarbonyl.

Another preferred embodiment of the present invention provides compounds of Formula III wherein E is aryl, substituted aryl or cycloalkyl.

Another preferred embodiment of the present invention provides compounds of Formula III wherein E is substituted aryl.

Another preferred embodiment of the present invention provides compounds of Formula III wherein A and B are, independently, alkyl; D is O, S or NH; $R_1$ and $R_2$ are, independently, halo, alkoxy, alkyl or H; X is N or CH; G is alkyl where alkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, carboxyl, oxo, carbamoyl, alkylcarbamoyl, dialkylcarbamoyl, where the alkyl groups of dialkylcarbamoyl may be the same or different, and heterocycyclylcarbonyl; and E is aryl, substituted aryl or cycloalkyl.

In other preferred embodiments, the present invention provides any of the compounds as described in the Examples.

The present invention provides salts of the AXL and c-MET inhibitory compounds described herein. Preferably, the salts are pharmaceutically acceptable. Pharmaceutically acceptable acid addition salts of the compounds described herein include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoracetate, propionate, caprylate, isobutyrate, oxalate, malonate, succinate, suberate, sebacate, fumarate, mandelate, benzoate, chlorobenzoate, methylbenzoate, dinitrobenzoate, phthalate, benzenesulfonate, toluenesulfonate, phenylacetate, citrate, lactate, ascorbate, pyroglutamate, maleate, tartrate, and methanesulfonate. Also contemplated are the salts of amino acids such as arginate, gluconate, galacturonate, and the like; see, for example, Berge et al., "Pharmaceutical Salts," J. of Pharmaceutical Science, 1977; 66:1-19.

The acid addition salts of basic compounds described herein may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are in general equivalent to their respective free base for purposes of the present invention.

Pharmaceutically acceptable base addition salts of compounds described herein are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine; see, for example, Berge et al., supra., 1977.

The base addition salts of acidic compounds may be prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are in general equivalent to their respective free acid for purposes of the present invention.

Some of the compounds in the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have carbocyclyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

III. Pharmaceutical Compositions

The present invention further provides pharmaceutical compositions comprising a compound of the present invention, or a pharmaceutically acceptable salt thereof, together with a pharmaceutically acceptable carrier, diluent, or excipient therefor. The pharmaceutical composition may contain two or more compounds of the present invention (i.e., two or more compounds of the present invention may be used together in the pharmaceutical composition). Preferably, the pharmaceutical composition contains a therapeutically effective amount of at least one compound of the present invention.

In another embodiment, these compositions are useful in the treatment of an AXL- or c-MET-mediated disorder or condition. The compounds of the invention can also be combined in a pharmaceutical composition that also comprises compounds that are useful for the treatment of cancer or another AXL- or c-MET-mediated disorder.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with an AXL or c-MET-mediated disorder as measured quantitatively or qualitatively.

For preparing a pharmaceutical composition from a compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component (i.e., compound of the present invention). In tablets, the active component is mixed with the carrier having the necessary binding properties in suitable proportions and compacted in the shape and size desired.

The powders and tablets contain from 1% to 95% (w/w) of the active compound (i.e., compound of the present invention). In another embodiment, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The dose administered to a subject, in the context of the present invention, should be sufficient to effect a beneficial therapeutic response in the subject over time. The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 10 mg/kg for a typical subject. Many different administration methods are known to those of skill in the art.

For administration, compounds of the present invention can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

IV. Methods of Treatment

In another aspect, the present invention provides a method of treating a subject suffering from an AXL- or c-MET-mediated disorder or condition comprising administering to the subject a therapeutically effective amount of a compound of the present invention or a pharmaceutically acceptable salt form thereof. In another aspect, the present invention provides a compound of the present invention or a pharmaceutically acceptable salt form thereof for use in treating a subject suffering from an AXL or c-MET-mediated disorder or condition. Preferably, the compound of the present invention or a pharmaceutically acceptable salt form thereof is administered to the subject in a pharmaceutical composition comprising a pharmaceutically acceptable carrier. In another aspect, the present invention provides a pharmaceutical composition comprising a compound of the present invention or a pharmaceutically acceptable salt form thereof for use in treating a subject suffering from an AXL- or c-MET-mediated disorder or condition. In another embodiment, the AXL- or c-MET-mediated condition or disorder is cancer. In another embodiment, the AXL- or c-MET-mediated disorder or condition is the development of resistance to cancer therapies. In another embodiment, the AXL or c-MET-mediated condition is selected from chronic myelogenous leukemia, chronic myeloproliferative disorder, lung cancer, prostate cancer, esophageal cancer, ovarian cancer, pancreatic cancer, gastric cancer, liver cancer, thyroid cancer, renal cell carcinoma, glioblastoma, breast cancer, acute myeloid leukemia, colorectal cancer, uterine cancer, malignant glioma, uveal melanoma, osteosarcoma and soft tissue sarcoma.

The AXL- or c-MET-mediated disorder or condition can be treated prophylactically, acutely, and chronically using compounds of the present invention, depending on the nature of the disorder or condition. Typically, the host or subject in each of these methods is human, although other mammals can also benefit from the administration of a compound of the present invention.

In another embodiment, the present invention provides a method of treating a proliferative disorder in a subject in need thereof, comprising administering to the subject a therapeutically effective amount of a compound of the present invention or a pharmaceutically acceptable salt form thereof. In another aspect, the present invention provides a compound of the present invention or a pharmaceutically acceptable salt form thereof for use in treating a proliferative disorder in a subject in need thereof. Preferably, the compound of the present invention or a pharmaceutically acceptable salt form thereof is administered to the subject in a pharmaceutical composition comprising a pharmaceutically acceptable carrier. In another aspect, the present invention provides a pharmaceutical composition comprising a compound of the present invention or a pharmaceutically acceptable salt form thereof for use in treating a proliferative disorder in a subject. In certain embodiments, the proliferative disorder is AXL- or c-MET-mediated. In certain embodiments, the proliferative disorder is cancer. In certain embodiments, the proliferative disorder is selected from chronic myelogenous leukemia, chronic myeloproliferative disorder, lung cancer, prostate cancer, esophageal cancer, ovarian cancer, pancreatic cancer, gastric cancer, liver cancer, thyroid cancer, renal cell carcinoma, glioblastoma, breast cancer, acute myeloid leukemia, colorectal cancer, uterine cancer, malignant glioma, uveal melanoma, osteosarcoma and soft tissue sarcoma.

The proliferative disorder can be treated prophylactically, acutely, and chronically using compounds of the present invention, depending on the nature of the disorder or condition. Typically, the host or subject in each of these methods is human, although other mammals can also benefit from the administration of a compound of the present invention.

In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. In another embodiment, the compounds of the present invention are delivered orally. The compounds can also be delivered rectally, bucally or by insufflation.

The compounds utilized in the pharmaceutical method of the invention can be administered at the initial dosage of about 0.001 mg/kg to about 100 mg/kg daily. In another embodiment, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

V. Chemistry

Unless otherwise indicated, all reagents and solvents were obtained from commercial sources and used as received. $^1$H NMRs were obtained on a Bruker Avance at 400 MHz in the solvent indicated with tetramethylsilane as an internal standard. Analytical HPLC was run using a Zorbax RX-C8, 5×150 mm column eluting with a mixture of acetonitrile and water containing 0.1% trifluoroacetic acid with a gradient of 10-100%. LCMS results were obtained from a Bruker Esquire 2000 Mass Spec with the Agilent 1100 HPLC equipped with an Agilent Eclipse XDB-C8, 2×30 mm 3.5 micron column. The column was at room temperature, with a run time of five (5) minutes, a flow rate of 1.0 mL/min, and a solvent mixture of 10% (0.1% formic acid/water): 100% (acetonitrile/0.1% formic acid). Automated normal phase column chromatography was performed on a CombiFlash Companion (ISCO, Inc.). Reverse phase preparative HPLC was performed on a Gilson GX-281 equipped with Gilson 333 and 334 pumps using a Phenomenex 00F-4454-00-AX Gemini-NX 5µ C18 column. Melting points were taken on a Mel-Temp apparatus and are uncorrected.

Synthesis

The compounds of the present invention can be synthesized using the methods described below or by using methods known to one skilled in the art of organic chemistry or variations thereon as appreciated by those skilled in the art. The preferred methods include, but are not limited to or by, those described below. Unless otherwise stated, starting compounds are of commercial origin or are readily synthesized by standard methods well known to one skilled in the art of organic synthesis.

The reactions are performed in solvents appropriate to the reagents, and materials employed are suitable for the transformations being effected. Also, in the description of the synthetic methods below, it is to be understood that all proposed reaction conditions, including choice of solvent, reaction atmosphere, reaction temperature, duration of experiment and workup procedures are chosen to be conditions standard for that reaction which should be readily recognized by one skilled in the art of organic synthesis.

It is understood that the examples and embodiments described herein are for illustrative purposes only and that various modifications or changes in light thereof will be suggested to persons skilled in the art and are to be included within the spirit and purview of this application and the scope of the appended claims. Specific chemical transformations are listed in the ensuing schemes and one skilled in the art appreciates that a variety of different reagents may be used in place of those listed. Common replacements for such reagents can be found in, but not limited to, texts such as "Encyclopedia of Reagents for Organic Synthesis" Leo A. Paquette, John Wiley & Son Ltd (1995) or "Comprehensive Organic Transformations: A Guide to Functional Group Preparations" Richard C. Larock. Wiley-VCH and "Strategic Applications of Named Reactions in Organic Synthesis" Kurti and Czako, Elsevier, 2005 and references therein.

The examples of the present invention may be produced according to synthesis routes as depicted in Schemes 1 to 6, and by the synthetic procedures described herein and within the examples.

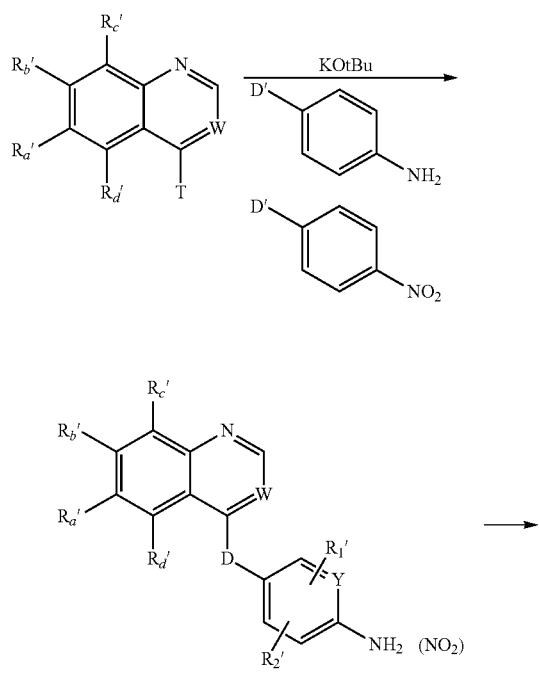

Scheme 1

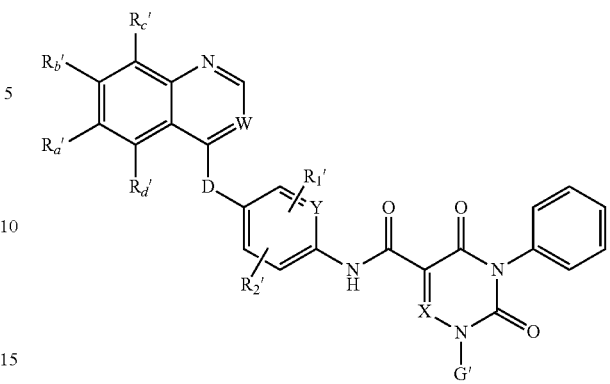

-continued

In Scheme 1, W and X are as defined herein. T is Br, Cl or I. D' is OH, SH, NH$_2$, or NH-alkyl. D is O, S, NH, or N-alkyl. R$_a$', R$_b$', R$_c$', R$_d$', R$_1$' and R$_2$' are R$_a$, R$_b$, R$_c$, R$_d$, R$_1$ and R$_2$, respectively, as defined herein, or are synthetic precursors thereto. Y is N, CH or C, where C may be substituted by one of the groups R$_1$' or R$_2$'.

Looking at Scheme 1, substituted 4-chloroquinolines or 4-bromoquinoline derivatives are known and can be synthesized as described in the literature from properly substituted arylamines and Meldrum's acid in the presence of trimethyl orthoformate (Bioorg. Medchem. Lett., 1997, 7, 789, WO9813350, US20080004273). Alternatively properly substituted quinolines can be synthesized from substituted acetophenones by methods described in the literature (for example J. Med. Chem. 2005, 48, 1359; EP 1153920; WO201145084). Quinazolines analogs may be synthesized by literature methods (described in J. Med. Chem. 2005, 48, 1359; J. Med. Chem. 2006, 49, 2186; J. Med. Chem. 2010, 53, 8089). The synthesizes of N, O, and S linker quinolines and quinazolines intermediates are described in J. Med. Chem. 2005, 48, 1359. A 4-(aminophenoxy)quinoline derivative may be produced by reacting a nitrophenol derivative with the 4-chloroquinoline derivative in a suitable solvent, for example, chlorobenzene, to synthesize a 4-(nitrophenoxy)-quinoline derivative or a corresponding quinazoline derivative and then reacting the 4-(nitrophenoxy)quinoline derivative in a suitable solvent, for example, N,N-dimethyl formamide, ethanol or ethyl acetate in the presence of a catalyst, for example, palladium hydroxide-carbon or palladium-carbon, under a hydrogen atmosphere. The nitro group can also be reduced with zinc or iron. Alternatively, the 4-(aminophenoxy)quinoline derivative can be produced by reacting an aminophenol derivative with the 4-chloroquinoline derivative in a suitable solvent, for example, dimethyl sulfoxide or N,N-dimethyl formamide, in the presence of a base, for example, sodium hydride or potassium t-butoxide. The 4-(aminophenoxy)-quinazoline derivative can be produced by dissolving an aminophenol derivative in an aqueous sodium hydroxide solution and subjecting the solution to a two phase reaction with a solution of the 4-chloroquinazoline derivative in a suitable solvent, DMF, THF, or ethyl methyl ketone, in the presence of a phase transfer catalyst, for example, tetra-n-butylammonium chloride.

An example of the synthesis of 2,4-dioxo-1,2,3,4-tetrahydro-pyrimidine-5-carboxylic acids is shown in Scheme 2.

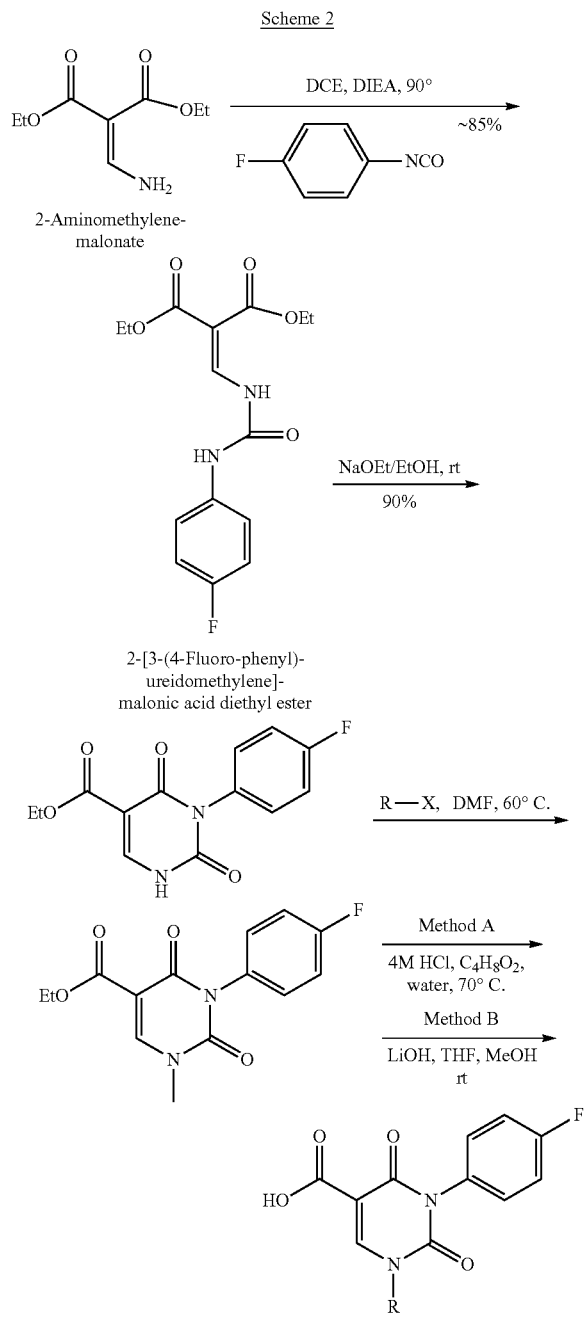

Where, in Scheme 2, DCE is dichloroethane, DIEA is diisopropylethylamine, NaOEt is sodium ethoxide, EtOH is ethanol, DMF is dimethylformamide, C₄H₈O₂ is dioxane, THF is tetrahydrofuran, MeOH is ethanol, and R—X is an alkyl halide.

Starting with a 2-aminomethylene malonate and reacting with any appropriate aryl, heteroaryl or alkyl isocyanate produces ureidomethylene-malonic acid esters. The ureidomethylene-malonic acid esters can be cyclized using a base such as KOH, NaOH or sodium ethoxide in ethanol to produce the N1-H 2,4-dioxo-1,2,3,4-tetrahydro-pyrimidine-5-carboxylic acid esters. Starting with an N-substituted 2-aminomethylene malonate produces an N1 substituted 2,4-dioxo-1,2,3,4-tetrahydro-pyrimidine-5-carboxylic acid ester. Starting with substitution on the methylene malonate, for example 2-(1-aminoethylidene)-malonic acid ester or 2-(1-amino-2-cyclopropyl-ethylidene)-malonic acid ester produces the corresponding C6 substituted 2,4-dioxo-1,2,3,4-tetrahydro-pyrimidine-6-methyl-5-carboxylic acid ester or 2,4-dioxo-1,2,3,4-tetrahydro-pyrimidine-6-cyclopropylmethyl-5-carboxylic acid ester. The N1-H intermediate may be alkylated under standard conditions using a base, for example $K_2CO_3$ in a solvent such as dimethylsulfoxide or dimethylformamide to produce the N1-substituted-2,4-dioxo-1,2,3,4-tetrahydro-pyrimidine-5-carboxylic acid ester.

2,4-dioxo-1,2,3,4-tetrahydro-pyrimidine-5-carboxylic acid esters that are N1 and N3 unsubstituted may be mono- or dialkylated using standard conditions as outlined in Scheme 3 or Scheme 4.

Scheme 3

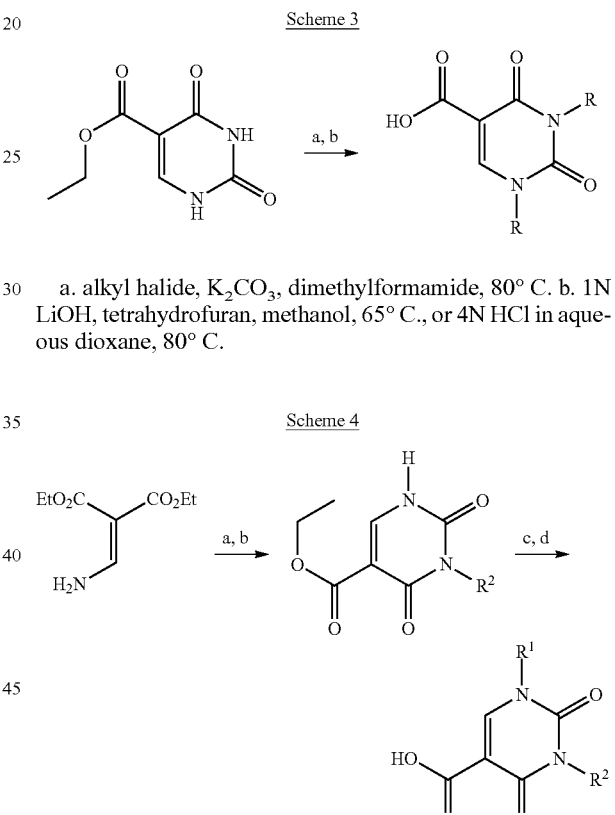

a. alkyl halide, $K_2CO_3$, dimethylformamide, 80° C. b. 1N LiOH, tetrahydrofuran, methanol, 65° C., or 4N HCl in aqueous dioxane, 80° C.

Scheme 4 a. $R^2NCO$, DIEA, dichloroethane, 100° C., 6 hr. b. sodium ethoxide, ethanol, rt, 18 hr. c. $R^1$halide, $K_2CO_3$, dimethylformamide, 80° C. d. 4N HCl in aqueous dioxane, 80° C., where $R^1$ and $R^2$ are alkyl Hydrolysis of the 2,4-dioxo-1,2,3,4-tetrahydro-pyrimidine-5-carboxylic acid esters may be achieved under standard acid or basic hydrolysis conditions to produce the acids.

Scheme 5

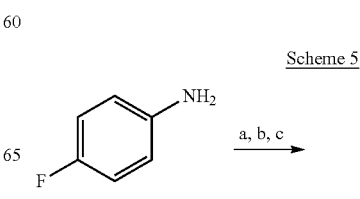

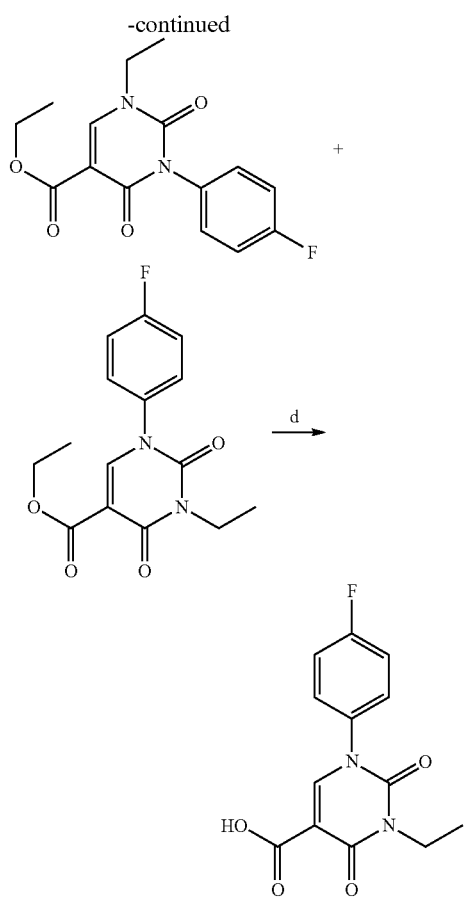

a. ethyl isocyanate, tetrahydrofuran, 0° C. b. diethyl ethoxymethylenemalonate, sodium ethoxide, ethanol, rt, 48 hr. c. ethyl acetate/hexanes. D. 1N LiOH, methanol, tetrahydrofuran, 60° C., 18 hr.

Examples where 2,4-dioxo-1,2,3,4-tetrahydro-pyrimidine-5-carboxylic acid amides are N1 aryl or N1 heteroaryl may be synthesized as outlined in Scheme 5. The synthesis of N1 4-fluorophenyl is delineated for Example 91. The sequential reaction of 4-fluoroaniline with ethyl isocyanate then diethyl ethoxymethylenemalonate produces 1-ethyl-3-(4-fluoro-phenyl)-2,4-dioxo-1,2,3,4-tetrahydro-pyrimidine-5-carboxylic acid ethyl ester and 3-ethyl-1-(4-fluoro-phenyl)-2,4-dioxo-1,2,3,4-tetrahydro-pyrimidine-5-carboxylic acid ethyl ester. The 1-(4-fluorophenyl) isomer is readily separated by crystallization. 3-Ethyl-1-(4-fluorophenyl)-2,4-dioxo-1,2,3,4-tetrahydro-pyrimidine-5-carboxylic acid is produced under basic hydrolysis and can also be synthesized under acid conditions, then coupled to (6,7-dimethoxyquinolin-4-yloxy)-3-fluorophenylamine to produce the N1 aryl amide example 91.

3,5-Dioxo-2,3,4,5-tetrahydro-[1,2,4]triazine-6-carboxylic acid esters may be synthesized as outlined in Scheme 6.

Scheme 6

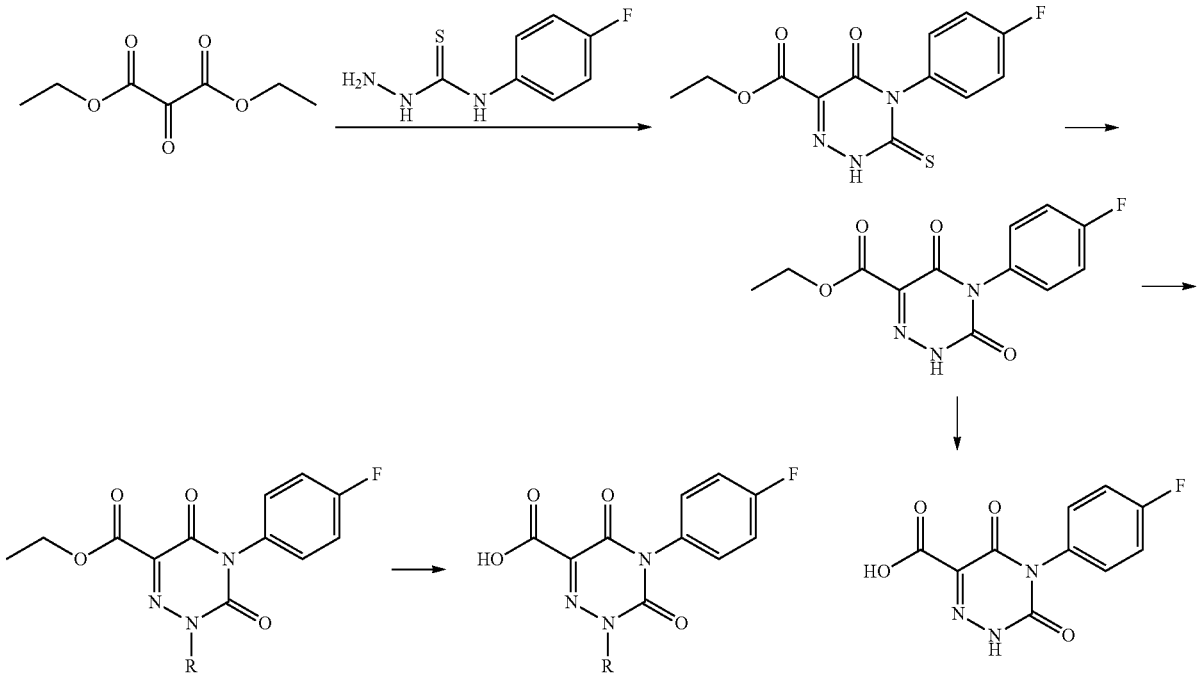

2-Oxo-malonic acid diethyl ester and 4-fluorophenyl thiosemicarbazide condensation produced 4-(4-fluorophenyl)-5-oxo-3-thioxo-2,3,4,5-tetrahydro-[1,2,4]triazine-6-carboxylic acid ethyl ester. Oxidation with, for example hydrogen peroxide and acetic acid produces 4-(4-fluorophenyl)-3,5-dioxo-2,3,4,5-tetrahydro-[1,2,4]triazine-6-carboxylic acid ethyl ester. Alkylation under conditions described for 2,4-dioxo-1,2,3,4-tetrahydro-pyrimidine-5-carboxylic acid esters produced N2-substituted 4-(4-fluorophenyl)-3,5-dioxo-2,3,4,5-tetrahydro-[1,2,4]triazine-6-carboxylic acid ethyl esters. N1 and or N4 unsubstituted 3,5-dioxo-2,3,4,5-tetrahydro-[1,2,4]triazine-6-carboxylic acid ethyl esters may be alkylated to produce the corresponding substituted 3,5-dioxo-2,3,4,5-tetrahydro-[1,2,4]triazine-6-carboxylic acid ethyl esters. Hydrolysis of the 3,5-dioxo-2,3,4,5-tetrahydro-[1,2,4]triazine-6-carboxylic acid ethyl esters may be achieved under acidic or basic conditions to produce 3,5-dioxo-2,3,4,5-tetrahydro-[1,2,4]triazine-6-carboxylic acids. Coupling aniline intermediates with these acids may be achieved using known standard procedures HATU, HOBT or EDCI, in an appropriate solvent such as DMF or THF or by converting the acid to the acid chloride and reacting with the amine in an inert solvent.

EXAMPLES

General synthesis methods for 2,4-dioxo-1,2,3,4-tetrahydropyrimidine-5-carboxylic acids Method A: 1-cyclopropylmethyl-3-(4-fluorophenyl)-2,4-dioxo-1,2,3,4-tetrahydropyrimidine-5-carboxylic acid a) 2-Aminomethylene-malonic acid diethyl ester (16.7 g, 89.2 mmol) and 4-fluorophenyl isocyanate (10.6 mL, 93.7 mmol) in 1,2-dichloroethane (25 mL, 320 mmol) was added N,N-diisopropylethylamine (17.1 mL, 98.1 mmol) and heated at 100° C. for 6 h. The mixture was cooled on an ice bath and the solid collected and washed with ether to give the urea (24.5 g, 85%). mp=198-200° C.; LCMS m/z=347 (M+23); $^1$H NMR (DMSO) δ: 10.57 (d, 1H, J=12.3 Hz), 10.41 (s, 1H), J=12.45 Hz), 8.45 (d, 1H, J=12.5 Hz), 7.48-7.53 (m, 2H), 7.16-7.21 (m, 2H), 4.24 (q, 2H, J=7 Hz), 4.15 (q, 2H, J=7 Hz), 1.22-1.28 (m, 6H).

b) 2-[3-(4-Fluorophenyl)ureidomethylene]malonic acid diethyl ester (24 g; 70 mmol) was suspended in Ethanol (100 mL) and added 21% NaOEt in EtOH (41.7 mL, 112 mmol) drop wise at rt. The mixture was stirred 4 h, upon which time the mixture became thick slurry. The mixture was concentrated and the residue partitioned between ethyl acetate (EtOAc) and 1M citric acid. The EtOAc layer was washed with water and brine, dried over MgSO$_4$ and was concentrated. The solid was triturated with ether-hexanes (⅓) to give 3-(4-fluorophenyl)-2,4-dioxo-1,2,3,4-tetrahydropyrimidine-5-carboxylic acid ethyl ester as a white solid. mp 206-8° C.; LCMS m/z=279 (M+1); $^1$H NMR (DMSO) δ: 12.0 (s, 1H), 8.25 (s, 1H), 7.31 (bs, 2H), 7.29 (d, 2H, J=3 Hz), 4.17 (q, 2H, J=7 Hz), 1.23 (t, 3H, J=7 Hz).

c) 3-(4-Fluorophenyl)-2,4-dioxo-1,2,3,4-tetrahydropyrimidine-5-carboxylic acid ethyl ester (3.50 g, 11.6 mmol), potassium carbonate (3.22 g, 23.3 mmol) and cyclopropylmethyl bromide (3.39 mL, 35.0 mmol) in N,N-dimethylformamide (DMF) (10 mL) was heated at 65° C. for 12 h. The mixture was cooled to rt, partitioned between EtOAc and 1N Na$_2$CO$_3$, water and brine and then dried over MgSO$_4$. LCMS m/z=333 (M+1); $^1$H NMR (CDCL$_3$): 8.42 (s, 1H), 7.16-7.19 (m, 4H), 4.35 (q, 2H, J=7 Hz), 3.74 (d, 2H, J=7 Hz), 1.35 (t, 3H, J=7 Hz), 1.25 (m, 1H), 0.72 (m, 2H), 0.42 (m, 2H).

d) The oil from step c was dissolved in methanol (10 mL) and tetrahydrofuran (10 mL) and 1 M of lithium hydroxide (10.6 mL) was added. After stirring at rt for 6 h the mixture was concentrated and extracted with 1N Na$_2$CO$_3$ (2×). The basic layer was acidified with 1N HCl on an ice bath and the product collected and dried to give 1-cyclopropylmethyl-3-(4-fluorophenyl)-2,4-dioxo-1,2,3,4-tetrahydropyrimidine-5-carboxylic acid as a white solid. LCMS m/z=305 (M+1); $^1$H NMR (DMSO) δ: 12.62 (s, 1H), 8.82 (s, 1H), 7.30-7.39 (m, 4H), 3.79 (d, 2H, J=7.2 Hz), 1.20 (m, 1H), 0.50-0.55 (m, 2H), 0.38-0.42 (m, 2H).

Method B: 3-(4-Fluorophenyl)-1-isopropyl-2,4-dioxo-1,2,3,4-tetrahydropyrimidine-5-carboxylic acid a) 3-(4-Fluorophenyl)-2,4-dioxo-1,2,3,4-tetrahydropyrimidine-5-carboxylic acid ethyl ester (15 g, 54 mmol), potassium carbonate (14.9 g, 108 mmol) and isopropyl iodide (10.8 mL, 108 mmol) in N,N-dimethylformamide (35 mL) was heated at 70° C. for 12 h. The mixture was concentrated, dissolved in EtOAc and was filtered. The EtOAc layer was washed with 1N Na$_2$CO$_3$, water and brine and was concentrated. The product was crystallized from EtOAc-ether-hexanes to give [3-(4-fluorophenyl)-1-isopropyl-2,4-dioxo-1,2,3,4-tetrahydropyrimidine-5-carboxylic acid ethyl ester as a white solid (15.5 g, 90%). mp 142-4° C.; LCMS m/z=321 (M+1), $^1$H NMR (CDCl$_3$) δ: 8.35 (s, 1H), 7.14-7.19 (m, 4H), (4.91 (h, 1H, J=6.8 Hz), 4.35 (q, 2, J=7.2 Hz), 1.44 (d, 6H, J=7 Hz), 1.36 (t, 3H, J=7.2 Hz).

b) [3-(4-Fluorophenyl)-1-isopropyl-2,4-dioxo-1,2,3,4-tetrahydropyrimidine-5-carboxylic acid ethyl ester (15 g, 47 mmol) was added 4M HCl in dioxane (18.7 mL, 216 mmol) and water (5 mL) and heated at 70° C. overnight. The product upon cooling precipitated, additional water (~10 mL) was added and the product collected and dried to give 3-(4-fluorophenyl)-1-isopropyl-2,4-dioxo-1,2,3,4-tetrahydropyrimidine-5-carboxylic acid as a white solid. mp 168-9° C.; LCMS m/z=293 (M+1); $^1$H NMR (DMSO) δ: 12.67 (s, 1H), 8.58 (s, 1H), 7.29-7.39 (M, 4H), 4.72 (h, 1H, J=6.8 Hz), 1.38 (d, 6H, J=6.8 Hz).

Method C. 3-(4-Fluorophenyl)-1-(3-methoxypropyl)-2,4-dioxo-1,2,3,4-tetrahydro-pyrimidine-5-carboxylic acid a) 3-(4-Fluorophenyl)-2,4-dioxo-1,2,3,4-tetrahydropyrimidine-5-carboxylic acid (0.25 g, 1.0 mmol), and potassium carbonate (0.55 g, 4.0 mmol) in N,N-dimethylformamide (5 mL, 60 mmol) was heated at 65° C. for 12 h. The mixture was filtered, concentrated and diluted with EtOAc. The EtOAc solution was washed with water and brine then dried over MgSO$_4$ and concentrated to give an oil.

b) This oil was dissolved in methanol/tetrahydrofuran (MeOH/THF) (1:1; 5 mL) and added 3 mL 1N LiOH, then heated at 60° C. for 1 h. The cooled solution was made acidic with concentrated HCl and the white solid collected to give 125 mg (40%) of 3-(4-fluorophenyl)-1-(3-methoxy-propyl)-2,4-dioxo-1,2,3,4-tetrahydropyrimidine-5-carboxylic acid as a white solid. LCMS m/z=323 (M+1); $^1$H NMR (DMSO) δ: 12.6 (s, 1H), 8.7

(s, 1H), 7.30-7.37 (m, 4H), 3.97 (t, 2H, J=7.2 Hz), 3.39 (t, 2H, J=6.3 Hz), 3.2 (s, 3H), 1.88 (q, 2H, J=6.2 Hz).

The following 2,4-dioxo-1,2,3,4-tetrahydro-pyrimidine-5-carboxylic acids were synthesized using methods A, B or C described above.

3-(4-Fluorophenyl)-2,4-dioxo-1,2,3,4-tetrahydropyrimidine-5-carboxylic acid. LCMS m/z=251 (M+1); $^1$H NMR (DMSO) δ: 12.56 (b, 1H), 12.39 (s, 1H), 8.36 (s, 1H), 7.29-7.38 (M, 4H).

1-Ethyl-3-(4-fluorophenyl)-2,4-dioxo-1,2,3,4-tetrahydropyrimidine-5-carboxylic acid. mp=166-8° C.; LCMS m/z=279 (M+1); $^1$H NNR (DMSO) δ: 12.6 (bs, 1H), 8.82 (s, 1H), 7.29-7.38 (m, 4H), 3.94 (q, 2H, J=7.3 Hz), 1.25 t, 3H, J=7 Hz).

3-(4-Fluorophenyl)-1-methyl-2,4-dioxo-1,2,3,4-tetrahydro-pyrimidine-5-carboxylic acid LCMS m/z=265 (M+1); $^1$H NMR (DMSO) δ: 12.59 (s, 1H), 8.80 (s, 1H), 7.3 (m, 4H), 3.56 (s, 3H).

1-Allyl-3-(4-fluorophenyl)-2,4-dioxo-1,2,3,4-tetrahydropyrimidine-5-carboxylic acid. LCMS m/z=291 (M+1); $^1$H NMR (DMSO) δ: 1H NMR (DMSO) δ: 12.66 (s, 1H), 8.72 (s, 1H), 7.27-7.41 (m, 4H), 5.89-5.99 (m, 1H), 5.24-5.35 (m, 2H), 4.53 (m, 2H).

1-(3,3-Difluoroallyl)-3-(4-fluorophenyl)-2,4-dioxo-1,2,3,4-tetrahydropyrimidine-5-carboxylic acid. LCMS m/z=327 (M+1); $^1$H NMR (DMSO) δ: 12.6 (s, 1H), 8.8 (s, 1H), 7.31-7.34 (m, 4H), 4.90-4.96 (m, 1H), 4.84-4.86 (m, 1H), 4.54 (d, 2H) 4.78 (m, 1H), 4.60-4.68 (M, 1H), 4.56-4.59 (m, 1H), 4.49 (m, 1H), 4.47 (m, 1H).

3-(4-Fluorophenyl)-1-(3-methyl-but-2-enyl)-2,4-dioxo-1,2,3,4-tetrahydro-pyrimidine-5-carboxylic acid. LCMS m/z=342 (M+23); $^1$H NMR (DMSO) δ: 12.6 (s, 1H), 8.7 (s, 1H), 7.30-7.38 (m, 4H), 5.3 (m, 1H), 4.49 (m, 2H), 1.7 (s, 6H).

3-(4-Fluorophenyl)-2,4-dioxo-1-propyl-1,2,3,4-tetrahydro-pyrimidine-5-carboxylic acid. LCMS m/z=293 (M+1); $^1$H NMR (DMSO) δ: 12.62 (s, 1H), 8.78 (s, 1H), 7.30-7.37 (m, 4H), 3.87 (t, 2H, J=7.5 Hz), 1.67 (q, 2H, J=7.5 Hz), 0.89 (t, 3H, J=7.5 Hz).

3-(4-Fluorophenyl)-1-isobutyl-2,4-dioxo-1,2,3,4-tetrahydro-pyrimidine-5-carboxylic acid. LCMS m/z=307 (M+1).

3-(4-Fluorophenyl)-2,4-dioxo-1-pentyl-1,2,3,4-tetrahydro-pyrimidine-5-carboxylic acid. LCMS m/z=321 (M+1); $^1$H NMR (DMSO) δ: 12.62 (s, 1H), 8.78 (s, 1H), 7.30-7.38 (m, 4H), 3.89 (m, 2H), 1.65 (m, 2H), 1.28 (m, 4H), 0.87 (t, 3H, J=7.4 Hz).

1-Ethyl-3-(4-fluorophenyl)-6-methyl-2,4-dioxo-1,2,3,4-tetrahydropyrimidine-5-carboxylic acid. LCMS m/z=293 (M+1); $^1$H NMR (DMSO) δ: 13.36 (s, 1H), 7.28-7.33 (m, 4H), 3.96 (q, 2H, J=7 Hz), 2.57 (s, 3H), 1.21 (t, 3H, J=7 Hz). 1-(2-Ethoxyethyl)-3-(4-fluorophenyl)-2,4-dioxo-1,2,3,4-tetrahydro-pyrimidine-5-carboxylic acid. LCMS m/z=323 (M+1); $^1$H NMR (DMSO) δ: 12.509 (s, 1H), 8.66 (s, 1H), 7.39-7.39 (m, 4H), 4.09 (t, 2H, J=5 Hz), 3.61 (t, 2H, J=5 Hz), 3.47 (q, 2H, J=7.2 Hz), 1.11 (t, 3H, J=7.2 Hz).

1-(2-Benzyloxyethyl)-3-(4-fluorophenyl)-2,4-dioxo-1,2,3,4-tetrahydropyrimidine-5-carboxylic acid. LCMS m/z=385 (M+1); $^1$H NMR (DMSO) δ: 12.59 (s, 1H), 8.72 (s, 1H), 7.31-7.34 (m, 9H), 4.52 (s, 2H), 4.15 (t, 2H, J=5 Hz), 3.68 (t, 2H, J=5 Hz).

3-(4-Fluorophenyl)-1-(2-isopropoxy-ethyl)-2,4-dioxo-1,2,3, 4-tetrahydropyrimidine-5-carboxylic acid. LCMS m/z=337 (M+1). $^1$H NMR (DMSO) δ: 12.57 (s, 1H), 8.67 (s, 1H), 7.32-7.36 (m, 4H), 4.06 (br, 2H), 3.6 (br, 3H), 1.07 (d, 6H, J=6 Hz).

1-(3-Benzyloxypropyl)-3-(4-fluorophenyl)-2,4-dioxo-1,2,3, 4-tetrahydropyrimidine-5-carboxylic acid. LCMS m/z=399 (M+1); $^1$H NMR (DMSO) δ: 12.59 (s, 1H), 8.75 (s, 1H), 7.24-7.35 (m, 9H), 4.43 (s, 2H), 4.01 (m, 2H), 3.53 (m, 2H), 1.74 (m, 2H).

3-(4-Fluorophenyl)-1-(2-morpholin-4-yl-ethyl)-2,4-dioxo-1,2,3,4-tetrahydro-pyrimidine-5-carboxylic acid; hydrochloride. LCMS m/z=400 (M+1). $^1$H NMR (DMSO) δ: 11.11 (br, 1H), 10.18 (br, 1H), 7.43 (m, 2H), 7.35 (m, 2H), 4.32 (br, 2H), 3.93 (m, 4H), 3.73-3.79 (m, 6H).

1-((S)-2,2-Dimethyl-1,3-dioxolan-4-ylmethyl)-3-(4-fluorophenyl)-2,4-dioxo-1,2,3,4-tetrahydropyrimidine-5-carboxylic acid. LCMS m/z=365 (M+1). $^1$H NMR (DMSO) δ: 12.60 (s, 1H), 8.66 (s, 1H), 7.34 (m, 4H), 4.34 (br, 1H), 4.12 (m, 1H), 4.01 (m, 2H), 3.72 (m, 1H), 1.30 (s, 3H), 1.27 (s, 3H).

1-(2-Dimethylaminoethyl)-3-(4-fluoro-phenyl)-2,4-dioxo-1,2,3,4-tetrahydropyrimidine-5-carboxylic acid; hydrochloride. LCMS m/z=358 (M+1); $^1$H NMR (DMSO) δ: 12.4 (b, 1H), 10.3 (s, 1H), 8.76 (s, 1H), 7.3-7.42 (m, 4H), 4.3 (t, 2H, J=7 Hz), 3.4 (m, 2H), 2.8 (d, 6H), 3-(4-Fluorophenyl)-2,4-dioxo-1-(2-pyrrolidin-1-yl-ethyl)-1, 2,3,4-tetrahydro-pyrimidine-5-carboxylic acid; hydrochloride. LCMS m/z=384 (M+1); $^1$H NMR (DMSO) δ: 12.63 (br s, 1H), 11.01 (s, 1H), 8.82 (s, 1H), 7.45 (m, 2H), 7.34 (m, 2H), 4.29 (t, 2H, J=5.2 Hz), 3.47 (m, 4H), 3.05 (m, 2H), 1.89-2.0 (m, 4H).

3-(4-Fluorophenyl)-2,4-dioxo-1-(2-piperidin-1-yl-ethyl)-1, 2,3,4-tetrahydropyrimidine-5-carboxylic acid; hydrochloride. LCMS m/z=398 (M+1).

3-Cyclohexyl-1-ethyl-2,4-dioxo-1,2,3,4-tetrahydro-pyrimidine-5-carboxylic acid. LCMS m/z=267 (M+1); $^1$H NMR (DMSO) δ: 12.87 (s, 1H), 8.70 (s, 1H), 4.67 (m, 1H), 3.98 (m, 2H), 2.26 (m, 2H), 1.78 (m, 2H), 1.60 (m, 3H), 1.07-1.33 (m, 6H).

1-(3-Dimethylaminopropyl)-3-(4-fluoro-phenyl)-2,4-dioxo-1,2,3,4-tetrahydro-pyrimidine-5-carboxylic acid; hydrochloride. LCMS m/z=372 (M+1).

3-(4-Fluorophenyl)-1-(3-morpholin-4-yl-propyl)-2,4-dioxo-1,2,3,4-tetrahydro-pyrimidine-5-carboxylic acid; hydrochloride. LCMS m/z=414 (M+1).

3-(4-Fluorophenyl)-2,4-dioxo-1-(tetrahydropyran-4-yl)-1,2, 3,4-tetrahydropyrimidine-5-carboxylic acid. LCMS m/z=335 (M+1); $^1$H NMR (DMSO) δ: 12.60 (s, 1H), 8.54 (s, 1H), 7.30-7.38 (m, 4H), 4.58 (m, 1H), 3.98 (m, 2H), 3.39 (m, 2H), 2.10 (m, 2H), 1.80 (m, 2H).

1-(4-Benzyloxybutyl)-3-(4-fluorophenyl)-2,4-dioxo-1,2,3, 4-tetrahydropyrimidine-5-carboxylic acid. LCMS m/z=413 (M+1); $^1$H NMR (DMSO) δ: 12.63 (s, 1H), 8/79 (s, 1H), 7.27-7.40 (m, 4H), 4.46 (m, 2H), 3.92 (m, 2H), 3.40 (m, 2H), 1.60-1.74 (m, 2H), 1.40-1.48 (m, 2H).

1-Cyclobutyl-3-(4-fluorophenyl)-2,4-dioxo-1,2,3,4-tetrahydropyrimidine-5-carboxylic acid. LCMS m/z=305 (M+1); $^1$H NMR (DMSO) δ: 12.64 (s, 1H), 8.82 (s, 0.5H), 8.52 (s, 0.5H), 7.30-7.39 (m, 4H), 4.74 (m, 0.5H), 3.78 (m, 0.5H), 2.29-2.40 (m, 2H), 1.75 (m, 1H), 1.22 (m, 0.5), 0.40-0.54 (m, 1.5H) NMR shows rotamers.

3-(4-Fluorophenyl)-2,4-dioxo-1-prop-2-ynyl-1,2,3,4-tetrahydropyrimidine-5-carboxylic acid. LCMS m/z=289 (M+1).

3-(4-Fluorophenyl)-1-(2-imidazol-1-yl-ethyl)-2,4-dioxo-1, 2,3,4-tetrahydropyrimidine-5-carboxylic acid. LCMS m/z=345 (M+1).

3-(4-Fluorophenyl)-2,4-dioxo-1-(2-pyrazol-1-yl-ethyl)-1,2, 3,4-tetrahydropyrimidine-5-carboxylic acid. LCMS m/z=345 (M+1).

3-(4-Fluorophenyl)-2,4-dioxo-1-phenethyl-1,2,3,4-tetrahydropyrimidine-5-carboxylic acid. LCMS m/z=355 (M+1).

1-(2-[1,3]Dioxolan-2-yl-ethyl)-3-(4-fluoro-phenyl)-2,4-dioxo-1,2,3,4-tetrahydro-pyrimidine-5-carboxylic acid. LCMS m/z=351 (M+1).

1-Diethylcarbamoylmethyl-3-(4-fluorophenyl)-2,4-dioxo-1,2,3,4-tetrahydropyrimidine-5-carboxylic acid amide. LCMS m/z=364 (M+1).

3-(4-Fluoro-phenyl)-1-(2-morpholin-4-yl-2-oxo-ethyl)-2,4-dioxo-1,2,3,4-tetrahydro-pyrimidine-5-carboxylic acid amide. LCMS m/z=376 (M+1).

3-(4-Fluorophenyl)-2,4-dioxo-1-[2-(2-oxo-pyrrolidin-1-yl)-ethyl]-1,2,3,4-tetrahydro-pyrimidine-5-carboxylic acid. LCMS m/z=362 (M+1).

1-(2-Fluoroethyl)-3-(4-fluoro-phenyl)-2,4-dioxo-1,2,3,4-tetrahydro-pyrimidine-5-carboxylic acid. LCMS m/z=397 (M+1).

1-tert-Butoxycarbonylmethyl-3-(4-fluorophenyl)-2,4-dioxo-1,2,3,4-tetrahydro-pyrimidine-5-carboxylic acid. LCMS m/z=365 (M+1).

3-(4-Fluoro-phenyl)-1-oxazol-2-ylmethyl-2,4-dioxo-1,2,3,4-tetrahydro-pyrimidine-5-carboxylic acid. LCMS m/z=332 (M+1).

3-(4-Fluoro-phenyl)-2,4-dioxo-1-(tetrahydrofuran-2-ylmethyl)-1,2,3,4-tetrahydro-pyrimidine-5-carboxylic acid. LCMS m/z=335 (M+1).

3-(4-Fluoro-phenyl)-2,4-dioxo-1-(tetrahydro-pyran-4-ylmethyl)-1,2,3,4-tetrahydro-pyrimidine-5-carboxylic acid. LCMS m/z=349 (M+1).

3-(4-Fluoro-phenyl)-1-(2-methyl-thiazol-4-ylmethyl)-2,4-dioxo-1,2,3,4-tetrahydro-pyrimidine-5-carboxylic acid. LCMS m/z=362 (M+1).

1-Cyclopentyl-3-(4-fluoro-phenyl)-2,4-dioxo-1,2,3,4-tetrahydropyrimidine-5-carboxylic acid. LCMS m/z=319 (M+1).

1-Benzyl-3-(4-fluoro-phenyl)-2,4-dioxo-1,2,3,4-tetrahydropyrimidine-5-carboxylic acid amide. LCMS m/z=340 (M+1).

3-(4-Fluorophenyl)-1-[2-(2-fluorophenyl)-ethyl]-2,4-dioxo-1,2,3,4-tetrahydro-pyrimidine-5-carboxylic acid amide. LCMS m/z=372 (M+1).

3-(4-Fluorophenyl)-1-[2-(4-fluoro-phenyl)-ethyl]-2,4-dioxo-1,2,3,4-tetrahydro-pyrimidine-5-carboxylic acid amide. LCMS m/z=372 (M+1).

1-(2-Cyclohexyl-ethyl)-3-(4-fluoro-phenyl)-2,4-dioxo-1,2,3,4-tetrahydro-pyrimidine-5-carboxylic acid. LCMS m/z=360 (M+1).

3-(4-Fluorophenyl)-2,4-dioxo-1-(3-phenylpropyl)-1,2,3,4-tetrahydro-pyrimidine-5-carboxylic acid. LCMS m/z=369 (M+1).

3-(4-Fluorophenyl)-2,4-dioxo-1-(2-oxo-2-pyrrolidin-1-yl-ethyl)-1,2,3,4-tetrahydro-pyrimidine-5-carboxylic acid. LCMS m/z=362 (M+1).

1-Dimethylcarbamoylmethyl-3-(4-fluoro-phenyl)-2,4-dioxo-1,2,3,4-tetrahydro-pyrimidine-5-carboxylic acid. LCMS m/z=336 (M+1).

1-(1-Dimethylcarbamoyl-2-oxo-propyl)-3-(4-fluoro-phenyl)-2,4-dioxo-1,2,3,4-tetrahydro-pyrimidine-5-carboxylic acid. LCMS m/z=378 (M+1).

Example 1

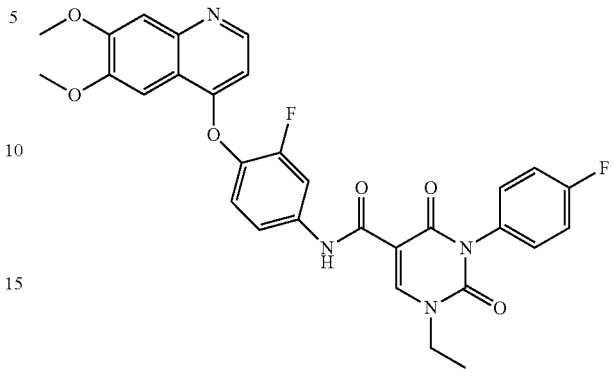

1-Ethyl-3-(4-fluorophenyl)-2,4-dioxo-1,2,3,4-tetrahydropyrimidine-5-carboxylicacid [4-(6,7-dimethoxyquinolin-4-yloxy)-3-fluorophenyl]amide Step a. 4-(6,7-Dimethoxyquinolin-4-yloxy)-3-fluorophenylamine.

Sodium hydride (60% disp. in mineral oil; 1.3 g, 33.5 mmol) was added to 4-amino-2-fluoro-phenol in dry N,N-dimethylformamide (50 mL) and stirred at rt for 30 min under an atmosphere of nitrogen. Then solid 4-chloro-6,7-dimethoxyquinoline (5.0 g, 22.4 mmol) was added and the reaction stirred at 100° C. for 30 h. The mixture was concentrated, dissolved in EtOAc (100 mL) and washed with 1N $Na_2CO_3$, water and brine, then dried over $MgSO_4$. The product was chromatographed on silica gel (5% methanol/dichloromethane (MeOH/DCM)) to give a tan solid 4.9 g, 70%. mp=172-5° C.; LCMS m/z=315 (M+1); $^1$H NMR (DMSO) δ: 8.48 (d, 1H, J=5.4 Hz), 7.50 (s, 1H), 7.38 (s, 1H), 7.07 (t, 1H, J=8.6 Hz), 6.53, 6.56 (dd, 1H, J=2.6, 13.4 Hz), 6.45, 6.47 (dd, 1H, J=2, 8 Hz), 6.38, 6.39 (dd, 1H, J=1, 5.4 Hz), 5.48 (s, 2H), 3.94 (s, 6H).

Step b. N,N,N',N'-Tetramethyl-O-(7-azabenzotriazol-1-yl)uronium hexafluorophosphate (HATU) (0.072 g, 0.19 mmol) and 1-ethyl-3-(4-fluorophenyl)-2,4-dioxo-1,2,3,4-tetrahydropyrimidine-5-carboxylic acid (0.053 g, 0.19 mmol) in N,N-dimethylformamide (2 mL) was added N,N-diisopropylethylamine (0.055 mL, 0.32 mmol). After 15 min stirring at rt, 4-(6,7-dimethoxyquinolin-4-yloxy)-3-fluorophenylamine (0.05 g, 0.2 mmol) was added. The reaction was stirred at rt for 12 h, diluted with EtOAc (25 mL), then washed with 1N $Na_2CO_3$, water and brine and then dried over MgSO4. The product was crystallized from MeOH to give 75 mg (68%) as a white solid. mp=151-4° C.; LCMS m/z=575 (M+1); $^1$H NMR (DMSO) δ: 11.04 (s, 1H), 8.89 (s, 1H), 8.47 (d, 1H, J=5.4 Hz), 7.98, 8.01 (dd, 1H, J=2.3, 12.6 Hz), 7.52-7.56 (m, 2H), 7.33-7.46 (m, 6H), 6.47 (d, 1H, J=5.4 Hz), 4.01 (q, 2H, J=7 Hz), 3.98 (d, 6H), 13.0 (t, 3H, J=7 Hz).

The following compounds were synthesized using procedures similar to those for Example 1.

Example 2

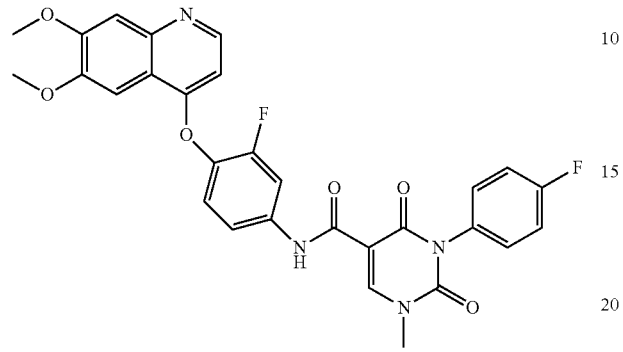

3-(4-Fluorophenyl)-1-methyl-2,4-dioxo-1,2,3,4-tetrahydropyrimidine-5-carboxylic acid [4-(6,7-dimethoxyquinolin-4-yloxy)-3-fluoro-phenyl]-amide. mp=158-60° C.; LCMS m/z=561 (M+1); $^1$H NMR (DMSO) δ: 11.03 (s, 1H), 8.9 (s, 1H), 8.48 (d, 1H, J=6 Hz), 7.99. 8.01 (dd, 1H, J=3, 12 Hz), 7.52 (m, 2H), 7.36-7.43 (m, 6H), 6.46 (d, 1H, J=6 Hz), 3.92 (s, 3H), 3.94 (s, 3H), 3.54 (s, 3H).

Example 3

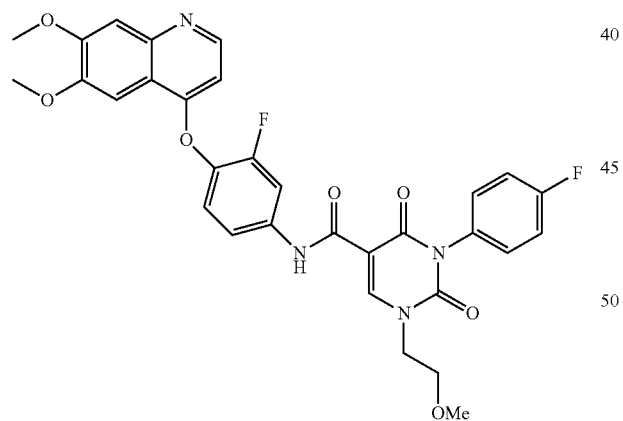

3-(4-Fluorophenyl)-1-(2-methoxyethyl)-2,4-dioxo-1,2,3,4-tetrahydropyrimidine-5-carboxylic acid [4-(6,7-dimethoxyquinolin-4-yloxy)-3-fluorophenyl]-amide. mp=118-21° C.; LCMS m/z=605 (M+1); $^1$H NMR (DMSO) δ: 11.0 (s, 1H), 8.74 (, s, 1H), 8.47 (d, 1H, J=6 Hz), 7.99, 8.01 (dd, 1H, J=3, 12 Hz), 7.52-7.55 (m, 2H), 7.33-7.46 (m, 6H), 6.48 (d, 1H, J=6 Hz), 4.17 (t, 2H, J=5 Hz), 3.94 (s, 3H), 3.95 (s, 3H), 3.16 (t, 2H, J=5 Hz).

Example 4

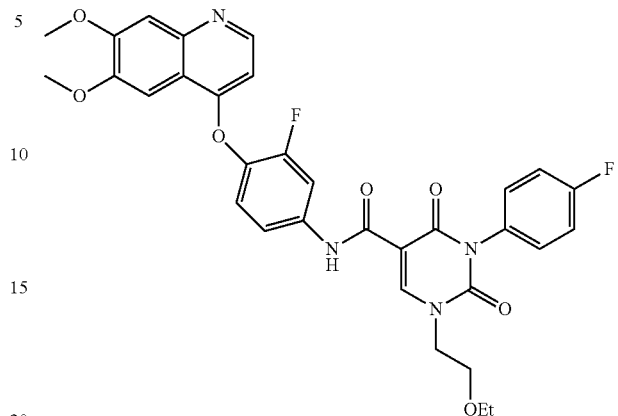

1-(2-Ethoxyethyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide. mp=128-30° C.; LCMS m/z=619 (M+1); 1H NMR (DMSO) δ: 11.0 (s, 1H), 8.76 (s, 1H), 8.47 (d, 1H, J=5.4 Hz), 7.98-8.01 (dd, 1H, J=2.4, 12 Hz), 7.52-7.55 (m, 2H), 7.40-7.46 (m, 4H), 7.34-7.38 (m, 2H), 6.48 (d, 1H, J=5 Hz), 4.16 (t, 2H, J=5 Hz), 3.94, 3.95 (ss, 6H), 3.65 (t, 2H, J=5 Hz), 3.51 (q, 2H, J=6.6 Hz), 1.13 (t, 3H, J=6.6 Hz).

Example 5

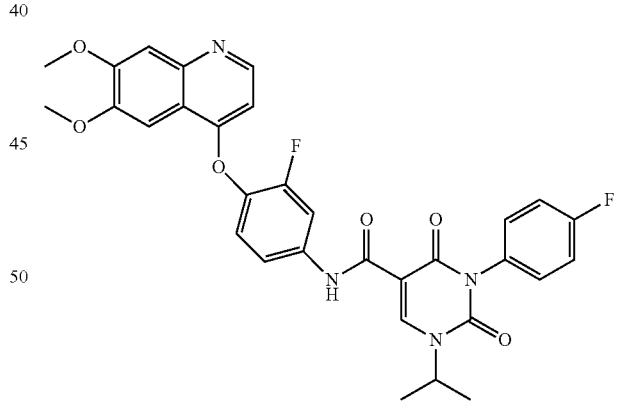

3-(4-Fluorophenyl)-1-isopropyl-2,4-dioxo-1,2,3,4-tetrahydropyrimidine-5-carboxylic acid [4-(6,7-dimethoxyquinolin-4-yloxy)-3-fluorophenyl]-amide. mp=146-48° C.; LCMS m/z=589 (M+1); $^1$H NMR (DMSO) δ: 11.9 (s, 1H), 8.68 (s, 1H), 8.48 (d, 1H, J=5.2 Hz), 7.99, 8.02 (dd, 1H, J=2.4, 12.4 Hz), 7.52-7.55 (m, 2H), 7.33-7.46 (m, 6H), 6.47 (d, 1H, J=5.2 Hz), 4.78 (m, 1H, J=7 Hz), 3.94 (ss, 6H), 1.43 (d, 6H, J=6.7 Hz).

Example 6

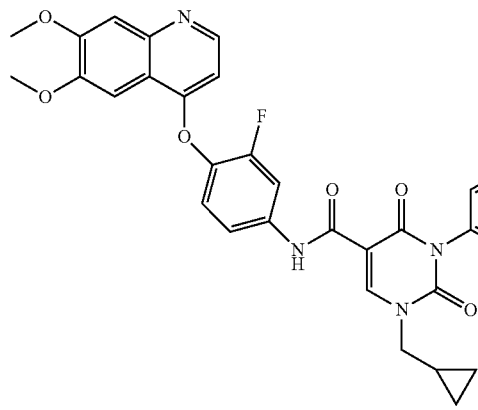

1-Cyclopropylmethyl-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide. mp=146-9° C.; LCMS (m/z=601 (M+1); $^1$H NM (DMSO) δ: 11.0 (s, 1H), 8.9 (s, 1H), 8.47 (d, 1H, J=5.2 Hz), 8.0, 8.02 (dd, 1H, J=2.3, 12 Hz), 7.52-7.55 (m, 2H), 7.34-7.46 (m, 6H), 6.47 (m, 1H, J=5.2 Hz), (3.94, ss, 6H), 3.86 (d, 1H, J=7.2 Hz), 1.25 (m, 1H), 0.57 (m, 2H), 0.44 (m, 2H).

Example 7

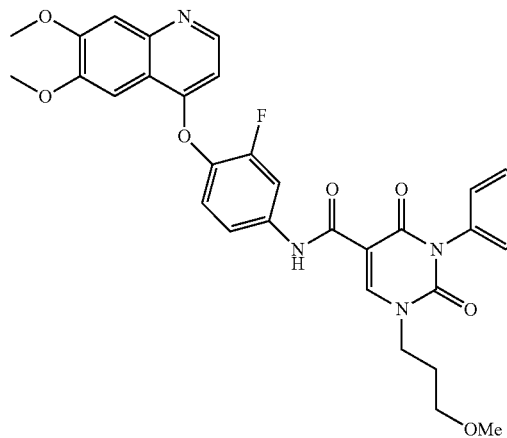

3-(4-Fluorophenyl)-1-(3-methoxypropyl)-2,4-dioxo-1,2,3,4-tetrahydropyrimidine-5-carboxylic acid [4-(6,7-dimethoxyquinolin-4-yloxy)-3-fluorophenyl]-amide. mp=126-7° C.; LCMS m/z=619 (M+1); $^1$H NMR (DMSO) δ: 11.0 (s, 1H), 8.8 (s, 1H), 8.47 (d, 1H, J=5.6 Hz), 7.99, 8.02 (dd, 1H, J=3.2, 13 Hz), 7.52-7.55 (m, 2H), 7.34-7.46 (m, 6H), 6.46 (d, 1H, J=5.2 Hz), 4.40 (t, 2H, J=7 Hz), 3.94 (ss, 6H), 3.42 (t, 2H, J=6.6 Hz), 3.24 (s, 3H), 1.191 (m, 2H).

Example 8

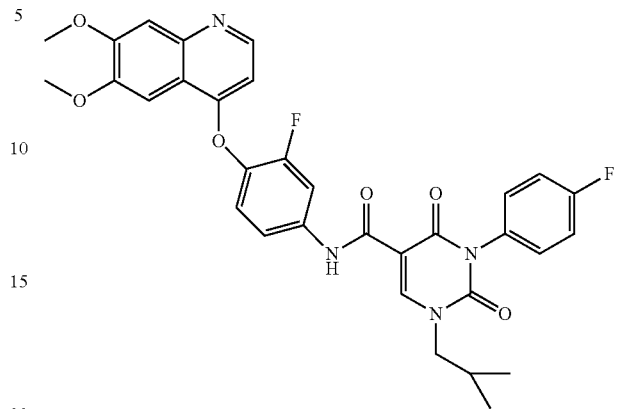

3-(4-Fluorophenyl)-1-isobutyl-2,4-dioxo-1,2,3,4-tetrahydropyrimidine-5-carboxylic acid [4-(6,7-dimethoxyquinolin-4-yloxy)-3-fluorophenyl]-amide. mp=136-40° C.; LCMS m/z=603 (M+1); $^1$H NMR (DMSO) δ: 11.0 (s, 1H), 8.81 (s, 1H), 8.48 (d, 1H, J=5.2 Hz), 8.0 (dd, 1H, J=2.2, 12 Hz), 7.52-7.55 (m, 2H), 7.33-7.46 (m, 6H), 6.47 (d, 1H, J=5.2 Hz), 3.94 (ss, 6H), 3.82 (d, 2H, J=7 Hz), 2.05 (m, 1H), 0.93 (d, 6H, J=7 Hz).

Example 9

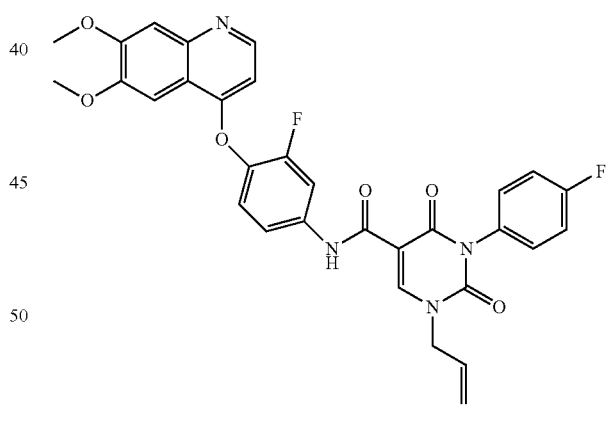

1-Allyl-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide. mp 128-30° C.; LCMS m/z=587 (M+1); 1H NMR (DMSO) δ: 11.0 (s, 1H), 8.80 (s, 1H), 8.48 (d, 1H, =5.2 Hz), 7.98, 8.02 (dd, 1H, J=2.5, 13 Hz), 7.53-7.55 (m, 1H), 7.52 (s, 1H), 7.34-7.46 (m, 6H), 6.47 (d, 1H, J=4.7 Hz), 5.94-6.02 (m, 1H), 5.36, 5.40 (dd, 1H, J=1.5, 17 Hz), 5.27, 5.30 (dd, 1H, J=1.5, 10 Hz), 4.62 (d, 2H, J=5.5 Hz), 3.94, 3.95 (ss, 6H).

Example 10

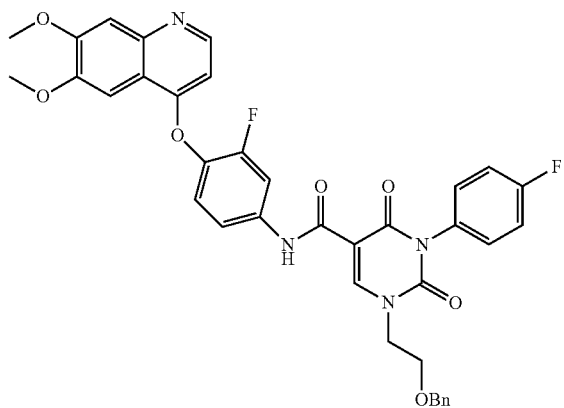 [SMILES: COc1cc2nccc(Oc3ccc(NC(=O)c4cn(CCOCc5ccccc5)c(=O)n(-c5ccc(F)cc5)c4=O)cc3F)c2cc1OC]

1-(2-Benzyloxyethyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide.
mp>102° C. (dec); LCMS m/z=681 (M+1); 1H NMR (DMSO) δ: 11.0 (s, 1H), 8.83 (s, 1H), 8.48 (d, 1H, J=5.3 Hz), 7.99, 8.02 (dd, 1H, J=2.4, 12.8 Hz), 7.54, 7.56 (dd, 1H, J=1.4, 8.8 Hz), 7.52 (s, 1H), 7.44 (t, 1H, J=8.8 Hz), 7.33-7.41 (m, 9H), 7.30 (m, 1H), 6.47 (d, 1H, J=5 Hz), 4.55 (s, 2H), 4.22 (t, 2H, J=4.7 Hz), 3.94, 3.95 (ss, 6H), 3.72 (t, 2H, J=4.8 Hz).

Example 11

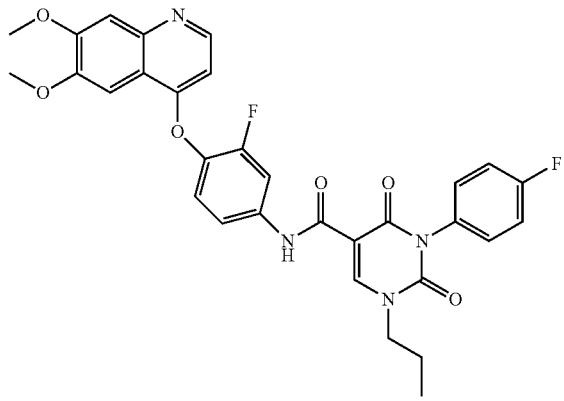 [SMILES: CCCn1cc(C(=O)Nc2ccc(Oc3ccnc4cc(OC)c(OC)cc34)c(F)c2)c(=O)n(-c2ccc(F)cc2)c1=O]

3-(4-Fluorophenyl)-2,4-dioxo-1-propyl-1,2,3,4-tetrahydropyrimidine-5-carboxylic acid [4-(6,7-dimethoxyquinolin-4-yloxy)-3-fluorophenyl]-amide. mp=134-6° C.; LCMS m/z=589 (M+1); $^1$H NMR (DMSO) δ: 11.0 (s, 1H), 8.86 (s, 1H), 8.47 (d, 1H, J=5.3 Hz), 7.98, 8.02 (dd, 1H, J=2.2, 12.6 Hz), 7.52-7.55 m, 2H), 7.40-7.46 (m, 4H), 7.34-7.38 (m, 2H), 6.47 (d, 1H, J=5.2 Hz), 3.92-3.97 (m, 8H), 1.71 (h, 2H, J=7.2 Hz), 0.93 (t, 3H, J=7.2 Hz).

Example 12

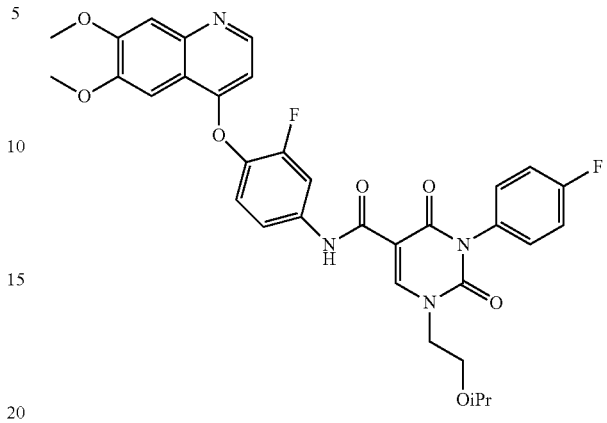

3-(4-Fluorophenyl)-1-(2-isopropoxyethyl)-2,4-dioxo-1,2,3,4-tetrahydropyrimidine-5-carboxylic acid [4-(6,7-dimethoxyquinolin-4-yloxy)-3-fluorophenyl]-amide.
mp=138-9° C.; LCMS m/z=633 (M+1); 1H NMR (DMSO) δ: 11.00 (s, 1H), 8.78 (s, 1H), 8.47 (d, 1H, J=4.7 Hz), 7.99 (d, 1H, J=13 Hz), 7.49-7.56 (m, 2H), 7.38-7.46 (m, 6H), 6.47 (d, 1H, J=4.6 Hz), 4.12 (m, 2H), 3.94 (d, 6H), 3.65 (m, 3H), 1.10 (d, 6H, J=6 Hz).

Example 13

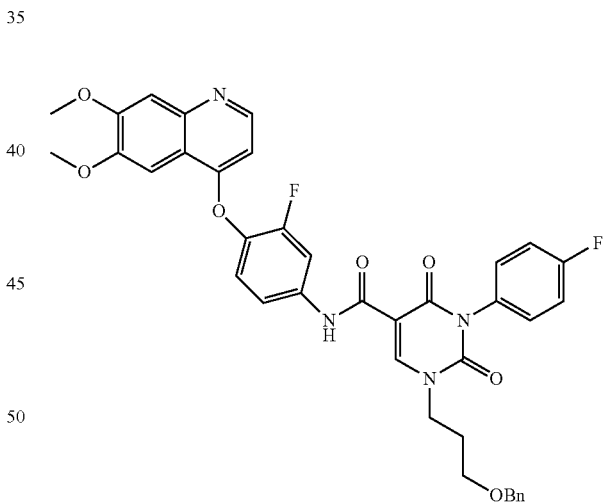

1-(3-Benzyloxypropyl)-3-(4-fluorophenyl)-2,4-dioxo-1,2,3,4-tetrahydropyrimidine-5-carboxylic acid [4-(6,7-dimethoxyquinolin-4-yloxy)-3-fluoro phenyl]-amide.
mp=94-96° C.; LCMS m/z=695 (M+1); $^1$H NMR (DMSO) δ: 11.00 (s, 1H), 8.83 (s, 1H), 8.47 (d, 1H, J=5 Hz), 7.98, 8.01 (dd, J=2.4, 12.6 Hz), 7.53-7.59 (m, 1H), 7.52 (s, 1H), 7.42-7.46 (m, 1H), 7.40 (s, 1H), 7.30-7.34 (m, 8H), 7.25-7.28 (m, 1H), 6.47 (dd, 1H, J=1, 5.2 Hz), 4.46 (s, 2H), 4.09 (t, 2H, J=7 Hz), 3.94 (d, 6H), 3.59 (t, 2H, J=5.8 Hz), 1.99 (t, 2H, J=6.4 Hz).

Example 14

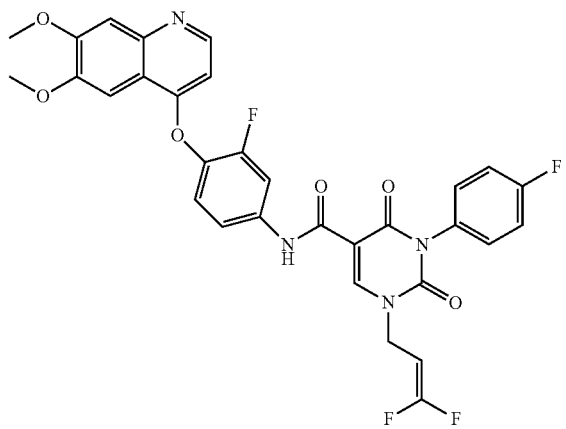 [SMILES: COc1cc2nccc(Oc3ccc(NC(=O)c4cn(CC=C(F)F)c(=O)n(-c5ccc(F)cc5)c4=O)cc3F)c2cc1OC]

1-(3,3-Difluoro-allyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide. mp=128-30° C.; LCMS m/z=623 (M+1); $^1$H NMR (DMSO) δ: 11.0 (s, 1H), 8.9 (s, 1H), 8.48 (d, 1H, J=5.5 Hz), 8.0, 7.98 (dd, 1H, J=2, 12.8 Hz), 7.52-7.56 (m, 2H), 7.34-7.46 (m, 6H), 6.46 (d, 1H, J=5 Hz), 4.88-4.99 (m, 1H), 4.62 (d, 2H, J=8 Hz), 3.94 (s, 6H).

Example 15

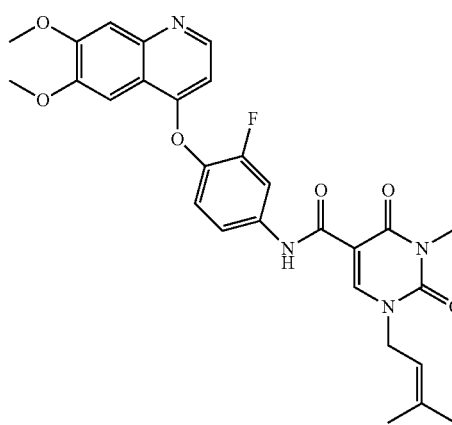

3-(4-Fluorophenyl)-1-(3-methyl-but-2-enyl)-2,4-dioxo-1,2,3,4-tetrahydropyrimidine-5-carboxylic acid [4-(6,7-dimethoxyquinolin-4-yloxy)-3-fluorophenyl]-amide. mp=119-121° C.; LCMS m/z=615 (M+1); $^1$H NMR (DMSO) δ: 11.0 (s, 1H), 8.78 9 (s, H), 8.47 (d, 1H, J=5.2 Hz), 8.0 (d, 1H, J=13 Hz), 7.52-7.54 (m, 2H), 7.33-7.45 (m, 6H), 6.47 (d. 1H. J=5.2 Hz), 5.34 (m, 1H), 4.56 (d, 2H, J=6.8 Hz), 3.94 (s, 6H), 1.76 (s, 3H), 1.74 (s, 3H).

Example 16

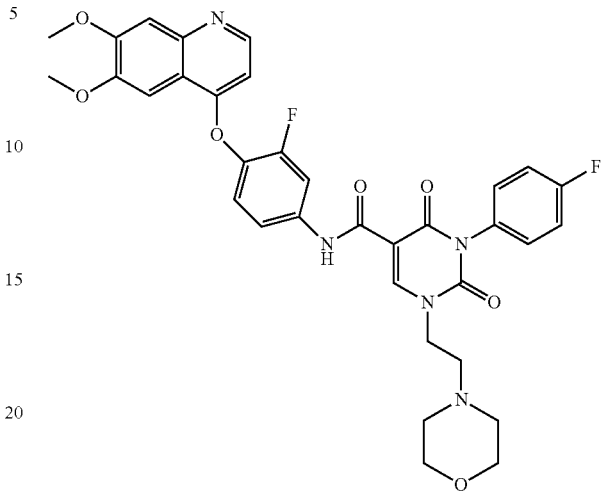

3-(4-Fluorophenyl)-1-(2-morpholin-4-yl-ethyl)-2,4-dioxo-1,2,3,4-tetrahydropyrimidine-5-carboxylic acid [4-(6,7-dimethoxyquinolin-4-yloxy)-3-fluoro phenyl]-amide. mp=124-6° C.; LCMS m/z=660 (M+1); $^1$H NMR (CDCl$_3$) δ: 10.9 (s, 1H), 8.65 (s, 1H), 8.49 (d, 1H, J=5.3 Hz), 7.87, 7.90 (dd, 1H, J=2.4, 12.4 Hz), 7.57 (s, 1H), 7.42 (s, 1H), 7.18-7.29 (m, 6H), 6.42 (dd, 1H, J=0.5, 5.2 Hz), 4.05-4.08 (m, 8H), 3.72 (t, 4H, J=4.7 Hz), 2.73 (t, 2H, J=5.7 Hz), 2.56 (m, 4H).

Example 17

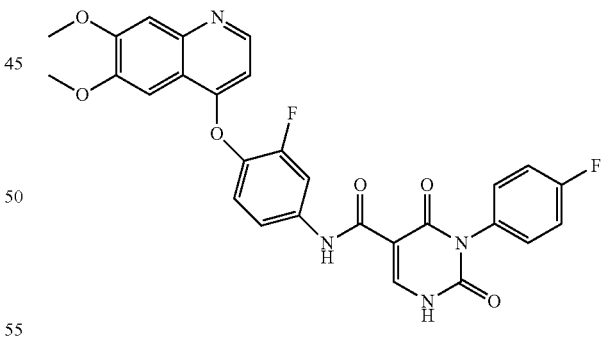

3-(4-Fluorophenyl)-2,4-dioxo-1,2,3,4-tetrahydropyrimidine-5-carboxylic acid [4-(6,7-dimethoxyquinolin-4-yloxy)-3-fluorophenyl]-amide. mp=276-8° C.; LCMS m/z=547 (M+1); $^1$H NMR (DMSO) δ: 12.4 (bs, 1H), 11.0 (s, 1H), 8.45 (s, 2H), 7.99 (d, 1H, J=12 Hz), 7.52 (s, 2H), 7.35-7.40 (m, 6H), 6.4 (s, 1H), 3.9 (s, 6H).

Example 18

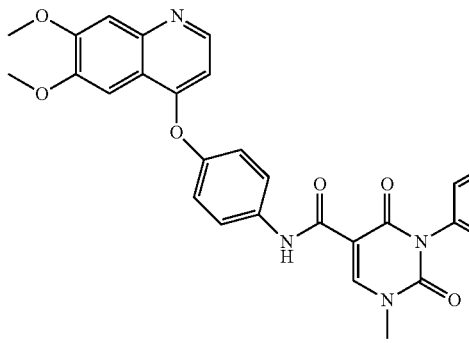

Step a. 4-(6,7-Dimethoxyquinolin-4-yloxy)-phenylamine.

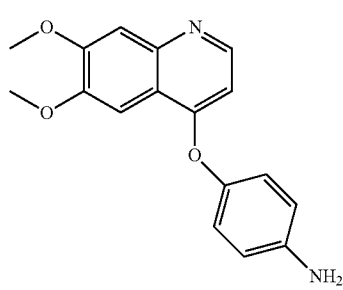 [SMILES: COc1cc2nccc(Oc3ccc(N)cc3)c2cc1OC]

4-(6,7-Dimethoxyquinolin-4-yloxy)phenylamine was synthesized using the methods for Example 1 step a. LCMS m/z=297 (M+1); $^1$H NMR (DMSO) δ: 8.42 (d, 1H, J=5.3 Hz), 7.50 (s, 1H), 7.36 (s, 1H), 7.91 (d, 2H, J=8 Hz), 6.67 (d, 2H, J=8 Hz), 6.36 (d, 1H, J=5.3 Hz), 5.14 (s, 2H), 3.93 (s, 6H).

Step b. 3-(4-Fluorophenyl)-1-methyl-2,4-dioxo-1,2,3,4-tetrahydropyrimidine-5-carboxylic acid [4-(6,7-dimethoxyquinolin-4-yloxy)-phenyl]-amide. mp=143-5° C.; LCMS m/z=543 (M+1); $^1$H NMR (DMSO) δ: 10.92 (s, 1H), 8.85 (s, 1H), 8.46 (d, 1H, J=5.2 Hz), 7.80 (d, 2H, J=9 Hz), 7.50 (s, 1H), 7.34-7.42 (m, 5H), 7.25 (d, 2H, J=9 Hz), 6.47 (d, 1H, J=5.2 Hz), 3.94 (s, 3H), 3.92 (s, 3H), 3.53 (s, 3H).

Example 19

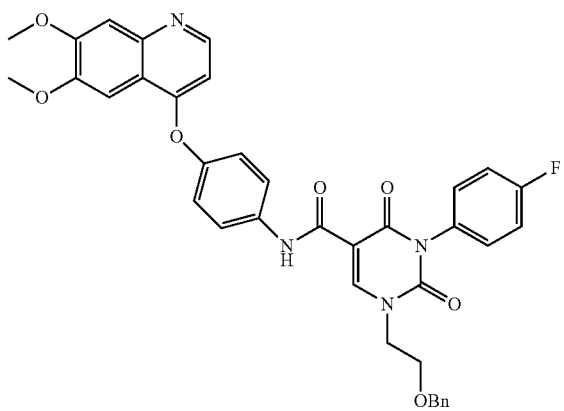 [SMILES: COc1cc2nccc(Oc3ccc(NC(=O)c4cn(CCOCc5ccccc5)c(=O)n(-c5ccc(F)cc5)c4=O)cc3)c2cc1OC]

1-(2-Benzyloxyethyl)-3-(4-fluoro-phenyl)-2,4-dioxo-1,2,3,4-tetrahydropyrimidine-5-carboxylic acid [4-(6,7-dimethoxyquinolin-4-yloxy)-phenyl]-amide. mp=163-4° C.; LCMS m/z=663 (M+1); 1H NMR (DMSO) δ: 10.89 (s, 1H), 8.81 (s, 1H), 8.47 (d, 1H, J=5.6 Hz), 8.80 (d, 2H, J=9 Hz), 7.50 (s, 1H), 7.25-7.41 (m, 12H), 6.49 (d, 1H, J=5.8 Hz), 4.56 (s, 2H), 4.21 (t, 2H, J=5 Hz), 3.94 (s, 3H), 3.92 (s, 3H), 3.72 (t, 2H, J=5 Hz).

Example 20

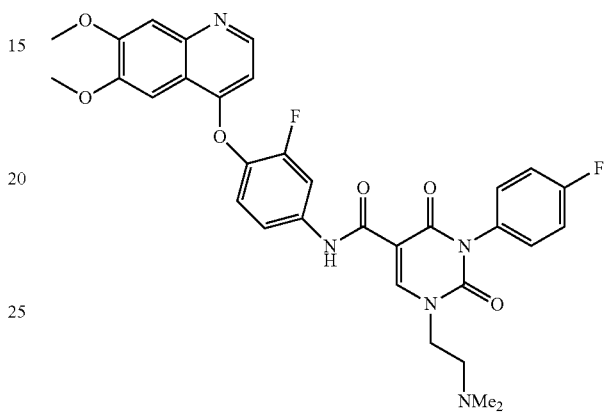

1-(2-Dimethylaminoethyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide. mp (HCl salt): 208-10° C.; LCMS m/z=618 (M+1); $^1$H NMR (DMSO) δ: 11.18 (s, 1H), 10.77 (s, 1H), 8.94 (s, 1H), 8.81 (d, 1H, J=6.6 Hz), 8.11, 8.08 (dd, 1H, J=2, 14 Hz), 7.74 (s, 1H), 7.65 (m, 2H), 7.50-7.60 (m, 3H), 7.37 (m, 2H), 6.95 (d, 1H, J=6.5 Hz), 4.39 (t, 1H, J=5.8 Hz), 4.04 (s, 3H), 4.03 (s, 3H), (2.82 (d, 6H).

Example 21

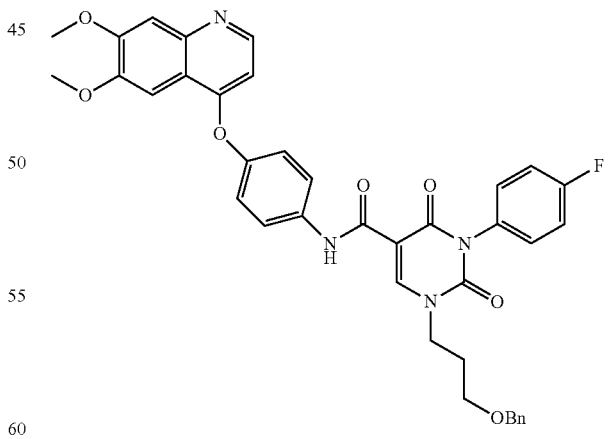

1-(3-Benzyloxypropyl)-3-(4-fluorophenyl)-2,4-dioxo-1,2,3,4-tetrahydropyrimidine-5-carboxylic acid [4-(6,7-dimethoxyquinolin-4-yloxy)phenyl]-amide. mp=100-104° C.; LCMS m/z=677 (M+1); $^1$H NMR (DMSO) δ: 10.90 (s, 1H), 8.81 (s, 1H), 8.47 (d, 1H, J=5 Hz), 7.80 (d, 2H, J=8.8 Hz), 7.50 (s, 1H), 7.40 (s, 1H), 7.25-7.33 (m, 11H), 6.49 (d, 1H, J=5.6 Hz), 4.45 (s, 2H), 4.08 (t, 2H, J=6.4 Hz), 3.94 (s, 3H), 3.92 (s, 3H), 3.56 (t, 2H, J=5.6 Hz), 1.98 (m, 2H).

Example 22

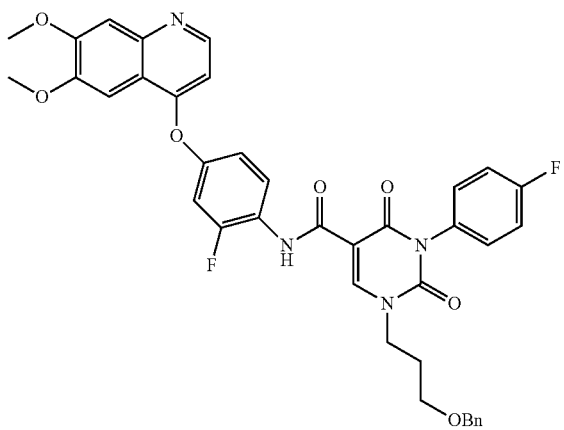 [SMILES: COc1cc2nccc(Oc3ccc(NC(=O)c4cn(CCCOCc5ccccc5)c(=O)n(-c5ccc(F)cc5)c4=O)c(F)c3)c2cc1OC]

1-(3-Benzyloxypropyl)-3-(4-fluorophenyl)-2,4-dioxo-1,2,3,4-tetrahydropyrimidine-5-carboxylic acid [4-(6,7-dimethoxyquinolin-4-yloxy)-2-fluorophenyl]-amide. mp 93-96° C.; LCMS m/z=695 (M+1); $^1$H NMR (DMSO) δ: 11.13 (s, 1H), 8.85 (s, 1H), 7.46-8.51 (m, 2H), 7.47 (s, 1H), 7.39-7.42 (m, 2H), 7.25-7.34 (m, 9H), 7.18 (d, 1H, J=10 Hz), 6.59 (d, 1H, J=5.3 Hz), 4.50 (s, 2H), 4.09 (t, 2H, J=6.5 Hz), 3.94 (s, 3H), 3.92 (s, 3H), 3.56 (t, 2H, J=6 Hz), 1.99 (q, 2H, J=6.2 Hz).

Example 23

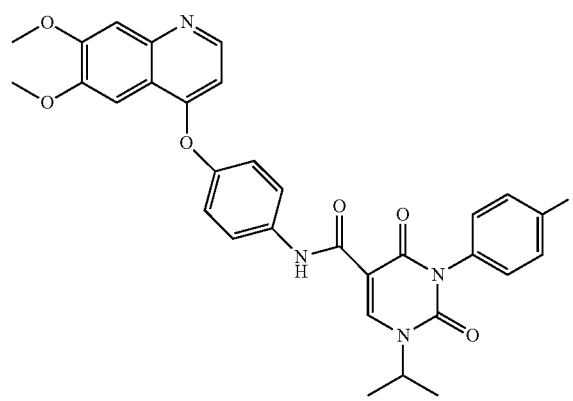

3-(4-Fluorophenyl)-1-isopropyl-2,4-dioxo-1,2,3,4-tetrahydropyrimidine-5-carboxylic acid [4-(6,7-dimethoxyquinolin-4-yloxy)phenyl]-amide. mp=253-6° C.; LCMS m/z=571 (M+1); $^1$H NMR (DMSO) δ: 10.93 (s, 1H), 8.67 (s, 1H), 8.47 (d, 1H, J=5.3 Hz), 7.78-7.82 (m, 2H), 7.49 (s, 1H), 7.33-7.45 (m, 5H), 7.23-7.27 (m, 2H), 6.48 (d, 1H, J=5.3 Hz), 4.77 (q, 1H, J=7 Hz), 3.94 (s, 3H), 3.92 (s, 3H), 1.42 (d, 6H, J=7.4 Hz).

Example 24

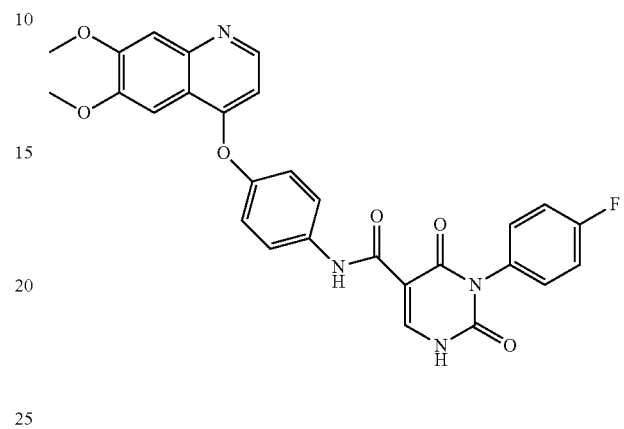

3-(4-Fluorophenyl)-2,4-dioxo-1,2,3,4-tetrahydropyrimidine-5-carboxylic acid [4-(6,7-dimethoxyquinolin-4-yloxy)phenyl]-amide. mp=211-3° C.; LCMS m/z=529 (M+1); $^1$H NMR (DMSO) δ: 12.36 (s, 1H), 10.90 (s, 1H), 8.46 (d, 1H, J=5.3 Hz), 8.43 (s, 1H), 7.77-7.80 (m, 2H), 7.49 (s, 1H), 7.39-7.43 (m, 3H), 7.32-7.37 (m, 2H), 7.22-7.25 (m, 2H), 6.47 (d, 1H, J=5.3 Hz), 3.94 (s, 3H), 3.92 (s, 3H).

Example 25

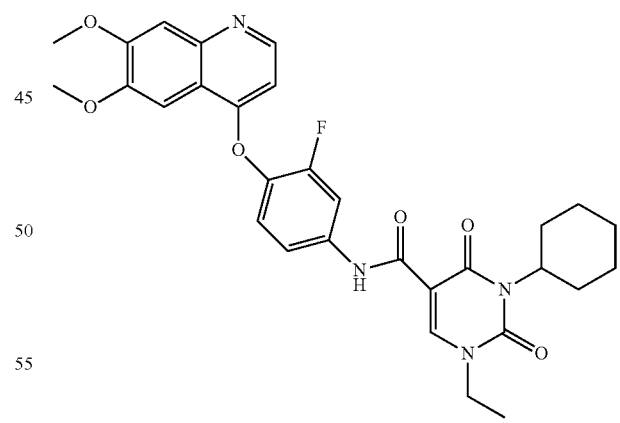

3-Cyclohexyl-1-ethyl-2,4-dioxo-1,2,3,4-tetrahydropyrimidine-5-carboxylic acid [4-(6,7-dimethoxyquinolin-4-yloxy)-3-fluorophenyl]-amide. mp 244-6° C.; LCMS m/z=563 (M+1); $^1$H NMR (DMSO) δ: 11.22 (s, 1H), 8.73 (s, 1H), 8.48 (d, 1H, J=5.2 Hz), 7.99,8.03 (dd, 1H, J=2.6, 12.6 Hz), 7.53-7.57 (m, 2H), 7.41-7.47 (m, 2H), 6.48 (d, 1H, J=5.2

Hz), 4.7 (m, 1H), 3.92-3.98 (m, 8H), 2.32 (m, 3H), 1.80 (m, 2H), 1.62 (m, 3H), 1.29 (m, 2H), 1.25 (m, 3H).

Example 26

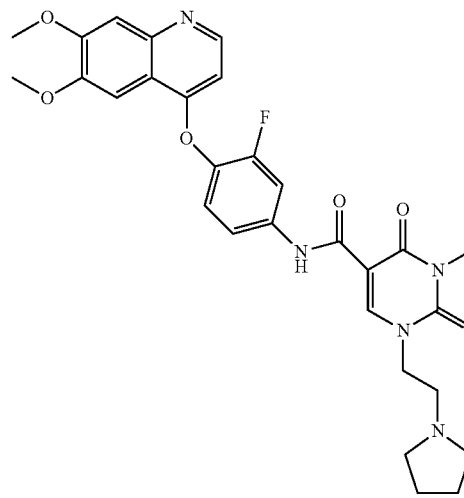

3-(4-Fluorophenyl)-2,4-dioxo-1-(2-pyrrolidin-1-yl-ethyl)-1,2,3,4-tetrahydropyrimidine-5-carboxylic acid [4-(6,7-dimethoxyquinolin-4-yloxy)-3-fluoro phenyl]-amide. mp=118-120° C.; LCMS m/z=644 (M+1); $^1$H NMR (DMSO) δ: 11.00 (s, 1H), 8.79 (s, 1H), 8.47 (d, 1H, J=5.2 Hz), 8.01, 7.98 (dd, 1H, J=2.3, 13 Hz), 7.52-7.55 (m, 2H), 7.33-7.45 (m, 6H), 6.46 (dd, 1H, J=1, 5.3 Hz), 4.08 (t, 2H, J=6.3 Hz), 3.94 (d, 6H), 2.73 (t, 2H, J=6 Hz), 2.54 (m, 4H), 1.70 (m, 4H).

Example 27

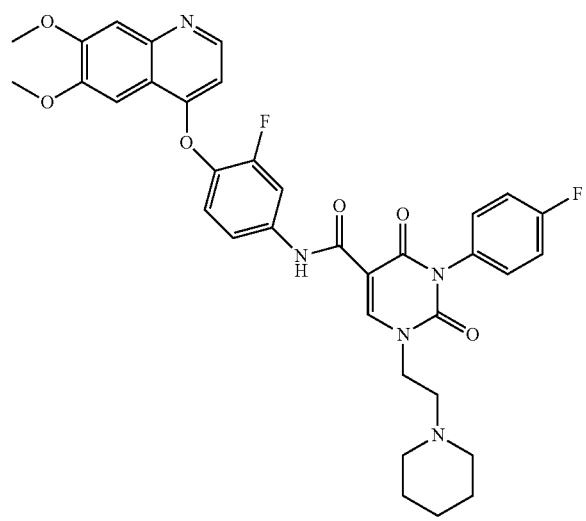 [SMILES: COc1cc2nccc(Oc3ccc(NC(=O)c4cn(CCN5CCCCC5)c(=O)n(-c5ccc(F)cc5)c4=O)cc3F)c2cc1OC]

3-(4-Fluorophenyl)-2,4-dioxo-1-(2-piperidin-1-yl-ethyl)-1,2,3,4-tetrahydropyrimidine-5-carboxylic acid [4-(6,7-dimethoxyquinolin-4-yloxy)-3-fluorophenyl]-amide. mp=137-40° C.; LCMS m/z=658 (M+1); $^1$H NMR (DMSO) δ: 11.00 (s, 1H), 8.78 (s, 1H), 8.47 (d, 1H, J=5.5 Hz), 7.97, 8.01 (dd, 1H, J=2.3, 13 Hz), 7.50-7.56 (m, 2H), 7.34-7.46 (m, 6H), 6.46 (d, 1H, J=5.5 Hz), 4.06 (t, 2H, J=5.5 Hz), 3.94 (s, 6H), 2.55 (m, 2H), 2.44 (b, 4H), 1.49 (m, 4H), 1.39 (m, 2H).

Example 28

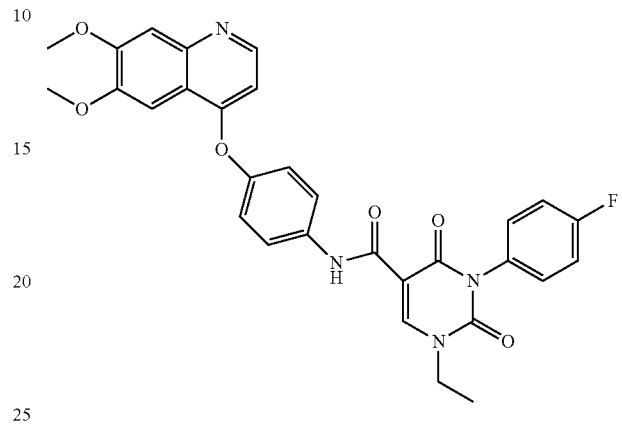

1-Ethyl-3-(4-fluorophenyl)-2,4-dioxo-1,2,3,4-tetrahydropyrimidine-5-carboxylic acid [4-(6,7-dimethoxyquinolin-4-yloxy)-phenyl]-amide. mp=282-4° C.; LCMS m/z=557 (M+1); $^1$H NMR (DMSO) δ: 10.92 (s, 1H), 8.87 (s, 1H), 8.47 (d, 1H, J=5.4 Hz), 7.80 (m, 2H, J=8 Hz), 7.49 (s, 1H), 7.33-7.44 (m, 5H), 7.24-7.26 (m, 2H), 6.48 (d, 1H, J=5.2 Hz), 4.01 (q, 2H, J=7.1 Hz), 3.94 (s, 3H), 3.92 (s, 3H), 1.29 (t, 3H, J=7.1 Hz).

Example 29

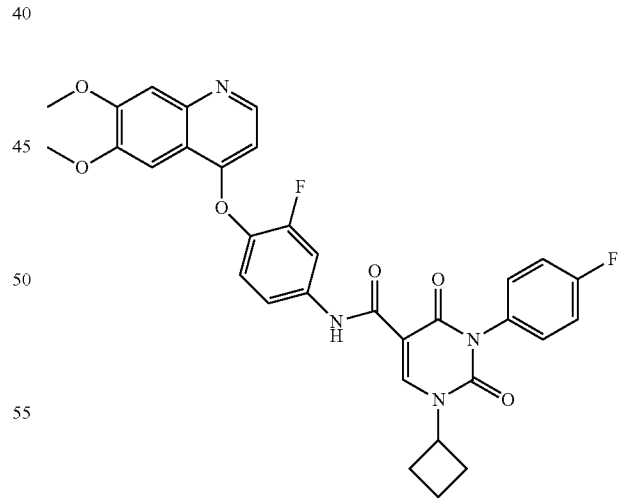

1-Cyclobutyl-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide. mp 148-50° C.; LCMS m/z=601 (M+1); $^1$H NMR (DMSO) δ: 11.02 (s, 1H), 8.91 (s, 0.4H), 8.64 (s, 0.6H), 8.48 (d, 1H, J=5.4 Hz), 7.99, 8.03 (dd, 1H, J=2.2, 13 Hz), 7.52-7.55 (m, 2H), 7.33-7.46 (m, 6H), 6.47 (d, 1H, J=5.4 Hz), 3.94 (d, 6H), 4.8 (m, 0.6H), 3.8

(m, 0.4H), 2.32-2.46 (m, 3H), 1.74-1.83 (m, 1H), 1.23-1.27, 0.54-0.57 (m, 1H), 0.43-0.46 (m, 1H).

Example 30

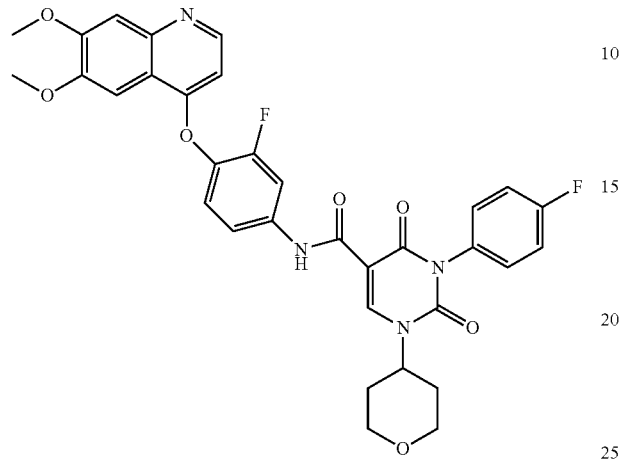

3-(4-Fluorophenyl)-2,4-dioxo-1-(tetrahydropyran-4-yl)-1,2,3,4-tetrahydropyrimidine-5-carboxylic acid [4-(6,7-dimethoxyquinolin-4-yloxy)-3-fluoro phenyl]-amide. mp=164-167° C.; LCMS m/z=631 (M+1); $^1$H NMR (DMSO) δ: 11.0 (s, 1H), 8.65 (s, 1H), 8.48 (d, 1H, J=5.3 Hz), 7.99, 8.02 (dd, 1H, J=2.5, 13 Hz), 7.52-7.56 (m, 2H), 7.34-7.46 (m, 6H), 6.48 (d, 1H, J=5 Hz), 4.64 (m, 1H), 3.98-4.02 (m, 2H), 3.94 (d, 6H), 3.45 (m, 2H), 1.99-2.09 (m, 2H), 1.86-1.89 (m, 2H).

Example 31

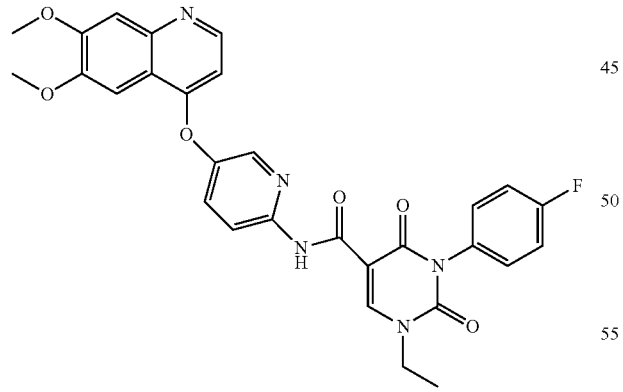

1-Ethyl-3-(4-fluorophenyl)-2,4-dioxo-1,2,3,4-tetrahydropyrimidine-5-carboxylic acid [5-(6,7-dimethoxyquinolin-4-yloxy)-pyridin-2-yl]-amide was synthesized starting with 5-(6,7-dimethoxyquinolin-4-yloxy)-pyridin-2-ylamine. mp=172-4° C.; LCMS m/z=558 (M+1); $^1$H NMR (DMSO) δ: 11.39 (s, 1H), 8.93 (s, 1H), 8.48 (d, 1H, J=5.2 Hz), 8.35-8.38 (m, 2H), 7.84, 7.88 (dd, 1H, J=2.3, 9.3 Hz), 7.52 (s, 1H), 7.33-7.44 (m, 5H), 6.54 (d, 1H, J=5.2 Hz). 4.02 (q, 2H, J=7.4 Hz), 3.93 (d, 6H), 1.29 (t, 3H, J=7.2 Hz).

Example 32

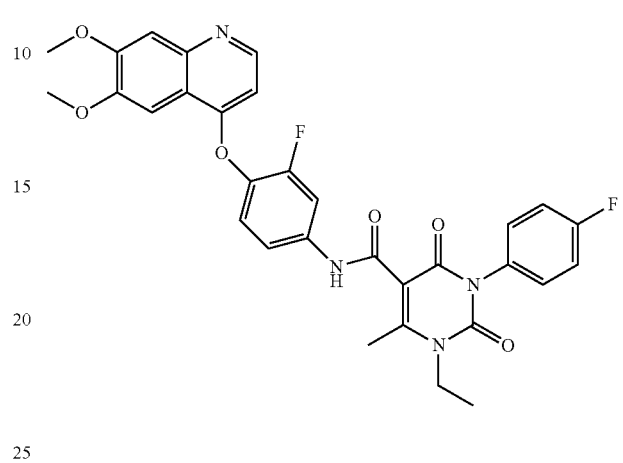

1-Ethyl-3-(4-fluorophenyl)-6-methyl-2,4-dioxo-1,2,3,4-tetrahydropyrimidine-5-carboxylic acid [4-(6,7-dimethoxyquinolin-4-yloxy)-3-fluorophenyl]-amide. mp=260-4° C.; LCMS m/z=589 (M+1); $^1$H NMR (DMSO) δ: 10.71 (s, 1H), 8.46 (d, 1H, J=5.2 Hz), 7.90, 7.94 (dd, 1H, J=2.3, 12.7 Hz), 7.53 (s, 1H), 7.40-7.47 (m, 3H), 7.32-7.36 (m, 4H), 6.46 (d, 1H, J=5.2 Hz), 3.97 (q, 2H, J=7 Hz), 3.94 (s, 6H), 2.47 (s, 3H), 1.25 (t, 3H, J=7.2 Hz).

Example 33

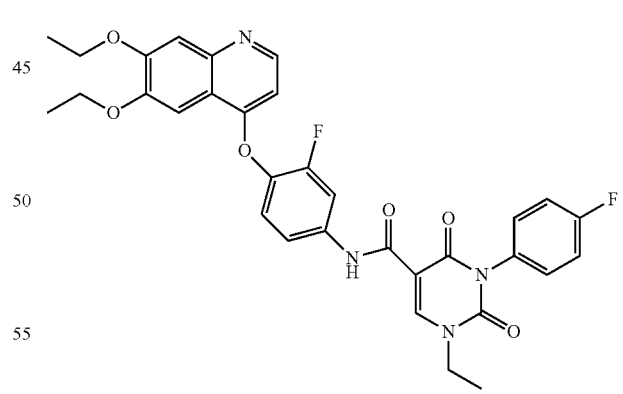

1-Ethyl-3-(4-fluorophenyl)-2,4-dioxo-1,2,3,4-tetrahydropyrimidine-5-carboxylic acid [4-(6,7-diethoxyquinolin-4-yloxy)-3-fluorophenyl]-amide. mp=216-8° C.; LCMS m/z=603 (M+1); $^1$H NMR (DMSO) δ: 11.03 (s, 1H), 8.89 (s, 1H), 8.45 (d, 1H, J=5.2 Hz), 7.98, 8.02 (dd, 1H, J=2.2, 13 Hz), 7.50-7.54 (m, 2H), 7.31-7.45 (m, 6H), 6.45 (d, 1H, J=5.2 Hz), 4.21 (m, 4H), 4.01 (q, 2H, J=6.4 Hz), 1.42 (m, 6H), 1.29 (t, 3H, J=7.2 Hz).

Example 34

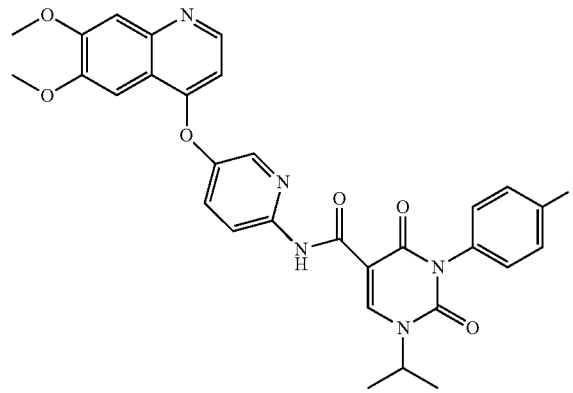

3-(4-Fluorophenyl)-1-isopropyl-2,4-dioxo-1,2,3,4-tetrahydropyrimidine-5-carboxylic acid [5-(6,7-dimethoxyquinolin-4-yloxy)-pyridin-2-yl]-amide was synthesized using the method for example 31. mp=220-4° C.; LCMS m/z=572 (M+1); $^1$H NMR DMSO δ: 11.40 (s, 1H), 8.72 (s, 1H), 8.49 (d, 1H, J=5.2 Hz), 8.36 (d, 1H, J=6.5 Hz), 8.35 (s, 1H), 8.86, 7.84 (dd, 1H, J=3.0, 9.3 Hz), 7.52 (s, 1H), 7.41-7.45 (m, 3H), 7.34-7.39 (m, 2H), 6.55 (d, 1H, J=5.4 Hz), 4.78 (h, 1H, J=6.8 Hz), 3.94, 3.93 (d, 6H), 1.43 (d, 6H, J=6.9 Hz).

Example 35

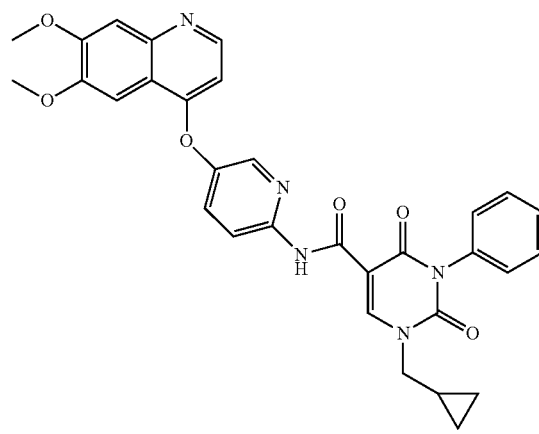

1-Cyclopropylmethyl-3-(4-fluorophenyl)-2,4-dioxo-1,2,3,4-tetrahydropyrimidine-5-carboxylic acid [5-(6,7-dimethoxyquinolin-4-yloxy)pyridin-2-yl]-amide was synthesized using the method for example 31. LCMS m/z=584 (M+1); $^1$H NMR (DMSO) δ: 11.43 (s, 1H), 8.97 (s, 1H), 8.74 (m, 1H), 8.44 (m, 2H), 7.96 (m, 1H), 7.70 (s, 1H), 7.50 (s, 1H), 7.42-7.46 (m, 2H), 7.34-7.39 (m, 2H), 6.91 (m, 1H), 4.0, 4.02 (ss, 6H), 3.88 (m, 2H), 1.21 (m, 1H), 0.55 (m, 2H), 0.45 (m, 2H).

Example 36

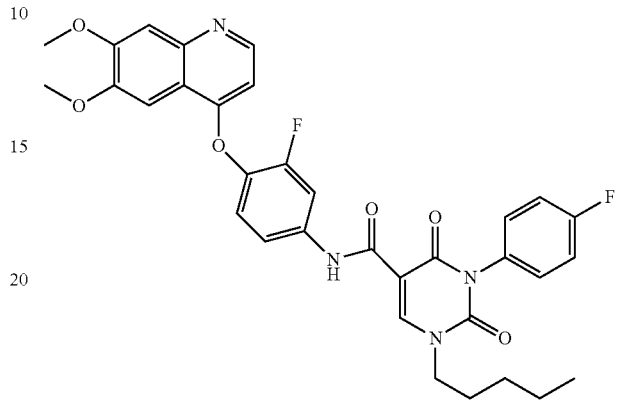

3-(4-Fluorophenyl)-2,4-dioxo-1-pentyl-1,2,3,4-tetrahydropyrimidine-5-carboxylic acid [4-(6,7-dimethoxyquinolin-4-yloxy)-3-fluorophenyl]-amide. mp=128-30° C.; LCMS m/z=617 (M+1); $^1$H NMR (DMSO) δ: 11.0 (s, 1H), 8.85 (s, 1H), 8.47 (d, 1H, J=4.7 Hz), 8.0 (d, 1H, J=12.6 Hz), 7.52-7.55 (m, 2H), 7.33-7.45 (m, 6H), 6.46 (d, 1H, J=4.5 Hz), 3.95 (bm, 8H), 1.70 (brm, 2H), 1.32 (bm, 4H), 0.89 (bm, 3H).

Example 37

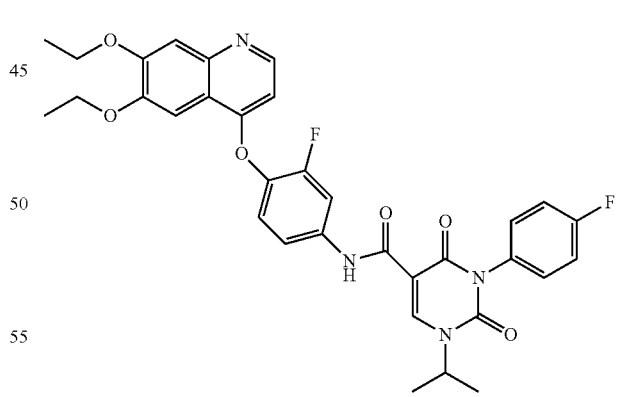

3-(4-Fluorophenyl)-1-isopropyl-2,4-dioxo-1,2,3,4-tetrahydropyrimidine-5-carboxylic acid [4-(6,7-diethoxyquinolin-4-yloxy)-3-fluoro-phenyl]-amide. mp=128-130° C.; LCMS m/z=617 (M+1); $^1$H NMR (DMSO) δ: 11.0 (s, 1H), 8.68 (s, 1H), 8.45 (d, 1H, J=5 Hz), 7.99 (d, 1H, J=13 Hz), 7.50-7.54 (m, 2H), 7.33-7.45 (m, 6H), 6.45 (d, 1H, J=5 Hz), 4.78 (m, 1H), 4.20 (m, 4H), 1.42 (m, 12H).

Example 38

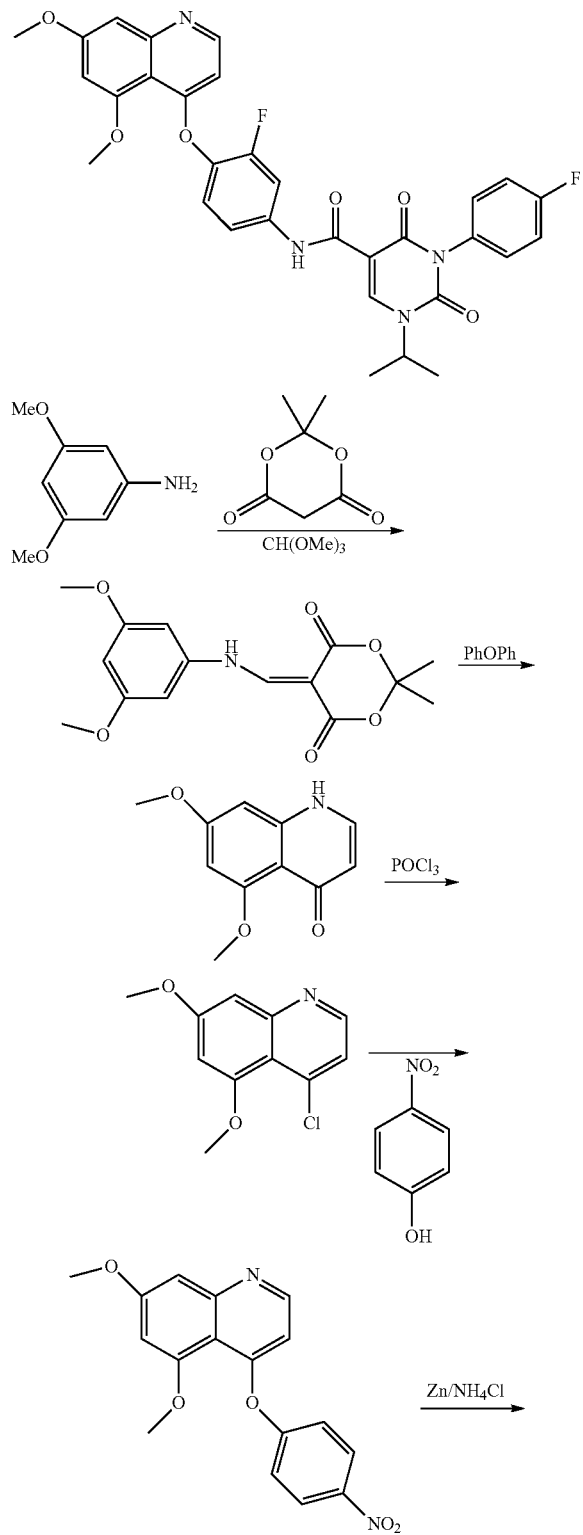

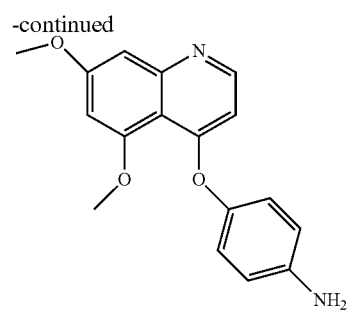

Step a. Meldrum acid (470 mg, 3.20 mmol) in triethylorthoformate (4 mL) and heated at 100° C. for 1.5 h. 3,5-Dimethoxyaniline (500 mg, 3.2 mmol) was added and heated and heated at 100° C. for 4 h. The reaction mixture was cooled to rt and hexanes added and stirred. The yellow solid was collected and dried to yield a yellow solid. LCMS m/z=308 (M+1); $^1$H NMR (CDCl$_3$) δ; 8.61 (d, 1H, J=14.0 Hz), 6.365 (m, 3H), 3.82 (s, 6H), 1.76 (s, 6H).

Step b. 5-[(3,5-Dimethoxyphenylamino)-methylene]-2,2-dimethyl[1,3]dioxane-4,6-dione (400 mg, 1.30 mmol) in diphenyl ether (5 mL) and heated at 200° C. for 30 min. The reaction mixture was cooled to rt and hexane was added and stirred for 30 min. The brown solid was filtered and dried to yield 5,7-dimethoxy-1H-quinolin-4-one LCMS m/z=206 (M+1).

Step c. 5,7-dimethoxy-1H-quinolin-4-one (300 mg, 1.4 mmol) in POCl$_3$ (5 mL) was heated to reflux for 15 h. The reaction mixture was cooled to rt and poured into ice-water. The mixture was then basified to pH 7 with NaHCO$_3$ and stirred overnight. The solid was filtered and washed with water and dried to give 4-chloro-5,7-dimethoxyquinoline. LCMS m/z=224 (M+1); $^1$H NMR (CDCl$_3$) δ: 8.56 (d, 1H, J=4.4 Hz), 7.23 (d, 1H, J=4.4 Hz), 7.05 (s, 1H), 6.58 (s, 1H), 3.93 (s, 6H).

Step d. 4-Chloro-5,7-dimethoxyquinoline (100 mg, 0.40 mmol) and p-nitrophenol (124 mg, 0.89 mmol) in chlorobenzene (2 mL) was heated at reflux for 14 h. Then the reaction mixture was cooled to rt, filtered, and the residue washed with toluene. The solid was suspended in 10% NaOH solution and stirred for 1 h at rt. The yellow solid was collected and washed with EtOAc to give 5,7-dimethoxy-4-(4-nitrophenoxy)quinoline. LCMS m/z=327 (M+1); $^1$H NMR (CDCl$_3$) δ: 8.60 (d, 1H, J=6.0 Hz), 8.44 (d, 2, J=8.8 Hz), 7.72 (s, 1H), 7.35 (d, 2H, J=8.4 Hz) 6.71 (s, 1H), 6.69 (d, 2H, J=6.4 Hz), 4.08 (s, 3H), 3.97 (s, 3H).

Step e. A mixture of 5,7-dimethoxy-4-(4-nitrophenoxy) quinoline (50 mg, 0.15 mmol), Zn dust (100 mg, 1.50 mmol) and ammonium chloride (32 mg, 0.60 mmol) in methanol (3 mL) was heated at reflux for 1 h. The mixture was filtered through celite and washed with CHCl$_3$. The organic layer was washed with 10% NaOH solution and brine, dried over Na$_2$SO$_4$, and concentrated to afford 4-(5,7-dimethoxyquinolin-4-yloxy)phenylamine as an off white solid. LCMS m/z=298 (M+1); $^1$H NMR (CDCl$_3$) δ: 8.44 (d, 1H, J=4.8 Hz), 7.00 (s, 1H), 6.83 (d, 2H, J=8.8 Hz), 6.65-6.63 (m, 3H), 6.32 (d, 1H, J=4.8 Hz), 5.11 (br s, 2H), 3.89 (s, 3H), 3.86 (s, 3H).

3-(4-Fluorophenyl)-1-isopropyl-2,4-dioxo-1,2,3,4-tetrahydropyrimidine-5-carboxylic acid [4-(5,7-dimethoxyquinolin-4-yloxy)phenyl]-amide. mp=122-4° C.; LCMS m/z=571 (M+1); $^1$H NMR (DMSO) δ: 10.87 (s, 1H), 8.65 (s, 1H), 8.53 (d, 1H, J=5.3 Hz), 7.73 (d, 2H, J=9 Hz), 7.42 (m, 2H), 7.35 (m, 2H), 7.07 (d, 2H, J=9 Hz), 6.99 (d, 1H, J=2 Hz), 6.63 (d, 1H, J=2 Hz), 6.50 (d, 1H, J=5 Hz), 4.78 (q, 1H, J=7 Hz), 3.90 (s, 3H), 3.80 (s, 3H), 1.42 (d, 6H, J=7 Hz).

Example 39

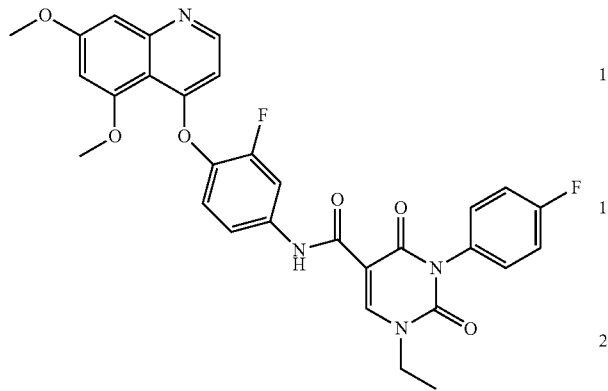

1-Ethyl-3-(4-fluorophenyl)-2,4-dioxo-1,2,3,4-tetrahydropyrimidine-5-carboxylic acid [4-(5,7-dimethoxyquinolin-4-yloxy)-phenyl]-amide was synthesized using 4-(5,7-dimethoxyquinolin-4-yloxy)phenylamine and 3-(4-fluorophenyl)-1-ethyl-2,4-dioxo-1,2,3,4-tetrahydropyrimidine-5-carboxylic acid by the method for example 38. mp=128-9° C.; LCMS m/z=557 (M+1); $^1$H NMR (DMSO) δ: 10.87 (s, 1H), 8.85 (s, 1H), 8.52 (m, 1H), 7.72 (m, 2H), 7.33-7.41 (m, 4H), 7.07 (m, 2H), 6.99 (m, 1H), 6.63 (m, 1H), 6.49 (m, 1H), 4.01 (m, 2H), 3.90 (s, 3H), 3.81 (s, 3H), 1.28 (m, 3H).

Example 40

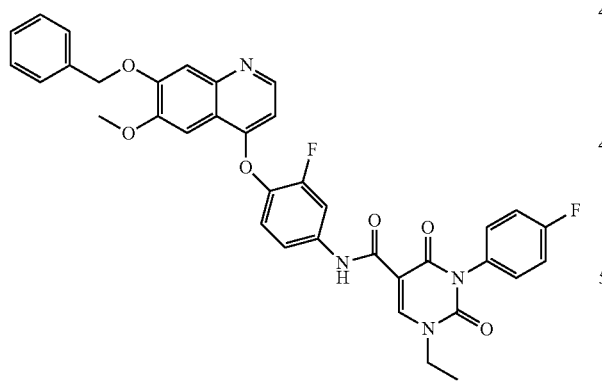

Step a. 4-(7-Benzyloxy-6-methoxyquinolin-4-yloxy)-3-fluorophenylamine. Sodium hydride (60% disp. in mineral oil, 0.534 g, 13.3 mmol) was added to 4-amino-2-fluorophenol in dry N,N-dimethylformamide (10.3 mL) at rt and stirred for 30 min under an atmosphere of nitrogen. Then solid 7-benzyloxy-4-chloro-6-methoxyquinoline (2.00 g, 6.67 mmol) was added and the reaction stirred at 100° C. for 30 h. The mixture was concentrated, dissolved in EtOAc (about 75 mL), and washed with 1N Na$_2$CO$_3$, water and brine, then dried over MgSO$_4$. The product was chromatographed on silica gel (5% MeOH/DCM) to give a brown solid 1.9 g (73%). LCMS m/z=391 (M+1); $^1$H NMR (DMSO) δ: 8.43 (s, 1H), 7.36-7.52 (m, 7H), 7.07 (m, 1H), 6.38-6.56 (m, 3H), 5.50 (m, 2H), 5.3 (s, 2H), 3.95 (s, 3H).

Step b. 1-Ethyl-3-(4-fluorophenyl)-2,4-dioxo-1,2,3,4-tetrahydropyrimidine-5-carboxylic acid [4-(7-benzyloxy-6-methoxyquinolin-4-yloxy)-3-fluorophenyl]-amide was synthesized using 4-(7-benzyloxy-6-methoxyquinolin-4-yloxy)-3-fluorophenylamine and 3-(4-fluorophenyl)-1-ethyl-2,4-dioxo-1,2,3,4-tetrahydropyrimidine-5-carboxylic acid by the method for example 1. mp=142-4° C.; LCMS m/z=651 (M+1); $^1$H NMR (DMSO) δ: 11.0 (s, 1H), 8.89 (s, 1H), 8.47 (d, 1H, J=5.3 Hz), 7.98, 8.02 (dd, 1H, J=2.3, 13 Hz), 7.50-7.54 (m, 5H), 7.41-7.46 (m, 5H), 7.33-7.38 (m, 3H), 6.48 (d, 1H, J=5 Hz), 5.31 (s, 2H), 4.90 (q, 2H, J=7 Hz), 3.95 (s, 3H), 1.29 (t, 3H, J=7 Hz).

Example 41

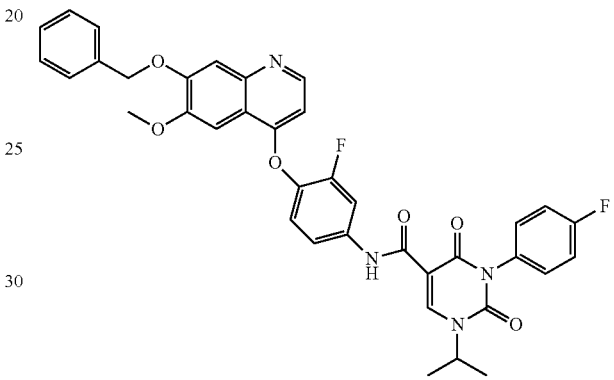

3-(4-Fluorophenyl)-1-isopropyl-2,4-dioxo-1,2,3,4-tetrahydropyrimidine-5-carboxylic acid [4-(7-benzyloxy-6-methoxyquinolin-4-yloxy)-3-fluorophenyl]-amide was synthesized using the method for example 40 and 3-(4-fluorophenyl)-1-isopropyl-2,4-dioxo-1,2,3,4-tetrahydropyrimidine-5-carboxylic acid. mp=184-6° C.; LCMS m/z=665 (M+1); $^1$H NMR (DMSO) δ: 11.0 (s, 1H), 8.6 (s, 1H), 8.46 (d, 1H, J=5.3 Hz), 8.0, 8.02 (dd, 1H, J=2.4, 12.6 Hz), 7.48-7.54 (m, 5H), 7.41-7.46 (m, 5H), 7.33-7.38 (m, 3H), 6.47 (d, 1H, J=5 Hz), 5.31 (s, 2H), 6.78 (m, 1H), 3.95 (s, 3H), 1.43 (d, 6H, J=5.5 Hz).

Example 42

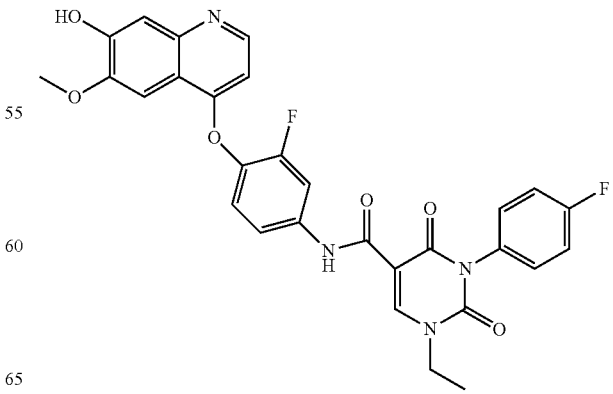 [SMILES: CCOc1cc2nccc(Oc3ccc(NC(=O)c4cn(CC)c(=O)n(-c5ccc(F)cc5)c4=O)cc3F)c2cc1OCC]

1-Ethyl-3-(4-fluorophenyl)-2,4-dioxo-1,2,3,4-tetrahydropyrimidine-5-carboxylic acid [3-fluoro-4-(7-hydroxy-6-methoxyquinolin-4-yloxy)phenyl]-amide. Example 40 (0.50 g, 0.77 mmol) and 20% Pd(OH)2/C, 50% wet (10:40:50, palladium hydroxide:carbon black:Water, 0.1 g, 0.07 mmol) in N,N-dimethylformamide (10 mL) was hydrogenated on a Parr apparatus under an atmosphere of hydrogen 40 psi for 12 h. The solvent was removed and the product was triturated with ether to give 42-mg (97%) as a while solid. mp>200° C. dec; LCMS m/z=561 (M+1); $^1$H NMR (DMSO) δ: 11.75 (bs, 1H), 11.11 (s, 1H), 8.89 (s, 1H), 8.73 (d, 1H, J=6.5 Hz), 8.07, 8.11 (dd, 1H, J=2.3, 12.5 Hz), 7.72 (s, 1H), 7.54-7.64 (m, 3H), 7.41-7.45 (m, 2H), 7.34-7.39 (m, 2H), 6.90 (d, 1H, J=6.5 Hz), 4.0-4.05 (s, m, 5H), 1.30 (t, 3H, J=7.2 Hz).

Example 43

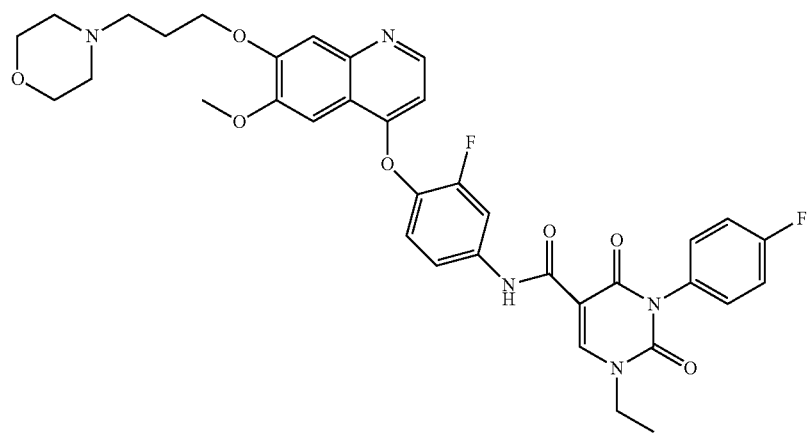 [SMILES: CCn1cc(C(=O)Nc2ccc(Oc3ccnc4cc(OCCCN5CCOCC5)c(OC)cc34)c(F)c2)c(=O)n(-c2ccc(F)cc2)c1=O]

1-Ethyl-3-(4-fluorophenyl)-2,4-dioxo-1,2,3,4-tetrahydropyrimidine-5-carboxylic acid {3-fluoro-4-[6-methoxy-7-(3-morpholin-4-yl-propoxy)quinolin-4-yloxy]phenyl}-amide. Example 42 (0.100 g, 0.178 mmol), methanesulfonic acid 3-morpholin-4-yl-propyl ester (0.0438 g, 0.196 mmol) and cesium carbonate (0.116 g, 0.357 mmol) in N,N-dimethylformamide (2 mLl) was heated at 65° C. for 8 h. The mixture was diluted with EtOAc and extracted with 1N Na$_2$CO$_3$, water and brine solutions then dried over MgSO$_4$. The solid was triturated with ether, then the ether decanted and the product precipitated with hexanes to give a white solid. mp=92-5° C.; LCMS m/z=688 (M+1); $^1$H NMR (DMSO) δ: 11.04 (s, 1H), 8.89 (s, 1H), 8.46 (d, 1H, J=5.3 Hz), 7.98, 8.02 (dd, 1H, J=2.4, 13 Hz), 7.51-7.55 (m, 2H), 7.33-7.46 (m, 6H), 6.46 (d, 1H, J=5.4 Hz, 4.20 (t, 2H, J=6.4 Hz), 4.01 (q, 2H, J=7.4 Hz), 3.94 (s, 3H), 3.58 (t, 4H, J=4.8 Hz), 2.45 (m, 2H), 2.39 (b, 4H), 1.98 (m, 2H), 1.29 (t, 3H, J=7.2 Hz).

Example 44

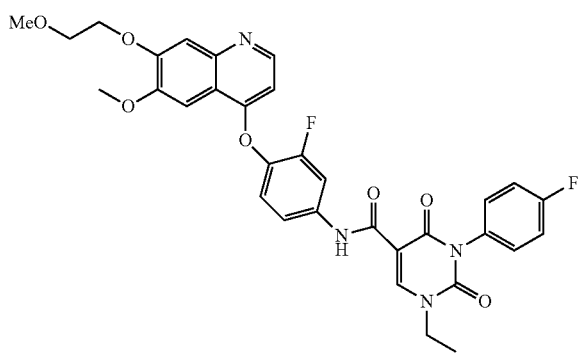 [SMILES: CCn1cc(C(=O)Nc2ccc(Oc3ccnc4cc(OCCOC)c(OC)cc34)c(F)c2)c(=O)n(-c2ccc(F)cc2)c1=O]

1-Ethyl-3-(4-fluorophenyl)-2,4-dioxo-1,2,3,4-tetrahydropyrimidine-5-carboxylic acid {3-fluoro-4-[6-methoxy-7-(2-methoxyethoxy)quinolin-4-yloxy]-phenyl}-amide. Example 44 was synthesized by the procedure for example 43 using example 42 and 1-bromo-2-methoxyethane. mp=178-80° C.; LCMS m/z=619 (M+1); $^1$H NMR (DMSO) δ: 11.00 (s, 1H), 8.89 (s, 1H), 8.46 (d, 1H, J=5 Hz), 7.98, 8.00 (dd, 1H, J=2, 13 Hz), 7.52-7.55 (m, 2H), 7.42-7.46 (m, 4H), 7.33-7.38 (m, 2H), 6.47 (d, 1H, J=5.4 Hz), 4.28 (m, 2H), 4.01 (q, 2H, J=7.1 Hz), 3.95 (s, 3H), 3.76- (m, 2H), 3.34 (s, 3H), 1.29 (t, 3H, J=7.1 Hz).

Example 45

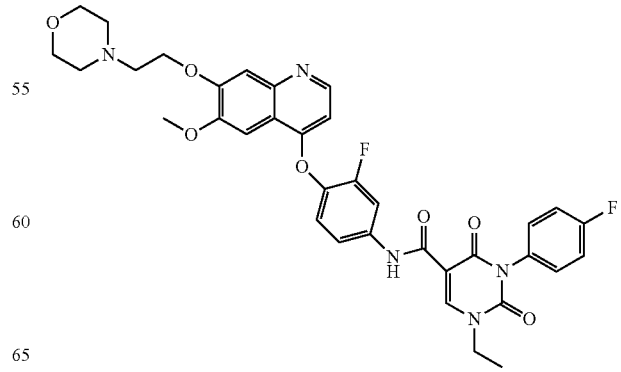

1-Ethyl-3-(4-fluorophenyl)-2,4-dioxo-1,2,3,4-tetrahydropyrimidine-5-carboxylic acid {3-fluoro-4-[6-methoxy-7-(2-morpholin-4-yl-ethoxy)-quinolin-4-yloxy]phenyl}-amide. Example 45 was synthesized by the procedure for example 43 using example 42 and 4-(2-chloroethyl)morpholine hydrochloride. mp=222-224° C.; LCMS m/z=674 (M+1); $^1$H NMR (DMSO) δ: 11.0 (s, 1H), 8.89 (s, 1H), 8.47 (d, 1H, J=5.4 Hz), 7.98, 8.01 (dd, 1H, J=2.4, 12.6 Hz), 7.52-7.55 (m, 2H), 7.41-7.46 (m, 4H), 7.33-7.38 (m, 2H), 6.46 (d, 1H, J=5.4 Hz), 4.27 (t, 2H, J=6 Hz), 4.02 (q, 2H, J=7.4 Hz), 3.94 (s, 3H), 3.59 (t, 4H, J=4.6 Hz), 2.79 (t, 2H, J=5.8 Hz), 2.53 (m, 4H), 1.29 (t, 3H, J=7.4 Hz).

Example 46

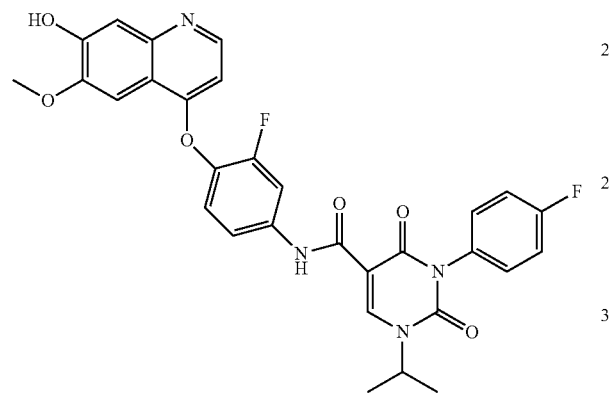

3-(4-Fluorophenyl)-1-isopropyl-2,4-dioxo-1,2,3,4-tetrahydropyrimidine-5-carboxylic acid [3-fluoro-4-(7-hydroxy-6-methoxyquinolin-4-yloxy)-phenyl]-amide.
Example 46 was synthesized using example 41 and the procedure for example 42. mp=205-7° C.; LCMS m/z=575 (M+1); $^1$H NMR (DMSO) δ: 11.7 (s, 1H), 11.1 (s, 1H), 8.73 (d, 1H, J=7 Hz), 8.68 (s, 1H), 8.07, 8.11 (dd, 1H, J=2.4, 12.7 Hz), 7.72 (s, 1H), 7.54-7.64 (m, 3H), 7.34-7.45 (m, 4H), 6.89 (d, 1H, J=6.5 Hz), 4.78 (m, 1H), 4.0 (s, 3H), 1.42 (d, 6H, J=7 Hz).

Example 47

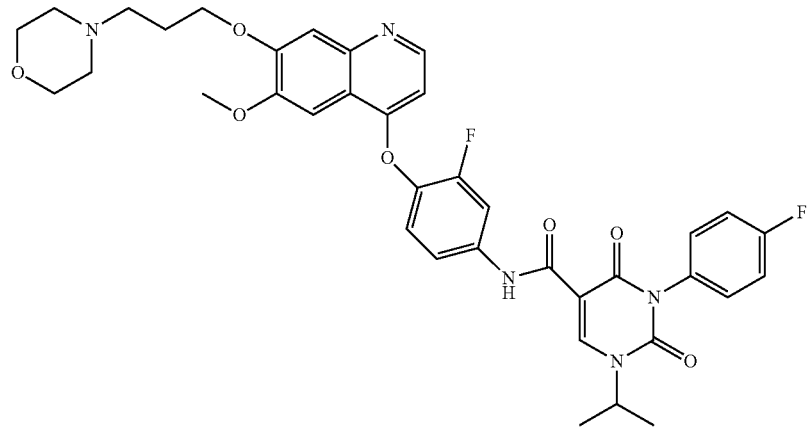 [SMILES: COc1cc2c(Oc3ccc(NC(=O)c4cn(C(C)C)c(=O)n(-c5ccc(F)cc5)c4=O)cc3F)ccnc2cc1OCCCN1CCOCC1]

3-(4-Fluorophenyl)-1-isopropyl-2,4-dioxo-1,2,3,4-tetrahydropyrimidine-5-carboxylic acid {3-fluoro-4-[6-methoxy-7-(3-morpholin-4-yl-propoxy)-quinolin-4-yloxy]phenyl}-amide. Example 47 was synthesized by the procedure for example 43 using example 46. mp=160-162° C.; LCMS m/z=701 (M+1); $^1$H NMR (DMSO) δ: 11.0 (s, 1H), 8.68 (s, 1H), 8.47 (d, 1H, 5.3 Hz), 7.99, 8.02 (dd, 1H, J=2.3, 13 Hz), 7.5'-7.55 (m, 2H), 7.33-7.45 (m, 6H), 6.46 (d, 1, J=5.3 Hz), 4.78 (m, 1H), 4.2 (t, 2H, J=6.8 Hz), 3.94 (s, 3H), 3.58 (m, 4H), 2.45 (m, 2H), 2.38 (m, 4H), 1.97 (m, 2H), 1.42 (d, 6H, J=7 Hz).

Example 48

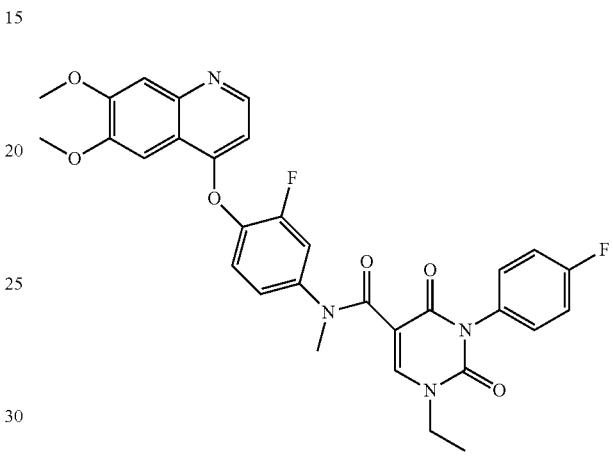

1-Ethyl-3-(4-fluorophenyl)-2,4-dioxo-1,2,3,4-tetrahydropyrimidine-5-carboxylic acid [4-(6,7-dimethoxyquinolin-4-yloxy)-3-fluoro-phenyl]-methyl-amide. Example 1 (0.050 g, 0.087 mmol) in N,N-dimethylformamide (2 mL) at 5° C. (ice bath) was added sodium hydride, 60% disp. in mineral oil (0.0052 g, 0.13 mmol). The mixture was stirred 0.5 h, and then methyl iodide (0.0081 mL, 0.13 mmol) was added. After 2 h, EtOAc was added, washed with 1N Na$_2$CO$_3$, water and brine. The product was purified by prep LC/MS. The fractions were combined and concentrated and the solid was crystallized with EtOAc, ether and hexanes to give a white solid as the TFA salt. mp=112-5° C.; LCMS m/z=589 (M+1); $^1$H NMR (DMSO) δ: 8.66 (d, 1H, J=5.9 Hz), 8.23 (s, 1H), 7.65 (s, 1H), 7.51-7.60 (m, 3H), 7.25-7.30 (m, 3H), 7.13-7.16 (m, 2H), 6.6 (d, 1H, J=5.8 Hz), 4.01 (d, 6H), 3.8 (q, 2H, J=7 Hz), 3.35 (s, 3H), 1.22 (t, 3H, J=7 Hz).

Example 49

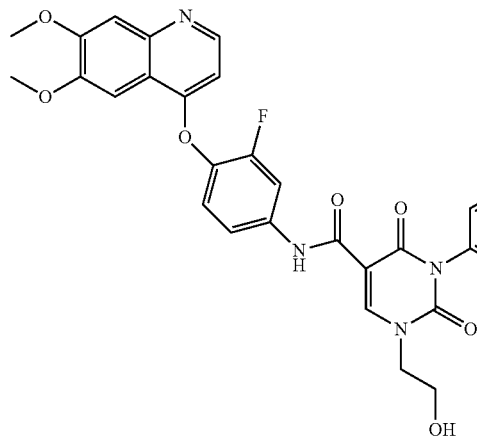

3-(4-Fluorophenyl)-1-(2-hydroxyethyl)-2,4-dioxo-1,2,3,4-tetrahydropyrimidine-5-carboxylic acid [4-(6,7-dimethoxyquinolin-4-yloxy)-3-fluorophenyl]-amide. Example 10 (0.06 g, 0.09 mmol) and palladium hydroxide (20%) on carbon (0.016 g, 0.024 mmol) in ethyl acetate (7 mL) and MeOH (3 mL) was added 2 drops of 5N HCl. The mixture was hydrogenated under an atmosphere of hydrogen on a Parr apparatus at 40 psi for 2 h. The mixture was diluted with EtOAc and washed with 1N Na$_2$CO$_3$, and brine, then dried over MgSO$_4$. The solution was concentrated and the product was triturated with ether-hexanes and the solid collected and dried at 60° C. under vacuum. mp=166-8° C.; LCMS m/z=591 (M+1); $^1$H NMR (DMSO) δ: 11.00 (s, 1H), 8.75 (s, 1H), 8.47 (d, 1H, J=5.4 Hz), 7.98, 8.01 (dd, 1H, J=2.2, 13 Hz), 7.52-7.55 (m, 2H), 7.34-7.46 (m, 6H), 6.47 (d, 1H, J=5 Hz), 5.03 (t, 1H, J=5.4 Hz), 4.05 (m, 2H), 3.94 (d, 6H), 3.67 (m, 2H).

Example 50

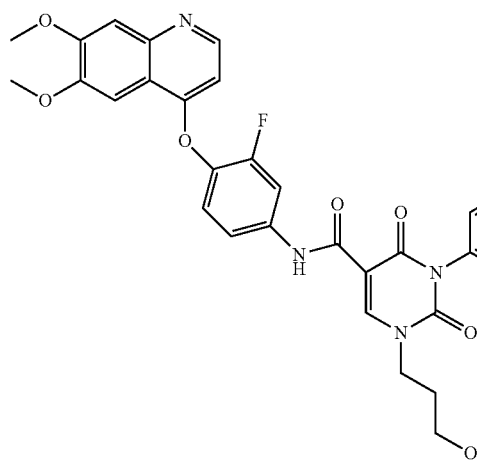

3-(4-Fluorophenyl)-1-(3-hydroxypropyl)-2,4-dioxo-1,2,3,4-tetrahydropyrimidine-5-carboxylic acid [4-(6,7-dimethoxyquinolin-4-yloxy)-3-fluorophenyl]-amide.
Example 50 was synthesized using example 13 by the procedure for example 49. mp=124-6° C.; LCMS m/z=605 (M+1); 1H NMR (DMSO) δ: 11.00 (s, 1H), 8.82 (s, 1H), 8.47 (d, 1H, J=5.4 Hz), 7.98, 8.01 (dd, 1H, J=2.5, 13 Hz), 7.52-7.55 (m, 2H), 7.33-7.46 (m, 6H), 6.47 (d, 1H, J=6 Hz), 4.63 (t, 1H, J=5 Hz), 4.05 (t, 2H, J=7 Hz), 3.94 (s, s, 6H), 3.50 (q, 2H, J=5 Hz), 1.85 (p, 2H, J=6.2 Hz).

Example 51

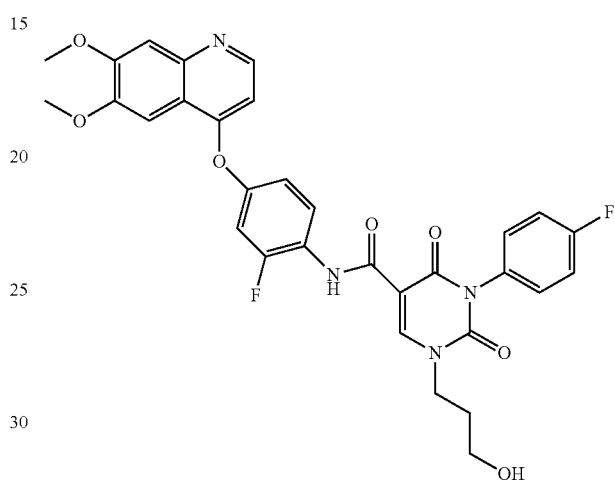

3-(4-Fluorophenyl)-1-(3-hydroxypropyl)-2,4-dioxo-1,2,3,4-tetrahydropyrimidine-5-carboxylic acid [4-(6,7-dimethoxy-quinolin-4-yloxy)-2-fluoro-phenyl]-amide.
Example 51 was synthesized using example 22 by the procedure for example 49. mp=220-4° C.; LCMS m/z=605 (M+1); $^1$H NMR (DMSO) δ: 11.16 (s, 1H), 8.83 (s, 1H), 8.45-8.50 (m, 2H), 7.47 (s, 1H), 7.33-7.44 (m, 6H), 7.16 (d, 1H, J=9 Hz), 6.58 (d, 1H, J=5 Hz), 4.63 (t, 1H, J=4.9 Hz), 4.04 (t, 2H, J=7 Hz), 3.94 (s, 3H), 3.92 (s, 3H), 3.50 (q, 2H, J=5.4 Hz), 1.84 (q, 2H, J=7 Hz).

Example 52

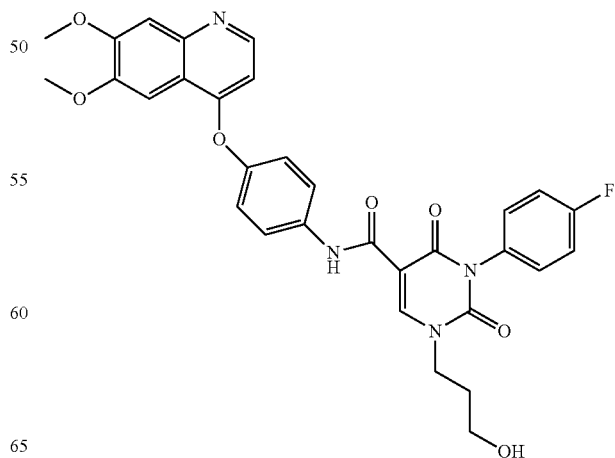

3-(4-Fluorophenyl)-1-(3-hydroxypropyl)-2,4-dioxo-1,2,3,4-tetrahydropyrimidine-5-carboxylic acid [4-(6,7-dimethoxyquinolin-4-yloxy)phenyl]-amide. Example 52 was synthesized using example 21 by the procedure for example 49. mp=123-6° C.; LCMS m/z=587 (M+1); $^1$H NMR (DMSO) δ: 10.93 (s, 1H), 8.79 (s, 1H), 8.47 (d, 1H, J=5 Hz), 7.8) d, 2H, J=9 Hz), 7.50 (s, 1H), 7.33-7.44 (m, 5H), 7.25 (d, 2H, J=9 Hz), 6.47 (d, 1H, j=5.6 Hz), 4.63 (t, 1H, J=5 Hz), 4.04 (t, 2H, J=7 Hz), 3.94 (s, 3H), 3.92 (s, 3H), 3.50 (q, 2H, J=5 Hz).

Example 53

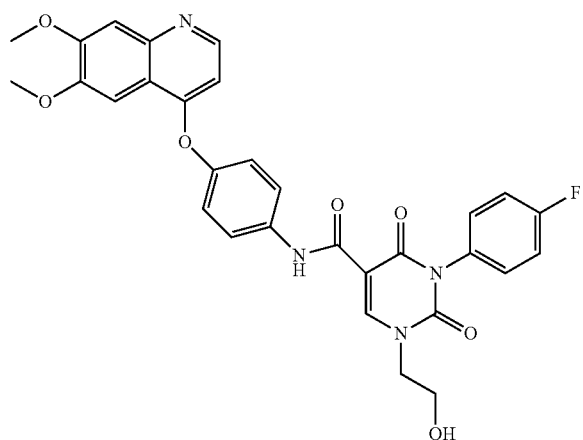 [SMILES: COc1cc2nccc(Oc3ccc(NC(=O)c4cn(CCO)c(=O)n(-c5ccc(F)cc5)c4=O)cc3)c2cc1OC]

3-(4-Fluorophenyl)-1-(2-hydroxyethyl)-2,4-dioxo-1,2,3,4-tetrahydropyrimidine-5-carboxylic acid [4-(6,7-dimethoxyquinolin-4-yloxy)phenyl]-amide. Example 53 was synthesized using example 19 by the procedure for example 49. mp=153-4° C.; LCMS m/z=573 (M+1); 1H NMR (DMSO) δ: 10.91 (s, 1H), 8.74 (s, 1H), 8.47 (d, 1H, J=5.8 Hz), 7.80 (d, 2H, J=9 Hz), 7.49 (s, 1H), 7.34-7.43 (m, 5H), 7.26 (d, 2H, J=9 Hz), 6.48 (d, 1H, J=5.4 Hz), 5.02 (t, 1H, J=5.2 Hz), 4.03 (m, 2H), 3.94 (s, 3H), 3.92 (s, 3H), 3.67 (m, 2H).

Example 54

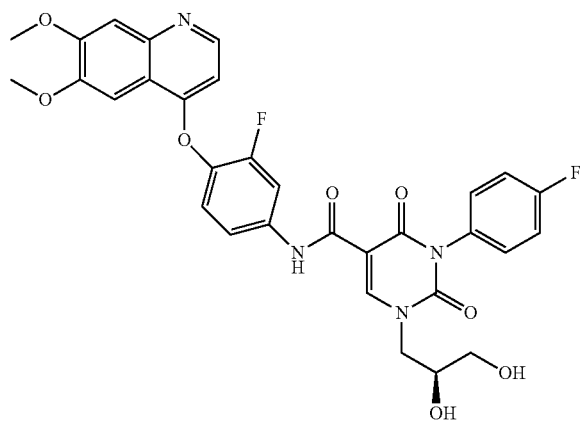 [SMILES: COc1cc2nccc(Oc3ccc(NC(=O)c4cn(C[C@H](O)CO)c(=O)n(-c5ccc(F)cc5)c4=O)cc3F)c2cc1OC]

1-((S)-2,3-Dihydroxypropyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide. 1-((S)-2,2-Dimethyl-1,3-dioxolan-4-ylmethyl)-3-(4-fluorophenyl)-2,4-dioxo-1,2,3,4-tetrahydropyrimidine-5-carboxylic acid (0.0446 g, 0.122 mmol) and N,N,N',N'-tetramethyl-O-(7-azabenzotriazol-1-yl)uronium hexafluorophosphate (0.0466 g, 0.122 mmol) in N,N-dimethylformamide (2.00 mL) was added N,N-diisopropylethylamine (0.0388 mL, 0.223 mmol) and stirred at rt for 15 min. 4-(6,7-Dimethoxyquinolin-4-yloxy)-3-fluorophenylamine (0.035 g, 0.11 mmol) was added and stirred overnight. The solution was diluted with EtOAc, washed with 1N Na$_2$CO$_3$, water and brine then dried over MgSO4 and concentrated. MeOH was added (1 mL) and a solid separated. This material was dissolved in 4 M of hydrogen chloride in 1,4-dioxane (2 mL, 8 mmol), stirred for 2 h and then concentrated. To this product was added MeOH and the precipitate collected to give a white solid. mp=165-6° C.; LCMS m/z=621 (M+1); $^1$H NMR (DMSO) δ: 11.0 (s, 1H), 8.72 (s, 1H), 8.48 9 d, 1H, J=5.4 Hz), 8.01, 7.98 (dd, 1H, J=2.4, 13.5 Hz), 7.52-7.55 (j, 1H), 7.34-7.46 (m, 6H), 6.47 (d, 1H, J=5.4 Hz), 6.17 (d, 1H, J=5 Hz), 4.78 (t, 1H, J=5.7 Hz), 4.22 (d, 1H, J=10 Hz), 3.94 (d, 6H), 3.75-3.78 (m, 2H), 3.3 (m, 2H).

Example 55

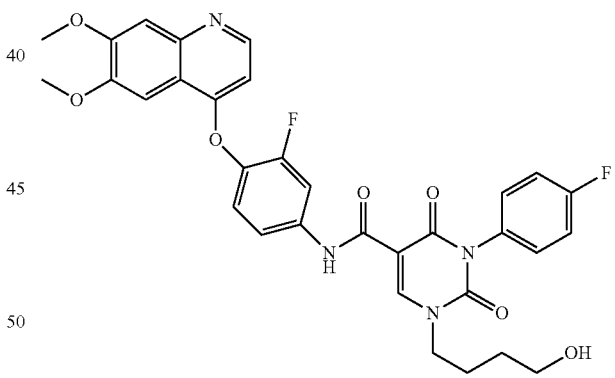

3-(4-Fluorophenyl)-1-(4-hydroxybutyl)-2,4-dioxo-1,2,3,4-tetrahydropyrimidine-5-carboxylic acid [4-(6,7-dimethoxyquinolin-4-yloxy)-3-fluorophenyl]-amide. LCMS m/z=619 (M+1); $^1$H NMR (DMSO) δ: 11.04 (s, 1H), 8.86 (s, 1H), 8.47 (d, 1H, J=5 Hz), 8.00 (d, 1H, J=12 Hz), 7.52-7.55 (m, 2H), 7.33-7.46 (m, 6H), 6.47 (d, 1H, J=5 Hz), 4.48 (t, 1H, J=4.5 Hz), 3.99 (m, 2H), 3.94 (d, 6H), 3.42 (m, 2H), 1.73 (m, 2H), 1.48 (m, 2H).

Example 56

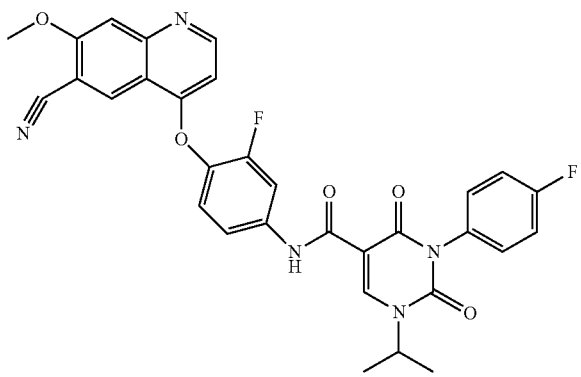 [SMILES: COc1cc2nccc(Oc3ccc(NC(=O)c4cn(C(C)C)c(=O)n(-c5ccc(F)cc5)c4=O)cc3F)c2cc1C#N]

4-(2-fluoro-4-methylaminophenoxy)-7-methoxyquinoline-6-carbonitrile was synthesized by the method described for 4-(5,7-dimethoxyquinolin-4-yloxy)phenylamine example 38 starting with 4-amino-2-methoxybenzonitrile; LCMS m/z=309 (M+1); $^1$H NMR (DMSO-d6) δ: 8.73 (s, 1H), 8.71 (d, 1H, J=5.2 Hz), 7.58 (s, 1H), 6.95 (d, 2H, J=8.8 Hz), 6.67 (d, 2H, J=8.4 Hz), 6.48 (d, 1H, J=5.6 Hz), 5.20 (br s, NH, 2H), 4.06 (s, 3H). 3-(4-Fluorophenyl)-1-isopropyl-2,4-dioxo-1,2,3,4-tetrahydropyrimidine-5-carboxylic acid [4-(6-cyano-7-methoxy-quinolin-4-yloxy)-phenyl]-amide. N,N,N',N'-Tetramethyl-O-(7-azabenzotriazol-1-yl)uronium hexafluorophosphate (0.066 g, 0.17 mmol) and 3-(4-fluorophenyl)-1-isopropyl-2,4-dioxo-1,2,3,4-tetrahydropyrimidine-5-carboxylic acid (0.062 g, 0.21 mmol) in N,N-dimethylformamide (2 mL, 20 mmol) was added N,N-diisopropylethylamine (0.055 mL, 0.32 mmol). After 15 min stirring at rt 4-(4-aminophenoxy)-7-methoxyquinoline-6-carbonitrile (0.05 g, 0.2 mmol) was added. The reaction was stirred at rt overnight, diluted with EtOAc, washed with 1N Na$_2$CO$_3$, water and brine solutions then dried over MgSO$_4$. The product was recrystallized from MeOH then dried overnight at 65° C. under vacuum to give a tan solid. mp=202-3° C.; LCMS m/z=566 (M+1); $^1$H NMR (DMSO) δ: 10.96 (s, 1H), 8.77 (s, 1H), 8.74 (d, 1H, J=5 Hz), 8.67 (s, 1H), 7.83 (d, 2H, J=7.3 Hz), 7.61 (s, 1H), 7.42-7.45 (m, 2H), 7.30-7.38 (m, 5H), 6.56 (d, 1H, J=5.5 Hz), 4.78 (q, 1H, J=7 Hz), 4.07 (s, 3H), 1.43 (d, 6H, J=7 Hz).

Example 57

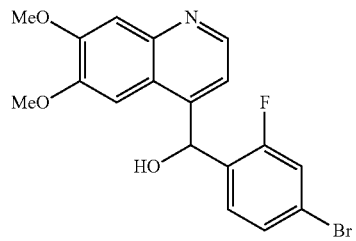 [SMILES: COc1cc2nccc(C(O)c3ccc(Br)cc3F)c2cc1OC]

Step a. (4-Bromo-2-fluoro-phenyl)-(6,7-dimethoxy-quinolin-4-yl)-methanol. A solution of 4-bromo-6,7-dimethoxyquinoline (0.5 g, 1.8 mmol) in tetrahydrofuran (6 mL) was cooled at −78° C. n-Butyllithium (0.89 mL, 2.23 mmol, 2.5 M solution in hexane) was added dropwise under an argon atmosphere and further stirred at −78° C. for 1 h. 4-Bromo-2-fluoro-benzaldehyde (0.45, 2.2 mmol) in 3 mL of tetrahydrofuran was added dropwise. The reaction mixture was stirred at −78° C. for 1 h and slowly warmed to 0° C. for 1.5 h. The reaction was quenched with satd. NH$_4$Cl solution and extracted three times with CH$_2$Cl$_2$ and the combined organics were washed with brine, dried (Na$_2$SO$_4$), filtered, and evaporated to yield a crude product. The crude product was purified by silica gel column chromatography to produce (4-bromo-2-fluoro-phenyl)-(6,7-dimethoxy-quinolin-4-yl)-methanol (0.45 g, 62%) as a yellow solid. MS m/z=393 (M+1).

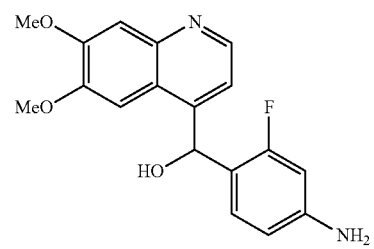 [SMILES: COc1cc2nccc(C(O)c3ccc(N)cc3F)c2cc1OC]

Step b. (4-Amino-2-fluoro-phenyl)-(6,7-dimethoxy-quinolin-4-yl)-methanol. A mixture of 4-bromo-2-fluoro-phenyl)-(6,7-dimethoxy-quinolin-4-yl)-methanol (0.72 g, 1.8 mmol), bis(dibenzylideneacetone)palladium(0) (0.19 g, 0.33 mmol), tri-t-butylphosphine (0.54 mL, 10% solution), lithium hexamethyldisilazide (6.24 mL, 3.46 mmol, 1 M solution in THF) and toluene (5 mL) was charged in a pressure reaction vessel with a screw cap. The mixture was heated at 80° C. for 3 h under an argon atmosphere and quenched with MeOH. The crude product was purified by Gilson prep. HPLC to produce 4-amino-2-fluoro-phenyl)-(6,7-dimethoxy-quinolin-4-yl)-methanol (0.4 g, 66%). MS m/z=329 (M+1).

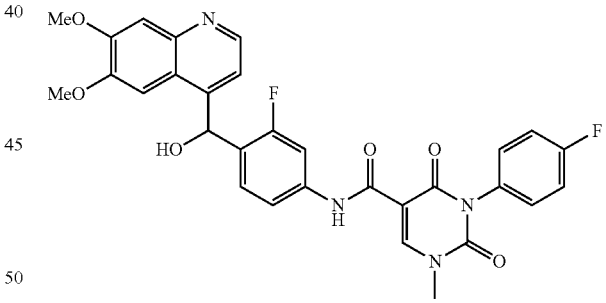

Step c. 3-(4-fluoro-phenyl)-1-methyl-2,4-dioxo-1,2,3,4-tetrahydro-pyrimidine-5-carboxylic acid {4-[(6,7-dimethoxy-quinolin-4-yl)-hydroxy-methyl]-3-fluoro-phenyl}-amide. To a well stirred mixture of 3-(4-fluorophenyl)-1-methyl-2,4-dioxo-1,2,3,4-tetrahydropyrimidine-5-carboxylic acid (0.058 g, 0.252 mmol) and N,N,N',N'-tetramethyl-O-(7-azabenzotriazol-1-yl)-uronium hexafluorophosphate (0.096 g, 0.25 mmol) in N, N-dimethylformamide (2 mL) was added N,N-diisopropylethylamine (0.26 mL, 1.5 mmol). After stirring for 10 min, 4-amino-2-fluoro-phenyl)-(6,7-dimethoxyquinolin-4-yl)-methanol (0.072 g, 0.21 mmol) was added. The reaction mixture was stirred at rt overnight and purified by Gilson prep. HPLC to produce (0.02 g, 17%) as a solid. mp 164-166°; LCMS m/z=546 (M+1). $^1$H NMR (DMSO-d$_6$) δ: 10.92 (s, 1H), 8.82

(s, 1H), 8.68 (d, 1H, J=4.6 Hz), 7.73 (dd, 1H. J=1.9 Hz, J=12.8 Hz), 7.52 (d, 1H, J=4.56 Hz), 7.31-7.39 (m, 6H), 7.25-7.27 (m, 2H), 6.5 (d, 1H, J=4.5 Hz), 6.28 (d, 1H, J=4.6 Hz), 3.88 (s, 3H), 3.81 (s, 3H), 3.50 (s, 3H).

Example 58

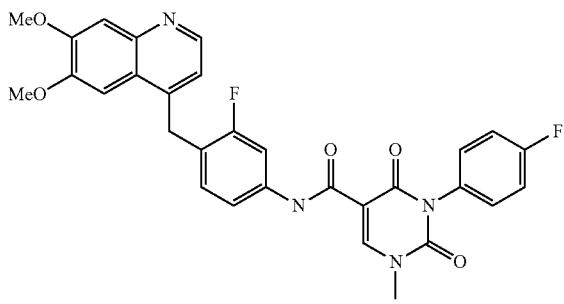 [SMILES: COc1cc2nccc(Cc3ccc(NC(=O)c4cn(C)c(=O)n(-c5ccc(F)cc5)c4=O)cc3F)c2cc1OC]

3-(4-fluoro-phenyl)-1-methyl-2,4-dioxo-1,2,3,4-tetrahydro-pyrimidine-5-carboxylic acid [4-(6,7-dimethoxy-quinolin-4-ylmethyl)-3-fluoro-phenyl]-amide. A mixture of example 57 (0.08 g, 0.13 mmol) and zinc (1.4 g, 21.5 mmol) in formic acid (5 mL) was heated at 60° C. for 5 h. The reaction mixture was diluted with $CH_2Cl_2$ and filtered over a celite and washed with $CH_2Cl_2$. The filtrate was evaporated and purified by Gilson prep. HPLC to give a white solid (33 mg, 42%), mp 293-295° C.; MS m/z=559 (M+H). $^1$H NMR (DMSO-$d_6$) δ: 10.92 (s, 1H), 8.84 (s, 1H), 8.55 (d, 1H, J=4.5 Hz), 7.78 (dd, 1H, J=1.80 Hz, J=12.4 Hz), 7.32-7.39 (m, 6H), 7.21-7.29 (m, 2H), 7.01 (d, 1H, J=4.48 Hz), 4.38 (s, 2H), 3.91 (s, 3H), 3.90 (s, 3H), 3.51 (s, 3H).

Example 59

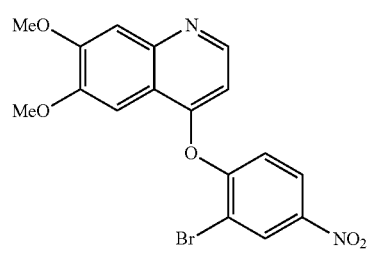

Step a. 4-(2-Bromo-4-nitro-phenoxy)-6,7-dimethoxy-quinoline. A mixture of 4-chloro-6,7-dimethoxyquinoline (0.82 g, 3.67 mmol), 2-bromo-4-nitrophenol (0.80 g, 3.67 mmol) and 4-dimethylaminopyridine (0.067 g, 0.549 mmol) in chlorobenzene (8 mL) was heated at 140° C. for 2 days under an argon atmosphere. The crude product was purified by silica gel column chromatography followed by crystallization from a mixture of $CH_2Cl_2$, MeOH, ether, and hexane to produce 4-(2-bromo-4-nitrophenoxy)-6,7-dimethoxyquinoline (0.74 g, 50%), LCMS m/z=406 (M+1).

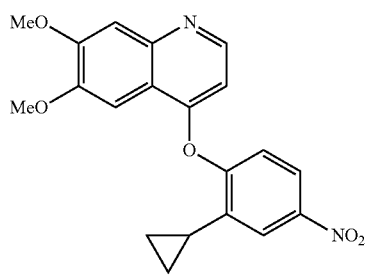 [SMILES: COc1cc2nccc(Oc3ccc([N+](=O)[O-])cc3C3CC3)c2cc1OC]

Step b. 4-(2-Cyclopropyl-4-nitro-phenoxy)-6,7-dimethoxy-quinoline. A mixture of 4-(2-bromo-4-nitro-phenoxy)-6,7-dimethoxy-quinoline (0.74 g, 1.8 mmol), potassium cyclopropyltrifluoroborate (0.49 g, 3.39 mmol), palladium acetate (0.07 g, 0.31 mmol), butyl-ditricyclo [3.3.1.1(3,7)]decan-1-yl-phosphane (0.12 g, 0.34 mmol), and cesium carbonate (3.07 g, 9.44 mmol) in a mixture of toluene (24 mL) and water (3.4 mL) was heated at 85° C. for overnight. The reaction mixture was diluted with $CH_2Cl_2$ and filtered over a pad of celite, washed with $CH_2Cl_2$. The filtrate was evaporated and purified by Gilson prep. HPLC to produce 4-(2-cyclopropyl-4-nitro-phenoxy)-6,7-dimethoxyquinoline (0.44 g, 65%). LCMS m/z=367 (M+1).

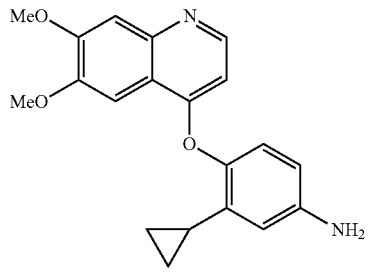 [SMILES: COc1cc2nccc(Oc3ccc(N)cc3C3CC3)c2cc1OC]

Step c. 3-Cyclopropyl-4-(6,7-dimethoxy-quinolin-4-yloxy)-phenylamine. A mixture of 4-(2-cyclopropyl-4-nitrophenoxy)-6,7-dimethoxy-quinoline (0.30 g, 0.82 mmol) and tin(II) chloride dihydrate (0.92 g, 4.09 mmol) in a mixture of ethanol (10 mL) and ethyl acetate (3 mL) was refluxed for 2 h. The reaction mixture was evaporated and partitioned between $CH_2Cl_2$ and satd. $NaHCO_3$ solution. The heterogeneous mixture was filtered over celite, washed with $CH_2Cl_2$ and the filtrate was separated into two phases. The aqueous phase was extracted two times with $CH_2Cl_2$ and the combined organics was washed with brine, dried ($Na_2SO_4$), filtered, and evaporated to yield a crude product. The crude product was purified by silica gel column chromatography to produce 3-cyclopropyl-4-(6,7-dimethoxy-quinolin-4-yloxy)-phenylamine (0.22 g, 80%), MS m/z=337 (M+1). $^1$H NMR (CDCl$_3$) δ: 8.54 (d, 1H, J=5.2 Hz), 8.1 (dd, 1H, J=2.73 Hz, J=8.9 Hz), 7.90 (d, 1H, J=2.72 Hz), 7.52 (s, 1H), 7.46 (s, 1H), 7.16 (d, 1H, J=8.85 Hz), 6.43 (d, 1H, J=5.2 Hz), 4.06 (s, 3H), 4.04 (s, 3H), 2.04-2.14 (m, 1H), 1.59 (brs, 2H), 0.95-1.04 (m, 2H), 0.78-0.86 (m, 2H).

Step d.

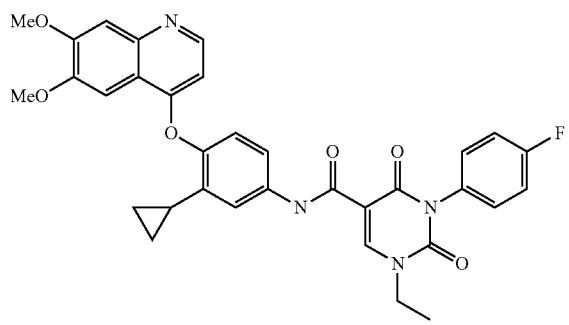 [SMILES: CCn1cc(C(=O)Nc2ccc(Oc3ccnc4cc(OC)c(OC)cc34)c(C3CC3)c2)c(=O)n(-c2ccc(F)cc2)c1=O]

1-Ethyl-3-(4-fluoro-phenyl)-2,4-dioxo-1,2,3,4-tetrahydropyrimidine-5-carboxylic acid [3-cyclopropyl-4-(6,7-dimethoxy-quinolin-4-yloxy)-phenyl]-amide was synthesized from 3-cyclopropyl-4-(6,7-dimethoxyquinolin-4-yloxy)phenylamine (0.06 g, 0.20 mmol) and 3-(4-fluorophenyl)-1-ethyl-2,4-dioxo-1,2,3,4-tetrahydropyrimidine-5-carboxylic acid (0.06 g, 0.21 mmol) in an analogous manner to Example 1. mp 183-185° C.; LCMS m/z=597 (M+1). $^1$H NMR (DMSO-d$_6$) δ: 10.84 (s, 1H), 8.86 (s, 1H), 8.44 (d, 1H, J=5.2 Hz), 7.71 (d d, 1H, J=2.53 Hz, J=8.73 Hz), 7.58 (s 1H), 7.31-7.46 (m, 5H), 7.27 (d, 1H, J=2.53 Hz), 7.17 (d, 1H, J=8.73 Hz), 6.33 (d, 1H, J=5.2 Hz), 4.00 (q, 2H, J=7.04 Hz), 3.94 (s, 6H), 1.77-1.87 (m, 1H), 1.29 (t, 3H, J=7.04 Hz), 0.72-0.82 (m, 2H), 0.62-0.71 (m, 2H).

Example 60

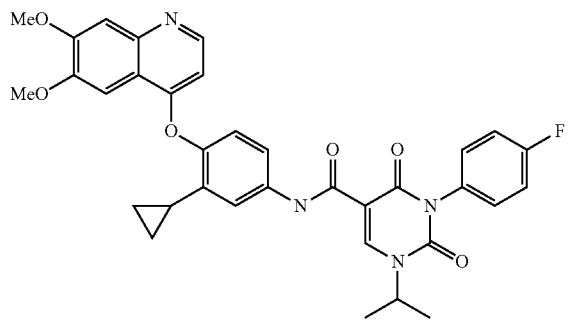 [SMILES: COc1cc2nccc(Oc3ccc(NC(=O)c4cn(C(C)C)c(=O)n(-c5ccc(F)cc5)c4=O)cc3C3CC3)c2cc1OC]

3-(4-Fluoro-phenyl)-1-isopropyl-2,4-dioxo-1,2,3,4-tetrahydro-pyrimidine-5-carboxylic acid [3-cyclopropyl-4-(6,7-dimethoxy-quinolin-4-yloxy)-phenyl]-amide. This compound was synthesized from 3-cyclopropyl-4-(6,7-dimethoxyquinolin-4-yloxy)phenylamine (0.06 g, 0.20 mmol) and 3-(4-fluorophenyl)-1-isopropyl-2,4-dioxo-1,2,3,4-tetrahydropyrimidine-5-carboxylic acid (0.063 g, 0.21 mmol) in an analogous manner to Example 59. mp 172-174° C.; LCMS m/z=611 (M+1). $^1$H NMR (DMSO-d$_6$) δ: 10.86 (s, 1H), 8.67 (s, 1H), 8.44 (d, 1H, J=5.24 Hz), 7.65 (dd, 1H, J=2.52 Hz, J=7.65 Hz), 7.58 (s, 1H), 7.31-7.48 (m, 6H), 7.16 (d, 1H, J=8.73 Hz), 6.34 (d, 1H, J=5.20 Hz), 4.70-4.85 (m, 1H), 3.94 (s, 6H), 1.78-1.88 (m, 1H), 0.73-0.82 (m, 2H), 0.62-0.69 (m, 2H).

The following examples were synthesized using the procedures for Example 1.

Example 61

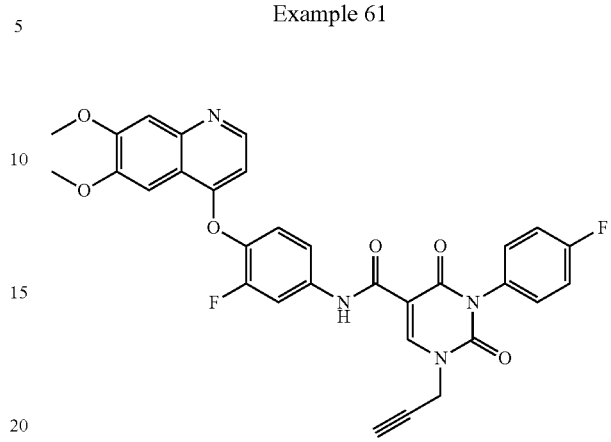

3-(4-Fluoro-phenyl)-2,4-dioxo-1-prop-2-ynyl-1,2,3,4-tetrahydro-pyrimidine-5-carboxylic acid [4-(6,7-dimethoxy-quinolin-4-yloxy)-3-fluoro-phenyl]-amide. mp 155-157° C.; LCMS m/z=585 (M+1); $^1$H NMR (DMSO) δ: 10.97 (s, 1H), 8.95 (s, 1H), 8.48 (d, 1H, J=5.5 Hz), 8.01 (dd, 1H, J=2.5 Hz, J=13 Hz), 7.56 (bd, 1H, J=9.0 Hz), 7.53 (s, 1H), 7.47-7.42 (m, 3H), 7.41 (s, 1H), 7.40-7.32 (m, 2H), 6.48 (d, 1H, J=5.0 Hz), 4.85 (d, 2H, J=2.5 Hz), 3.95 (s, 3H), 3.94 (s, 3H), 2.69 (s, 1H).

Example 62

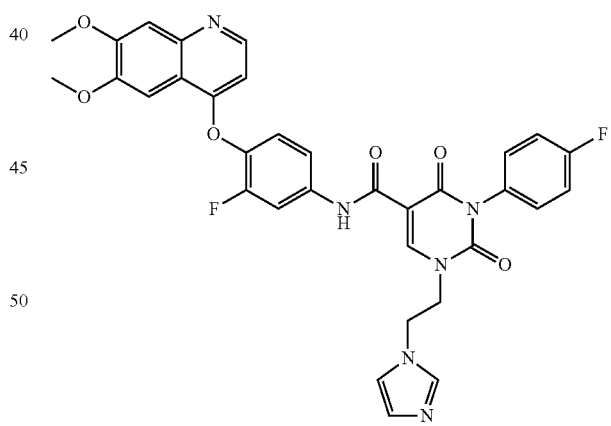

3-(4-Fluoro-phenyl)-1-(2-imidazol-1-yl-ethyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 218-221° C.; LCMS m/z=641 (M+1); $^1$H NMR (DMSO) δ: 11.05 (s, 1H), 9.20 (s, 1H), 8.77 (s, 1H), 8.75 (m, 1H), 8.06 (dd, 1H, J=2.5 Hz, J=13 Hz), 7.85 (t, 1H, J=1.7 Hz), 7.71 (t, 1H, J=1.7 Hz), 7.68 (s, 1H), 7.62 (dd, 1H, J=1.7 Hz, J=9.0 Hz), 7.57 (s, 1H), 7.55 (t, 1H, J=9.0 Hz), 7.39 (s, 2H), 7.27 (s, 2H), 6.84 (m, 1H), 4.59 (t, 2H, J=6.5 Hz), 4.45 (t, 2H, J=6.5 Hz), 4.02 (s, 3H), 4.01 (s, 3H).

(m, 11H), 6.48 (d, 1H, J=5.6 Hz), 4.20 (t, 2H, J=6.8 Hz), 3.95 (s, 3H), 3.94 (s, 3H), 3.02 (t, 2H, J=6.9 Hz).

Example 63

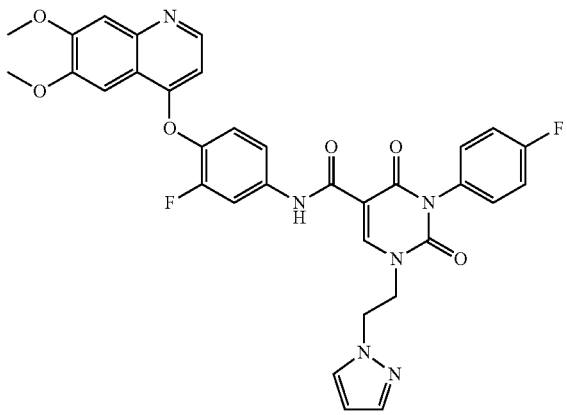 [SMILES: COc1cc2nccc(Oc3ccc(NC(=O)c4cn(CCn5cccn5)c(=O)n(-c5ccc(F)cc5)c4=O)cc3F)c2cc1OC]

3-(4-Fluoro-phenyl)-2,4-dioxo-1-(2-pyrazol-1-yl-ethyl)-1,2,3,4-tetrahydro-pyrimidine-5-carboxylic acid [4-(6,7-dimethoxy-quinolin-4-yloxy)-3-fluoro-phenyl]-amide. mp 149-151° C.; LCMS m/z=641 (M+1); $^1$H NMR (DMSO) δ: 10.92 (s, 1H), 8.49 (d, 1H, J=6.6 Hz), 8.36 (s, 1H), 7.97 (dd, 1H, J=2.5 Hz, J=12.5 Hz), 7.81 (d, 1H, J=2.0 Hz), 7.54-7.50 (m, 3H), 7.46-7.34 (m, 6H), 6.48 (d, 1H, J=4.8 Hz), 6.27 (t, 1H, J=2.0 Hz), 4.48 (t, 2H, J=5.7 Hz), 4.38 (t, 2H, J=5.4 Hz), 3.95 (s, 3H), 3.94 (s, 3H).

Example 65

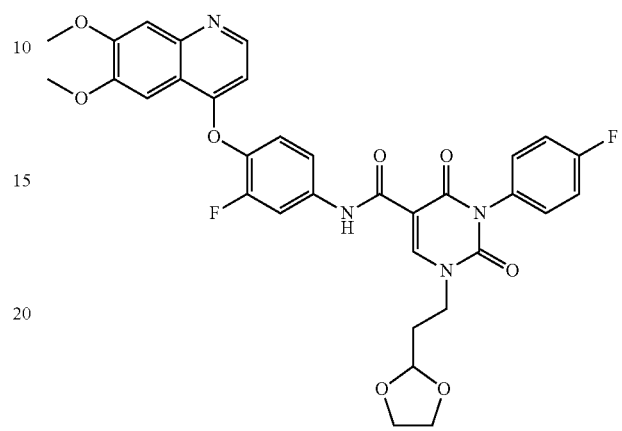

1-[2-(1,3-Dioxolan-2-yl-ethyl)]-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 138-140° C.; LCMS m/z=647 (M+1); $^1$H NMR (DMSO) δ: 11.01 (s, 1H), 8.82 (s, 1H), 8.48 (d, 1H, J=5.4 Hz), 8.00 (dd, 1H, J=2.3 Hz, J=12.5 Hz), 7.55 (bd, 1H, J=9.7 Hz), 7.54 (s, 1H), 7.49-7.34 (m, 6H), 6.47 (d, 1H, J=5.3 Hz), 4.93 (t, 1H, J=4.2 Hz), 4.10 (t, 2H, J=6.9 Hz), 3.95 (s, 3H), 3.94 (s, 3H), 3.94-3.90 (m, 2H), 3.81-3.77 (m, 2H), 2.05 (q, 2H, J=4.5 Hz).

Example 64

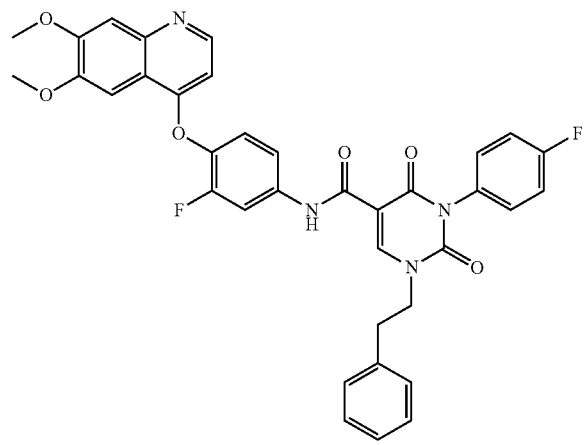 [SMILES: COc1cc2nccc(Oc3ccc(NC(=O)c4cn(CCc5ccccc5)c(=O)n(-c5ccc(F)cc5)c4=O)cc3F)c2cc1OC]

3-(4-Fluoro-phenyl)-2,4-dioxo-1-phenethyl-1,2,3,4-tetrahydro-pyrimidine-5-carboxylic acid [4-(6,7-dimethoxy-quinolin-4-yloxy)-3-fluoro-phenyl]-amide. mp 168-170° C.; LCMS m/z=651 (M+1); $^1$H NMR (DMSO) δ: 11.00 (s, 1H), 8.79 (s, 1H), 8.48 (d, 1H, J=4.8 Hz), 7.99 (dd, 1H, J=2.5 Hz, J=12.5 Hz), 7.56 (bd, 1H, J=9.0 Hz), 7.52 (s, 1H), 7.47-7.23

Example 66

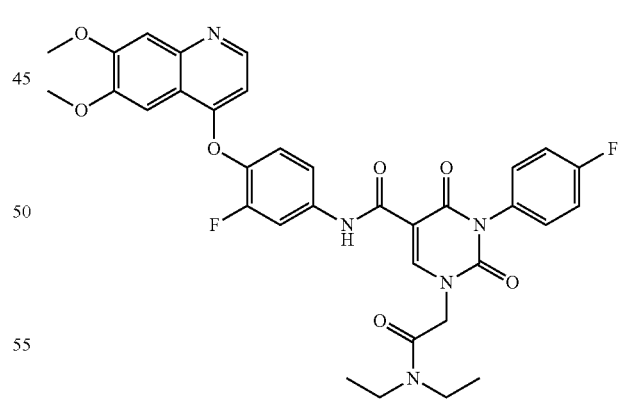

1-Diethylcarbamoylmethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 147-149° C.; LCMS m/z=660 (M+1); $^1$H NMR (DMSO) δ: 10.98 (s, 1H), 8.86 (s, 1H), 8.48 (d, 1H, J=4.5 Hz), 8.00 (dd, 1H, J=3.1 Hz, J=12.5 Hz), 7.56 (bd, 1H, J=9.3 Hz), 7.53 (s, 1H), 7.47-7.34 (m, 6H), 6.48 (d, 1H, J=4.6 Hz), 4.96 (s, 2H), 3.95 (s, 3H), 3.94 (s, 3H), 3.39-3.28 (m, 4H), 1.18 (t, 3H, J=7.0 Hz), 1.05 (t, 3H, J=7.1 Hz).

Example 67

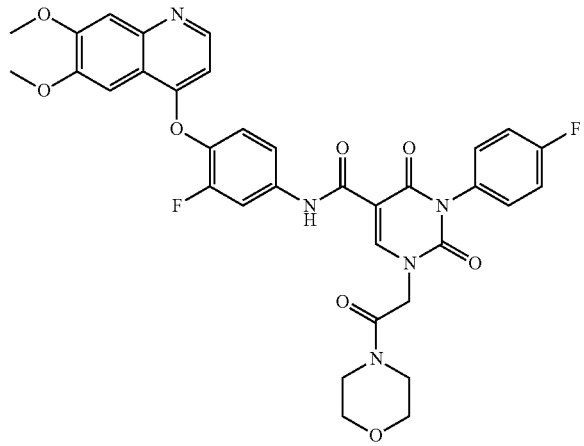 [SMILES: COc1cc2nccc(Oc3ccc(NC(=O)c4cn(CC(=O)N5CCOCC5)c(=O)n(-c5ccc(F)cc5)c4=O)cc3F)c2cc1OC]

3-(4-fluoro-phenyl)-1-(2-morpholin-4-yl-2-oxo-ethyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 159-161° C.; LCMS m/z=674 (M+1); $^1$H NMR (DMSO) δ: 10.97 (s, 1H), 8.82 (s, 1H), 8.49 (d, 1H, J=5.3 Hz), 8.00 (dd, 1H, J=2.6 Hz, J=12.6 Hz), 7.56 (bd, 1H, J=9.5 Hz), 7.53 (s, 1H), 7.48-7.34 (m, 6H), 6.49 (d, 1H, J=5.0 Hz), 5.00 (s, 2H), 3.95 (s, 3H), 3.94 (s, 3H), 3.65 (t, 2H, J=4.4 Hz), 3.60 (t, 2H, J=4.4 Hz), 3.52-3.46 (m, 4H).

Example 68

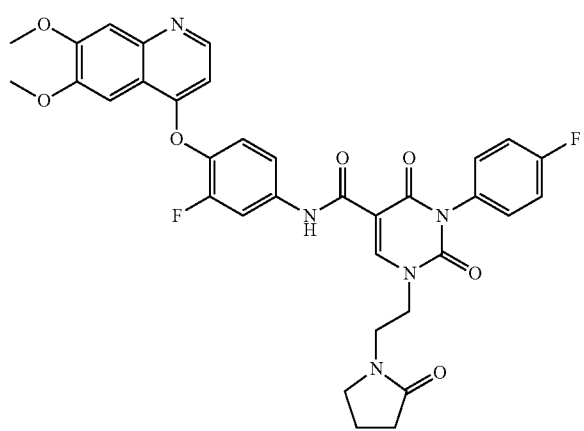 [SMILES: COc1cc2nccc(Oc3ccc(NC(=O)c4cn(CCN5CCCC5=O)c(=O)n(-c5ccc(F)cc5)c4=O)cc3F)c2cc1OC]

3-(4-Fluoro-phenyl)-2,4-dioxo-1-[2-(2-oxo-pyrrolidin-1-yl)-ethyl]-1,2,3,4-tetrahydro-pyrimidine-5-carboxylic acid [4-(6,7-dimethoxy-quinolin-4-yloxy)-3-fluoro-phenyl]-amide. mp 157-159° C.; LCMS m/z=658 (M+1); $^1$H NMR (DMSO) δ: 10.97 (s, 1H), 8.80 (s, 1H), 8.48 (d, 1H, J=5.3 Hz), 8.00 (dd, 1H, J=2.6 Hz, J=12.6 Hz), 7.55 (bd, 1H, J=9.5 Hz), 7.53 (s, 1H), 7.47-7.36 (m, 6H), 6.48 (d, 1H, J=5.0 Hz), 4.16

(t, 2H, J=4.6 Hz), 3.95 (s, 3H), 3.94 (s, 3H), 3.54-3.49 (m, 4H), 2.12 (t, 2H, J=7.8 Hz), 1.93 (p, 2H, J=8.2 Hz).

Example 69

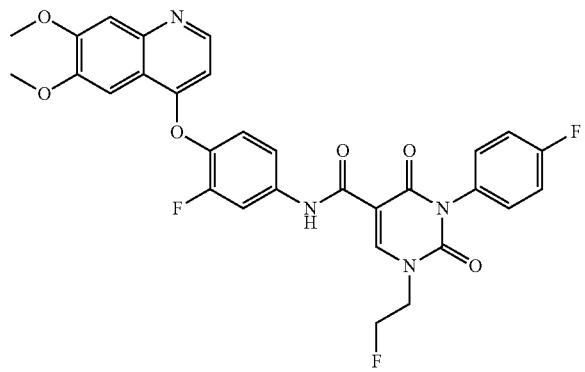 [SMILES: COc1cc2nccc(Oc3ccc(NC(=O)c4cn(CCF)c(=O)n(-c5ccc(F)cc5)c4=O)cc3F)c2cc1OC]

1-(2-Fluoro-ethyl)-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 138-140° C.; LCMS m/z=593 (M+1); $^1$H NMR (DMSO) δ: 11.00 (s, 1H), 8.82 (s, 1H), 8.48 (d, 1H, J=5.2 Hz), 8.01 (dd, 1H, J=2.4 Hz, J=13 Hz), 7.55 (bd, 1H, J=8.9 Hz), 7.52 (s, 1H), 7.48-7.33 (m, 6H), 6.48 (d, 1H, J=5.1 Hz), 4.73 (dt, 2H, J=4.2 Hz, J=42 Hz), 4.36 (dt, 2H, J=4.2 Hz, J=28 Hz), 3.95 (s, 3H), 3.94 (s, 3H).

Example 70

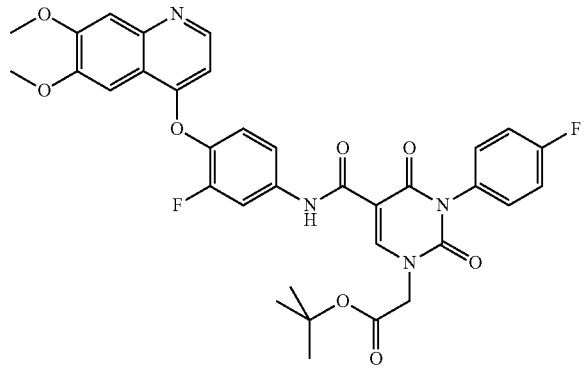 [SMILES: COc1cc2nccc(Oc3ccc(NC(=O)c4cn(CC(=O)OC(C)(C)C)c(=O)n(-c5ccc(F)cc5)c4=O)cc3F)c2cc1OC]

[5-[4-(6,7-Dimethoxy-quinolin-4-yloxy)-3-fluoro-phenylcarbamoyl]-3-(4-fluoro-phenyl)-2,4-dioxo-3,4-dihydro-2H-pyrimidin-1-yl]-acetic acid tert-butyl ester. mp 138-143° C.; LCMS m/z=661 (M+1); $^1$H NMR (DMSO) δ: 10.94 (s, 1H), 8.94 (s, 1H), 8.48 (d, 1H, J=5.2 Hz), 8.00 (dd, 1H, J=2.5 Hz, J=12.8 Hz), 7.56 (bd, 1H, J=8.9 Hz), 7.52 (s, 1H), 7.48-

7.35 (m, 6H), 6.48 (d, 1H, J=4.9 Hz), 4.76 (s, 2H), 3.95 (s, 3H), 3.94 (s, 3H), 1.44 (s, 9H).

Example 71

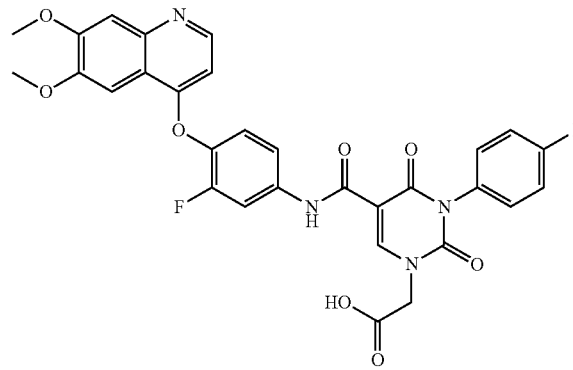

[5-[4-(6,7-Dimethoxyquinolin-4-yloxy)-3-fluorophenyl-carbamoyl]-3-(4-fluorophenyl)-2,4-dioxo-3,4-dihydro-2H-pyrimidin-1-yl]-acetic acid. Example 70 was hydrolyzed using trifluoroacetic acid in dichloromethane at room temperature for 18 to give Example 71 mp 225° C. dec.; LCMS m/z=605 (M+1); $^1$H NMR (DMSO) δ: 13.42 (bs, 1H), 11.00 (s, 1H), 8.95 (s, 1H), 8.72 (d, 1H, J=6.2 Hz), 8.07 (dd, 1H, J=2.5 Hz, J=13 Hz), 7.69 (s, 1H), 7.62 (bd, 1H, J=8.6 Hz), 7.54 (t, 1H, J=9.1 Hz), 7.50 (s, 1H), 7.44-7.34 (m, 4H), 6.84 (bs, 1H), 4.79 (s, 2H), 4.01 (s, 3H), 4.00 (s, 3H).

Example 72

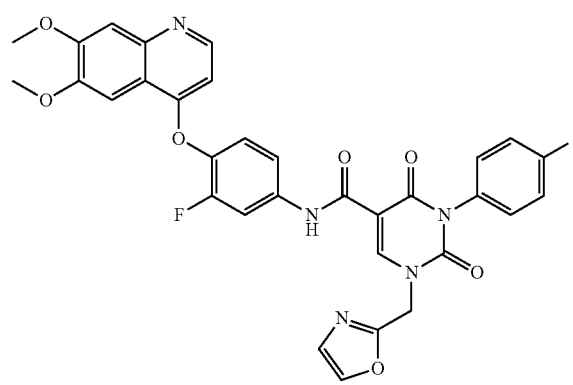

3-(4-Fluoro-phenyl)-1-oxazol-2-ylmethyl-2,4-dioxo-1,2,3,4-tetrahydro-pyrimidine-5-carboxylic acid [4-(6,7-dimethoxy-quinolin-4-yloxy)-3-fluoro-phenyl]-amide. mp 148-150° C.; LCMS m/z=628 (M+1); $^1$H NMR (DMSO) δ: 10.85 (s, 1H), 9.05 (s, 1H), 8.48 (d, 1H, J=5.2 Hz), 8.17 (s, 1H), 8.01 (dd, 1H, J=2.3 Hz, J=13 Hz), 7.56 (bd, 1H, J=8.5 Hz), 7.52 (s, 1H), 7.48-7.33 (m, 6H), 7.25 (s, 1H), 6.48 (d, 1H, J=5.0 Hz), 5.41 (s, 2H), 3.95 (s, 3H), 3.94 (s, 3H).

Example 73

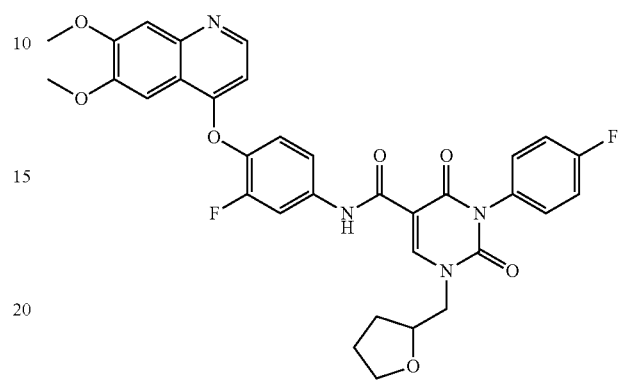

3-(4-Fluoro-phenyl)-2,4-dioxo-1-(tetrahydro-furan-2-yl-methyl)-1,2,3,4-tetrahydro-pyrimidine-5-carboxylic acid [4-(6,7-dimethoxy-quinolin-4-yloxy)-3-fluoro-phenyl]-amide. mp 127-130° C.; LCMS m/z=631 (M+1); $^1$H NMR (DMSO) δ: 11.01 (s, 1H), 8.77 (s, 1H), 8.48 (d, 1H, J=5.2 Hz), 8.01 (dd, 1H, J=2.3 Hz, J=13 Hz), 7.54 (bd, 1H, J=9.5 Hz), 7.52 (s, 1H), 7.47-7.33 (m, 6H), 6.48 (d, 1H, J=5.3 Hz), 4.17-4.09 (m, 2H), 3.99-3.93 (m, 1H), 3.95 (s, 3H), 3.94 (s, 3H), 3.88-3.81 (m, 1H), 3.74-3.68 (m, 1H), 2.04-1.77 (m, 3H), 1.65-1.55 (m, 1H).

Example 74

3-(4-Fluoro-phenyl)-2,4-dioxo-1-(tetrahydro-pyran-4-yl-methyl)-1,2,3,4-tetrahydro-pyrimidine-5-carboxylic acid [4-(6,7-dimethoxy-quinolin-4-yloxy)-3-fluoro-phenyl]-amide. mp 185-187° C.; LCMS m/z=645 (M+1); $^1$H NMR (DMSO) δ: 11.05 (s, 1H), 8.83 (s, 1H), 8.48 (d, 1H, J=5.4 Hz), 8.01 (dd, 1H, J=2.4 Hz, J=13 Hz), 7.54 (bd, 1H, J=8.6 Hz), 7.52 (s, 1H), 7.46-7.33 (m, 6H), 6.47 (bd, 1H, J=5.4 Hz), 3.95 (s, 3H), 3.94

(s, 3H), 3.92-3.85 (m, 4H), 3.26 (bd, 2H, J=11.1 Hz), 1.60 (bd, 2H, J=12.2 Hz), 1.32-1.23 (m, 3H).

Example 75

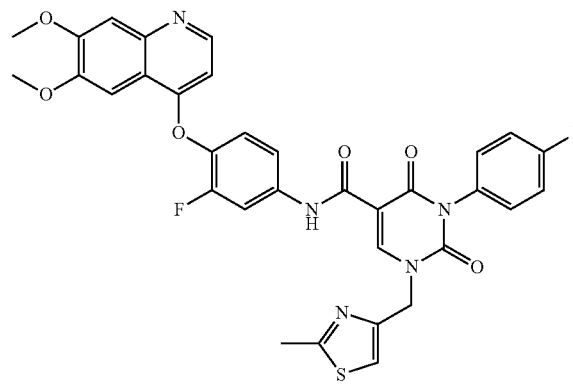

3-(4-Fluoro-phenyl)-1-(2-methyl-thiazol-4-ylmethyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 196-198° C.; LCMS m/z=658 (M+1); $^1$H NMR (DMSO) δ: 11.01 (s, 1H), 8.95 (s, 1H), 8.48 (d, 1H, J=5.3 Hz), 8.01 (dd, 1H, J=2.3 Hz, J=12.5 Hz), 7.55 (bd, 1H, J=9 Hz), 7.54 (s, 1H), 7.52 (s, 1H), 7.47-7.33 (m, 6H), 6.48 (bd, 1H, J=5.9 Hz), 5.24 (s, 1H), 3.95 (s, 3H), 3.94 (s, 3H), 2.66 (s, 3H).

Example 76

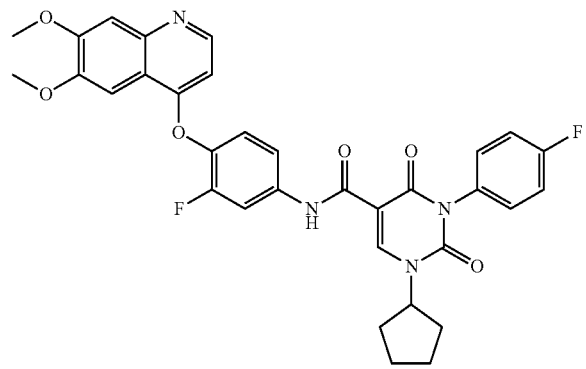 [SMILES: COc1cc2nccc(Oc3ccc(NC(=O)c4cn(C5CCCC5)c(=O)n(-c5ccc(F)cc5)c4=O)cc3F)c2cc1OC]

1-Cyclopentyl-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 222-224° C.; LCMS m/z=615 (M+1); $^1$H NMR (DMSO) δ: 11.03 (s, 1H), 8.63 (s, 1H), 8.48 (d, 1H, J=5.4 Hz), 8.01 (dd, 1H, J=2.5 Hz, J=13 Hz), 7.54 (bd, 1H, J=9 Hz), 7.52 (s, 1H), 7.46-7.33 (m, 6H), 6.48 (bd, 1H, J=5.4 Hz), 4.90-4.81 (m, 1H), 3.95 (s, 3H), 3.94 (s, 3H), 2.12-2.04 (m, 2H), 1.93-1.78 (m, 4H), 1.69-1.63 (m, 2H).

Example 77

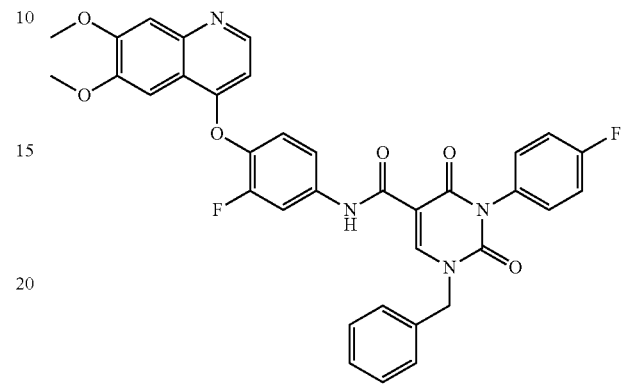

1-Benzyl-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 242-244° C.; LCMS m/z=637 (M+1); $^1$H NMR (DMSO) δ: 11.01 (s, 1H), 8.97 (s, 1H), 8.48 (d, 1H, J=5.8 Hz), 8.00 (dd, 1H, J=2.5 Hz, J=13 Hz), 7.54 (bd, 1H, J=9 Hz), 7.52 (s, 1H), 7.47-7.33 (m, 11H), 6.47 (bd, 1H, J=5.4 Hz), 5.22 (s, 2H), 3.95 (s, 3H), 3.94 (s, 3H).

Example 78

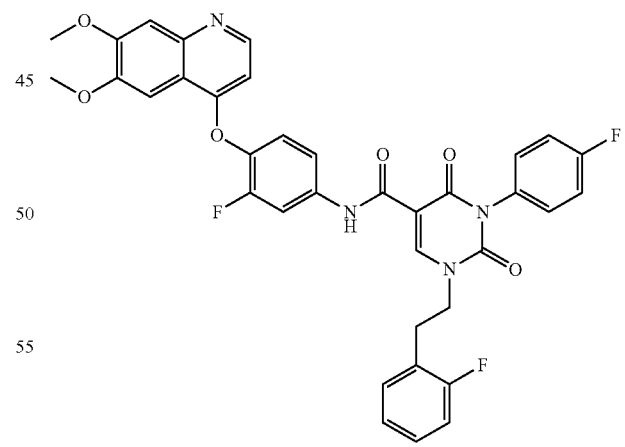

3-(4-Fluoro-phenyl)-1-[2-(2-fluoro-phenyl)-ethyl]-2,4-dioxo-1,2,3,4-tetrahydro-pyrimidine-5-carboxylic acid [4-(6,7-dimethoxy-quinolin-4-yloxy)-3-fluoro-phenyl]-amide. mp 178-180° C.; LCMS m/z=669 (M+1); $^1$H NMR (DMSO) δ: 10.98 (s, 1H), 8.72 (s, 1H), 8.48 (d, 1H, J=5.4 Hz), 7.98 (dd, 1H, J=2.4 Hz, J=13 Hz), 7.53 (bd, 1H, J=9 Hz), 7.52 (s, 1H), 7.46-7.28 (m, 8H), 7.22-7.16 (m, 2H), 6.47 (bd, 1H, J=5.3 Hz), 4.23 (t, 2H, J=7.4 Hz), 3.95 (s, 3H), 3.94 (s, 3H), 3.07 (t, 2H, J=7.3 Hz).

Example 79

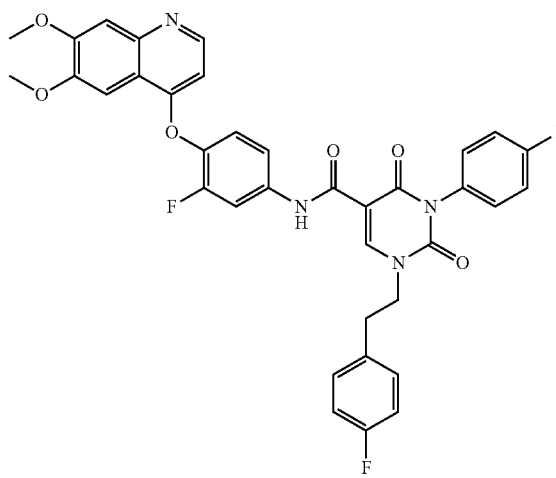

3-(4-Fluoro-phenyl)-1-[2-(4-fluoro-phenyl)-ethyl]-2,4-dioxo-1,2,3,4-tetrahydro-pyrimidine-5-carboxylic acid [4-(6,7-dimethoxy-quinolin-4-yloxy)-3-fluoro-phenyl]-amide. mp 203-205° C.; LCMS m/z=669 (M+1); $^1$H NMR (DMSO): 11.00 (s, 1H), 8.79 (s, 1H), 8.48 (d, 1H, J=5.4 Hz), 7.99 (dd, 1H, J=2.4 Hz, J=13 Hz), 7.53 (bd, 1H, J=9 Hz), 7.52 (s, 1H), 7.47-7.33 (m, 8H), 7.20-7.14 (m, 2H), 6.47 (bd, 1H, J=5.3 Hz), 4.18 (t, 2H, J=7.4 Hz), 3.95 (s, 3H), 3.94 (s, 3H), 3.01 (t, 2H, J=7.3 Hz).

Example 80

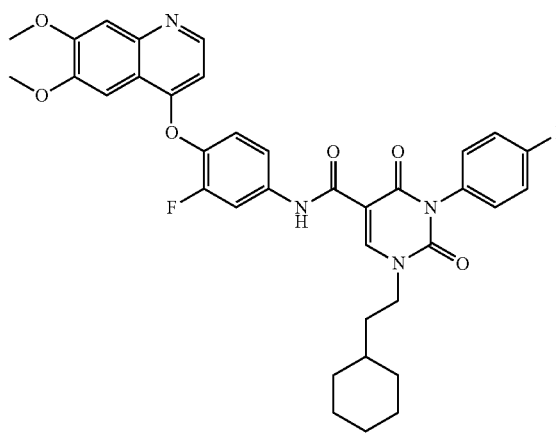

1-(2-Cyclohexyl-ethyl)-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 186-190° C.; LCMS m/z=657 (M+1); $^1$H NMR (DMSO) δ: 11.04 (s, 1H), 8.86 (s, 1H), 8.48 (d, 1H, J=5.2 Hz), 8.01 (dd, 1H, J=2.3 Hz, J=13 Hz), 7.54 (bd, 1H, J=9.5 Hz), 7.52 (s, 1H), 7.46-7.27 (m, 6H), 6.48 (d, 1H, J=5.3 Hz), 4.00 (t, 2H, J=7.2 Hz), 3.95 (s, 3H), 3.94 (s, 3H), 1.75-1.57 (m, 8H), 1.23-1.15 (m, 3H), 0.99-0.90 (m, 2H).

Example 81

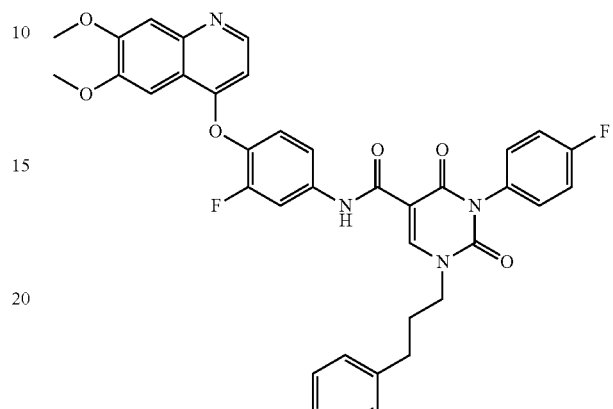

3-(4-Fluoro-phenyl)-2,4-dioxo-1-(3-phenyl-propyl)-1,2,3,4-tetrahydro-pyrimidine-5-carboxylic acid [4-(6,7-dimethoxy-quinolin-4-yloxy)-3-fluoro-phenyl]-amide. mp 128-131° C.; LCMS m/z=665 (M+1); $^1$H NMR (DMSO) δ: 11.02 (s, 1H), 8.84 (s, 1H), 8.48 (d, 1H, J=5.4 Hz), 8.01 (dd, 1H, J=2.5 Hz, J=10 Hz), 7.54 (bd, 1H, J=11 Hz), 7.52 (s, 1H), 7.46-7.16 (m, 11H), 6.48 (d, 1H, J=4.9 Hz), 4.03 (t, 2H, J=7.2 Hz), 3.95 (s, 3H), 3.94 (s, 3H), 2.68 (dd, 2H, J=7.2 Hz, J=16 Hz), 2.03 (t, 2H, J=7.2 Hz).

Example 82

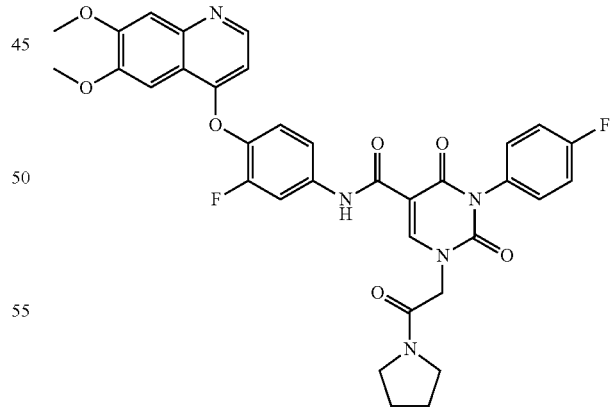

3-(4-Fluoro-phenyl)-2,4-dioxo-1-(2-oxo-2-pyrrolidin-1-yl-ethyl)-1,2,3,4-tetrahydro-pyrimidine-5-carboxylic acid [4-(6,7-dimethoxy-quinolin-4-yloxy)-3-fluoro-phenyl]-amide. mp 189-192° C.; LCMS m/z=658 (M+1); $^1$H NMR (DMSO) δ: 10.97 (s, 1H), 8.80 (s, 1H), 8.48 (d, 1H, J=5.3 Hz), 8.00 (dd, 1H, J=2.4 Hz, J=12 Hz), 7.56 (bd, 1H, J=8.5 Hz), 7.53 (s, 1H), 7.47-7.35 (m, 6H), 6.48 (d, 1H, J=5.2 Hz), 4.88

(s, 2H), 3.95 (s, 3H), 3.94 (s, 3H), 3.48 (t, 2H, J=6.6 Hz), 3.35 (t, 2H, J=6.9 Hz), 1.93 (p, 2H, J=6.7 Hz), 1.80 (p, 2H, J=6.9 Hz).

Example 83

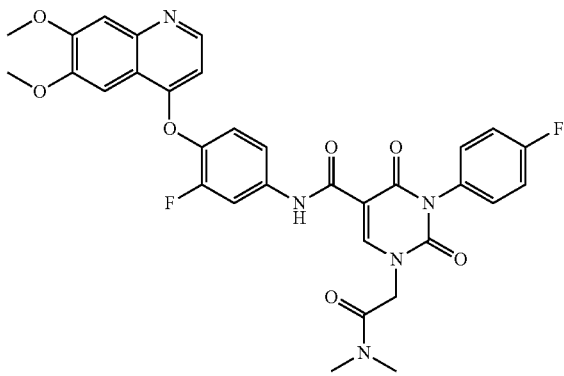 [SMILES: COc1cc2nccc(Oc3ccc(NC(=O)c4cn(CC(=O)N(C)C)c(=O)n(-c5ccc(F)cc5)c4=O)cc3F)c2cc1OC]

1-Dimethylcarbamoylmethyl-3-(4-fluorophenyl)-2,4-dioxo-1,2,3,4-tetrahydro-pyrimidine-5-carboxylic acid [4-(6,7-dimethoxy-quinolin-4-yloxy)-3-fluorophenyl]-amide. mp 163-166° C.; LCMS m/z=632 (M+1); $^1$H NMR (DMSO) δ: 10.96 (s, 1H), 8.79 (s, 1H), 8.48 (d, 1H, J=5.0 Hz), 8.00 (dd, 1H, J=2.5 Hz, J=13 Hz), 7.56 (bd, 1H, J=9.4 Hz), 7.53 (s, 1H), 7.47-7.35 (m, 6H), 6.48 (d, 1H, J=5.4 Hz), 4.97 (s, 2H), 3.95 (s, 3H), 3.94 (s, 3H), 3.03 (s, 3H), 2.89 (s, 3H).

Example 84

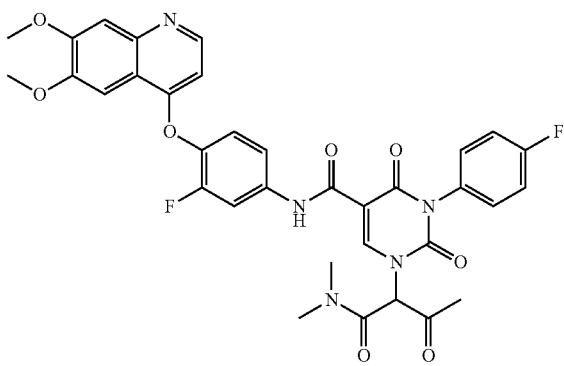 [SMILES: COc1cc2nccc(Oc3ccc(NC(=O)c4cn(C(C(C)=O)C(=O)N(C)C)c(=O)n(-c5ccc(F)cc5)c4=O)cc3F)c2cc1OC]

1-(1-Dimethylcarbamoyl-2-oxo-propyl)-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 137-140° C.; LCMS m/z=674 (M+1); $^1$H NMR (DMSO) δ: 10.93 (s, 1H), 8.56 (s, 1H), 8.48 (d, 1H, J=5.3 Hz), 8.00 (dd, 1H, J=2.3 Hz, J=13 Hz), 7.55 (bd, 1H, J=9 Hz), 7.52 (s, 1H), 7.47-7.33 (m, 6H), 6.72 (s, 1H), 6.48 (d, 1H, J=5.7 Hz), 3.95 (s, 3H), 3.94 (s, 3H), 3.17 (s, 3H), 2.97 (s, 3H), 2.31 (s, 3H).

Example 85

Step a. 4-(6,7-Dimethoxyquinolin-4-yloxy)-2-fluoro-phenylamine. A mixture of 3-fluoro-4-nitrophenol (0.644 g, 4.10 mmol) and 60% sodium hydride (0.215 g, 5.60 mmol) in dimethylformamide (20 mL) was stirred 15 min. 4-Bromo-6,7-dimethoxyquinoline (1.0 g, 3.73 mmol) was added and the mixture stirred at 110° C. for 18 h. After partitioning between water and ethyl acetate, the organics were washed with water and brine. The solvent was removed under vacuum, and the residue was purified by column chromatography (0-5% methanol in dichloromethane).

Step b. The nitro intermediate (0.52 g, 1.51 mmol) from step a in ethanol (20 mL) was hydrogenated on a Parr apparatus at 50 psi with 10% palladium on carbon (0.05 g) for 4 h. The solution was filtered and the product purified by column chromatography (0-5% MeOH in dichloromethane) to give 4-(6,7-dimethoxyquinolin-4-yloxy)-2-fluorophenylamine in 36% yield. $^1$H NMR (DMSO) δ: 8.80 (d, 1H, J=6.5 Hz), 7.72 (s, 1H), 7.70 (s, 1H), 7.26 (dd, 1H, J=2.6 Hz, J=12 Hz), 7.03-6.96 (m, 2H), 6.90 (d, 1H, J=6.5 Hz), 4.69 (bs, 2H), 4.04 (s, 3H), 4.03 (s, 3H).

The following examples were synthesized using 4-(6,7-dimethoxy-quinolin-4-yloxy)-2-fluorophenylamine and the method for Example 1.

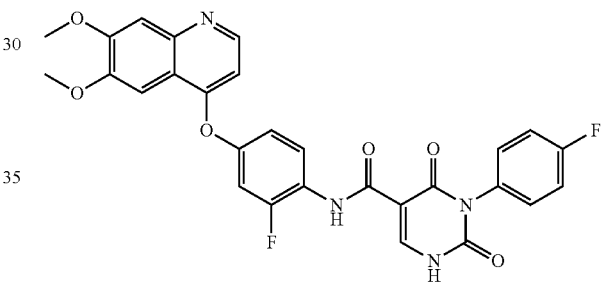

3-(4-Fluoro-phenyl)-2,4-dioxo-1,2,3,4-tetrahydro-pyrimidine-5-carboxylic acid [4-(6,7-dimethoxy-quinolin-4-yloxy)-2-fluoro-phenyl]-amide. mp 238-243° C.; LCMS m/z=547 (M+1); $^1$H NMR (DMSO) δ: 12.44 (bs, 1H), 11.16 (bs, 1H), 8.52-8.46 (m, 3H), 7.47 (s, 1H), 7.44-7.33 (m, 5H) 7.40 (s, 1H), 7.14 (d, 1H, J=9.0 Hz), 6.59 (d, 1H, J=5.0 Hz), 3.95 (s, 3H), 3.92 (s, 3H).

Example 86

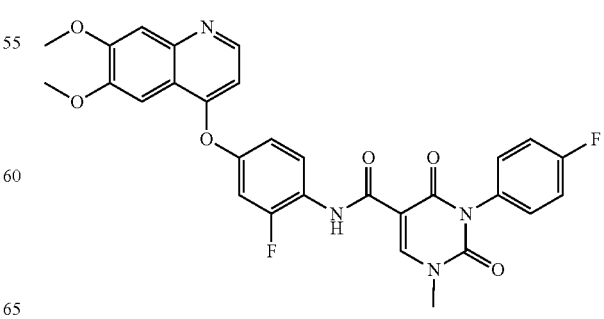

3-(4-Fluoro-phenyl)-1-methyl-2,4-dioxo-1,2,3,4-tetrahydro-pyrimidine-5-carboxylic acid [4-(6,7-dimethoxy-quinolin-4-yloxy)-2-fluoro-phenyl]-amide. mp 208-210° C.; LCMS m/z=561 (M+1); $^1$H NMR (DMSO) δ: 11.17 (bs, 1H), 8.90 (s, 1H), 8.51-8.46 (m, 2H), 7.47 (s, 1H), 7.43-7.34 (m, 6H) 7.40 (s, 1H), 7.16 (d, 1H, J=9.0 Hz), 6.59 (d, 1H, J=5.0 Hz), 3.95 (s, 3H), 3.92 (s, 3H), 3.54 (s, 3H).

Example 87

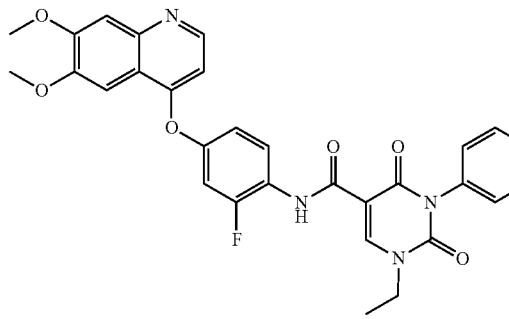

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-2-fluoro-phenyl]-amide. mp 142-144° C.; LCMS m/z=575 (M+1); $^1$H NMR (DMSO) δ: 11.18 (bs, 1H), 8.91 (s, 1H), 8.50 (d, 1H, J=5.2 Hz), 8.48 (t, 1H, J=9.8 Hz), 7.47 (s, 1H), 7.45-7.33 (m, 6H), 7.16 (bd, 1H, J=8.3 Hz), 6.59 (d, 1H, J=5.2 Hz), 4.02 (q, 2H, J=7.0 Hz), 3.95 (s, 3H), 3.92 (s, 3H), 1.30 (t, 3H, J=7.0 Hz).

Example 88

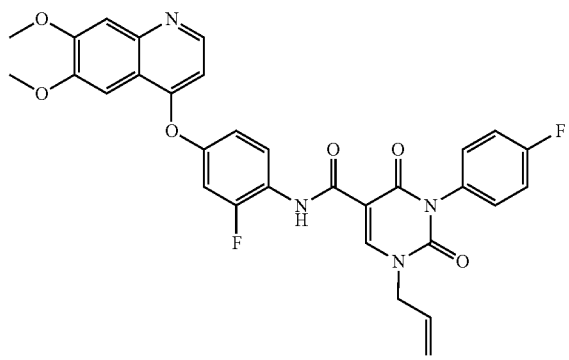 [SMILES: C=CCn1cc(C(=O)Nc2ccc(Oc3ccnc4cc(OC)c(OC)cc34)cc2F)c(=O)n(-c2ccc(F)cc2)c1=O]

1-Allyl-3-(4-fluoro-phenyl)-2,4-dioxo-1,2,3,4-tetrahydro-pyrimidine-5-carboxylic acid [4-(6,7-dimethoxy-quinolin-4-yloxy)-2-fluoro-phenyl]-amide. mp 134-136° C.; LCMS m/z=587 (M+1); $^1$H NMR (DMSO) δ: 11.16 (s, 1H), 8.82 (s, 1H), 8.50 (d, 1H, J=5.5 Hz), 8.47 (t, 1H, J=8.0 Hz), 7.47 (s, 1H), 7.46-7.34 (m, 6H), 7.16 (bd, 1H, J=8.6 Hz), 6.59 (d, 1H, J=5.4 Hz), 6.03-5.93 (m, 1H), 5.38 (d, 1H, J=17 Hz), 5.29 (d, 1H, J=10.6 Hz), 4.63 (d, 2H, J=5.7 Hz), 3.95 (s, 3H), 3.92 (s, 3H).

Example 89

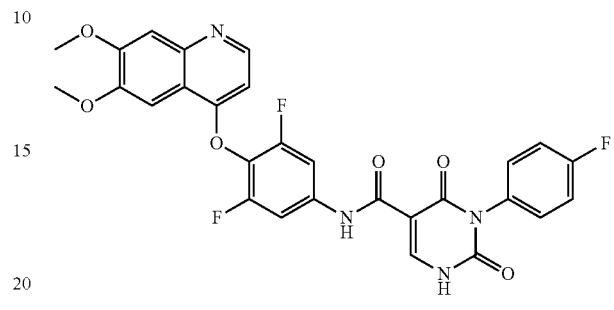

3-(4-Fluoro-phenyl)-2,4-dioxo-1,2,3,4-tetrahydropyrimidine-5-carboxylic acid [4-(6,7-dimethoxy-quinolin-4-yloxy)-3,5-difluoro-phenyl]-amide. Example 89 was synthesized using the 4-(6,7-dimethoxyquinolin-4-yloxy)-3,5-difluorophenylamine (synthesized using the method for example 85 starting with 2,6-difluoro-4-nitrophenol; LCMS m/z=333 M+1); LCMS m/z=565 (M+1); $^1$H NMR (CDCl$_3$) δ: 8.50 (bd, 1H), 8.47 (s, 1H), 7.60 (d, 1H, J=4.0 Hz), 7.46 (bd, 2H, J=15 Hz), 7.24-7.12 (m, 6H), 6.36 (d, 1H, J=8.9 Hz), 5.88 (d, 1H, J=8.1 Hz), 4.07 (s, 3H), 4.05 (s, 3H).

Example 90

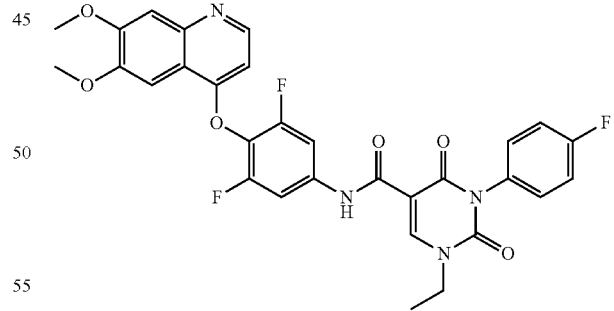

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3,5-difluoro-phenyl]-amide. mp 166-170° C.; LCMS m/z=593 (M+1); $^1$H NMR (DMSO) δ: 11.13 (s, 1H), 8.91 (s, 1H), 8.50 (d, 1H, J=6.8 Hz), 7.83 (d, 2H, J=9.8 Hz), 7.54 (s, 1H), 7.45-7.32 (m, 5H), 6.59 (d, 1H, J=6.5 Hz), 4.02 (q, 2H, J=6.5 Hz), 3.96 (s, 6H), 2.69 (t, 3H, J=6.5 Hz).

Example 91

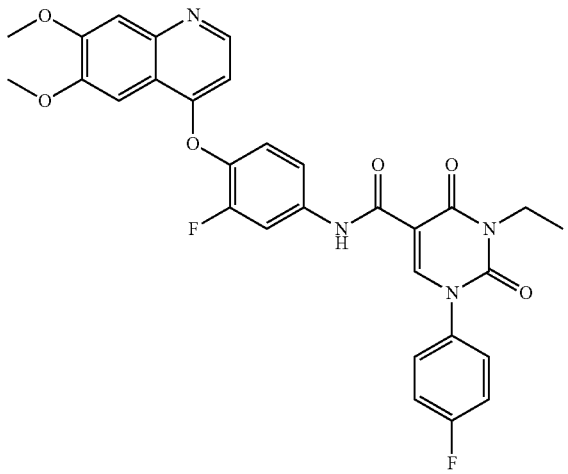 [SMILES: CCn1c(=O)c(C(=O)Nc2ccc(Oc3ccnc4cc(OC)c(OC)cc34)c(F)c2)cn(-c2ccc(F)cc2)c1=O]

3-Ethyl-1-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide. To a solution of 4-fluoroaniline (1.0 g, 9.01 mmol) in THF (20 mL) at 0° C., was slowly added ethyl isocyanate (0.70 g, 10.0 mmol). After stirring 30 min. at 0° C., the solution was warmed to rt and the solvent was removed under vacuum. To the residue was added ethanol (30 mL), diethyl ethoxymethylenemalonate (1.95 g, 9.01 mmol) and 21% NaOEt in ethanol (2.92 mL, 9.01 mmol)) and the reaction stirred 48 h at rt. The solvent was removed under vacuum and cold conc. HCl was added to pH 6. The aqueous layer was removed under vacuum and the solids were crystallized from ethyl acetate and hexanes. 3-Ethyl-1-(4-fluorophenyl)-2,4-dioxo-1,2,3,4-tetrahydro-pyrimidine-5-carboxylic acid ethyl ester isomer was isolated in 25% yield. $^1$H NMR (CDCl$_3$) δ: 8.32 (s, 1H), 7.20-7.14 (m, 4H), 4.35 (q, 2H, J=7.1 Hz), 3.95 (q, 2H, J=7.2 Hz), 1.42 (t, 3H, J=7.2 Hz), 1.36 (t, 3H, J=7.2 Hz).

3-Ethyl-1-(4-fluorophenyl)-2,4-dioxo-1,2,3,4-tetrahydro-pyrimidine-5-carboxylic acid ethyl ester was hydrolyzed with 1N LiOH in MeOH and THF at 65° C. The acid was coupled with 4-(6,7-Dimethoxyquinolin-4-yloxy)-3-fluorophenylamine using the method for example 1 to give 3-ethyl-1-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide mp 140-142° C.; LCMS m/z=575 (M+1); $^1$H NMR (DMSO) δ: 11.18 (s, 1H), 8.49 (d, 1H, J=2.5 Hz), 8.46 (s, 1H), 8.03 (dd, 1H, J=3 Hz, J=13 Hz), 7.65-7.39 (m, 6H), 7.55 (s, 1H), 7.41 (s, 1H), 6.49 (d, 1H, J=5.0 Hz), 4.00 (q, 2H, J=7.4 Hz), 3.95 (s, 6H), 1.23 (t, 3H, J=7.3 Hz).

Example 92

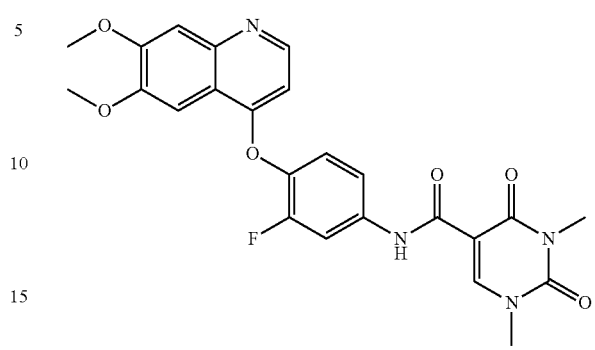

1,3-Dimethyl-2,4-dioxo-1,2,3,4-tetrahydropyrimidine-5-carboxylic acid [4-(6,7-dimethoxy-quinolin-4-yloxy)-3-fluorophenyl]-amide.

Step a. A mixture of 2,4-dioxo-1,2,3,4-tetrahydropyrimidine-5-carboxylic acid ethyl ester (0.100 g, 0.543 mmol), iodomethane (0.130 mL, 1.63 mmol), and potassium carbonate (0.225 g, 1.63 mmol) was slurred in N,N-dimethylformamide (5 mL, 60 mmol) at 80° C. 18 h. The mixture was poured into water and extracted with ethyl acetate. The residue was hydrolyzed with 1 equivalent of 1N LiOH in THF/MeOH (1:1; 6 mL) at 60° C. 4 h. The organics were removed under vacuum, and the aqueous was washed with ethyl acetate. The aqueous was then cooled and acidified with conc. HCl. The 1,3-dimethyl-2,4-dioxo-1,2,3,4-tetrahydro-pyrimidine-5-carboxylic acid was filtered off in 60% yield. $^1$H NMR (DMSO) δ: 12.78 (bs, 1H), 8.72 (s, 1H), 3.45 (s, 3H), 3.22 (s, 3H).

This intermediate acid was coupled with 4-(6,7-dimethoxyquinolin-4-yloxy)-3-fluorophenylamine as described in example 1. mp 258-260° C.; LCMS m/z=481 (M+1); $^1$H NMR (DMSO) δ: 11.22 (s, 1H), 8.76 (s, 1H), 8.49 (d, 1H, J=5.3 Hz), 8.02 (dd, 1H, J=2.5 Hz, J=13 Hz), 7.54 (d, 1H, J=8 Hz), 7.54 (s, 1H), 7.47 (t, 1H, J=9.0 Hz), 7.41 (s, 1H), 6.49 (d, 1H, J=9.0 Hz), 3.95 (s, 6H), 3.51 (s, 3H), 3.29 (s, 3H).

Examples 92-98 intermediate acids were synthesized as in Scheme 2 and described in Example 92 and coupled using methods described for Example 1.

Example 93

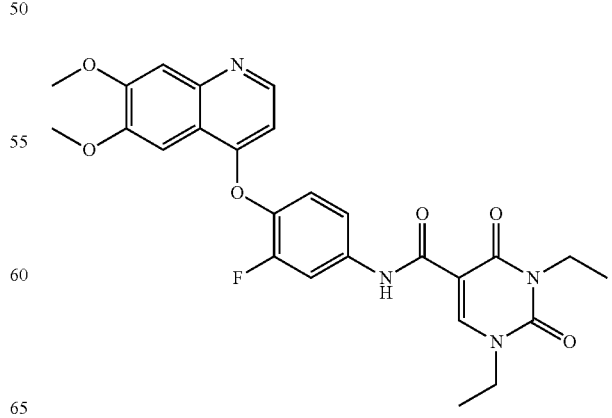

1,3-Diethyl-2,4-dioxo-1,2,3,4-tetrahydro-pyrimidine-5-carboxylic acid [4-(6,7-dimethoxy-quinolin-4-yloxy)-3-fluoro-phenyl]-amide. mp 178-180° C.; LCMS m/z=509 (M+1); $^1$H NMR (DMSO) δ: 11.22 (s, 1H), 8.76 (s, 1H), 8.49 (d, 1H, J=5.5 Hz), 8.02 (dd, 1H, J=2.5 Hz, J=13 Hz), 7.55 (d, 1H, J=8 Hz), 7.54 (s, 1H), 7.46 (t, 1H, J=9.0 Hz), 7.41 (s, 1H), 6.49 (d, 1H, J=9.0 Hz), 4.02-3.96 (m, 4H), 3.95 (s, 6H), 1.27 (t, 3H, J=7.4 Hz), 1.18 (t, 3H, J=7.5 Hz).

Example 94

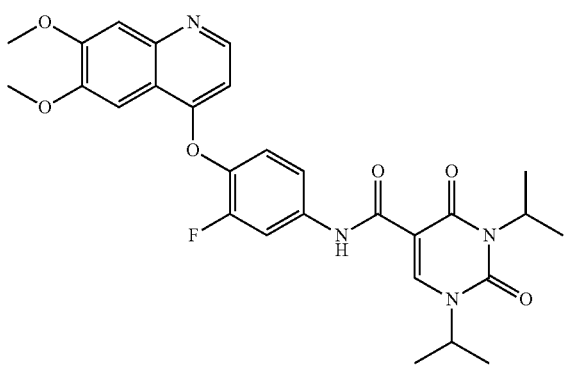 [SMILES: COc1cc2nccc(Oc3ccc(NC(=O)c4cn(C(C)C)c(=O)n(C(C)C)c4=O)cc3F)c2cc1OC]

1,3-Diisopropyl-2,4-dioxo-1,2,3,4-tetrahydro-pyrimidine-5-carboxylic acid [4-(6,7-dimethoxy-quinolin-4-yloxy)-3-fluoro-phenyl]-amide. mp 113-116° C.; LCMS m/z=537 (M+1); $^1$H NMR (DMSO) δ: 11.22 (s, 1H), 8.54 (s, 1H), 8.49 (d, 1H, J=5.0 Hz), 8.02 (dd, 1H, J=2.5 Hz, J=13 Hz), 7.54 (bd, 1H, J=9 Hz), 7.53 (s, 1H), 7.46 (t, 1H, J=8.1 Hz), 7.42 (s, 1H), 6.49 (d, 1H, J=5.6 Hz), 5.18 (h, 1H, J=6.7 Hz), 4.78 (h, 1H, J=6.8 Hz), 3.95 (s, 6H), 1.45 (d, 6H, J=6.7 Hz), 1.38 (d, 6H, J=6.4 Hz).

Example 95

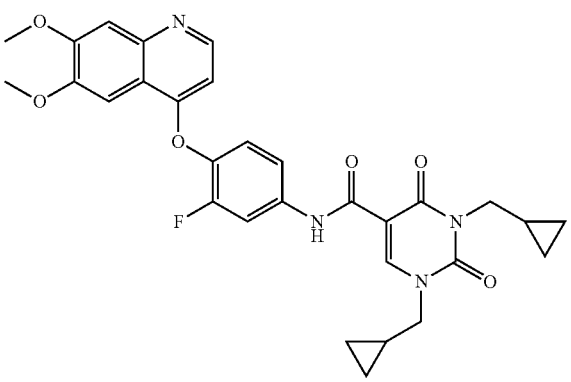 [SMILES: COc1cc2nccc(Oc3ccc(NC(=O)c4cn(CC5CC5)c(=O)n(CC5CC5)c4=O)cc3F)c2cc1OC]

1,3-Bis-cyclopropylmethyl-2,4-dioxo-1,2,3,4-tetrahydro-pyrimidine-5-carboxylic acid [4-(6,7-dimethoxy-quinolin-4-yloxy)-3-fluoro-phenyl]-amide. mp 63-65° C.; LCMS m/z=561 (M+1); $^1$H NMR (DMSO) δ: 11.192 (s, 1H), 8.83 (s, 1H), 8.49 (d, 1H, J=5.3 Hz), 8.03 (dd, 1H, J=2.3 Hz, J=13.5 Hz), 7.55 (bd, 1H, J=9 Hz), 7.54 (s, 1H), 7.46 (t, 1H, J=8.9 Hz), 7.41 (s, 1H), 6.49 (d, 1H, J=5.1 Hz), 3.95 (s, 6H), 3.84 (t, 4H, J=7.1 Hz), 1.16-1.08 (m, 2H), 0.56-0.38 (m, 8H).

Example 96

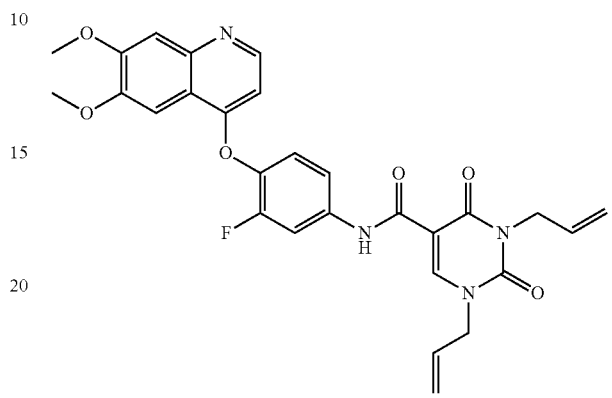

1,3-Diallyl-2,4-dioxo-1,2,3,4-tetrahydro-pyrimidine-5-carboxylic acid [4-(6,7-dimethoxy-quinolin-4-yloxy)-3-fluoro-phenyl]-amide. mp 172-174° C.; LCMS m/z=529 (M+1); $^1$H NMR (DMSO) δ: 11.10 (s, 1H), 8.72 (s, 1H), 8.49 (d, 1H, J=5.2 Hz), 8.02 (dd, 1H, J=2.5 Hz, J=13 Hz), 7.56 (bd, 1H, J=8.9 Hz), 7.53 (s, 1H), 7.46 (t, 1H, J=8.8 Hz), 6.49 (d, 1H, J=5.2 Hz), 6.03-5.03 (m, 2H), 5.31-5.27 (m, 1H), 5.27-5.25 (m, 1H), 5.20-5.17 (m, 1H), 5.16-5.14 (m, 1H), 4.60 (d, 2H, J=5.5 Hz), 4.53 (d, 2H, J=5.5 Hz), 3.95 (s, 3H), 3.94 (s, 3H).

Example 97

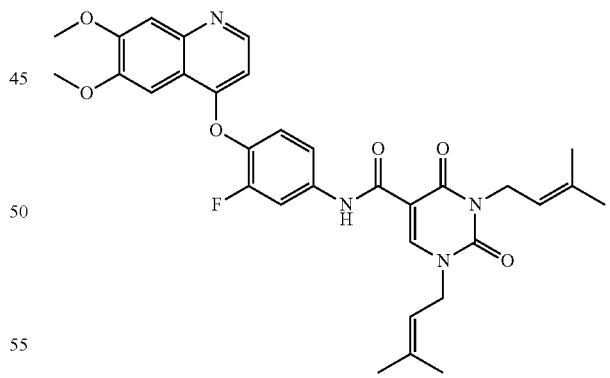

1,3-Bis-(3-methyl-but-2-enyl)-2,4-dioxo-1,2,3,4-tetrahydro-pyrimidine-5-carboxylic acid [4-(6,7-dimethoxy-quinolin-4-yloxy)-3-fluoro-phenyl]-amide. mp 184-186° C.; LCMS m/z=589 (M+1); $^1$H NMR (DMSO) δ: 11.15 (s, 1H), 8.65 (s, 1H), 8.49 (d, 1H, J=5.7 Hz), 8.02 (dd, 1H, J=2. Hz, J=13 Hz), 7.54 (bd, 1H, J=9 Hz), 7.52 (s, 1H), 7.46 (t, 1H, J=9.5 Hz), 7.71 (s, 1H), 6.49 (bd, 1H, J=5 Hz), 5.30 (m, 1H), 5.19 (m, 1H), 4.53 (dd, 4H, J=6.7 Hz, J=15.3 Hz), 3.95 (s, 6H), 1.78 (bs, 3H), 1.77 (bs, 3H), 1.74 (bs, 3H), 1.69 (bs, 3H).

Example 98

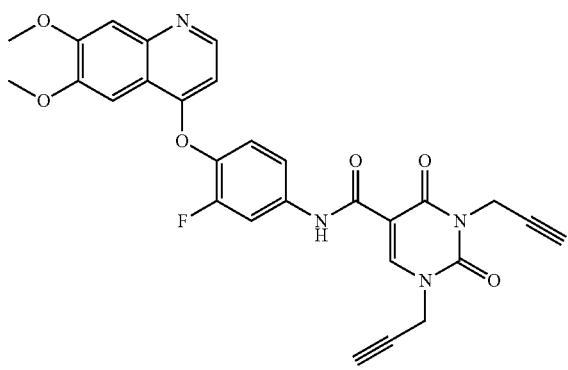 [SMILES: C#CCn1cc(C(=O)Nc2ccc(Oc3ccnc4cc(OC)c(OC)cc34)c(F)c2)c(=O)n(CC#C)c1=O]

2,4-Dioxo-1,3-di-prop-2-ynyl-1,2,3,4-tetrahydro-pyrimidine-5-carboxylic acid [4-(6,7-dimethoxy-quinolin-4-yloxy)-3-fluoro-phenyl]-amide. mp 133-138° C.; LCMS m/z=529 (M+1); $^1$H NMR (DMSO) δ: 10.94 (s, 1H), 8.88 (s, 1H), 8.49 (d, 1H, J=6.5 Hz), 8.03 (dd, 1H, J=2.5 Hz, J=13 Hz), 7.59 (bd, 1H, J=8.5 Hz), 7.54 (s, 1H), 7.48 (t, 6H, J=9.1 Hz), 6.50 (d, 1H, J=5.3 Hz), 4.84 (d, 2H, J=2.4 Hz), 4.42 (d, 2H, J=2.2 Hz), 3.96 (s, 6H), 3.61 (t, 1H, J=2.5 Hz), 3.25 (t, 1H, J=2.5 Hz).

Example 99

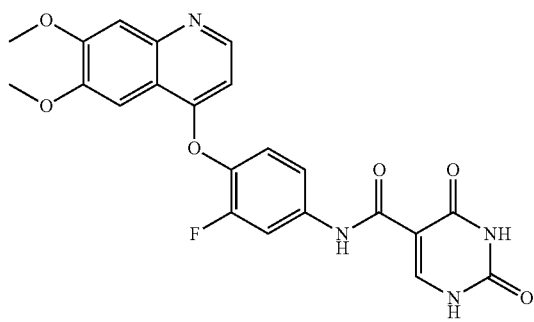 [SMILES: COc1cc2nccc(Oc3ccc(NC(=O)c4c[nH]c(=O)[nH]c4=O)cc3F)c2cc1OC]

2,4-Dioxo-1,2,3,4-tetrahydro-pyrimidine-5-carboxylic acid [4-(6,7-dimethoxy-quinolin-4-yloxy)-3-fluoro-phenyl]-amide. A solution of 2,4-dioxo-1,2,3,4-tetrahydro-pyrimidine-5-carboxylic acid (0.156 g, 1.00 mmol) in thionyl chloride (2 mL, 30 mmol) was stirred at 100° C. 3 h. After the solvent was removed under vacuum, [4-(6,7-dimethoxy-quinolin-4-yloxy)-3-fluoro-phenylamine (0.314 g, 1.00 mmol) and pyridine (2 mL, 20 mmol) were added and stirred at room temperature 18 hr. The solvent was removed under vacuum and the residue was purified on HPLC. 0.15 g of the trifluoracetic acid salt was isolated in 27% yield. mp 251-255° C.; LCMS m/z=453 (M+1); $^1$H NMR (DMSO) δ: 11.99 (bs, 1H), 11.93 (s, 1H), 11.18 (s, 1H), 8.74 (d, 1H, J=4.5 Hz), 8.31 (d, 1H, J=7.5 Hz), 8.06 (d, 1H, J=12 Hz), 7.70 (s, 1H), 7.55 (m, 2H), 7.51 (s, 1H), 6.85 (m, 1H), 4.02 (s, 3H), 4.01 (s, 3H).

Example 100

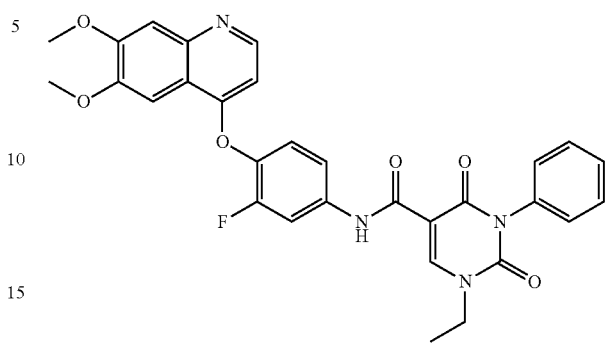

1-Ethyl-2,4-dioxo-3-phenyl-1,2,3,4-tetrahydro-pyrimidine-5-carboxylic acid [4-(6,7-dimethoxy-quinolin-4-yloxy)-3-fluoro-phenyl]-amide. To a solution of 2-aminomethylene-malonic acid diethyl ester (0.75 g, 4.0 mmol) and phenyl isocyanate (0.57 g, 4.4 mmol) in 1,2-dichloroethane (20 mL) was added N,N-diisopropylethylamine (0.77 mL, 4.4 mmol) and heated at 100° C. 6 h. The mixture was cooled and filtered. The solids were purified by column chromatography with 0-5% MeOH in methylene chloride. This intermediate urea was suspended in ethanol (10 mL) and 21% NaOEt in ethanol (1.29 mL, 4.0 mmol) was added. After 18 h the solvent was removed under vacuum and the residue was slurred in ethyl acetate. The organics were washed with 1M citric acid solution, water and brine. The solvent was removed under vacuum and the residue was purified by chromatography with 0-5% MeOH in dichloromethane to give 0.50 g (40%). The ester was alkylated and hydrolyzed using methods for example 92 to give 1-ethyl-2,4-dioxo-3-phenyl-1,2,3,4-tetrahydro-pyrimidine-5-carboxylic acid. $^1$H NMR (DMSO) δ: 12.65 (bs, 1H), 8.82 (s, 1H), 7.54-7.43 (m, 3H), 7.32-7.29 (m, 2H), 4.02 (q, 2H, J=7.1 Hz), 1.26 (t, 3H, J=7.1 Hz).

This intermediate acid was coupled to 4-(6,7-dimethoxyquinolin-4-yloxy)-3-fluorophenylamine as described in example 1 to give Example 100. mp 282-285° C.; LCMS m/z=557 (M+1); $^1$H NMR (DMSO) δ: 11.01 (s, 1H), 8.89 (s, 1H), 8.48 (d, 1H, J=4.6 Hz), 8.00 (dd, 1H, J=2.3 Hz, J=13 Hz), 7.56-7.34 (m, 9H), 6.47 (d, 1H, J=4.6 Hz), 4.02 (q, 2H, J=6.9 Hz), 3.95 (s, 3H), 3.94 (s, 3H), 1.3 (t, 3H, J=7.4 Hz).

Example 101

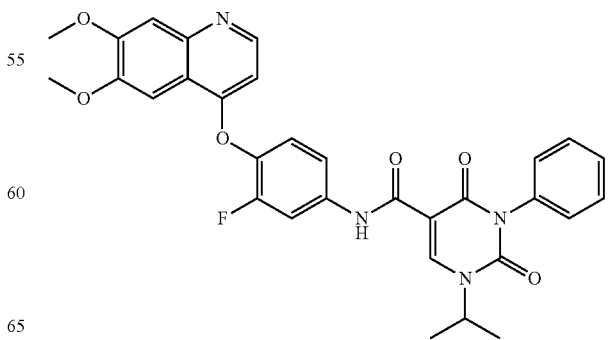

1-Isopropyl-2,4-dioxo-3-phenyl-1,2,3,4-tetrahydro-pyrimidine-5-carboxylic acid [4-(6,7-dimethoxy-quinolin-4-yloxy)-3-fluoro-phenyl]-amide. mp 235-237° C.; LCMS m/z=571 (M+1); $^1$H NMR (DMSO) δ: 11.07 (s, 1H), 8.69 (s, 1H), 8.48 (d, 1H, J=4.6 Hz), 8.01 (dd, 1H, J=2.3 Hz, J=13 Hz), 7.55-7.35 (m, 9H), 6.48 (d, 1H, J=4.6 Hz), 4.79 (h, 1H, J=6.9 Hz), 3.95 (s, 3H), 3.94 (s, 3H), 1.43 (d, 6H, J=6.8 Hz).

Example 102

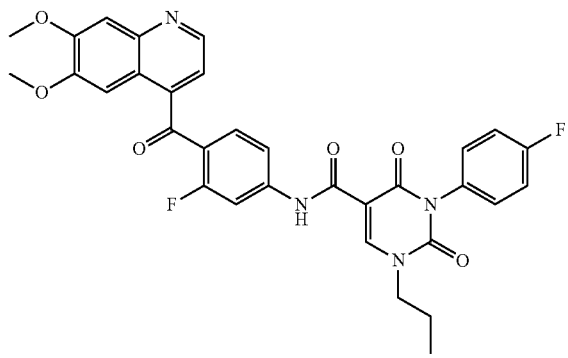 [SMILES: CCCn1cc(C(=O)Nc2ccc(C(=O)c3ccnc4cc(OC)c(OC)cc34)c(F)c2)c(=O)n(-c2ccc(F)cc2)c1=O]

3-(4-Fluoro-phenyl)-2,4-dioxo-1-propyl-1,2,3,4-tetrahydro-pyrimidine-5-carboxylic acid [4-(6,7-dimethoxy-quinoline-4-carbonyl)-3-fluoro-phenyl]-amide.

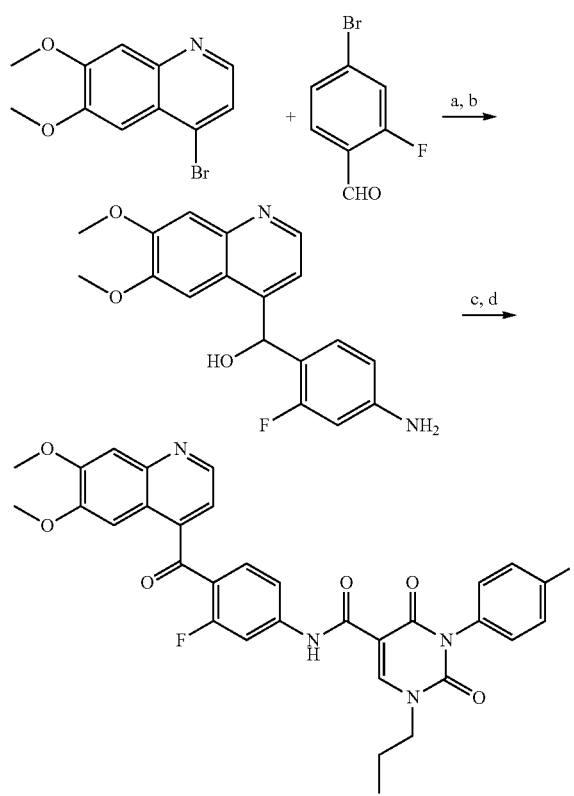

Step a. A solution of 4-bromo-6,7-dimethoxyquinoline (1.0 g, 3.73 mmol) in dry THF (20 mL) was cooled to −78° C. A solution of 2.5M n-butyllithium in hexanes (1.50 mL, 3.73 mmol) was added and stirred 15 min. A solution of 4-bromo-2-fluoro-benzaldehyde (0.757 g, 3.73 mmol) in THF (10 mL) was added dropwise over 5 min. After stirring 30 min. at −78° C., saturated ammonium chloride solution (1 mL) was added. The solvent was removed under reduced pressure. The residue was dissolved in ethyl acetate and washed with water. After the solvent was removed under vacuum, the residue was purified by chromatography with 0-5% MeOH in dichloromethane to give (4-bromo-2-fluoro-phenyl)-(6,7-dimethoxy-quinolin-4-yl)-methanol in 52% yield. $^1$H NMR (CDCl$_3$) δ: 8.63 (d, 1H, J=4.1 Hz), 7.57 (d, 1H, J=4.7 Hz), 7.34 (s, 1H), 7.25-7.17 (m, 2H), 7.08 (s, 1H), 6.67 (s, 1H), 4.02-3.96 (m, 1H), 3.94 (s, 3H), 3.88 (s, 3H).

Step b. The intermediate from step a (0.196 g, 0.50 mmol) was dissolved in THF (5 mL) and 1M lithium hexamethyldisilazane in THF (0.55 mL, 0.55 mmol), bis(dibenzylideneacetone)palladium (0.014 g, 5 mol %) and tri-tert-butylphosphine (0.061 mL, 5 mol %) were added. The sealed tube was heated at 65° C. 18 hr. After cooling, concentrated HCl was added to pH 1 and stirred 1 hr. The solvent was removed under vacuum, ethyl acetate and saturated sodium bicarbonate solution was added until slightly basic. The organics were separated, the solvent removed under vacuum and the residue purified by chromatography with 0-5% MeOH in dichloromethane to give (4-amino-2-fluoro-phenyl)-(6,7-dimethoxy-quinolin-4-yl)methanone in 60% yield. $^1$H NMR (CDCl$_3$) δ: 8.78 (d, 1H, J=4.7 Hz), 7.69 (d, 1H, J=4.7 Hz), 7.42 (s, 1H), 7.10 (s, 1H), 6.90 (t, 1H, J=8.3 Hz), 6.65 (s, 1H), 6.41 (dd, 1H, J=2.2 Hz, J=12.1 Hz), 6.33 (dd, 1H, J=2.2 Hz, J=8.4 Hz), 4.00 (s, 3H), 3.90 (s, 3H), 3.80 (bs, 2H), 2.33 (bs, 1H).

Steps c and d. 3-(4-Fluoro-phenyl)-2,4-dioxo-1-propyl-1,2,3,4-tetrahydro-pyrimidine-5-carboxylic acid [4-(6,7-dimethoxy-quinoline-4-carbonyl)-3-fluoro-phenyl]-amide. The intermediate from step b was coupled with 3-(4-fluorophenyl)-2,4-dioxo-1-propyl-1,2,3,4-tetrahydro-pyrimidine-5-carboxylic acid using the methods for Example 1. The alcohol (0.075 g, 0.12 mmol) product was dissolved in dichloromethane (5 mL) and cooled to 0° C. Dess-Martin periodinane (0.076 g, 0.18 mmol) was added slowly and the solution warmed to room temperature for 4 h. The organics were washed with saturated sodium bicarbonate and the solvent removed under vacuum. The residue was purified by column chromatography with 5% MeOH in dichloromethane to give 0.063 g (84%) mp 125-127° C.; LCMS m/z=601 (M+1); $^1$H NMR (DMSO) δ: 11.30 (s, 1H), 8.88 (s, 1H), 8.79 (d, 1H, J=4.0 Hz), 7.87 (dd, 1H, J=1.9 Hz, J=13 Hz), 7.72 (t, 1H, J=8.5 Hz), 7.56 (dd, 1H, J=1.8 Hz, J=8.7 Hz), 7.49 (s, 1H), 7.45-7.32 (m, 5H), 7.29 (s, 1H), 3.96 (s, 3H), 3.94 (t, 2H, J=7.4 Hz), 3.77 (s, 3H), 1.71 (q, 2H, J=7.8 Hz), 0.92 (t, 3H, J=8.3 Hz).

Synthesis of 3,5-dioxo-2,3,4,5-tetrahydro-[1,2,4]triazine-6-carboxylic acid

Method A.
Step a. 4-(4-fluorophenyl)-5-oxo-3-thioxo-2,3,4,5-tetrahydro-[1,2,4]triazine-6-carboxylic acid ethyl ester. A mixture of 2-oxo-malonic acid diethyl ester (2.5 mL, 16 mmol) and 4-fluorophenyl thiosemicarbazide (3.0 g, 16 mmol) in ethanol (60 mL, 1000 mmol) was heated at reflux for 3 days. The mixture was cooled to rt and the separated solid was filtered, washed with cold ethanol and dried to give 3.44 g (71%). LCMS m/z=296 (M+1); $^1$H NMR (DMSO) δ: 7.35 (m, 4H), 4.30 (q, 2H, J=7.1 Hz), 1.27 (t, 3H, J=7.1 Hz).

Step b. 4-(4-Fluorophenyl)-3,5-dioxo-2,3,4,5-tetrahydro-[1,2,4]triazine-6-carboxylic acid ethyl ester. To a solution of 4-(4-fluorophenyl)-5-oxo-3-thioxo-2,3,4,5-tetrahydro-1,2,4-triazine-6-carboxylic acid ethyl ester (11 g, 37 mmol) in N,N-dimethylformamide (100 mL) and acetic acid (40 mL, 700 mmol) was added 50% aq. hydrogen peroxide (11 mL, 190 mmol). The mixture was stirred at rt 2 days, the solvent was removed and the product was taken up in ethylacetate and washed successively with water and brine. After drying, the solvent was evaporated. The solid obtained was triturated with ether, filtered and washed with cold ether to yield 9.85 g (95%). LCMS m/z=280 (M+1); $^1$H NMR (DMSO) δ: 13.1 (s, 1H), 7.42-7.28 (2 m, 4H), 4.29 (q, 2H, J=7.1 Hz), 1.27 (t, 3H, J=7.1 Hz).

Step c. 4-(4-Fluorophenyl)-2-isopropyl-3,5-dioxo-2,3,4,5-tetrahydro-[1,2,4]triazine-6-carboxylic acid ethyl ester. 4-(4-Fluorophenyl)-3,5-dioxo-2,3,4,5-tetrahydro-1,2,4-triazine-6-carboxylic acid ethyl ester (1000 mg, 4 mmol), isopropyl iodide (0.72 mL, 7.16 mmol) and potassium carbonate (544 mg, 3.94 mmol) in N,N-dimethylformamide (20 mL) was heated at 65° C. for 60 min. The reaction mixture was cooled to rt and was concentrated, diluted with EtOAc and was filtered through a pad of celite. The filtrate was concentrated and the product purified by flash chromatography (hexane: EtOAc 3:1) to give a white solid (1.1 g, 96%). LCMS m/z=322 (M+1); $^1$H NMR (DMSO) δ: 7.41-7.31 (m, 4H), 4.86 (m, 1H), 4.31 (q, 2H, J=7.0 Hz), 1.31-1.26 (overlapping t and d, 9H).

Step d. 4-(4-Fluorophenyl)-2-isopropyl-3,5-dioxo-2,3,4,5-tetrahydro[1,2,4]triazine-6-carboxylic acid. Sulfuric acid (10 mL, 200 mmol) was carefully added to a mixture of 4-(4-fluorophenyl)-2-isopropyl-3,5-dioxo-2,3,4,5-tetrahydro-1,2,4-triazine-6-carboxylic acid ethyl ester (1100 mg, 3.4 mmol) and water (2 mL). The mixture became homogenous after a few minutes. The reaction mixture was stirred at 40° C. overnight, was cooled to rt and was carefully added to ice. The mixture was saturated with solid NaCl and was extracted repeatedly from EtOAc (3×). The combined EtOAc layer was washed with brine, dried over magnesium sulfate, and concentrated to give the product as foam (100%). LCMS m/z=294 (M+1); $^1$H NMR (Methanol d4) δ: 7.35-7.31 (2 m, 4H), 4.95 (m, 1H), 4.31 (q, 2H, J=7.0 Hz), 1.41 (d, 6H, J=6.6 Hz).

The following 3,5-dioxo-2,3,4,5-tetrahydro[1,2,4]triazine-6-carboxylic acids were synthesized using the previous procedure.

2-Ethyl-4-(4-fluorophenyl)-3,5-dioxo-2,3,4,5-tetrahydro-[1,2,4]triazine-6-carboxylic acid. LCMS m/z=280 (M+1); $^1$H NMR (Methanol-d4) a: 7.34-7.18 (m, 4H), 4.10 (q, 2H, J=7.2 Hz), 1.38 (t, 3H, J=7.2 Hz).

4-(4-Fluorophenyl)-2-(2-hydroxyethyl)-3,5-dioxo-2,3,4,5-tetrahydro-[1,2,4]triazine-6-carboxylic acid. Synthesized from 2-[2-(t-butyldimethylsilanyloxy)ethyl]-4-(4-fluorophenyl)-3,5-dioxo-2,3,4,5-tetrahydro-[1,2,4]triazine-6-carboxylic acid. LCMS m/z=296 (M+1); $^1$H NMR (DMSO) δ: 7.41-7.36 (m, 4H), 4.09-4.01 (2 m, 3H), 3.72 (m, 2H).

Tert-4-(4-Fluorophenyl)-3,5-dioxo-2-(2-oxo-propyl)-2,3,4,5-tetrahydro-[1,2,4]triazine-6-carboxylic acid. (from the ester precursor, 4-(4-fluorophenyl)-3,5-dioxo-2-prop-2-ynyl-2,3,4,5-tetrahydro-[1,2,4]triazine-6-carboxylic acid ethyl ester). LCMS m/z=308 (M+1); $^1$H NMR (DMSO) δ: 7.46-7.32 (m, 4H), 4.95 (s, 2H2.21 (s, 3H).

2-Cyclopropylmethyl-4-(4-fluoro-phenyl)-3,5-dioxo-2,3,4,5-tetrahydro-[1,2,4]triazine-6-carboxylic acid. LCMS m/z=306 (M+1.

4-(4-Fluorophenyl)-3,5-dioxo-2,3,4,5-tetrahydro-[1,2,4]triazine-6-carboxylic acid. 4-(4-Fluoro-phenyl)-3,5-dioxo-2,3,4,5-tetrahydro-1,2,4-triazine-6-carboxylic acid ethyl ester (300 mg, 1 mmol) in THF (3 mL) and MeOH (7 mL) was added 5M NaOH (2 mL, 2 mmol). The mixture was stirred at rt for 1h and was concentrated. Water was added and the mixture was extracted with ether. The aq. layer was made acidic with HCl at 0° C. and was extracted with EtOAc and concentrated. LCMS m/z=274 (M+Na); $^1$H NMR (DMSO) δ: 13.03 (s, 1H), 7.35-7.30 (m, 4H).

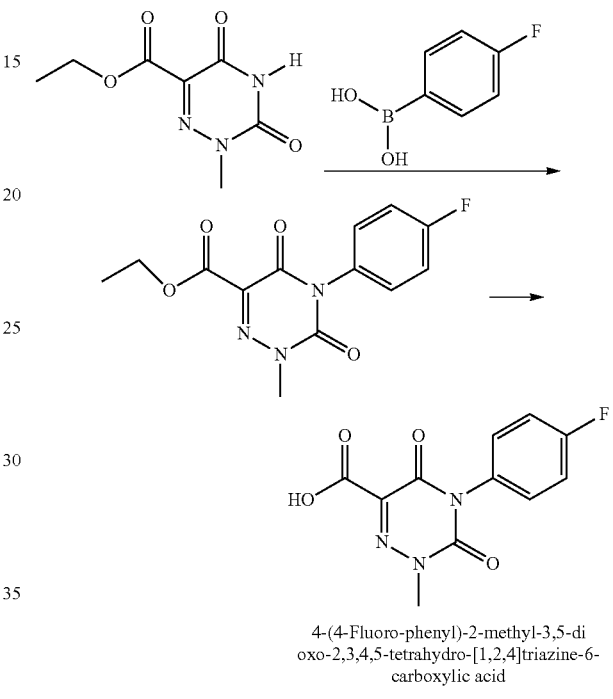

4-(4-Fluoro-phenyl)-2-methyl-3,5-dioxo-2,3,4,5-tetrahydro-[1,2,4]triazine-6-carboxylic acid Method B Step a. 4-(4-Fluoro-phenyl)-2-methyl-3,5-dioxo-2,3,4,5-tetrahydro-[1,2,4]triazine-6-carboxylic acid. To a mixture of 2-methyl-3,5-dioxo-2,3,4,5-tetrahydro-[1,2,4]triazine-6-carboxylic acid ethyl ester (220 mg, 1.1 mmol) (Yuen, K. *J Org. Chem*. 1962, 27, 976), 4-Fluorophenyl boronic acid (230 mg, 1.6 mmol) and triethylamine (0.46 mL, 3.3 mmol) in methylene chloride (5 mL, 80 mmol) was added copper acetate (150 mg, 1.2 mmol). The mixture was stirred under argon at rt 18 h. The solvent was removed and the product was purified by flash chromatography (hexane: EtOAc 60:40) to yield 34 mg (10%). LCMS=294 (M+1).

Step b. 4-(4-Fluorophenyl)-2-methyl-3,5-dioxo-2,3,4,5-tetrahydro-[1,2,4]triazine-6-carboxylic acid. 4-(4-fluorophenyl)-2-methyl-3,5-dioxo-2,3,4,5-tetrahydro-1,2,4-triazine-6-carboxylic acid ethyl ester (30 mg, 0.1 mmol) was dissolved in THF-MeOH (1:1, 2 mL) and 1M of lithium hydroxide (0.102 mL, 0.102 mmol) was added. After stirring at rt overnight, the solution was concentrated, dissolved in 1N Na$_2$CO$_3$ and washed with EtOAc. The aqueous layer was filtered and made acidic with 5N HCl and extracted with EtOAc. The combined organics were washed with water and brine, dried (MgSO4) and evaporated to give a white solid (30 mg, 100%). LCMS m/z=266 (M+1); ¹H NMR (Methanol d4): 7.55-7.52 (m, 2H), 7.07-7.03 (m, 2H), 3.52 (s, 3H).

Example 103

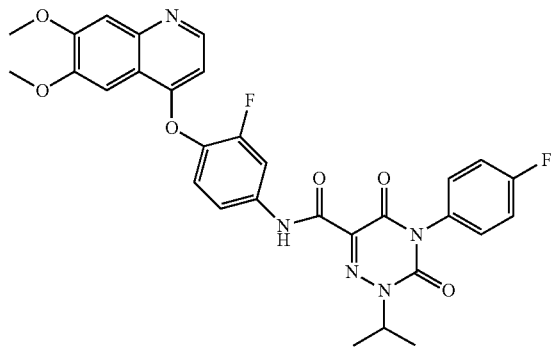 [SMILES: COc1cc2nccc(Oc3ccc(NC(=O)c4nn(C(C)C)c(=O)n(-c5ccc(F)cc5)c4=O)cc3F)c2cc1OC]

4-(4-Fluoro-phenyl)-2-isopropyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide. A mixture of 4-(4-fluorophenyl)-2-isopropyl-3,5-dioxo-2,3,4,5-tetrahydro-1,2,4-triazine-6-carboxylic acid (500 mg, 2 mmol), 4-(6,7-dimethoxyquinolin-4-yloxy)-3-fluorophenylamine (535 mg, 1.70 mmol), N,N,N',N'-tetramethyl-O-(7-azabenzotriazol-1-yl)uronium hexafluorophosphate (639 mg, 1.68 mmol) and N,N-diisopropylethylamine (279 uL, 1.60 mmol) in N,N-dimethylformamide (8 mL) was stirred at rt for 3 h. The solvent was removed and the residue dissolved in EtOAc and washed with saturated NaHCO₃ solution water and brine. After drying over magnesium sulfate, solvent was evaporated and the product was purified by ISCO silica gel chromatography (hexane: EtOAc 1:4) to give 835 mg (83%), which triturated with ether and dried. mp=225-226° C.; LCMS m/z=590 (M+1); ¹H NMR DMSO) δ: 10.87 (s, 1H), 8.49 (d, 1H, J=5.2 Hz), 7.97 (dd, 1H, J=12.6, 2.2 Hz), 7.59-7.36 (m, 8H), 6.50 (d, 1H, J=4.9 Hz), 4.90 (m, 1H), 3.95 (s, 6H), 3.32 (s, 3H), 1.38 (d, 6H, J=6.6 Hz).

The following examples were synthesized using the procedure for Example 103.

Example 104

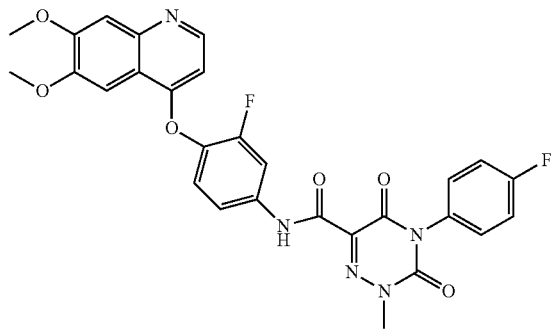 [SMILES: COc1cc2nccc(Oc3ccc(NC(=O)c4nn(C)c(=O)n(-c5ccc(F)cc5)c4=O)cc3F)c2cc1OC]

4-(4-Fluorophenyl)-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt. The product was purified by reverse phase HPLC (Gilson) and the fractions showing product were concentrated as the TFA salt to give an off-white solid. LCMS m/z=562 (M+1); ¹H NMR (DMSO) δ: 10.98 (s, 1H), 8.74 (d, 1H, J=6.1 Hz), 8.02 (dd, 1H, J=12.7, 2.3 Hz), 7.70 (s, 1H), 7.67-7.56 (2 m, 2H), 7.52 (s, 1H), 7.43-7.37 (m, 4H), 6.88 (d, 1H, J=5.5 Hz), 4.02 (s, 3H), 4.01 (s, 3H), 3.69 (s, 3H).

Example 105

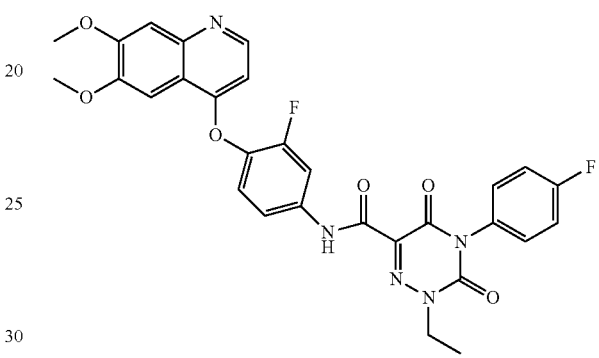

2-Ethyl-4-(4-fluoro-phenyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt. off-white solid, LCMS m/z=576 (M+1); 1H NMR (DMSO) δ: 10.99 (s, 1H), 8.78 (d, 1H, J=6.2 Hz), 8.03 (dd, 1H, J=12.7, 2.3 Hz), 7.72 (s, 1H), 7.67-7.58 (m, 2H), 7.54 (s, 1H), 7.45-7.32 (2 m, 4H), 6.93 (d, 1H, J=6.1 Hz), 4.08 (q, 2H, J=7.1 Hz), 4.03 (s, 3H), 4.02 (s, 3H), 1.35 (t, 3H, J=7.1 Hz).

Example 106

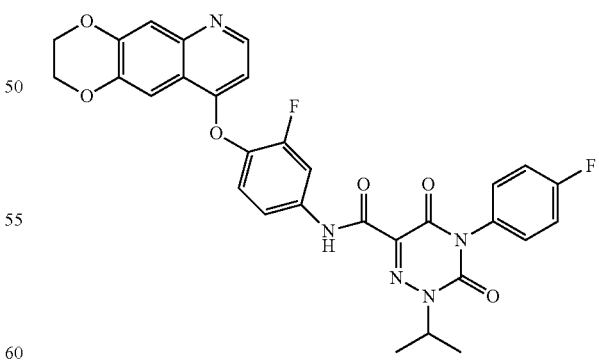

4-(4-Fluorophenyl)-2-isopropyl-3,5-dioxo-2,3,4,5-tetrahydro-[1,2,4]triazine-6-carboxylic acid [4-(2,3-dihydro-[1,4]dioxino[2,3-g]quinolin-9-yloxy)-3-fluorophenyl]-amide TFA salt. This compound was synthesized from 4-(2,3-dihydro[1,4]dioxino[2,3-g]quinolin-9-yloxy)-3- fluorophenylamine; hydrochloride (synthesized using the procedure for example 111 step a; LCMS m/z=313 (M+1); $^1$H NMR (DMSO) δ: 8.85 (d, 1H, J=6.5 Hz), 7.87 (s, 1H), 7.76 (s, 1H), 7.26 (t, 1H, J=8.9 Hz), 6.88 (dd, 1H, J=6.6, 0.8 Hz), 6.78 (dd, 1H, J=8.6, 1.9 Hz), 6.67 (br d, 1H, J=8.6 Hz), 4.52 (m, 4H)) and 4-(4-fluorophenyl)-2-isopropyl-3,5-dioxo-2,3,4,5-tetrahydro-1,2,4-triazine-6-carboxylic acid using the procedure for example 103 to give an off-white solid, LCMS m/z=588 (M+1); $^1$H NMR (DMSO) δ: 10.94 (s, 1H), 8.74 (d, 1H, J=6.0 Hz), 8.02 (dd, 1H, J=12.6, 2.3 Hz), 7.80 (s, 1H), 7.63-7.53 (2 m & s, 3H), 7.54 (s, 1H), 7.45-7.36 (m, 4H), 6.81 (d, 1H, J=5.9 Hz), 4.90 (q, 1H, J=6.6 Hz), 4.48 (m, 4H), 1.38 (d, 6H, J=6.6 Hz).

Example 107

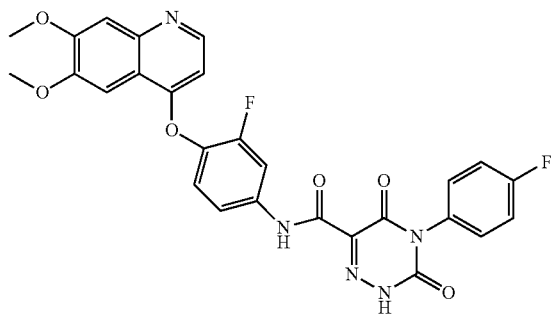 [SMILES: COc1cc2nccc(Oc3ccc(NC(=O)c4n[nH]c(=O)n(-c5ccc(F)cc5)c4=O)cc3F)c2cc1OC]

4-(4-Fluoro-phenyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt. Off-white solid, LCMS m/z=548 (M+1); 1H NMR DMSO) δ: 13.30 (s, 1H), 10.97 (s, 1H), 8.71 (d, 1H, J=6.0 Hz), 8.02 (dd, 1H, J=12.7, 2.3 Hz), 7.68 (s, 1H), 7.65 (m, 1H), 7.65 (m, 1H), 7.56 (m, 1H), 7.5 (s, 1H), 7.46-7.31 (2 m, 4H), 6.83 (d, 1H, J=6.3 Hz), 4.01 (s, 6H).

Example 108

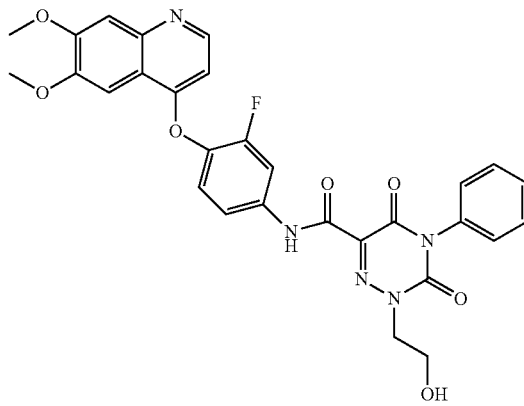

4-(4-Fluorophenyl)-2-(2-hydroxyethyl)-3,5-dioxo-2,3,4,5-tetrahydro-[1,2,4]triazine-6-carboxylic acid [4-(6,7-dimethoxyquinolin-4-yloxy)-3-fluorophenyl]-amide. TFA salt Off-white solid; LCMS m/z=592 (M+1); $^1$H NMR DMSO) δ: 10.96 (s, 1H), 8.75 (d, 1H, J=6.2 Hz), 8.02 (dd 1H, J=12.6, 2.4 Hz), 7.70 (s, 1H), 7.66-7.57 (m, 2H), 7.51 (s, 1H), 7.41-7.39 (m and s, 4H), 6.89 (d, 1H, J=5.4 Hz), 4.11 (m, 2H), 4.02 (2 s, 6H), 3.77 (m, 2H).

Example 109

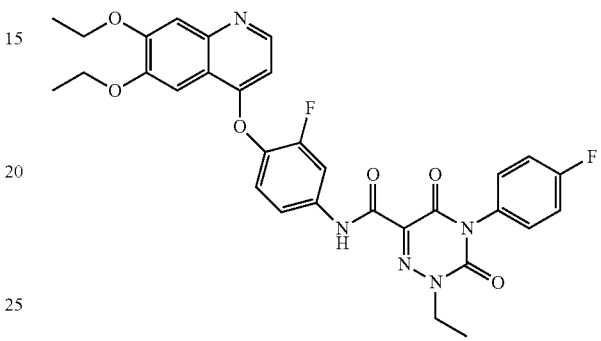

2-Ethyl-4-(4-fluorophenyl)-3,5-dioxo-2,3,4,5-tetrahydro-[1,2,4]triazine-6-carboxylic acid [4-(6,7-diethoxy-quinolin-4-yloxy)-3-fluoro-phenyl]-amide. TFA salt Off-white solid; LCMS m/z=604 (M+1); $^1$H NMR (DMSO) δ: 10.98 (s, 1H), 8.74 (d, 1H, J=6.2 Hz), 8.03 (dd 1H, J=12.6, 2.2 Hz), 7.69 (s, 1H), 7.66-7.54 (m, 2H), 7.51 (s, 1H), 7.46-7.34 (m, 4H), 6.89 (d, 1H, J=5.0 Hz), 4.29 (m, 4H), 4.09 (q, 2H, J=7.1 Hz) 1.45 (overlapping triplets, 6H), 1.35 (t, 3H, J=7.1 Hz).

Example 110

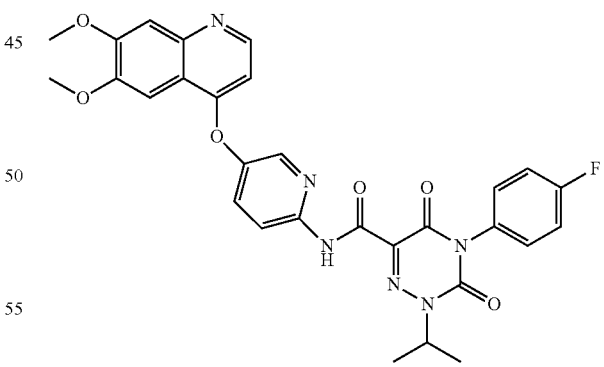

4-(4-Fluoro-phenyl)-2-isopropyl-3,5-dioxo-2,3,4,5-tetrahydro-[1,2,4]triazine-6-carboxylic acid [5-(6,7-dimethoxy-quinolin-4-yloxy)-pyridin-2-yl]-amide di-TFA salt. Off-white solid, LCMS m/z=573 (M+1); $^1$H NMR DMSO) δ: 11.29 (s, 1H), 8.75 (d, 1H, J=6.2 Hz), 8.50 (d, 1H, J=2.8 Hz), 8.42 (m, 1H), 7.99 (dd, 1H, J=9, 2.9 Hz), 7.70 (s, 1H), 7.51 (s, 1H), 7.45-7.37 (m, 4H), 6.93 (d, 1H, J=6.1 Hz), 4.91 (m, 1H), 4.02 (s, 3H), 4.01 (s, 3H), 1.38 (d, J=6.6 Hz).

J=9.8 Hz), 8.04 (dd, 1H, J=12.6, 2.2 Hz), 7.63-7.34 (m, 8H), 6.88 (d, 1H, J=6.0 Hz), 4.90 (m, 1H), 1.38 (d, 6H, J=6.6 Hz).

Example 111

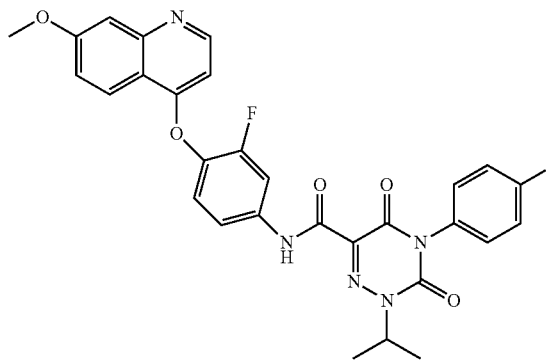

3-Fluoro-4-(7-methoxy-quinolin-4-yloxy)-phenylamine; Hydrochloride

Step a. A mixture of 4-chloro-7-methoxyquinoline (1.0 g mg, 5 mmol), (3-fluoro-4-hydroxyphenyl)-carbamic acid t-butyl ester (1.88 mg, 8.26 mmol) and 4-dimethylaminopyridine (1010 mg, 8.26 mmol) in N,N-dimethylformamide (25 mL) was stirred at 145° C. for 5 h. The mixture was cooled to rt, the solvent was removed and the residue was taken in DCM and washed with water and brine. After drying, the solvent was evaporated. The crude product was purified by flash chromatography (hexanes:EtOAc 1:1) to give a white solid; LCMS=385 (M+1).

Step b. The intermediate from step-a was treated with 4M HCl in dioxane (4 mL, 50 mmol) and the mixture was stirred at rt overnight. The solvent was removed and the mixture was triturated with ether and dried to 368 mg (20%, two steps) of 3-fluoro-4-(7-methoxy-quinolin-4-yloxy)-phenylamine; hydrochloride. LCMS m/z=285 (M+1); $^1$H NMR (DMSO) δ: 8.98 (d, 1H, J=6.6 Hz), 8.50 (d, 1H, J=9.3 Hz), 7.78 (d, 1H, J=2.4 Hz), 7.42 (t, 1H), 7.61 (m, 1H), 7.04-6.84 (m, 4H), 4.03 (s, 3H), 3.72 (s, 3H).

Step c. 4-(4-Fluorophenyl)-2-isopropyl-3,5-dioxo-2,3,4,5-tetrahydro-[1,2,4]triazine-6-carboxylic acid [3-fluoro-4-(7-methoxyquinolin-4-yloxy)-phenyl]-amide TFA salt. This compound was synthesized from 3-fluoro-4-(7-methoxy-quinolin-4-yloxy)-phenylamine hydrochloride and 4-(4-fluorophenyl)-2-isopropyl-3,5-dioxo-2,3,4,5-tetrahydro-1,2,4-triazine-6-carboxylic acid using the procedure for example 103 to give a white solid, LCMS m/z=560 (M+1); $^1$H NMR (DMSO) δ: 10.98 (s, 1H), 8.88 (d, 1H, J=6.1 Hz), 8.43 (d, 1H, Example 112

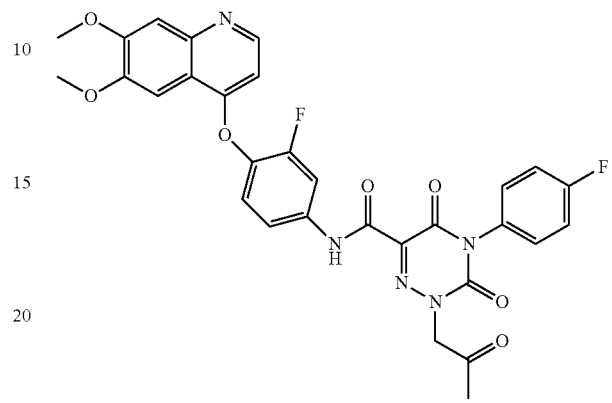

4-(4-Fluorophenyl)-3,5-dioxo-2-(2-oxo-propyl)-2,3,4,5-tetrahydro-[1,2,4]triazine-6-carboxylic acid [4-(6,7-dimethoxyquinolin-4-yloxy)-3-fluorophenyl]-amide. TFA salt off-white solid, LCMS m/z=604 (M+1); $^1$H NMR (DMSO) δ: 11.04 (s, 1H), 8.78 (d, 1H, J=6.3 Hz), 8.02 (dd 1H, J=11.5, 2.1 Hz), 7.73 (s, 1H), 7.62 (m, 2H), 7.55 (s, 1H), 7.39-7.34 (m, 4H), 6.94 (d, 1H, J=6.2 Hz), 4.02 (2 s, 6H), 2.25 (s, 3H).

Example 113

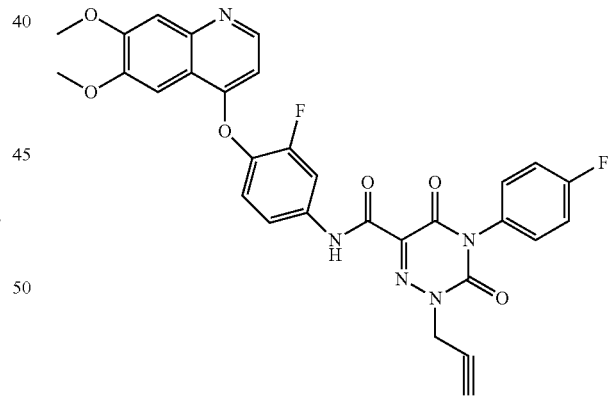

4-(4-Fluoro-phenyl)-3,5-dioxo-2-prop-2-ynyl-2,3,4,5-tetrahydro-[1,2,4]triazine-6-carboxylic acid [4-(6,7-dimethoxy-quinolin-4-yloxy)-3-fluoro-phenyl]-amide TFA salt. A mixture of example 107 (25 mg, 0.046 mmol), propargyl bromide (10 uL, 0.1 mmol), and potassium carbonate (10 mg, 0.07 mmol) in N,N-dimethylformamide (1 mL) was stirred at rt 18 h. The mixture was filtered, solvent was removed and the product was purified by reverse phase HPLC to give an off-white solid (7 mg, 30%). LCMS m/z=586 (M+1); $^1$H NMR (DMSO) δ: 10.99 (s, 1H), 8.71 (d, 1H, J=6.1 Hz), 8.0 (dd, 1H, J=2.3, 12.7 Hz), 7.68 (s, 1H), 7.65-7.58 (m, 2H), 7.4 (s, 1H), 7.37-7.35 (m, 4H), 6.84 (d, 1H, J=5.8 Hz), 4.88 (d, 2H, J=2.3 Hz), 4.01 (2 s, 6H), 3.53 (s, 3H).

Example 114

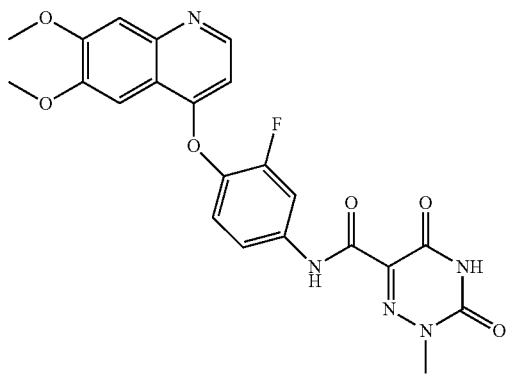 [SMILES: COc1cc2nccc(Oc3ccc(NC(=O)c4nn(C)c(=O)[nH]c4=O)cc3F)c2cc1OC]

2-Methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide. TFA salt. A mixture of 2-methyl-3,5-dioxo-2,3,4,5-tetrahydro-1,2,4-triazine-6-carboxylic acid (500 mg, 3 mmol) (Yuen, K. *J Org. Chem.* 1962, 27, 976), 4-(6,7-dimethoxyquinolin-4-yloxy)-3-fluorophenylamine (0.80 g, 2.54 mmol) and N,N,N',N'-tetramethyl-O-(7-azabenzotriazol-1-yl)uronium hexafluorophosphate (1.06 g, 2.80 mmol) and N,N-diisopropylethylamine (1.33 mL, 7.64 mmol) in N,N-dimethylformamide (8 mL) was stirred at rt 18 h. The solvent was removed and the residue was triturated with DCM collected and dried. Yield-quantitative, LCMS m/z=468 (M+1); $^1$H NMR (DMSO) δ: 12.69 (br s, 1H), 11.01 (s, 1H), 8.77 (d, 1H, J=6.2 Hz), 8.01 (dd, 1H, J=2.2, 11.4 Hz), 7.72 (s, 1H), 7.64-7.57 (m, 2H), 7.56 (s, 1H), 6.92 (d, 1H, J=5.6 Hz), 4.03 (2 s, 6H), 3.58 (s, 3H).

Example 115

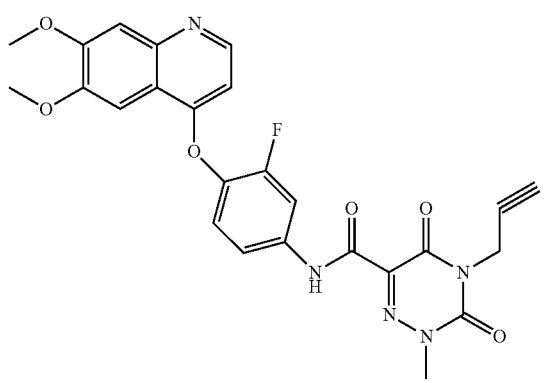 [SMILES: C#CCn1c(=O)c(C(=O)Nc2ccc(Oc3ccnc4cc(OC)c(OC)cc34)c(F)c2)nn(C)c1=O]

2-Methyl-3,5-dioxo-4-prop-2-ynyl-2,3,4,5-tetrahydro-[1,2,4]triazine-6-carboxylic acid [4-(6,7-dimethoxy-uinolin-4-yloxy)-3-fluoro-phenyl]-amide. TFA salt. A mixture of example 114 (100 mg, 0.2 mmol), propargyl bromide (60 uL, 0.7 mmol), and potassium carbonate (44.4 mg, 0.321 mmol) in N,N-dimethylformamide (3 mL) was stirred at rt 18 h. The mixture was filtered and the solvent was removed. The product was purified by reverse phase HPLC to give an off-white solid (36 mg, 30%). LCMS m/z=506 (M+1); $^1$H NMR (DMSO) δ: 10.98 (s, 1H), 8.79 (d, 1H, J=6.2 Hz), 8.00 (dd, 1H, J=2.3, 12.5 Hz), 7.72 (s, 1H), 7.66-7.58 (m, 2H), 7.53 (s, 1H), 6.92 (d, 1H, J=6.1 Hz), 4.61 (d, 2H, J=2.4 Hz), 4.03 (2 s, 6H), 3.65 (s, 3H), 3.29 (t, 1H, J=2.4 Hz).

The following examples were synthesized from Example 114 using the procedure for Example 115.

Example 116

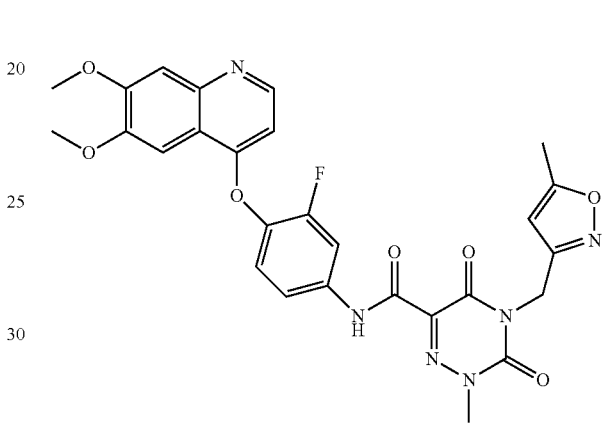

2-Methyl-4-(5-methyl-isoxazol-3-ylmethyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide. TFA salt. Off-white solid; LCMS m/z=563 (M+1); $^1$H NMR (DMSO) δ: 10.99 (s, 1H), 8.76 (d, J=6.2 Hz, 1H), 8.0 (dd, 1H, J=2.2, 12.6 Hz), 7.71 (s, 1H), 7.66-7.53 (m, 2H), 7.71 (s, 1H), 6.80 (d, 1H, J=6.0 Hz), 6.27 (s, 1H), 5.05 (s, 2H), 4.02 (2 xs, 6H), 3.66 (s, 3H), 2.38 (s, 3H).

Example 117

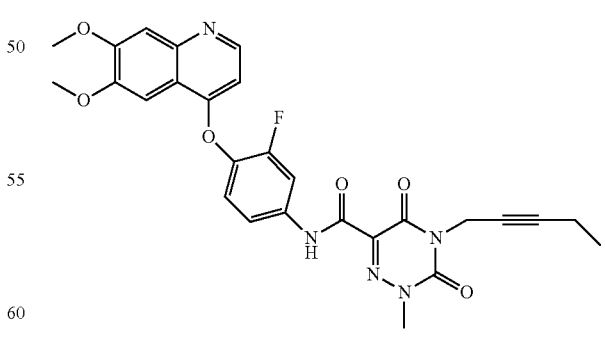

2-Methyl-3,5-dioxo-4-pent-2-ynyl-2,3,4,5-tetrahydro-[1,2,4]triazine-6-carboxylic acid [4-(6,7-dimethoxy-uinolin-4-yloxy)-3-fluoro-phenyl]-amide. TFA salt. yellowish solid. LCMS m/z=534 (M+1); $^1$H NMR (DMSO) δ: 10.98 (s, 1H), 8.75 (d, 1H, J=6.2 Hz), 8.00 (dd, 1H, J=2.3, 12.5 Hz), 7.71 (s, 1H), 7.66-7.57 (m, 2H), 7.53 (s, 1H), 6.89 (d, 1H, J=6.0 Hz), 4.56 (s, 2H), 4.02 (2 s, 6H), 3.65 (s, 3H), 2.18 (m, 2H), 1.04 (t, 3H, J=7.5 Hz).

Example 118

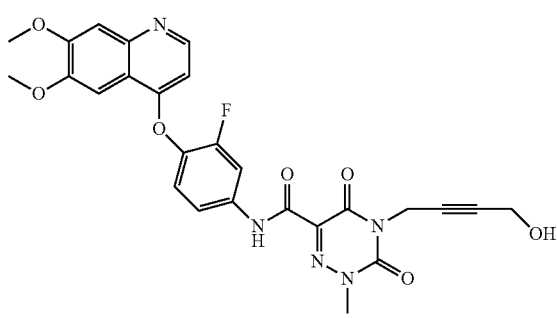 [SMILES: COc1cc2nccc(Oc3ccc(NC(=O)c4nn(C)c(=O)n(CC#CCO)c4=O)cc3F)c2cc1OC]

4-(4-Hydroxy-but-2-ynyl)-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide. TFA salt Off-white solid; LCMS m/z=536 (M+1); $^1$H NMR (DMSO) δ: 10.98 (s, 1H), 8.74 (d, J=6.1 Hz, 1H), 7.99 (dd, 1H, J=2.1, 12.7 Hz), 7.70 (s, 1H), 7.65-7.54 (m, 2H), 7.51 (s, 1H), 6.87 (d, 1H, J=5.9 Hz), 4.65 (s, 2H), 4.07 (s, 2H), 4.02 (2xs, 6H), 3.65 (s, 2H).

Example 119

4-(1,5-Dimethyl-1H-pyrazol-3-ylmethyl)-2-methyl-3,5-dioxo-2,3,4,5-tetrahydro-[1,2,4]triazine-6-carboxylic acid [4-(6,7-dimethoxyquinolin-4-yloxy)-3-fluorophenyl]-amide. TFA salt Off-white solid; LCMS m/z=576 (M+1); $^1$H NMR (DMSO) δ: 11.00 (s, 1H), 8.81 (d, 1H, J=6.3 Hz), 8.01 (d, 1H, 11.2 Hz), 7.74 (s, 1H), 7.65-7.59 (s, m, 3H), 6.96 (d, 1H, J=5.9 Hz), 6.02 (s, 1H), 5.01 (s, 2H), 4.04 (s, 6H), 3.84 (s, 3H), 3.65 (s, 3H), 2.07 (s, 3H). 13.30 (s, 1H), 10.97 (s, 1H), 8.71 (d, 1H, J=6.0 Hz), 8.02 (dd, 1H, J=12.7, 2.3 Hz), 7.68 (s, 1H), 7.65 (m, 1H), 7.65 (m, 1H), 7.56 (m, 1H), 7.5 (s, 1H), 7.46-7.31 (2 m, 4H), 6.83 (d, 1H, J=6.3 Hz), 4.01 (s, 6H).

Example 120

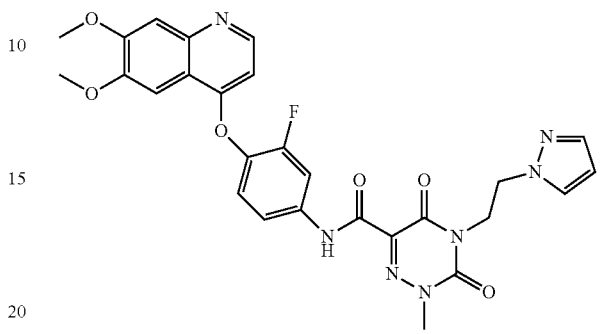

2-Methyl-3,5-dioxo-4-(2-pyrazol-1-yl-ethyl)-2,3,4,5-tetrahydro-[1,2,4]triazine-6-carboxylic acid [4-(6,7-dimethoxyquinolin-4-yloxy)-3-fluorophenyl]-amide. TFA salt Off-white solid. LCMS m/z=562 (M+1); $^1$H NMR (DMSO) δ: 10.98 (s, 1H), 8.77 (d, 1H, J=6.0 Hz), 8.01 (dd, 1H, J=2.2, 12.6 Hz), 7.77 (d, 1H, J=2.0 Hz), 7.72 (s, 2H), 7.66-7.57 (m, 2H), 7.55 (s, 1H), 7.42 (d, 1H, J=1.4 Hz), 6.90 (d, 1H, J=6.0 Hz)), 6.22 (d, 1H, J=1.9 Hz), 4.39 (m, 2H), 4.22 (m, 2H), 4.03 (2 s, 6H), 3.61 (s, 3H).

Example 121

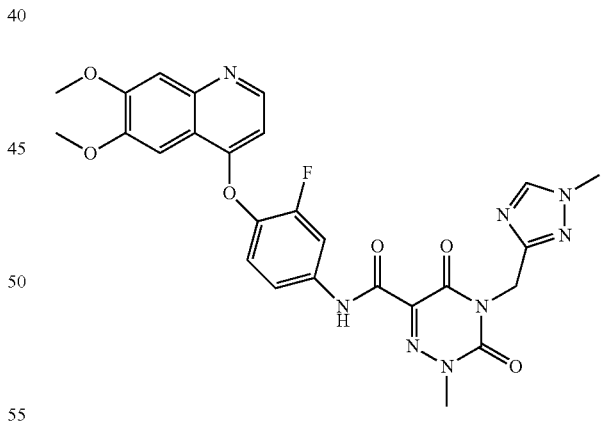

2-Methyl-4-(1-methyl-1H-[1,2,4]triazol-3-ylmethyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt Off-white solid; LCMS m/z=563 (M+1); $^1$H NMR (DMSO) δ: 11.06 (s, 1H), 8.78 (d, 1H, J=6.3 Hz), 8.39 (s, 1H), 7.99 (dd, 1H, J=2.3, 12.5 Hz), 7.93 (s, 1H), 7.68-7.58

(m, 2H), 7.73 (s, 1H), 6.93 (d, 1H, J=6.2 Hz), 5.06 (s, 2H), 4.03 (s, 3H), 4.02 (s, 3H), 3.81 (s, 3H), 3.66 (s, 3H).

Example 122

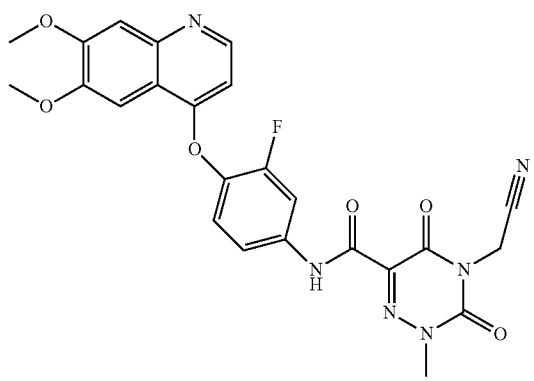 [SMILES: COc1cc2nccc(Oc3ccc(NC(=O)c4nn(C)c(=O)n(CC#N)c4=O)cc3F)c2cc1OC]

4-Cyanomethyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide. TFA salt; LCMS m/z=507 (M+1); $^1$H NMR (DMSO) δ: 10.95 (s, 1H), 8.76 (d, 1H, J=6.2 Hz), 7.81 (dd, 1H, J=2.2, 12.6 Hz), 7.72 (s, 1H), 7.68-7.58 (m, 2H), 7.56 (s, 1H), 4.92 (s, 2H), 4.03 (s, 3H), 4.02 (s, 3H), 3.66 (s, 3H).

Example 123

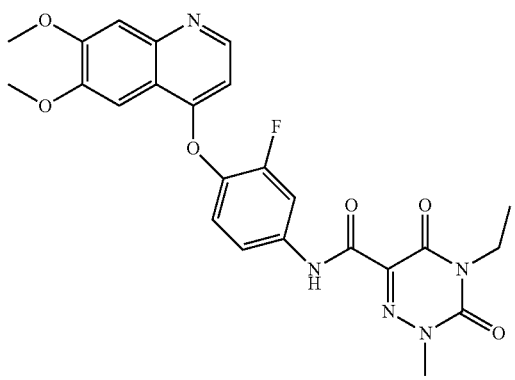 [SMILES: CCn1c(=O)c(C(=O)Nc2ccc(Oc3ccnc4cc(OC)c(OC)cc34)c(F)c2)nn(C)c1=O]

4-Ethyl-2-methyl-3,5-dioxo-2,3,4,5-tetrahydro-[1,2,4]triazine-6-carboxylic acid [4-(6,7-dimethoxyquinolin-4-yloxy)-3-fluoro-phenyl]-amide TFA salt. LCMS m/z=496 (M+1); $^1$H NMR (DMSO) δ: 11.03 ((s, 1H), 8.78 (d, 1H, J=6.2 Hz), 8.04 (dd, 1H, J=2.2, 12.6 Hz), 7.72 (s, 1H), 7.67-

7.58 (m, 2H), 7.55 (s, 1H), 6.92 (d, 1H, J=6.2 Hz), 4.03 (s, 6H), 3.89 (q, 2H, J=7.1 Hz), 3.64 (s, 3H), 1.18 (t, 3H, J=7.1 Hz).

Example 124

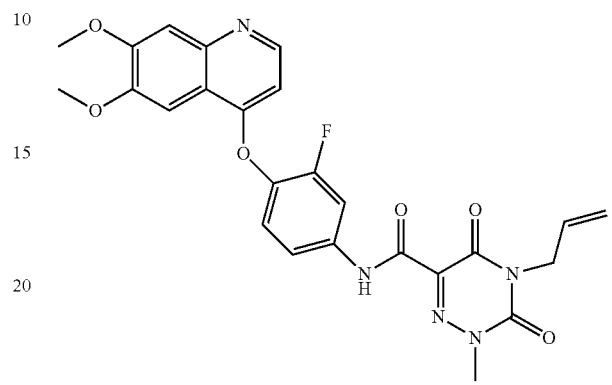

4-Allyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt. LCMS m/z=508 (M+1); $^1$H NMR DMSO) δ: 11.00 (s, 1H), 8.76 (d, 1H, J=6.2 Hz), 8.02 (dd, 1H, J=2.0, 12.6 Hz), 7.72 (s, 1H), 7.67-7.57 (m, 2H), 7.53 (s, 1H), 6.90 (d, 1H, J=6.0 Hz), 5.84 (m, 1H), 5.23 (ddd, 2H, J=25.8, 7.2 and 1.4 Hz), 4.46 (d, 1H, J=4.3 Hz), 4.03 (2 s, 6H), 3.65 (s, 3H).

Example 125

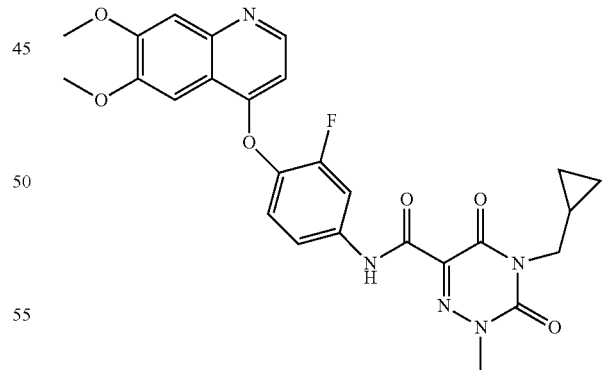

4-Cyclopropylmethyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt. LCMS m/z=522 (M+1); $^1$H NMR (DMSO) δ: 11.01 (s, 1H), 8.74 (d, 1H, J=6.1 Hz), 8.01 (m, 1H), 7.70 (s, 1H), 7.65-7.59 (m, 2H), 7.53 (s, 1H), 6.87 (d, 1H, J=6.0 Hz), 4.02

(2 s, 6H), 3.92 (m, 1H), 3.75 (d, 1H, J=7.0 Hz), 3.64 (s, 3H), 2.36 (m, 2H), 1.18 (m, 1H), 0.49 (m, 1H), 0.38 (m, 1H).

2H), 7.53 (s, 1H), 6.90 (d, 1H, J=5.9 Hz), 4.03 (2 s, 6H), 3.70 (d, 2H, J=7.3 Hz), 3.64 (s, 3H), 2.07 (m, 1H), 0.90 (d, 6H, J=6.7 Hz).

Example 126

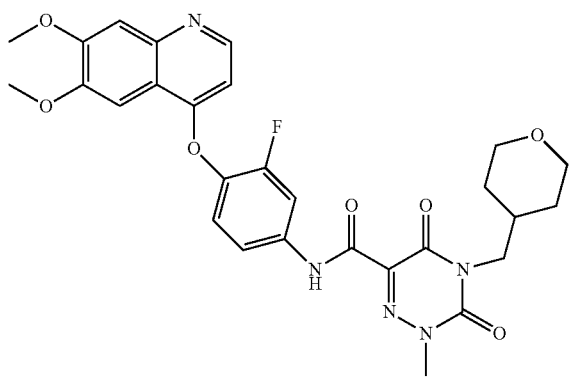 [SMILES: COc1cc2nccc(Oc3ccc(NC(=O)c4nn(C)c(=O)n(CC5CCOCC5)c4=O)cc3F)c2cc1OC]

2-Methyl-3,5-dioxo-4-(tetrahydro-pyran-4-ylmethyl)-2,3,4,5-tetrahydro-[1,2,4]triazine-6-carboxylic acid [4-(6,7-dimethoxy-quinolin-4-yloxy)-3-fluoro-phenyl]-amide TFA salt LCMS m/z=566 (M+1); ¹H NMR (DMSO) δ: 10.99 (s, 1H), 8.75 (d, 1H, J=6.1 Hz), 8.01 (dd, 1H, J=12.6, 2.3 Hz), 7.71 (s, 1H), 7.65-7.57 (m, 2H), 7.52 (s, 1H), 6.88 (d, 1H, J=6.1 Hz), 4.02 (2 s, 6H), 3.84 (m, 2H), 3.76 (d, 2H, J=7.0 Hz), 3.64 (s, 3H), 3.24 (m, 3H), 2.02 (m, 1H), 1.57 (m, 2H), 1.27 (m, 2H).

Example 127

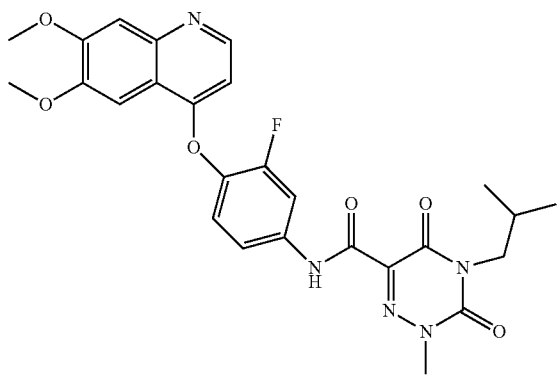 [SMILES: COc1cc2nccc(Oc3ccc(NC(=O)c4nn(C)c(=O)n(CC(C)C)c4=O)cc3F)c2cc1OC]

4-Isobutyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt. LCMS m/z=524 (M+1); ¹H NMR (DMSO) δ: 11.02 (s, 1H), 8.76 (d, 1H, J=6.2 Hz), 8.01 (dd, 1H, J=2.3, 12.6 Hz), 7.71 (s, 1H), 7.66-7.57 (m, Example 128

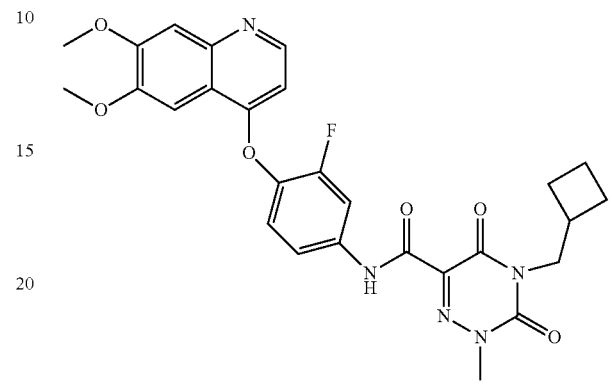

4-Cyclobutylmethyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide. TFA salt. LCMS m/z=536 (M+1); ¹H NMR (DMSO) δ: 11.02 (s, 1H), 8.79 (d, 1H, J=6.3 Hz), 8.01 (dd, 1H, J=2.2, 12.4 Hz), 7.74 (s, 1H), 7.69-7.58 (m, 2H), 7.55 (s, 1H), 6.95 (d, 1H, J=6.2 Hz), 4.03 (s, 6H), 3.92 (d, 2H, J=7.0 Hz), 3.63 (s, 3H), 2.66 (m, 1H), 1.99 (m, 2H), 1.81 (m, 4H).

Example 129

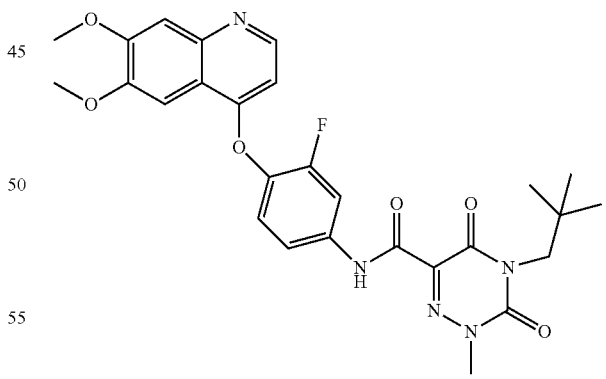

4-(2,2-Dimethylpropyl)-2-methyl-3,5-dioxo-2,3,4,5-tetrahydro-[1,2,4]triazine-6-carboxylic acid [4-(6,7-dimethoxyquinolin-4-yloxy)-3-fluorophenyl]-amide TFA salt. LCMS m/z=538 (M+1); ¹H NMR (DMSO) δ: 11.0 (s, 1H), 8.72 (d, 1H, J=6.0 Hz), 7.99 (dd, 1H, J=2.2, 12.5 Hz), 7.69 (s, 1H), 7.63-7.55 (m, 2H), 7.50 (s, 1H), 6.83 (d, 1H, J=5.8 Hz), 4.01 (2 s, 6H), 3.63 (s, 3H), 0.94 (s, 9H).

Example 130

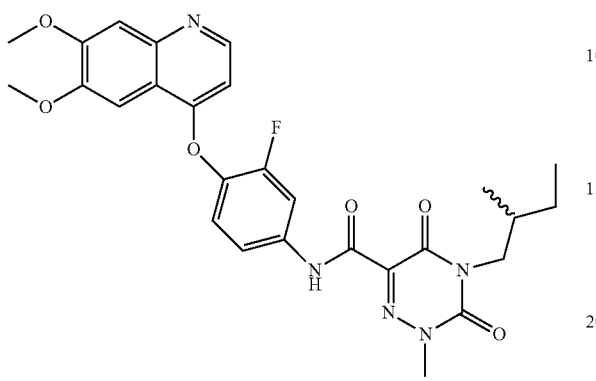

±2-Methyl-4-(2-methyl-butyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt. LCMS m/z=538 (M+1); $^1$H NMR (DMSO) δ: 11.01 (s, 1H), 8.76 (d, 1H, J=6.2 Hz), 8.01 (dd, 1H, J=2.2, 12.6 Hz), 7.71 (s, 1H), 7.66-7.57 (m, 2H), 7.53 (s, 1H), 6.89 (d, 1H, J=6.1 Hz), 4.03 (2 s, 6H), 3.76 (m, 2H), 3.64 (s, 3H), 1.87 (m, 1H), 1.40 (m, 1H), 1.17 (m, 1H), 0.87 (m, 6H).

Example 131

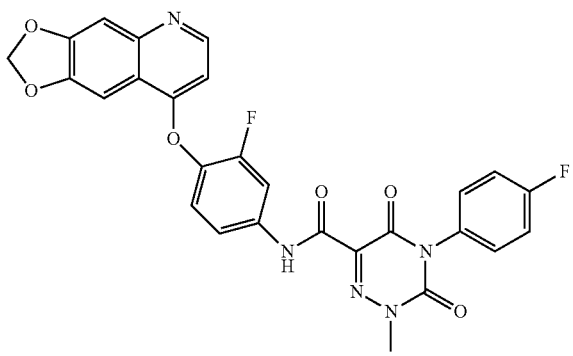 [SMILES: Cn1nc(C(=O)Nc2ccc(Oc3ccnc4cc5c(cc34)OCO5)c(F)c2)c(=O)n(-c2ccc(F)cc2)c1=O]

3-(4-Fluoro-phenyl)-1-methyl-2,4-dioxo-1,2,3,4-tetrahydro-pyrimidine-5-carboxylic acid [4-([1,3]dioxolo[4,5-g]quinolin-8-yloxy)-3-fluoro-phenyl]-amide, TFA salt. This compound was synthesized from 3-(4-fluorophenyl)-1-methyl-2,4-dioxo-1,2,3,4-tetrahydro-pyrimidine-5-carboxylic acid and 4-(1,3-dioxolo[4,5-g]quinolin-8-yloxy)-3-fluoro-phenylamine hydrochloride (LCMS m/z=299 (M+1); $^1$H NMR (DMSO) δ: 8.80 (d, 1H, J=6.6 Hz), 7.85 (s, 1H), 7.74 (s, 1H), 7.31 (t, 1H, J=8.9 Hz), 6.94 (dd, 1H, J=6.6, 0.8 Hz), 6.87 (dd, 1H, J=12.6, 2.2 Hz), 6.76 (d, 1H, J=12.6, 2.1 Hz), 6.43 (s, 2H); synthesized using the procedure for example 111 steps a-b)) using the procedure for examples 103. LCMS m/z=545 (M+1); $^1$H NMR (DMSO) δ: 11.08 (s, 1H), 8.89 (s, 1H), 8.69 (d, 1H, J=6.0 Hz), 8.43 (d, 1H, J=9.8 Hz), 8.05 (dd, 1H, J=12.8, 2.4 Hz), 7.76 (s, 1H), 7.68-7.52 (2 m and a s, 3H), 7.48-7.31 (m, 4H), 6.84 (d, 1H, J=5.9 Hz), 6.36 (s, 2H), 3.54 (s, 3H).

Example 132

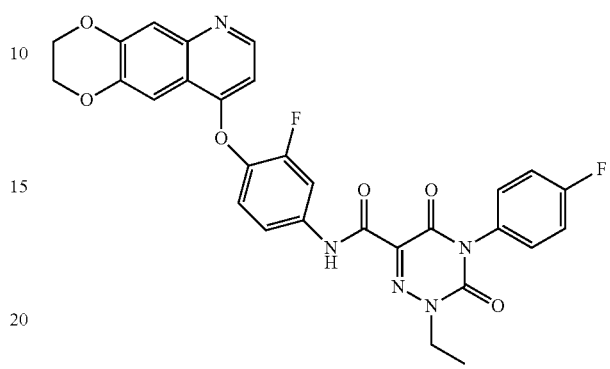

1-Ethyl-3-(4-fluorophenyl)-2,4-dioxo-1,2,3,4-tetrahydro-pyrimidine-5-carboxylic acid [4-(2,3-dihydro-[1,4]dioxino[2,3-g]quinolin-9-yloxy)-3-fluoro-phenyl]-amide TFA salt. This compound was synthesized from 1-ethyl-3-(4-fluorophenyl)-2,4-dioxo-1,2,3,4-tetrahydropyrimidine-5-carboxylic acid and 4-(2,3-dihydro-[1,4]dioxino[2,3-g]quinolin-9-yloxy)-3-fluorophenylamine using the procedure for examples 103. LCMS m/z=545 (M+1); $^1$H NMR (DMSO) δ: 11.09 (s, 1H), 8.89 (s, 1H), 8.78 (d, 1H, J=6.2 Hz), 8.43 (d, 1H, J=9.8 Hz), 8.07 (dd, 1H, J=12.8, 2.2 Hz), 7.83 (s, 1H), 7.62-7.50 (2 m and a s, 3H), 7.44-7.32 (2 m, 4H), 6.85 (d, 1H, J=6.1 Hz), 4.49 (m, 4H), 4.02 (q, 2H, J=7.0 Hz), 1.30 (t, 3H, J=7.0 Hz).

Example 133

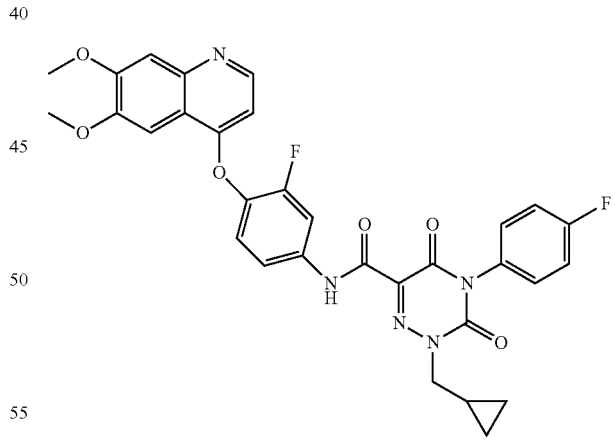

2-Cyclopropylmethyl-4-(4-fluorophenyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide TFA salt. This compound was synthesized from 1-cyclopropylmethyl-3-(4-fluorophenyl)-2,4-dioxo-1,2,3,4-tetrahydropyrimidine-5-carboxylic acid and 4-(6,7-dimethoxyquinolin-4-yloxy)-3-fluorophenylamine using the procedure for example 103. LCMS m/z=602 (M+1); $^1$H NMR (DMSO) δ: 10.98 (s, 1H), 8.72 (d, 1H, J=5.9 Hz), 8.02 (dd 1H, J=12.6, 2.2 Hz), 7.69 (s, 1H), 7.66-7.56 (m, 2H), 7.50 (s, 1H), 7.45-7.36 (m and s, 4H), 7.27 (m, 1H), 6.85 (d, 1H, J=5.1 Hz), 5.12 (m, 1H), 4.02 (m and 2 s, 7H), 2.49 (m, 1H), 2.32 (m, 2H), 1.80 (m, 2H).

Example 134

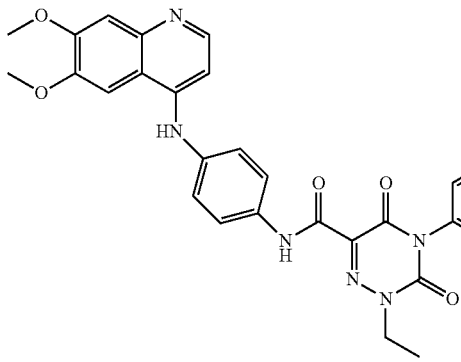

Step a. 4-Chloro-6,7-dimethoxyquinoline (0.40 g, 1.79 mmol, p-nitroaniline (0.414 g, 2.68 mmol) and p-toluenesulfonic acid (0.154 g, 0.894 mmol) in 1-methoxy-2-propanol (5 mL) were heated to 120° C. for 8 h. The mixture was cooled to rt, triturated with ether and filtered to yield (6,7-dimethoxyquinolin-4-yl)-(4-nitrophenyl)amine (0.43 g, 73%). LCMS m/z=326 (M+1); $^1$H NMR (DMSO) δ: 14.37 (s, 1H), 10.72 (s, 1H), 8.54 (d, 1H, J=6.80 Hz), 8.39 (d, 2H, J=9.08 Hz), 8.05 (s, 1H), 7.74 (d, 2H, J=9.09 Hz), 7.47 (d, 1H, 8.13 Hz), 7.43 (s, 1H), 7.19 (d, 1H, J=6.85), 7.10 (d, 1H, J=7.84), 4.02 (d, 7H, J=5.48), 2.28, (s, 1H).

Step b. N-(6,7-Dimethoxyquinolin-4-yl)-benzene-1,4-diamine. (6,7-Dimethoxyquinolin-4-yl)-(4-nitrophenyl)amine (0.425 g, 1.31 mmol), palladium hydroxide (0.0844 g, 0.601 mmol) and potassium carbonate (0.542 g, 3.92 mmol) in methanol (106 mL) were hydrogenation on a Parr apparatus at 40 psi overnight. The mixture was filtered through Celite and concentrated to yield a crude product which was purified by prep. HPLC to yield N-(6,7-dimethoxyquinolin-4-yl)-benzene-1,4-diamine (0.13 g, 33%). LCMS m/z=296 (M+1).

Step c. 1-Ethyl-3-(4-fluoro-phenyl)-2,4-dioxo-1,2,3,4-tetrahydro-pyrimidine-5-carboxylic acid [4-(6,7-dimethoxyquinolin-4-ylamino)-phenyl]-amide 1-Ethyl-3-(4-fluorophenyl)-2,4-dioxo-1,2,3,4-tetrahydropyrimidine-5-carboxylic acid (0.104 g, 0.372 mmol), and N,N,N',N'-tetramethyl-O-(7-azabenzotriazol-1-yl)uranium hexafluorophosphate (0.154 g, 0.406 mmol) in N,N-dimethylformamide (5 mL) was added N,N-diisopropylethylamine (0.425 mL, 2.44 mmol). After 15 min N-(6,7-dimethoxyquinolin-4-yl)-benzene-1,4-diamine (0.10 g, 0.34 mmol) was added and stirred at rt for 18 h. The reaction mixture was evaporated under vacuum, quenched with saturated NaHCO$_3$ solution and extracted with CH$_2$Cl$_2$. The combined organics were washed with brine, dried (Na$_2$SO$_4$), filtered and concentrated to obtain a crude product which was purified by prep. HPLC to give a brown solid (0.58 g, 31%). mp=178-181° C. (CHCl$_2$, MeOH, ether and hexane); LCMS m/z=556 (M+H); $^1$H NMR (DMSO-d6) δ: 10.85 (s, 1H), 8.85 (s, 1H), 8.65 (s, 1H), 8.25 (d, 1H, J=6.3 Hz), 7.70 (d, 2H, J=8.8 Hz), 7.65 (s, 2H), 7.45-7.29 (m, 7H), 7.23 (s, 1H), 6.74 (d, 1H, J=5.3 Hz), 4.01 (d, 2H, J=7.1 Hz), 3.91 (d, 7H, J=10.6), 1.30 (t, 3H, J=7.1).

Example 135

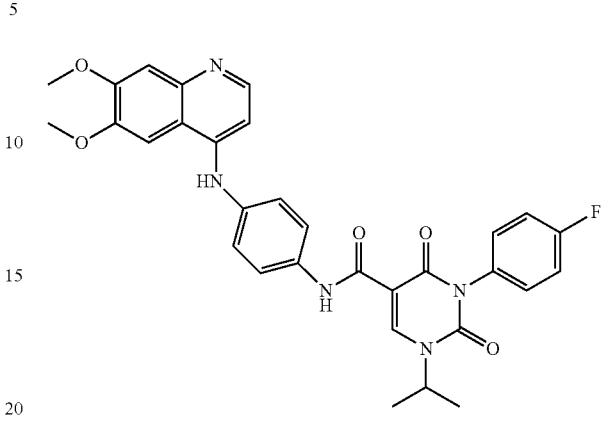

3-(4-Fluorophenyl)-1-isopropyl-2,4-dioxo-1,2,3,4-tetrahydropyrimidine-5-carboxylic acid [4-(6,7-dimethoxyquinolin-4-ylamino)-phenyl]-amide. This compound was synthesized using N-(6,7-dimethoxyquinolin-4-yl)-benzene-1,4-diamine and 3-(4-fluorophenyl)-1-isopropyl-2,4-dioxo-1,2,3,4-tetrahydropyrimidine-5-carboxylic acid the method for example 134. mp=190-193° C.; LCMS m/z=570 (M+1); $^1$H NMR (DMSO-d$_6$) δ: 10.85 (s, 1H), 8.65 (brs, 2H), 8.26 (d, 1H, J=5.3 Hz), 7.71 (d, 2H, J=8.8 Hz), 7.65 (s, 1H), 7.27-7.47 (m, 7H), 7.23 (s, 1H), 6.75 (d, 1H, J=5.3 Hz), 4.72-4.84 (m, 1H), 3.92 (s, 3H), 3.90 (s, 3H), 1.42 (d, 7H, J=6.8 Hz).

Example 136

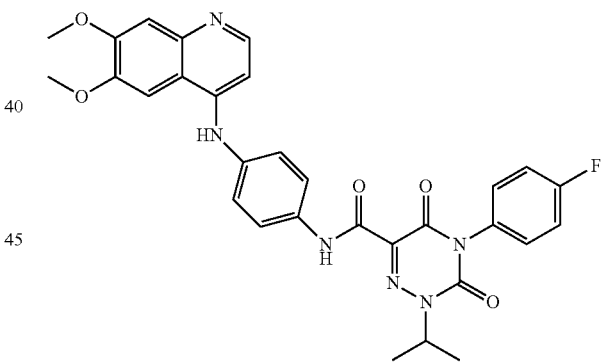

4-(4-Fluoro-phenyl)-2-isopropyl-3,5-dioxo-2,3,4,5-tetrahydro-[1,2,4]triazine-6-carboxylic acid [4-(6,7-dimethoxy-quinolin-4-ylamino)-phenyl]-amide. This compound was synthesized using N-(6,7-dimethoxyquinolin-4-yl)-benzene-1,4-diamine and 4-(4-fluorophenyl)-2-isopropyl-3,5-dioxo-2,3,4,5-tetrahydro[1,2,4]triazine-6-carboxylic acid by the method for example 134. mp=152-155° C.; LCMS m/z=571 (M+1); $^1$H NMR (DMSO-d$_6$) δ: 8.67 (s, 1H), 7.68 (d, 2H, J=8.87 Hz), 7.54 (d, 2H, J=8.68 Hz), 7.20-7.34 (m, 12H), 7.10 (brs, 1H), 6.99 (s, 1H), 6.60 (d, 2H, J=8.6 Hz), 4.04 (d, 7H, J=2.2 Hz), 3.79 (brs, 2H), 1.21 (t, 1H, J=7.0 Hz), 0.81-0.91 (m, 1H).

Example 137

Step a. 4-[(6,7-dimethoxy-4-quinolyl)sulfanyl]aniline. 4-Chloro-6,7-dimethoxyquinoline (0.40 g, 1.79 mmol) and 4-aminothiophenol (0.379 g, 2.68 mmol) in N,N-dimethylformamide (5 mL) was stirred at rt for 8 h. The product was extracted with calcium carbonate, washed with brine, dried with sodium sulfate, filtered and concentrated. The crude product was dissolved in CH₂Cl₂ and was recrystallized with ether and hexanes, and was filtered to yield 4-[(6,7-dimethoxy-4-quinolyl)sulfanyl]aniline (0.49 g, 88%) as a yellow solid. mp=235-238° C. LCMS m/z=313 (M+1); ¹H NMR (CDCl₃) δ: δ 8.58 (d, 1H, J=6.41 Hz), 7.51 (s, 1H), 7.46 (s, ¹H), 7.31 (d, 2H, J=8.7 Hz), 6.81 (d, 1H, J=6.1 Hz), 6.77 (d, 2H, J=8.6 Hz), 4.03 (d, 7H, J=5.6 Hz).

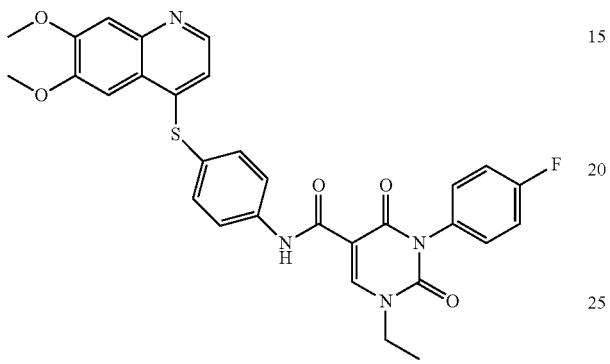

Step b. 1-Ethyl-3-(4-fluorophenyl)-2,4-dioxo-1,2,3,4-tetrahydro-pyrimidine-5-carboxylic acid [4-(6,7-dimethoxy-quinolin-4-ylsulfanyl)-phenyl]-amide. 1-Ethyl-3-(4-fluorophenyl)-2,4-dioxo-1,2,3,4-tetrahydropyrimidine-5-carboxylic acid and 4-(6,7-dimethoxyquinolin-4-ylsulfanyl)phenylamine were coupled using the procedure for example 134 to produce 1-ethyl-3-(4-fluoro-phenyl)-2,4-dioxo-1,2,3,4-tetrahydro-pyrimidine-5-carboxylic acid [4-(6,7-dimethoxy-quinolin-4-ylsulfanyl)-phenyl]-amide as a white solid, mp=241-244° C.; LCMS m/z=573 (M+1); ¹H NMR (DMSO-d₆) δ: 11.04 (s, 1H), 8.88 (s, 1H), 8.43 (d, 1H, J=4.8 Hz), 7.84 (d, 2H, J=8.72 Hz), 7.58 (d, 2H, J=8.7 Hz), 7.30-7.44 (m, 6H), 6.64 (d, 1H, J=4.9 Hz), 4.01 (q, 2H, J=7.05 Hz), 3.96 (q, 7H, J=6.4 Hz), 1.29 (t, 3H, J=7.1 Hz).

Example 138

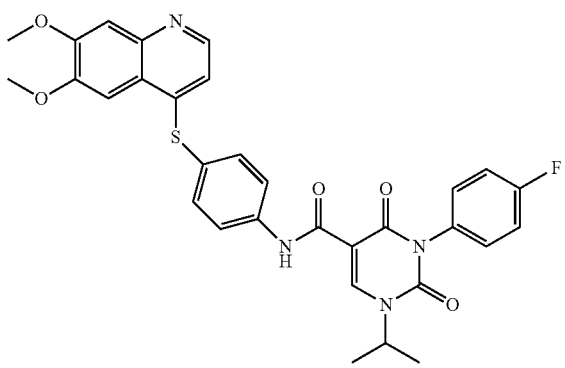 [SMILES: COc1cc2nccc(Sc3ccc(NC(=O)c4cn(C(C)C)c(=O)n(-c5ccc(F)cc5)c4=O)cc3)c2cc1OC]

3-(4-Fluoro-phenyl)-1-isopropyl-2,4-dioxo-1,2,3,4-tetrahydro-pyrimidine-5-carboxylic acid [4-(6,7-dimethoxy-quinolin-4-ylsulfanyl)-phenyl]-amide. This compound was synthesized using the procedure for example 134 to give a light tan solid. mp=236-239° C.; LCMS m/z=587 (M+1); ¹H NMR (DMSO-d₆) a: 11.04 (s, 1H), 8.67 (s, 1H), 8.44 (d, 1H, J=4.8 Hz), 7.84 (d, 2H, J=8.78 Hz), 7.58 (d, 2H, J=8.7 Hz), 7.30-7.47 (m, 7H), 6.71 (d, 2H, J=4.9 Hz), 4.72-4.81 (m, 1H), 3.92 (d, 7H, J=7.1 Hz), 1.42 (d, 7H, J=6.8).

Example 139

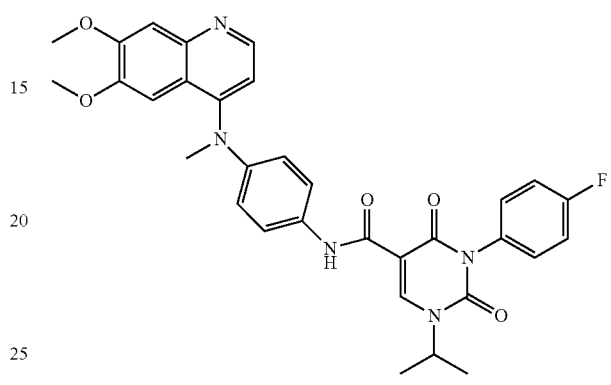

Step a. 4-Chloro-6,7-dimethoxyquinoline (0.50 g, 2.24 mmol), N-methyl(4-nitrophenyl)amine; (0.564 g, 3.35 mmol) and p-toluenesulfonic acid (0.192 g, 1.12 mmol) in 1-methoxy-2-propanol (6.56 mL, 67.1 mmol) were heated to 120° C. for 8 h. The reaction was cooled to rt, triturated with ether and filtered to yield (6,7-dimethoxyquinolin-4-yl)methyl(4-nitrophenyl)amine (0.40 g, 40%). LCMS m/z=340 (M+1); ¹H NMR (CDCl3) δ: 8.80 (d, 1H, J=4.8 Hz), 8.10 (d, 2H, J=9.4 Hz), 7.5 (brs, 1H), 7.16 (d, 1H, J=4.8), 6.84 (s, 1H), 6.64 (d, 2H, J=9.4 Hz), 4.05 (s, 3H), 3.81 (s, 3H), 3.52 (s, 3H).

Step b. (6,7-Dimethoxyquinolin-4-yl)-methyl-(4-nitrophenyl)amine (0.30 g, 0.88 mmol), potassium carbonate (1.3 g, 9.4 mmol) and palladium hydroxide (1.00 g, 7.12 mmol) was hydrogenated in a mixture of ethanol (32 mL, 540 mmol), N,N-dimethylformamide (5 mL, 60 mmol) and methylene chloride (19 mL, 290 mmol) at 40 psi overnight. The mixture was filtered through Celite, and washed with calcium carbonate solution and brine then dried over sodium sulfate and concentrated to yield a crude product. This material was purified by prep. HPLC to yield [N-(6,7-Dimethoxy-quinolin-4-yl)-N-methyl-benzene-1,4-diamine (0.180 g, 66%). LCMS m/z=310 (M+1).

Step c. 3-(4-Fluorophenyl)-1-isopropyl-2,4-dioxo-1,2,3,4-tetrahydropyrimidine-5-carboxylic acid {4-[(6,7-dimethoxy-quinolin-4-yl)-methyl-amino]-phenyl}-amide. This compound was synthesized using 3-(4-fluorophenyl)-1-isopropyl-2,4-dioxo-1,2,3,4-tetrahydro-pyrimidine-5-carboxylic acid and N-(6,7-dimethoxyquinolin-4-yl)-N-methyl-benzene-1,4-diamine by the method described for example 134. mp=224-227° C.; LCMS m/z=584 (M+1); ¹H NMR (CDCl₃) δ: 10.66 (s, 1H), 8.65 (s, 1H), 8.64 (d, 1H, J=5.0 Hz), 7.51 (d, 2H, J=9.0 Hz), 7.38 (s, 1H), 7.00 (d, 1H, J=5.8 Hz), 6.90 (s, 1H), 6.86 (d, 2H, J=9.0 Hz), 4.90-5.00 (m, 1H), 4.00 (t, 3H), 3.63 (t, 3H), 3.44 (t, 3H).

Example 140

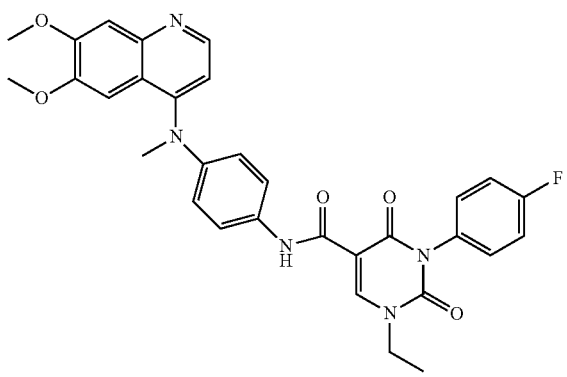 [SMILES: CCn1cc(C(=O)Nc2ccc(N(C)c3ccnc4cc(OC)c(OC)cc34)cc2)c(=O)n(-c2ccc(F)cc2)c1=O]

1-Ethyl-3-(4-fluorophenyl)-2,4-dioxo-1,2,3,4-tetrahydro-pyrimidine-5-carboxylic acid {4-[(6,7-dimethoxy-quinolin-4-yl)-methylamino]-phenyl}-amide. This compound was synthesized using 1-ethyl-3-(4-fluorophenyl)-2,4-dioxo-1,2,3,4-tetrahydropyrimidine-5-carboxylic acid and N-(6,7-dimethoxyquinolin-4-yl)-N-methyl-benzene-1,4-diamine by the method described for example 134. mp=199-202° C.; LCMS m/z=570 (M+1); $^1$H NMR (CDCl$_3$) δ: 10.62 (s, 1H), 8.64 (d, 1H, J=5.0 Hz), 8.60 (s, 1H), 7.50 (d, 2H, J=9.0 Hz), 7.38 (s, 1H), 7.31 (s, 1H), 7.00 (d, 1H, J=5.3 Hz), 6.90 (s, 1H), 6.86 (d, 2H J=8.9 Hz), 4.01 (s, 1H), 4.00 (s, 3H), 3.63 (s, 3H), 3.44 (s, 3H).

Example 141

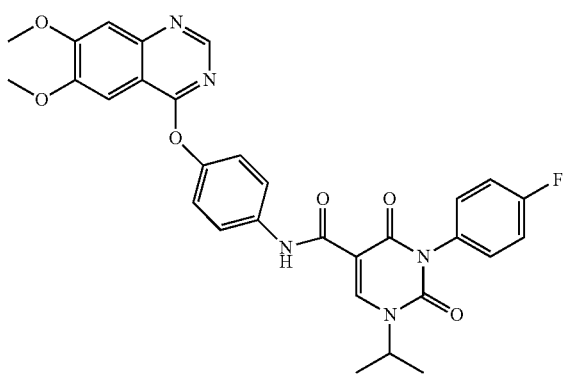 [SMILES: COc1cc2ncnc(Oc3ccc(NC(=O)c4cn(C(C)C)c(=O)n(-c5ccc(F)cc5)c4=O)cc3)c2cc1OC]

Step a. 4-(6,7-Dimethoxy-quinazolin-4-yloxy)-phenylamine. 4-Chloro-6,7-dimethoxy-quinazoline (0.500 g, 2.22 mmol), 4-aminophenol (0.291 g, 2.67 mmol), 2-butanone (4.01 mL, 44.5 mmol), 2N sodium hydroxide solution (1.00 mL, 0.213 mmol), and tetra-N-butylammonium bromide (0.308 g, 0.957 mmol) were combined and heated to reflux (80° C.) for 15 min. The reaction was cooled to rt. DCM was added and washed with calcium carbonate solution and brine, then dried over sodium sulfate and concentrated to yield a crude product. The solid was triturated with diethyl ether and hexanes to yield 4-(6,7-dimethoxyquinazolin-4-yloxy)-phenylamine (0.52 g, 78%). LCMS m/z=298 (M+1).

Step b. 3-(4-Fluoro-phenyl)-1-isopropyl-2,4-dioxo-1,2,3,4-tetrahydro-pyrimidine-5-carboxylic acid [4-(6,7-dimethoxy-quinazolin-4-yloxy)-phenyl]-amide. This compound was synthesized using 4-(6,7-dimethoxyquinazolin-4-yloxy)-phenylamine and 3-(4-fluorophenyl)-1-isopropyl-2,4-dioxo-1,2,3,4-tetrahydropyrimidine-5-carboxylic acid by the procedure for example 134. mp=238-241° C.; LCMS m/z=572 (M+1); $^1$H NMR (CDCl$_3$) δ: 10.86 (s, 1H), 8.70 (s, 1H), 8.62 (s, 1H), 7.76 (d, 2H, J=9.0 Hz), 7.54 (s, 1H), 7.32 (s, 1H), 4.90-5.03 (m, 1H), 4.06 (t, 7H, J=20 Hz).

Example 142

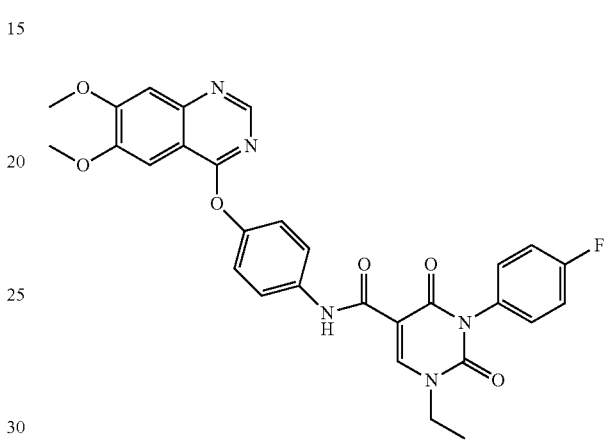

1-Ethyl-3-(4-fluorophenyl)-2,4-dioxo-1,2,3,4-tetrahydro-pyrimidine-5-carboxylic acid [4-(6,7-dimethoxy-quinazolin-4-yloxy)-phenyl]-amide. This compound was synthesized using 1-ethyl-3-(4-fluorophenyl)-2,4-dioxo-1,2,3,4-tetrahydropyrimidine-5-carboxylic acid and 4-(6,7-dimethoxy-quinazolin-4-yloxy)-phenylamine by the procedure for example 134. mp=238-241° C.; LCMS m/z=558 (M+H); 1H NMR (CDCl3): δ 10.82 (s, 1H), 8.63 (d, 2H J=6.5 Hz), 7.76 (d, 2H, J=9.0 Hz), 7.55 (s, 1H), 7.32 (s, 1H), 7.23 (d, 2H, J=8.9 Hz), 4.07 (s, 7H), 4.03 (q, 3H, J=7.2 Hz), 1.59 (s, 1H), 1.49 (s, 1H), 1.46 (t, 3H, 7.2 Hz), 1.20 (t, 1H, J=7.0 Hz), 1.03 (t, 1H, J=7.3 Hz).

Example 143

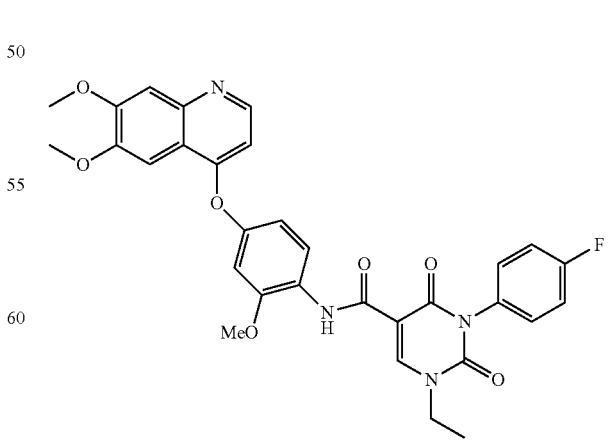

Step a. A solution of 4-chloro-6,7-dimethoxyquinoline (0.4 g, 2 mmol), 3-methoxy-4-nitrophenol (0.30 g, 1.8 mmol), and 4-dimethylaminopyridine (0.011 g, 0.089 mmol) in chlorobenzene (5 mL) was stirred at 140° C. overnight. After cooling to rt the solid that formed was filtered and dried to yield pure product 0.48 g (75%), MS: 357 (M+H).

Step b. 6,7-Dimethoxy-4-(3-methoxy-4-nitrophenoxy)quinoline was hydrogenated in EtOH/DMF using 10% Pd/C at 40 psi to yield 4-(6,7-dimethoxyquinolin-4-yloxy)-2-methoxy-phenylamine. LCMS m/z=327 (M+1); $^1$H NMR (DMSO) δ: 8.43 (d, 1H, J=6 Hz), 7.5 (s, 1H), 7.37 (s, 1H), 6.76 (d, 1H, J=2.6 Hz), 6.72 (d, 1H, J=9 Hz), 6.60 (dd, 1H, J=2.5, 8.5 Hz), 6.41 (d, 1H, J=5.6 Hz), 3.75 (s, 3H), 3.31 (s, 6H).

1-Ethyl-3-(4-fluorophenyl)-2,4-dioxo-1,2,3,4-tetrahydropyrimidine-5-carboxylic acid [4-(6,7-dimethoxy-quinolin-4-yloxy)-2-methoxyphenyl]-amide. This compound was synthesized using 4-(6,7-dimethoxyquinolin-4-yloxy)-2-methoxy-phenylamine and 1-ethyl-3-(4-fluorophenyl)-2,4-dioxo-1,2,3,4-tetrahydropyrimidine-5-carboxylic acid using the procedure for example 1. LCMS m/z=587 (M+1); $^1$H NMR (CDCl$_3$) δ: 11 (S, 1H), 8.63 (s, 1H), 8.54 (d, 1H, J=9 Hz), 8.49 (d, 1H, J=5 Hz), 7.55 (s, 1H), 7.42 (s, 1H), 7.26-7.23 (m, 3H), 6.82 (dd, 1H, J=3, 9 Hz), 6.74 (d, 1H, J=3 Hz), 6.52 (d, 1H, J=6 Hz), 4.05 (d, 6H), 4.01 (q, 2H, J=8 Hz), 3.85 (s, 3H), 1.45 (t, 3H, J=8 Hz).

Example 144

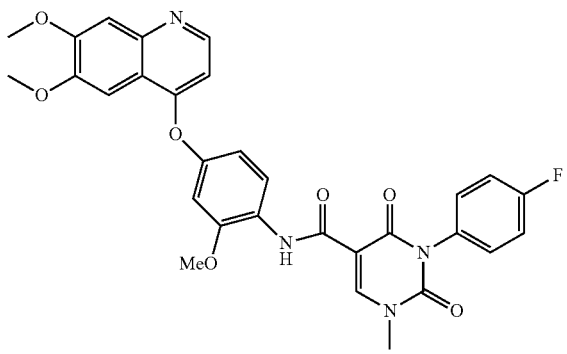 [SMILES: COc1cc(Oc2ccnc3cc(OC)c(OC)cc23)ccc1NC(=O)c1cn(C)c(=O)n(-c2ccc(F)cc2)c1=O]

1-Methyl-3-(4-fluoro-phenyl)-2,4-dioxo-1,2,3,4-tetrahydro-pyrimidine-5-carboxylic acid [4-(6,7-dimethoxy-quinolin-4-yloxy)-2-methoxy-phenyl]-amide. This compound was synthesized using 4-(6,7-dimethoxyquinolin-4-yloxy)-2-methoxy-phenylamine and 3-(4-fluorophenyl)-1-methyl-2,4-dioxo-1,2,3,4-tetrahydropyrimidine-5-carboxylic acid using the procedure for example 1. LCMS m/z=573 (M+1); $^1$H NMR (CDCl$_3$) δ: 11 (s, 1H), 8.61 (s, 1H), 8.54 (d, 1H, J=9 Hz), 8.49 (d, 1H, J=5 Hz), 7.55 (s, 1H), 7.42 (s, 1H), 7.26-7.23 (m, 4H), 6.81 (dd, 1H, J=3, 9 Hz), 6.74 (d, 1H, J=3 Hz), 6.5 (d, 1H, J=5 Hz), 4.05 (s, 6H), 3.84 (s, 3H), 3.61 (s, 3H).

Example 145

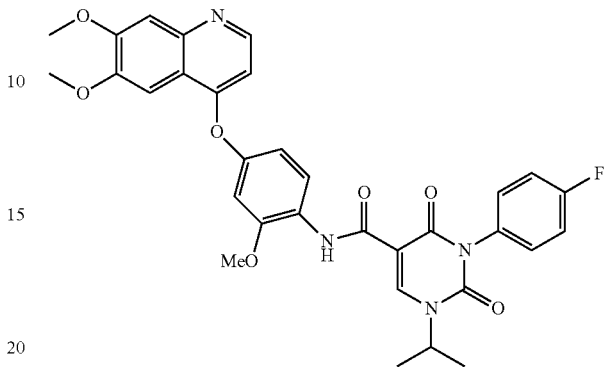

1-Isopropyl-3-(4-fluoro-phenyl)-2,4-dioxo-1,2,3,4-tetrahydro-pyrimidine-5-carboxylic acid [4-(6,7-dimethoxy-quinolin-4-yloxy)-2-methoxy-phenyl]-amide. This compound was synthesized using 4-(6,7-dimethoxyquinolin-4-yloxy)-2-methoxy-phenylamine and 3-(4-fluorophenyl)-1-isopropyl-2,4-dioxo-1,2,3,4-tetrahydropyrimidine-5-carboxylic acid using the procedure for example 1. LCMS m/z=601 (M+1); $^1$H NMR (CDCl$_3$) δ: 11.0 (s, 1H), 8.68 (s, 1H), 8.54 (d, 1H J=9 Hz), 8.5 (d, 1H, J=6 Hz), 7.55 (s, 1H), 7.42 (s, 1H), 7.25-7.23 (m, 3H), 6.81 (dd, 1H, J=3.9 Hz), 6.74 (d, 1H, J=3 Hz), 6.52 (d, 1H, J=6 Hz), 4.96 (p, 1H, J=7 Hz), 4.05 (d, 6H), 3.83 (s, 3H), 1.47 (d, 6H, J=6 Hz).

Example 146

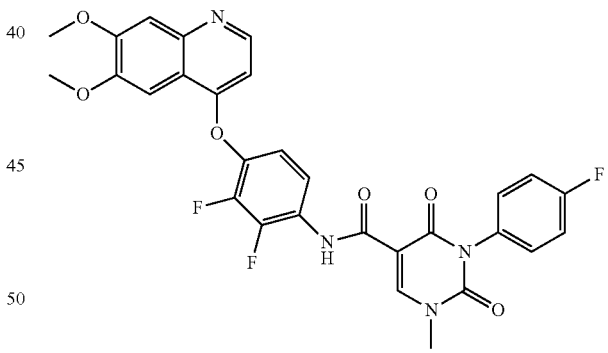

Step a. Potassium tert-butoxide (0.13 g, 1.12 mmol) was added to 4-amino-2-fluorophenol in dry N-methylpyrrolidinone (5 mL, 50 mmol) at rt and stirred for 30 min under an atmosphere of nitrogen. Then solid 4-bromo-6,7-dimethoxyquinoline (0.30 g, 1.1 mmol) was added and the reaction stirred at 100° C. for 30 h. The mixture was concentrated, dissolved in EtOAc (~75 mL), and washed 1× with 1N Na$_2$CO$_3$, water and NaCl solution, then dried over MgSO$_4$. The product was chromatographed on silica gel (5% MeOH/DCM) to give 4-(6,7-dimethoxyquinolin-4-yloxy)-2,3-difluoro-phenylamine 0.066 g (18%). LCMS m/z=333 (M+1). $^1$H NMR (CDCl$_3$) δ: 8.5 (d, 1H, J=8 Hz), 7.58 (s, 1H), 7.44 (s, 1H), 6.89-6.83 (m, 1H), 6.64-6.58 (m, 1H), 6.42 (d, 1H, J=5 Hz), 4.05 (d, 6H, J=5 Hz).

Step b. 1-Methyl-3-(4-fluorophenyl)-2,4-dioxo-1,2,3,4-tetrahydro-pyrimidine-5-carboxylic acid [4-(6,7-dimethoxy-quinolin-4-yloxy)-2,3-difluoro-phenyl]-amide. This compound was synthesized using 4-(6,7-dimethoxyquinolin-4-yloxy)-2,3-difluoro-phenylamine and 3-(4-fluorophenyl)-1-methyl-2,4-dioxo-1,2,3,4-tetrahydropyrimidine-5-carboxylic acid using the procedure for example 1. mp=226-267° C.; LCMS m/z=579 (M+1); $^1$H NMR (CDCl$_3$) δ: 11.07 (s, 1H), 8.62 (s, 1H), 8.51 (d, 1H, J=6 Hz), 8.25 (m, 1H), 7.55 (s, 1H), 7.43 (s, 1H), 7.25-7.23 (m, 4H), 7.05 (m, 1H), 6.46 (d, 1H, J=5 Hz), 4.05 (d, 6H), 3.65 (s, 3H).

Example 147

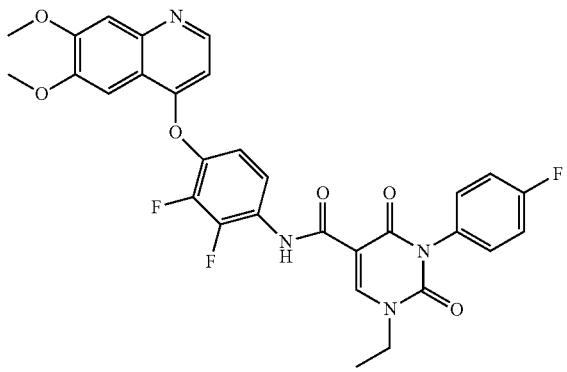 [SMILES: CCn1cc(C(=O)Nc2ccc(Oc3ccnc4cc(OC)c(OC)cc34)c(F)c2F)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-2,3-difluoro-phenyl]-amide. This compound was synthesized using 4-(6,7-dimethoxyquinolin-4-yloxy)-2,3-difluoro-phenylamine and 1-ethyl-3-(4-fluorophenyl)-2,4-dioxo-1,2,3,4-tetrahydropyrimidine-5-carboxylic acid using the procedure for example 1. mp=270-272° C.; LCMS m/z=593 (M+1); $^1$H NMR (CDCl$_3$) δ: 11.08 (s, 1H), 8.63 (s, 1H), 5.51 (d, 1H, J=6 Hz), 8.28-8.22 (m, 1H), 7.55 (s, 1H), 7.43 (s, 1H), 7.25-7.23 (m, 4H), 7.09-7.03 (m, 1H), 6.46 (d, 1H, J=5 Hz), 4.05 (d, 6H), 4.04-3.99 (m, 2H), 1.47 (t, 3H, J=8 Hz).

Example 148

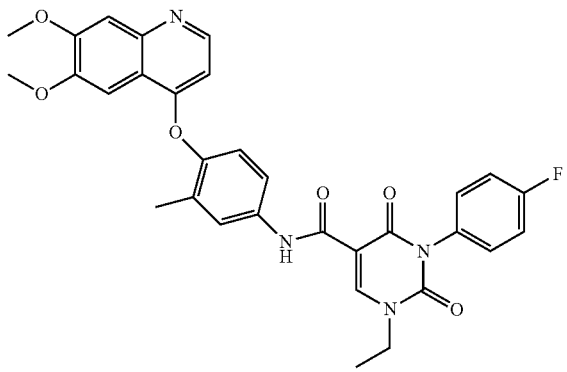 [SMILES: CCn1cc(C(=O)Nc2ccc(Oc3ccnc4cc(OC)c(OC)cc34)c(C)c2)c(=O)n(-c2ccc(F)cc2)c1=O]

Step a. 4-(6,7-Dimethoxy-quinolin-4-yloxy)-3-methylphenylamine was synthesized using the procedure for example 143 steps a/b. LCMS m/z=311 (M+1).

Step b. 1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-methyl-phenyl]-amide. This compound was synthesized using 4-(6,7-dimethoxy-quinolin-4-yloxy)-3-methylphenylamine and 1-ethyl-3-(4-fluorophenyl)-2,4-dioxo-1,2,3,4-tetrahydropyrimidine-5-carboxylic acid using the procedure for example 1. mp=265-267° C.; LCMS m/z=571 (M+1); $^1$H NMR (DMSO-d6) δ: 10.93 (s, 1H), 8.85 (s, 1H), 8.44 (d, 1H, J=5 Hz), 7.73 (dd, 1H, J=2, 8 Hz), 7.66 (d, 1H, J=3 Hz), 7.55 (s, 1H), 7.46-7.33 (m, 5H), 7.18 (d, 1H, J=8 Hz), 6.31 (d, 1H, J=5 Hz), 4.02 (q, 2H, J=8 Hz), 3.32 (s, 6H), 2.09 (s, 3H), 1.30 (t, 3H, J=8 Hz).

Example 149

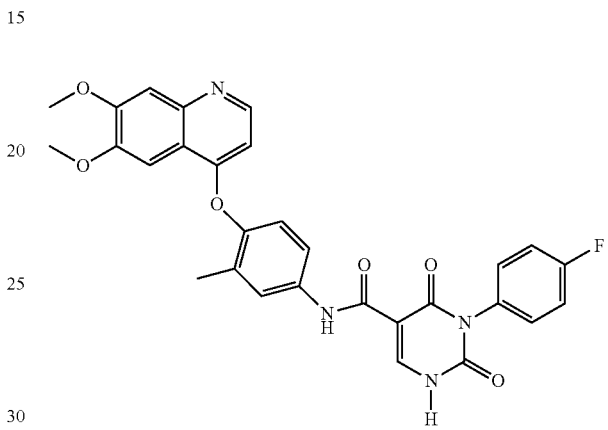

3-(4-Fluoro-phenyl)-2,4-dioxo-1,2,3,4-tetrahydro-pyrimidine-5-carboxylic acid [4-(6,7-dimethoxy-quinolin-4-yloxy)-3-methyl-phenyl]-amide. This compound was synthesized using 4-(6,7-dimethoxy-quinolin-4-yloxy)-3-methylphenylamine and 3-(4-fluorophenyl)-2,4-dioxo-1,2,3,4-tetrahydropyrimidine-5-carboxylic acid using the procedure for example 1. mp=240-242° C.; LCMS m/z=543 (M+1); $^1$H NMR (CDCl$_3$) δ: 10.74 (s, 1H), 8.61 (s, 1H), 8.45 (d, 1H, J=5 Hz), 7.63-7.61 (m, 1H), 7.60 (s, 1H), 7.58-7.53 (m, 1H), 7.44 (s, 1H), 7.29-7.26 (m, 3H), 7.08 (d, 1H, J=10 Hz), 6.30 (d, 1H, J=5 Hz), 5.30 (s, 1H), 4.05 (d, 6H, J=5 Hz), 2.05 (s, 3H).

Example 150

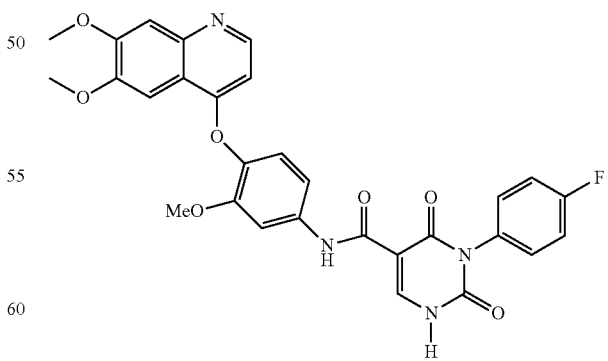

3-(4-Fluoro-phenyl)-2,4-dioxo-1,2,3,4-tetrahydro-pyrimidine-5-carboxylic acid [4-(6,7-dimethoxy-quinolin-4-yloxy)-3-methoxy-phenyl]-amide. This compound was synthesized using 4-(6,7-dimethoxy-quinolin-4-yloxy)-3- methoxy-phenylamine (LCMS m/z=327 (M+1)) and 3-(4-fluorophenyl)-2,4-dioxo-1,2,3,4-tetrahydropyrimidine-5-carboxylic acid using the procedure for example 1. LCMS m/z=559 (M+1); ¹H NMR (CDCl₃) δ: 10.94 (s, 1H), 8.69 (s, 1H), 8.45 (d, 1H, J=6 Hz), 8.2 (d, 1H, J=5 Hz), 7.61 (s, 1H), 7.42 (s, 1H), 7.32-7.26 (m, 3H), 7.2 (s, 1H), 6.57 (d, 1H, J=7 Hz), 6.33 (d, 1H, J=7 Hz), 5.30 (s, 1H), 4.05 (s, 6H), 3.76 (s, 3H).

Example 151

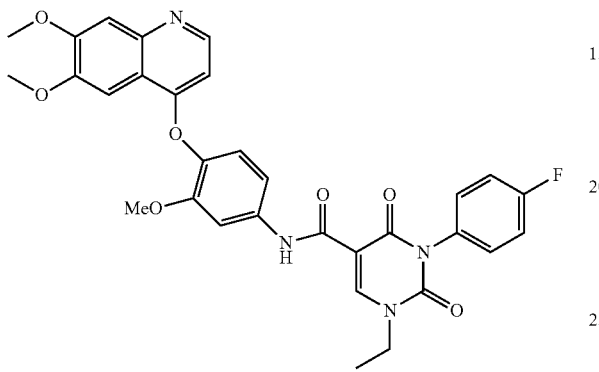

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-methoxy-phenyl]-amide. This compound was synthesized using 4-(6,7-dimethoxy-quinolin-4-yloxy)-3-methoxy-phenylamine and 1-ethyl-3-(4-fluorophenyl)-2,4-dioxo-1,2,3,4-tetrahydropyrimidine-5-carboxylic acid using the procedure for example 1. mp=245-247° C.; LCMS m/z=587 (M+1); ¹H NMR (DMSO-d6) δ: 10.98 (s, 1H), 8.89 (s, 1H), 8.46 (d, 1H, J=6 Hz), 7.56 (d, 1H, J=2 Hz), 7.53 (s, 1H), 7.49 (dd, 1H, J=3, 9 Hz), 7.45-7.41 (m, 2H), 7.39-7.34 (m, 3H), 7.25 (d, 1H, J=9 Hz), 6.36 (d, 1H, J=6 Hz), 4.01 (q, 2H, J=8 Hz), 3.95 (d, 6H), 3.71 (s, 3H), 1.3 (t, 3H, J=8 Hz).

Example 152

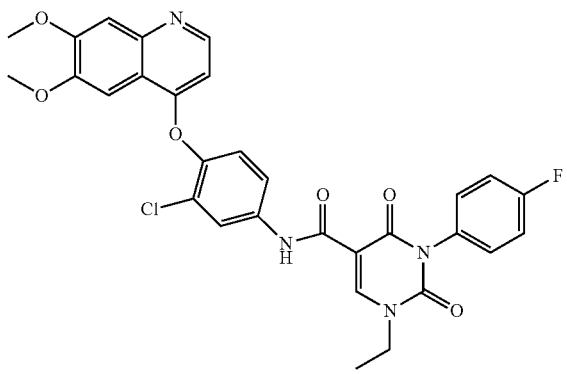 [SMILES: CCn1cc(C(=O)Nc2ccc(Oc3ccnc4cc(OC)c(OC)cc34)c(Cl)c2)c(=O)n(-c2ccc(F)cc2)c1=O]

3-Chloro-4-(6,7-dimethoxy-quinolin-4-yloxy)-phenylamine was synthesized using the procedure for example 146 step a, LCMS=331 (M+1).

1-Ethyl-3-(4-fluoro-phenyl)-2,4-dioxo-1,2,3,4-tetrahydro-pyrimidine-5-carboxylic acid [3-chloro-4-(6,7-dimethoxy-quinolin-4-yloxy)-3-methoxy-phenyl]-amide. This compound was synthesized using 3-chloro-4-(6,7-dimethoxy-quinolin-4-yloxy)phenylamine and 1-ethyl-3-(4-fluorophenyl)-2,4-dioxo-1,2,3,4-tetrahydropyrimidine-5-carboxylic acid using the procedure for example 1. mp=257-259° C.; LCMS m/z=591 (M+1); ¹H NMR (DMSO-d6) δ: 11.0 (s, 1H), 8.88 (s, 1H), 8.47 (d, 1H, J=6 Hz), 8.18 (d, 1H, J=3 Hz), 7.71 (dd, 1H, J=3, 9 Hz), 7.52 (s, 1H), 7.45-7.33 (m, 6H), 6.37 (d, 1H, J=6 Hz), 4.0 (q, 2H, J=7 Hz), 3.95 (d, 6H), 1.30 (t, 3H, J=7 Hz).

Example 153

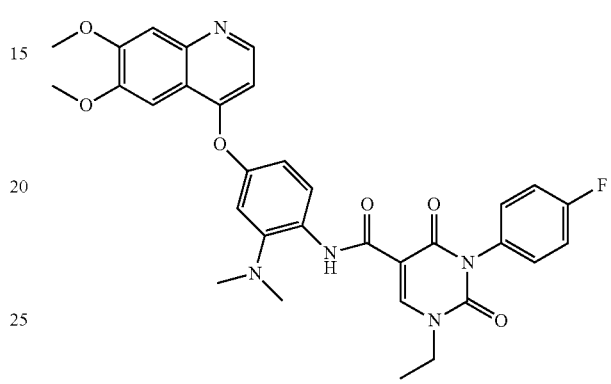

[5-(6,7-Dimethoxy-quinolin-4-yloxy)-2-methyl-phenyl]-dimethyl-amine was synthesized using the procedure for example 143 step a. LCMS m/z=340 (M+1). ¹H NMR (CDCl₃) δ: 8.48 (d, 1H, J=9 Hz), 7.89 (s, 1H), 7.63 (s, 1H), 6.83 (d, 1H, J=3 Hz), 6.80 (d, 1H, J=8 Hz), 6.74 (dd, 1H, J=3, 8.6 Hz), 6.66 (d, 1H, J=5 Hz), 4.10 (d, 6H), 2.69 (s, 6H).

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-2-dimethylamino-phenyl]-amide. This compound was synthesized using [5-(6,7-dimethoxyquinolin-4-yloxy)-2-methylphenyl]dimethylamine and 1-ethyl-3-(4-fluorophenyl)-2,4-dioxo-1,2,3,4-tetrahydropyrimidine-5-carboxylic acid using the procedure for example 1. mp=144-145° C.; LCMS m/z=600 (M+1); ¹H NMR (DMSO-d6) δ: 11.18 (s, 1H), 8.87 (s, 1H), 8.51 (d, 1H, J=9 Hz), 8.47 (d, 1H, J=5 Hz), 7.51 (s, 1H), 7.45-7.33 (m, 5H), 7.10 (d, 1H, J=3 Hz), 6.98 (dd, 1H, J=3, 9 Hz), 6.49 (d, 1H, J=5 Hz), 4.01 (q, 2H, J=7 Hz), 3.94 (d, 6H), 2.58 (s, 6H), 1.29 (t, 3H, J=7 Hz).

Example 154

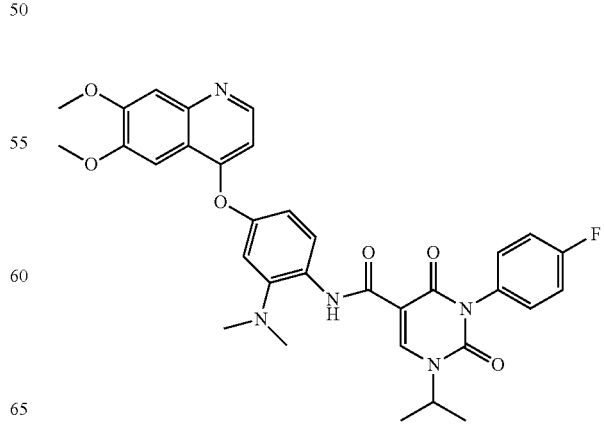

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-2-dimethylamino-phenyl]-amide. This compound was synthesized using [5-(6,7-dimethoxyquinolin-4-yloxy)-2-methylphenyl]dimethylamine and 3-(4-fluorophenyl)-1-isopropyl-2,4-dioxo-1,2,3,4-tetrahydropyrimidine-5-carboxylic acid using the procedure for example 1. mp=231-233° C.; LCMS m/z=614 (M+1); $^1$H NMR (DMSO-d6) δ: 11.19 (s, 1H), 8.67 (s, 1H), 8.52-8.46 (m, 2H), 7.50 (s, 1H), 7.45-7.33 (m, 5H), 7.11 (d, 1H, J=3 Hz), 6.97 (dd, 1H, J=3, 9 Hz), 6.50 (d, 1H, J=5 Hz), 4.78 (p, 1H, J=6 Hz), 3.94 (d, 6H), 2.58 (s, 6H), 1.42 (d, 6H, J=6 Hz).

Example 155

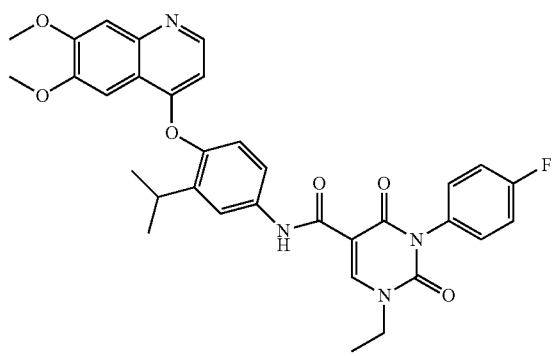

4-(6,7-Dimethoxy-quinolin-4-yloxy)-3-isopropyl-phenylamine was synthesized using the procedure for example 143 step a. LCMS m/z=338 (M+1); $^1$H NMR (CDCl3) δ: 8.45 (d, 1H, J=7 Hz), 7.63 (s, 1H), 7.27 (s, 1H), 6.88 (d, 1H, J=8.5 Hz), 6.73-6.71 (m, 1H), 6.63-6.58 (m, 1H), 6.44 (d, 1H, J=6 Hz), 4.07 (s, 6H), 2.98-2.90 (m, 1HO, 1.16 (d, 6H, J=6 Hz).

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-isopropyl-phenyl]-amide. This compound was synthesized using 4-(6,7-dimethoxy-quinolin-4-yloxy)-3-isopropyl-phenylamine and 1-ethyl-3-(4-fluorophenyl)-2,4-dioxo-1,2,3,4-tetrahydropyrimidine-5-carboxylic acid using the procedure for example 1. mp=173-175° C.; LCMS m/z=599 (M+1); $^1$H NMR (DMSO-d6) δ: 10.93 (s, 1H), 8.80 (s, 1H), 8.45 (d, 1H, J=6 Hz), 7.76 (dd, 1H, J=2, 8 Hz), 7.68 (d, 1H, J=2 Hz), 7.55 (s, 1H), 7.46-7.33 (m, 5H), 7.16 (d, 1H, J=8 Hz), 6.36 (d, 1H, J=5 Hz), 4.01 (q, 2H, J=8 Hz), 3.94 (d, 6H), 2.99 (m, 1H), 1.3 (t, 3H, J=7 Hz), 1.14 (d, 6H, J=7 Hz).

Example 156

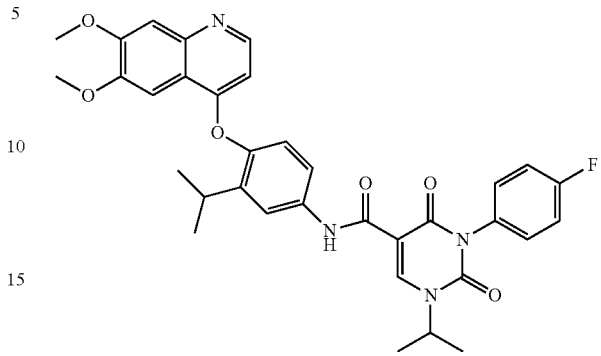

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-3-isopropyl-phenyl]-amide. This compound was synthesized using 4-(6,7-dimethoxy-quinolin-4-yloxy)-3-isopropyl-phenylamine and 3-(4-fluorophenyl)-1-isopropyl-2,4-dioxo-1,2,3,4-tetrahydropyrimidine-5-carboxylic acid using the procedure for example 1. mp=165-167° C.; LCMS m/z=613 (M+1); $^1$H NMR (CDCl$_3$) δ: 10.86 (s, 1H), 8.72 (s, 1H), 8.46 (d, 1H, J=5.5 Hz), 7.66 (dd, 1H, J=2.5, 8 Hz), 7.63 (d, 1H, J=2 Hz), 7.60 (s, 1H), 7.44 (s, 1H), 7.27-7.25 (m, 3H), 7.05 (d, 1H, J=9 Hz), 6.37 (d, 1H, J=5.5 Hz), 4.98 (p, 1H, J=8 Hz), 4.06 (s, 6H), 3.09 (p, 1H, J=8 Hz), 1.5 (d, 6H, J=7 Hz), 1.18 (d, 6H, J=7 Hz).

Example 157

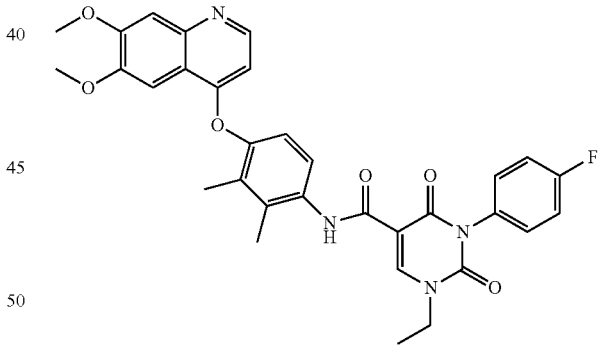

4-(6,7-Dimethoxy-quinolin-4-yloxy)-2,3-dimethyl-phenylamine was synthesized using the procedure for example 143 step a. LCMS m/z=325 (M+1); $^1$H NMR (CDCl$_3$) δ: 8.42 (d, 1H, J=7 Hz), 7.64 (s, 1H), 7.42 (s, 1H), 6.83 (d, 1H, J=8 Hz), 6.65 (d, 1H, J=8 Hz), 6.26 (d, 1H, J=8 Hz), 4.06 (d, 6H, J=4.5 Hz), 2.15 (s, 3H), 2.06 (s, 3H).

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-2,3-dimethyl-phenyl]-amide. This compound was synthesized using 4-(6,7-Dimethoxy-quinolin-4-yloxy)-2,3-dimethyl-phenylamine and 1-ethyl-3-(4-fluorophenyl)-2,4-dioxo-1,2,3,4-tetrahydropyrimidine-5-carboxylic acid using the procedure for example 1. mp=283-285° C.; LCMS m/z=585 (M+1); ¹H NMR (DMSO-d6) δ: 10.81 (s, 1H), 8.88 (s, 1H), 8.43 (d, 1H, J=5.5 Hz), 8.07 (d, 1H, J=8.5 Hz), 7.56 (s, 1H), 7.46-7.42 (m, 2H), 7.40 (s, 1H), 7.39-7.33 (m, 2H), 7.10 (d, 1H, J=9 Hz), 6.26 (d, 1H, J=6 Hz), 4.02 (q, 2H, J=7 Hz), 3.95 (s, 6H), 2.21 (s, 3H), 2.07 (s, 3H), 1.3 (t, 3H, J=7 Hz).

Example 158

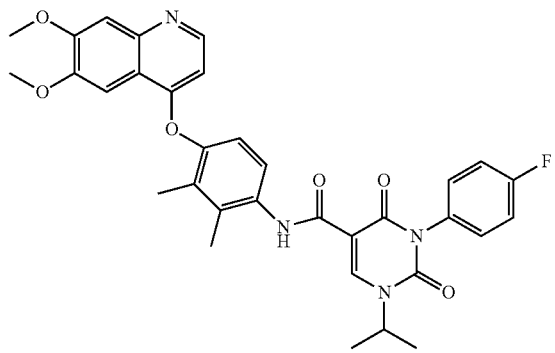 [SMILES: COc1cc2nccc(Oc3ccc(NC(=O)c4cn(C(C)C)c(=O)n(-c5ccc(F)cc5)c4=O)c(C)c3C)c2cc1OC]

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-2,3-dimethyl-phenyl]-amide. This compound was synthesized using 4-(6,7-Dimethoxy-quinolin-4-yloxy)-2,3-dimethyl-phenylamine and 3-(4-fluorophenyl)-1-isopropyl-2,4-dioxo-1,2,3,4-tetrahydropyrimidine-5-carboxylic acid using the procedure for example 1. mp=238-240° C.; LCMS m/z=599 (M+1); ¹H NMR (DMSO-d6) δ: 10.82 (s, 1H), 8.68 (s, 1H), 8.43 (d, 1H, J=5.5 Hz), 8.06 (d, 1H, J=9 Hz), 7.56 (s, 1H), 7.47-7.42 (m, 2H), 7.39-7.34 (m, 2H), 7.09 (d, 1H, J=9 Hz), 6.27 (d, 1H, J=5.5 Hz), 4.78 (p, 1H, J=8 Hz), 3.95 (s, 6H), 2.21 (s, 3H), 2.07 (s, 3H), 1.43 (d, 6H, J=6 Hz).

Example 159

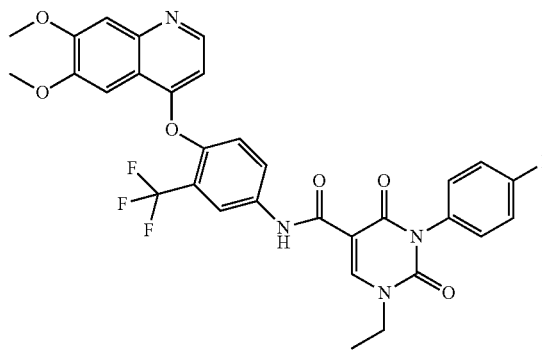

3-(1,1-Difluoro-ethyl)-4-(6,7-dimethoxy-quinolin-4-yloxy)-phenylamine was synthesized using the procedure for example 143 step a. LCMS m/z=365 (M+1). ¹H NMR (CDCl₃) δ: 8.48 (d, 1H, J=6 Hz), 7.56 (s, 1H), 7.42 (s, 1H), 7.06-7.01 (m, 2H) 6.90-6.86 (m, 1H), 6.41 (d, 1H, J=6 Hz), 4.05 (s, 6H).

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-trifluoromethyl-phenyl]-amide. This compound was synthesized using 3-(1,1-difluoroethyl)-4-(6,7-dimethoxy-quinolin-4-yloxy)-phenylamine and 1-ethyl-3-(4-fluorophenyl)-2,4-dioxo-1,2,3,4-tetrahydropyrimidine-5-carboxylic acid using the procedure for example 1. mp=260-262° C.; LCMS m/z=625 (M+1); ¹H NMR (DMSO-d6) δ: 11.08 (s, 1H), 8.89 (s, 1H), 8.51 (d, 1H, J=5 Hz), 8.37 (d, 1H, J=2.5 Hz), 7.45-7.41 (m, 5H), 7.36 (t, 2H, J=8.5 Hz), 6.58 (d, 1H, J=6 Hz), 4.02 (q, 2H, J=7.5 Hz), 3.90 (d, 6H), 1.30 (t, 3H, J=8 Hz).

Example 160

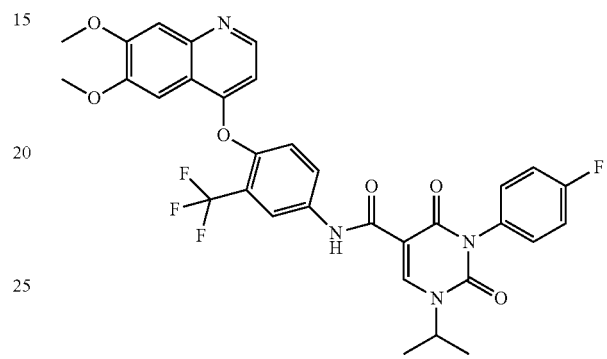

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-3-trifluoromethyl-phenyl]-amide. This compound was synthesized using 3-(1,1-difluoroethyl)-4-(6,7-dimethoxy-quinolin-4-yloxy)-phenylamine and 3-(4-fluorophenyl)-1-isopropyl-2,4-dioxo-1,2,3,4-tetrahydropyrimidine-5-carboxylic acid using the procedure for example 1. mp=228-230° C.; LCMS m/z=639 (M+1); ¹H NMR (DMSO-d6) δ: 11.08 (s, 1H), 8.89 (s, 1H), 8.51 (d, 1H, J=5 Hz), 8.37 (d, 1H, J=2.5 Hz), 7.45-7.41 (m, 5H), 7.36 (t, 2H, J=8.5 Hz), 6.58 (d, 1H, J=6 Hz), 4.02 (q, 2H, J=7.5 Hz), 3.90 (d, 6H), 1.30 (t, 6H, J=8 Hz).

Example 161

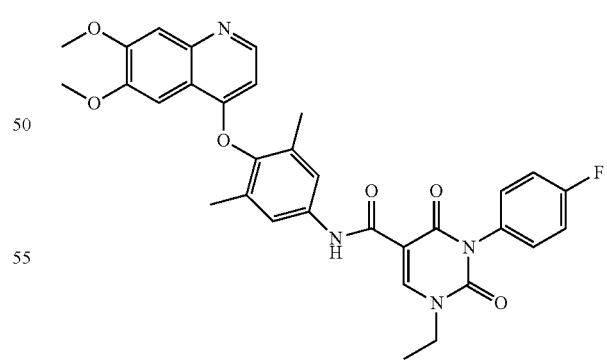

4-(6,7-Dimethoxy-quinolin-4-yloxy)-3,5-dimethyl-phenylamine was synthesized using the procedure for example 143 step a. LCMS m/z=325 (M+1). ¹H NMR (CDCl₃) δ: 8.43 (d, 1H, J=8 Hz), 7.65 (s, 1H), 7.48 (s, 1H), 6.48 (s, 2H), 6.26 (d, 1H, J=6 Hz), 4.07 (s, 6H), 2.03 (s, 6H).

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3,5-dimethyl-phenyl]-amide. This compound was synthesized using 4-(6,7-dimethoxy-quinolin-4-yloxy)-3,5-dimethyl-phenylamine and 1-ethyl-3-(4-fluorophenyl)-2,4-dioxo-1,2,3,4-tetrahydropyrimidine-5-carboxylic acid using the procedure for example 1. mp=240-242° C.; LCMS m/z=585 (M+1); $^1$H NMR (DMSO-d6) δ: 10.90 (s, 1H), 8.84 (s, 1H), 8.41 (d, 1H, J=5 Hz), 7.61 (s, 1H), 7.55 (s, 1H), 7.45-7.33 (m, 6H), 6.19 (d, 1H, J=6 Hz), 4.01 (q, 2H, J=8 Hz), 3.95 (d, 6H, J=5 Hz), 2.07 (s, 6H), 1.30 (t, 3H, J=7 Hz).

Example 162

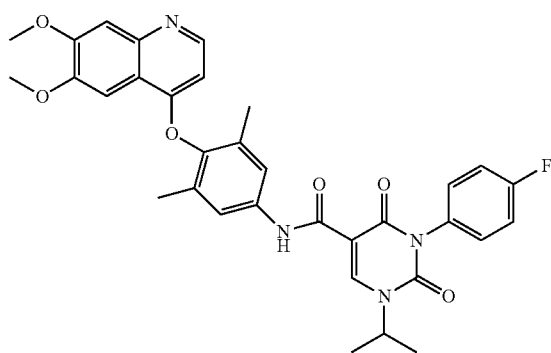 [SMILES: COc1cc2nccc(Oc3c(C)cc(NC(=O)c4cn(C(C)C)c(=O)n(-c5ccc(F)cc5)c4=O)cc3C)c2cc1OC]

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-3,5-dimethyl-phenyl]-amide. This compound was synthesized using 4-(6,7-dimethoxy-quinolin-4-yloxy)-3,5-dimethyl-phenylamine and 3-(4-fluorophenyl)-1-isopropyl-2,4-dioxo-1,2,3,4-tetrahydropyrimidine-5-carboxylic acid using the procedure for example 1. mp=180-182° C.; LCMS m/z=599 (M+1); $^1$H NMR (DMSO-d6) δ: 10.89 (s, 1H), 8.65 (s, 1H), 8.41 (d, 1H, J=5 Hz), 7.60 (s, 1H), 7.58 (s, 2H), 7.45-7.33 (m, 5H), 6.19 (d, 1H, J=7 Hz), 4.18 (p, 1H, J=7 Hz), 3.95 (d, 6H, J=6 Hz), 2.05 (s, 6H), 1.45 (d, 6H, J=7 Hz).

Example 163

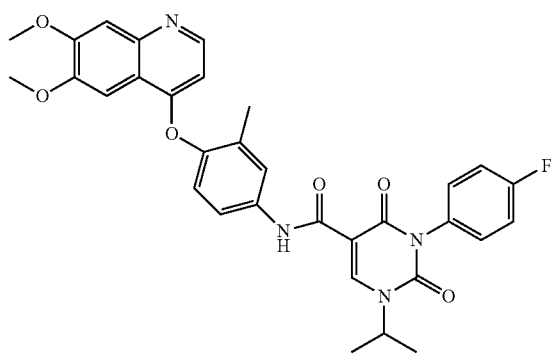

4-(6,7-Dimethoxy-quinolin-4-yloxy)-3-methyl-phenylamine was synthesized using the procedure for example 143 step a. LCMS m/z=311 (M+1).

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-3-methyl-phenyl]-amide. This compound was synthesized using 4-(6,7-Dimethoxy-quinolin-4-yloxy)-3-methyl-phenylamine and 3-(4-fluorophenyl)-1-isopropyl-2,4-dioxo-1,2,3,4-tetrahydropyrimidine-5-carboxylic acid using the procedure for example 1. mp=238-240° C.; LCMS m/z=585 (M+1); $^1$H NMR (DMSO-d6) δ: 10.92 (s, 1H), 8.65 (s, 1H), 8.44 (d, 1H, J=6 Hz), 7.73-7.67 (m, 2H), 7.55 (s, 1H), 7.45-7.41 (m, 2H), 7.39-7.34 (m, 3H), 7.17 (d, 1H, J=8 Hz), 6.31 (d, 1H, J=4.5 Hz), 4.78 (p, 1H, J=6 Hz), 3.95 (s, 6H), 2.09 (s, 3H), 1.43 (d, 6H, J=7 Hz).

Example 164

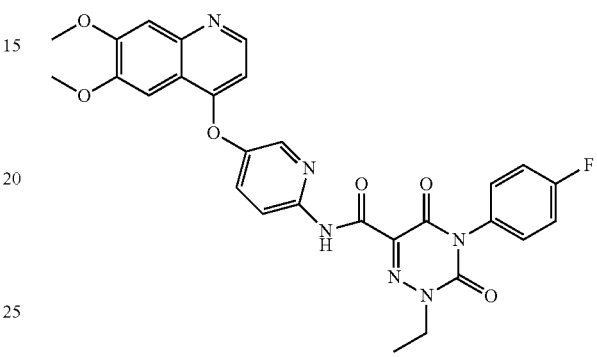

2-Ethyl-4-(4-fluoro-phenyl)-3,5-dioxo-2,3,4,5-tetrahydro-1,2,4-triazine-6-carboxylic acid [5-(6,7-dimethoxy-quinolin-4-yloxy)-pyridin-2-yl]-amide. This compound was synthesized using 5-(6,7-dimethoxyquinolin-4-yloxy)-pyridin-2-ylamine and 2-ethyl-4-(4-fluorophenyl)-3,5-dioxo-2,3,4,5-tetrahydro-[1,2,4]triazine-6-carboxylic acid using the procedure for example 1. mp=200-202° C.; LCMS m/z=585 (M+1); $^1$H NMR (CDCl$_3$) δ: 11.13 (s, 1H), 8.52 (d, 1H, J=5 Hz), 8.48 (d, 1H, J=8.5 Hz), 8.27 (d, 1H, J=2.6 Hz), 7.60 (dd, 1H, J=2, 9 Hz), 7.52 (s, 1H), 7.43 (s, 1H), 7.28-7.26 (m, 3H), 6.47 (d, 1H, J=4.3 Hz), 4.33 (q, 2H, J=8.5 Hz), 4.05 (d, 6H), 1.51 (t, 3H, J=8 Hz).

Example 165

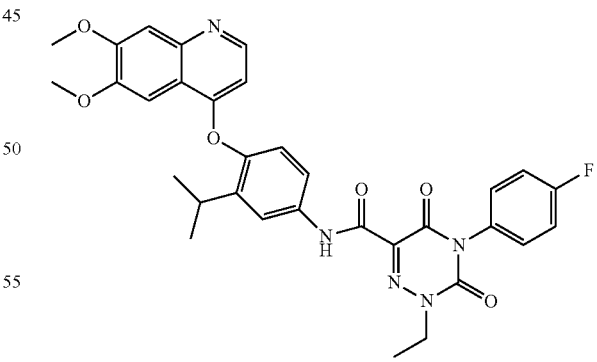

2-Ethyl-4-(4-fluoro-phenyl)-3,5-dioxo-2,3,4,5-tetrahydro-1,2,4-triazine-6-carboxylic acid [4-(6,7-dimethoxy-quinolin-4-yloxy)-3-isopropyl-phenyl]-amide. This compound was synthesized using 4-(6,7-dimethoxy-quinolin-4-yloxy)-3-isopropyl-phenylamine and 2-ethyl-4-(4-fluorophenyl)-3,5-dioxo-2,3,4,5-tetrahydro-[1,2,4]triazine-6-carboxylic acid using the procedure for example 1. mp=155-156° C.; LCMS m/z=600 (M+1); $^1$H NMR (CDCl$_3$)

δ: 10.78 (s, 1H), 8.47 (d, 1H, J=5.5 Hz). 7.72 (s, 1H), 7.66 (d, 1H, J=8 Hz), 7.59 (s, 1H), 7.43 (s, 1H), 7.31-7.24 (m, 3H), 7.07 (d, 1H, J=9 Hz), 6.35 (d, 1H, J=6 Hz), 4.34 (q, 2H, J=7.3 Hz), 4.05 (s, 6H), 3.11 (m, 1H), 1.58 (t, 3H, J=6 Hz), 1.19 (d, 6H, J=7 Hz).

Example 166

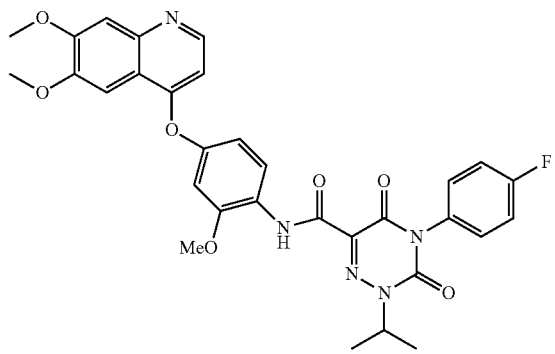 [SMILES: COc1cc(Oc2ccnc3cc(OC)c(OC)cc23)ccc1NC(=O)c1nn(C(C)C)c(=O)n(-c2ccc(F)cc2)c1=O]

4-(4-Fluoro-phenyl)-2-isopropyl-3,5-dioxo-2,3,4,5-tetrahydro-1,2,4-triazine-6-carboxylic acid [4-(6,7-dimethoxy-quinolin-4-yloxy)-2-methoxy-phenyl]-amide. This compound was synthesized using 4-(6,7-dimethoxyquinolin-4-yloxy)-2-methoxy-phenylamine and 4-(4-Fluorophenyl)-2-isopropyl-3,5-dioxo-2,3,4,5-tetrahydro[1,2,4]triazine-6-carboxylic acid using the procedure for example 1. mp=216-218° C.; LCMS m/z=602 (M+1); $^1$H NMR (CDCl$_3$) δ: 11.02 (s, 1H), 8.66 (d, 1H, J=8.5 Hz), 8.50 (d, 1H, J=5 Hz), 7.54 (s, 1H), 7.43 (s, 1H), 7.30-7.27 (m, 3H), 6.83 (dd, 1H, J=3.5, 10 Hz), 6.75 (d, 1H, J=2.5 Hz), 6.53 (d, 1H, J=5 Hz), 5.09 (m, 1H), 4.05 (s, 6H), 3.86 (s, 3H), 1.53 (d, 6H, J=6.5 Hz)

Example 167

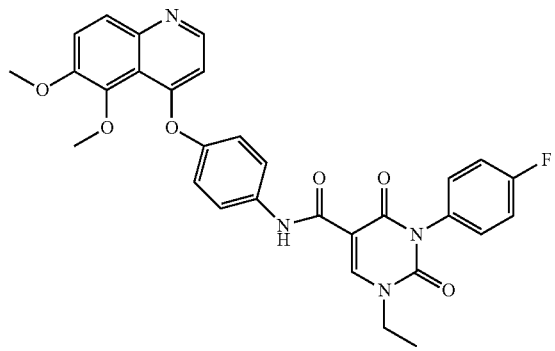 [SMILES: CCn1cc(C(=O)Nc2ccc(Oc3ccnc4ccc(OC)c(OC)c34)cc2)c(=O)n(-c2ccc(F)cc2)c1=O]

1-Ethyl-3-(4-fluoro-phenyl)-2,4-dioxo-1,2,3,4-tetrahydro-pyrimidine-5-carboxylic acid [4-(5,6-dimethoxy-quinolin-4-yloxy)-phenyl]-amide. This compound was synthesized using 4-(5,6-dimethoxy-quinolin-4-yloxy)-phenylamine and 1-ethyl-3-(4-fluorophenyl)-2,4-dioxo-1,2,3,4-tetrahydropyrimidine-5-carboxylic acid using the procedure for example 1. mp>250° C.; LCMS m/z=557 (M+1); 1H NMR (DMSO) δ: 10.92 (s, 1H), 8.86 (s, 1H), 8.48 (m, 1H), 7.79 (m, 2H), 7.49 (s, 1H), 7.35-7.42 (m, 5H), 7.24-7.27 (m, 2H), 6.49 (m, 1H), 4.00 (m, 2H), 3.94 (s, 3H), 3.92 (s, 3H), 1.29 (m, 3H).

Example 168

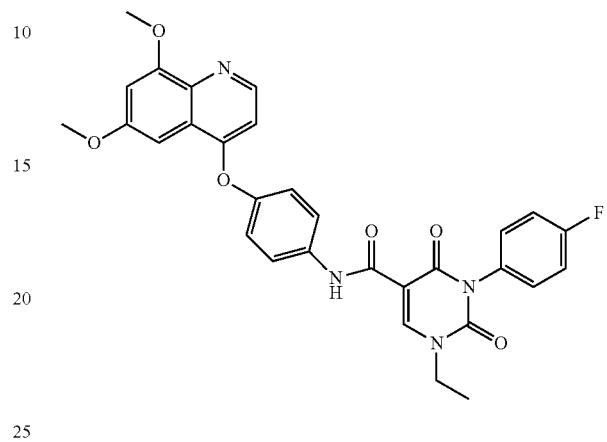

1-Ethyl-3-(4-fluoro-phenyl)-2,4-dioxo-1,2,3,4-tetrahydro-pyrimidine-5-carboxylic acid [4-(6,8-dimethoxy-quinolin-4-yloxy)-phenyl]-amide. This compound was synthesized using 4-(6,8-dimethoxy-quinolin-4-yloxy)-phenylamine and 1-ethyl-3-(4-fluorophenyl)-2,4-dioxo-1,2,3,4-tetrahydropyrimidine-5-carboxylic acid using the procedure for example 1. mp=127-9° C.; LCMS m/z=557 (M+1); 1H NMR (DMSO) δ: 10.93 (s, 1H), 8.87 (s, 1H), 8.45 (d, 1H, J=5 Hz), 7.79 (d, 2H, J=8.8 Hz), 7.41-7.45 (m, 2H), 7.33-7.37 (m, 2H), 7.24- (d, 2H, J=8.8 Hz), 7.10 (d, 1H, J=2.3 Hz), 6.86 (d, 1H, J=2.3 Hz), 6.61 (d, 1H, J=5 Hz), 4.01 (q, 2H, J=7 Hz), 3.94 (s, 3H), 3.89 (s, 3H), 1.29 (t, 3H, J=7 Hz).

Example 169

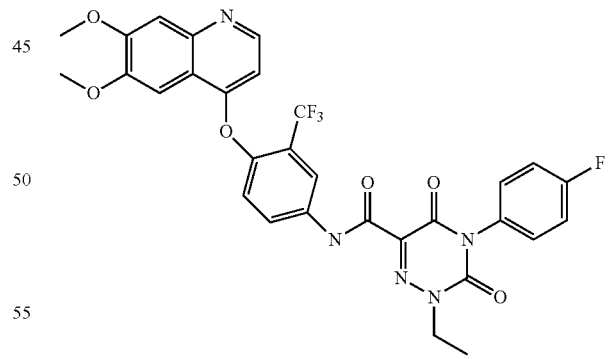

2-Ethyl-4-(4-fluoro-phenyl)-3,5-dioxo-2,3,4,5-tetrahydro-1,2,4-triazine-6-carboxylic acid [4-(6,7-dimethoxy-quinolin-4-yloxy)-3-trifluoromethyl-phenyl]-amide. This compound was synthesized using 4-(6,7-dimethoxy-quinolin-4-yloxy)-3-trifluoromethyl-phenylamine and 2-ethyl-4-(4-fluoro-phenyl)-3,5-dioxo-2,3,4,5-tetrahydro-1,2,4-triazine-6-carboxylic acid using the procedure for example 1. mp=148-50° C.; LCMS m/z=626 (M+1); $^1$H NMR (DMSO): 10.95 (s, 1H), 8.52 (d, 1H), 8.32 (s, 1H), 8.04 (m, 1H), 7.35-7.49 (m, 8H), 6.60 (m, 1H), 4.08 (q, 2H, J=7Hz), 3.97 (s, 3H), 3.89 (s, 3H), 1.35 (t, 3H, J=7Hz).

Example 170

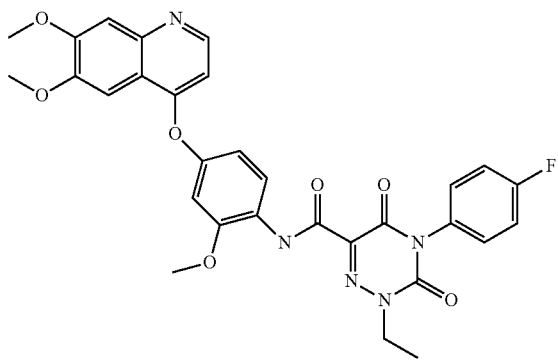 [SMILES: CCn1nc(C(=O)Nc2ccc(Oc3ccnc4cc(OC)c(OC)cc34)cc2OC)c(=O)n(-c2ccc(F)cc2)c1=O]

2-Ethyl-4-(4-fluoro-phenyl)-3,5-dioxo-2,3,4,5-tetrahydro-1,2,4-triazine-6-carboxylic acid [4-(6,7-dimethoxy-quinolin-4-yloxy)-2-methoxy-phenyl]-amide. This compound was synthesized using 4-(6,7-dimethoxy-quinolin-4-yloxy)-2-methoxy-phenylamine and 2-ethyl-4-(4-fluoro-phenyl)-3,5-dioxo-2,3,4,5-tetrahydro-1,2,4-triazine-6-carboxylic acid using the procedure for example 1. mp=264-6° C.; LCMS m/z=588 (M+1); ); $^1$H NMR (DMSO): 11.00 (s, 1H), 8.47-8.52 (m, 2H), 7.51 (s, 1H), 7.38-7.46 (m, 5H), 7.10 (m, 1H), 6.88 (m, 1H), 6.53 (d, 1H, J=5Hz), 4.10 (q, 2H, J=7 Hz), 3.94 (s, 3H), 3.93 (s, 3H), 3.84 (s, 3H), 1.35 (t, 3H, J=7Hz).

Example 171

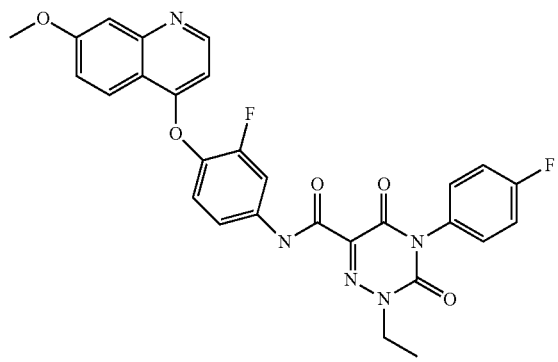 [SMILES: CCn1nc(C(=O)Nc2ccc(Oc3ccnc4cc(OC)ccc34)c(F)c2)c(=O)n(-c2ccc(F)cc2)c1=O]

2-Ethyl-4-(4-fluoro-phenyl)-3,5-dioxo-2,3,4,5-tetrahydro-1,2,4-triazine-6-carboxylic acid [3-fluoro-4-(7-methoxy-quinolin-4-yloxy)-phenyl]-amide. This compound was synthesized using 3-fluoro-4-(7-methoxy-quinolin-4-yloxy)-phenylamine and 2-ethyl-4-(4-fluoro-phenyl)-3,5-dioxo-2,3,4,5-tetrahydro-1,2,4-triazine-6-carboxylic acid. LCMS m/z=546 (M+1); ); $^1$H NMR (DMSO): 11.00 (s, 1H), 8.88 (m, 1H), 8.01-8.05 (m, 1H), 7.58-7.67 (m, 2H), 7.52-7.55 (m, 2H), 7.36-7.45 (m, 4H), 6.88 (m, 1H), 4.08 (q, 2H, J=7Hz), 4.01 (s, 3H), 1.35 (t, 3H, J=7Hz).

VI. Biology

AXL Kinase Assay

The ability of compounds to inhibit the kinase activity of recombinant human baculovirus-expressed AXL was measured by homogeneous TRF (HTRF) using Cisbio's KinEASE™ assay system in white 384-well Optiplates. Assay buffer contained 1 mM DTT, 2 mM MnCl$_2$, 2% DMSO, 50 nM supplement enzymatic buffer, and 1× enzymatic buffer. A 2× concentration of tyrosine kinase (TK) substrate-biotin/ATP mixture made in assay buffer was added to plates at 10 μL/well using the Multidrop Combi (Thermo Fisher Scientific, Waltham, Mass.). The final concentrations were 0.3 μM TK substrate-biotin, and 1.3 μM ATP. Compounds (100 nL), diluted in 100% DMSO on the Biomek FX, (Beckman Coulter, Inc., Brea, Calif.), were transferred to the assay plates using the Biomek FX pintool (2.5% final DMSO in assay). A 2× concentration (final=12 ng/mL) of GST-AXL (diluted in assay buffer) was added to plates at 10 uL/well using the Multidrop Combi. Plates were sealed, briefly shaken and incubated at 25° C. for 30 minutes. A 4× stock of Streptavidin-XL665 (final=18.8 nM) and a 1:100 diluted stock of TK antibody-cryptate were made in HTRF detection buffer and mixed together just prior to adding 20 μL/well on the Multidrop Combi. Plates were sealed, briefly shaken and incubated at 25° C. for 1 hour. The fluorescence of the resulting solution was measured using the PerkinElmer EnVision™ 2102 multi-label plate reader (PerkinElmer, Waltham, Mass.) with an excitation wavelength of 337 nm (laser) and emission wavelengths of 590 and 665 nm. Raw data was expressed as the ratio of 665/590×10,000.

C-MET Kinase Assay

The cMET kinase assay was performed in 384-well Fluotrac™ 200 HiBase microplates using the HTRF KinEASE™ assay described above for AXL except that the assay volume was reduced to half. Enzyme concentration was 8 ng/mL of recombinant human baculovirus-expressed cMET while the substrate concentrations were 0.1 μM and 0.02 μM for the biotinylated peptide and ATP, respectively. Instead of the Multidrop Combi, the BioRAPTR® FRD microfluidic workstation (Beckman Coulter, Brea, Calif.) was utilized for reagent additions.

Data Analysis

Inhibition curves for compounds were generated by plotting percent control activity versus log 10 of the concentration of compound. IC$_{50}$ values were calculated by nonlinear regression using the sigmoidal dose-response (variable slope) equation in GraphPad Prism as follows:

$$y = \text{bottom} + (\text{top} - \text{bottom})/(1 + 10(\log \text{IC}_{50} - x) * \text{Hill Slope})$$

where y is the % kinase activity at a given concentration of compound, x is the logarithm of the concentration of compound, bottom is the % of control kinase activity at the highest compound concentration tested, and top is the % of control kinase activity at the lowest compound concentration examined. The values for bottom and top were fixed at 0 and 100, respectively.

Results

Biological data for Example compounds is presented in the following Table 1. Unless otherwise specified in Table 1, IC$_{50}$ nanomolar value ranges designated as A, B, or C indicate the following ranges:

IC$_{50}$<10 nM A;
IC$_{50}$ 10 nM to 100 nM B; and
IC$_{50}$ 101 nM to 1,000 nM C;

"NT" denotes not tested.

Unless otherwise specified, all values are an average of two or more determinations.

TABLE 1

AXL and c-MET Inhibition

| Example | AXL IC$_{50}$ nM | c-MET IC$_{50}$ nM |
|---|---|---|
| 1 | A | A |
| 2 | A | A |
| 3 | A | B |
| 4 | A | B |
| 5 | A | B |
| 6 | A | A |
| 7 | A | B |
| 8 | A | B |
| 9 | A | A |
| 10 | B | B |
| 11 | A | B |
| 12 | B | B |
| 13 | B | B |
| 14 | A | A |
| 15 | B | B |
| 16 | A | A |
| 17 | A | A |
| 18 | A | B |
| 19 | B | B |
| 20 | A | B |
| 21 | A | B |
| 22 | A | B |
| 23 | A | A |
| 24 | A | A |
| 25 | B | C |
| 26 | A | B |
| 27 | A | B |
| 28 | A | A |
| 29 | A | B |
| 30 | A | B |
| 31 | A | B |
| 32 | A | A |
| 33 | A | B |
| 34 | A | B |
| 35 | B | B |
| 36 | B | B |
| 37 | B | C |
| 38 | B | NT |
| 39 | A | NT |
| 40 | B | B |
| 41 | C | C |
| 42 | B | B |
| 43 | B | B |
| 44 | B | B |
| 45 | B | B |
| 46 | B | A |
| 47 | B | B |
| 48 | C | C |
| 49 | A | A |
| 50 | A | A |
| 51 | A | A |
| 52 | A | B |
| 53 | A | A |
| 54 | A | B |
| 55 | A | B |
| 56 | B | B |
| 57 | A | C |
| 58 | A | B |
| 59 | B | B |
| 60 | B | C |
| 61 | A | A |
| 62 | A | A |
| 63 | A | A |
| 64 | A | B |
| 65 | A | B |
| 66 | A | A |
| 67 | A | B |
| 68 | A | A |
| 69 | A | A |
| 70 | B | B |
| 71 | A | A |
| 72 | A | B |
| 73 | A | B |
| 74 | A | B |
| 75 | A | NT |
| 76 | A | NT |
| 77 | A | B |
| 78 | A | B |
| 79 | A | B |
| 80 | B | C |
| 81 | B | B |
| 82 | A | B |
| 83 | A | B |
| 84 | B | B |
| 85 | A | A |
| 86 | A | B |
| 87 | A | B |
| 88 | A | B |
| 89 | B | C |
| 90 | A | B |
| 91 | A | B |
| 92 | C | NT |
| 93 | B | B |
| 94 | B | B |
| 95 | B | B |
| 96 | A | B |
| 97 | B | C |
| 98 | A | B |
| 99 | C | NT |
| 100 | A | B |
| 101 | A | B |
| 102 | A | A |
| 103 | A | B |
| 104 | A | A |
| 105 | A | B |
| 106 | A | B |
| 107 | A | A |
| 108 | A | A |
| 109 | B | B |
| 110 | A | B |
| 111 | A | B |
| 112 | A | B |
| 113 | A | A |
| 114 | B | B |
| 115 | A | B |
| 116 | B | B |
| 117 | B | C |
| 118 | C | C |
| 119 | C | NT |
| 120 | C | B |
| 121 | C | NT |
| 122 | C | NT |
| 123 | B | C |
| 124 | B | B |
| 125 | A | B |
| 126 | A | C |
| 127 | A | B |
| 128 | A | B |
| 129 | A | B |
| 130 | A | B |
| 131 | A | B |
| 132 | A | B |
| 133 | B | B |
| 134 | B | C |
| 135 | B | C |
| 136 | B | C |
| 137 | B | B |
| 138 | B | B |
| 139 | C | NT |
| 140 | C | NT |
| 141 | B | B |
| 142 | A | B |
| 143 | A | A |
| 144 | A | B |
| 145 | A | B |
| 146 | A | A |
| 147 | A | A |
| 148 | B | B |
| 149 | A | A |
| 150 | A | B |

TABLE 1-continued

AXL and c-MET Inhibition

| Example | AXL IC$_{50}$ nM | c-MET IC$_{50}$ nM |
|---|---|---|
| 151 | A | B |
| 152 | A | B |
| 153 | C | NT |
| 154 | B | C |
| 155 | B | B |
| 156 | B | B |
| 157 | B | C |
| 158 | B | C |
| 159 | A | B |
| 160 | B | C |
| 161 | B | B |
| 162 | B | B |
| 163 | B | B |
| 164 | A | B |
| 165 | B | B |
| 166 | B | C |
| 167 | A | NT |
| 168 | B | NT |
| 169 | B | A |
| 170 | A | B |
| 171 | A | A |

In one embodiment, the invention provides a compound of Formula I or a salt thereof having an AXL IC$_{50}$ of less than 1 μM. In one embodiment, the invention provides a compound of Formula I or a salt thereof having an AXL IC$_{50}$ of less than 100 nM. In one embodiment, the invention provides a compound of Formula I or a salt thereof having an AXL IC$_{50}$ of less than 10 nM. In one embodiment, the invention provides the exemplified compounds of Formula I or salts thereof having AXL IC$_{50}$s of less than 1 μM. In one embodiment, the invention provides the exemplified compounds of Formula I or salts thereof having AXL IC$_{50}$s of less than 100 nM. In one embodiment, the invention provides the exemplified compounds of Formula I or salts thereof having AXL IC$_{50}$s of less than 10 nM.

In one embodiment, the invention provides a compound of Formula I or a salt thereof having a c-Met IC$_{50}$ of less than 1 μM. In one embodiment, the invention provides a compound of Formula I or a salt thereof having a c-Met IC$_{50}$ of less than 100 nM. In one embodiment, the invention provides a compound of Formula I or a salt thereof having a c-Met IC$_{50}$ of less than 10 nM. In one embodiment, the invention provides the exemplified compounds of Formula I or salts thereof having c-Met IC$_{50}$s of less than 1 μM. In one embodiment, the invention provides the exemplified compounds of Formula I or salts thereof having c-Met IC$_{50}$s of less than 100 nM. In one embodiment, the invention provides the exemplified compounds of Formula I or salts thereof having c-Met IC$_{50}$s of less than 10 nM.

In one embodiment, the invention provides a compound of Formula I or a salt thereof having AXL and c-Met IC$_{50}$s of less than 1 μM. In one embodiment, the invention provides a compound of Formula I or a salt thereof having AXL and c-Met IC$_{50}$s of less than 100 nM. In one embodiment, the invention provides a compound of Formula I or a salt thereof having AXL and c-Met IC$_{50}$s of less than 10 nM. In one embodiment, the invention provides the exemplified compounds of Formula I or salts thereof having AXL and c-Met IC$_{50}$s of less than 1 μM. In one embodiment, the invention provides the exemplified compounds of Formula I or salts thereof having AXL and c-Met IC$_{50}$s of less than 100 nM. In one embodiment, the invention provides the exemplified compounds of Formula I or salts thereof having AXL and c-Met IC$_{50}$s of less than 10 nM.

Additional preferred Embodiments of the present invention include:

1. A compound of the formula

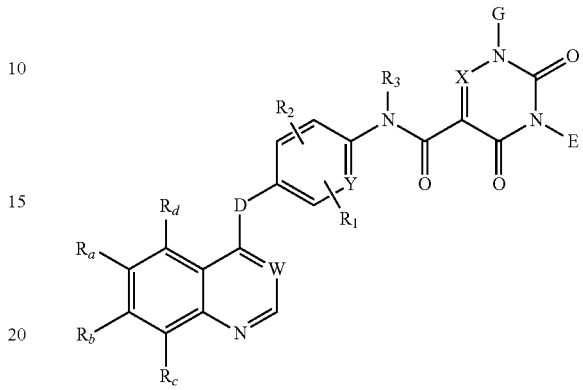

wherein:

$R_a$ is H, alkyl, halo, cyano, hydroxyl, amino, alkylamino, dialkylamino where the alkyl groups of dialkylamino may be the same or different, carbamoyl, N-alkylcarbamoyl, N,N-dialkylcarbamoyl, where the alkyl groups of dialkylcarbamoyl may be the same or different, trihalomethyl, or $R_a$ is OA;

$R_b$ is H, alkyl, halo, cyano, hydroxyl, amino, alkylamino, dialkylamino where the alkyl groups of dialkylamino may be the same or different, carbamoyl, N-alkylcarbamoyl, N,N-dialkylcarbamoyl, where the alkyl groups of dialkylcarbamoyl may be the same or different, trihalomethyl, or $R_b$ is OB;

$R_c$ is H, alkyl, halo, cyano, hydroxyl, amino, alkylamino, dialkylamino where the alkyl groups of dialkylamino may be the same or different, carbamoyl, N-alkylcarbamoyl, N,N-dialkylcarbamoyl, where the alkyl groups of dialkylcarbamoyl may be the same or different, trihalomethyl, or $R_c$ is OJ;

$R_d$ is H, alkyl, halo, cyano, hydroxyl, amino, alkylamino, dialkylamino where the alkyl groups of dialkylamino may be the same or different, carbamoyl, N-alkylcarbamoyl, N,N-dialkylcarbamoyl, where the alkyl groups of dialkylcarbamoyl may be the same or different, trihalomethyl, or $R_d$ is OL;

where A, B, J and L, are, independently, H, alkyl, alkoxyalkyl, cycloalkyl, cycloalkoxyalkyl, heterocyclylalkyl, heterocyclylalkoxyalkyl, arylalkyl or arylalkoxyalkyl, or A and B together with the oxygen atoms to which they are attached form

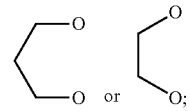

D is O, S, SO, SO$_2$, C=O, C(H)OH, CH$_2$, NH or N-alkyl;

E is H, alkyl, substituted alkyl, alkenyl, substituted alkenyl, alkynyl, substituted alkynyl, cycloalkyl, aryl, substituted aryl, heteroaryl, substituted heteroaryl, heterocyclyl or heteroarylalkyl, where the heteroaryl group of heteroarylalkyl may be substituted or unsubstituted;

G is H, aryl, substituted aryl, heteroaryl, substituted heteroaryl, heterocyclyl, alkyl or cycloalkyl, cycloalkylalkyl, alkenyl or alkynyl, where alkyl, alkenyl or cycloalkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, carboxyl, oxo, carbamoyl, alkylcarbamoyl, dialkylcarbamoyl, where the alkyl groups of dialkylcarbamoyl may be the same or different, and heterocycyclylcarbonyl;

W is CH or N;

X is C—$R_4$ or N, where $R_4$ is H, OH or alkyl, where the alkyl group may be substituted by hydroxyl, alkoxy, alkylamino, or dialkyl amino, where the alkyl groups of dialkylamino may be the same or different;

Y is N, CH or C where C may be substituted with one of the groups $R_1$ or $R_2$; and $R_1$ and $R_2$ are, independently, H, alkyl, cycloalkyl, halo, alkoxy, trihaloalkyl, amino, alkylamino, dialkylamino, where the alkyl groups on dialkylamino may be the same or different, or heterocyclyl; and $R_3$ is H, or alkyl; or a pharmaceutically acceptable salt thereof.

2. A compound according to preferred Embodiment 1 wherein W is CH.

3. A compound according to preferred Embodiment 1 wherein W is N.

4. A compound according to preferred Embodiment 1 of the formula

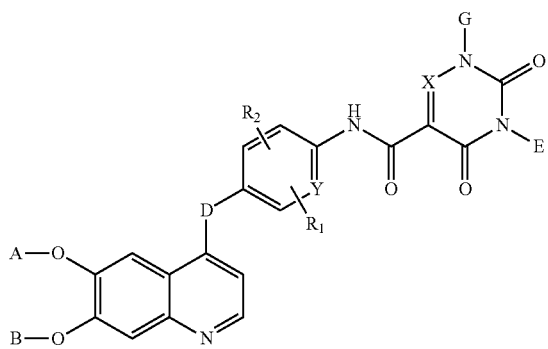

wherein:

A and B are, independently, H, alkyl, alkoxyalkyl, cycloalkyl, cycloalkoxyalkyl, heterocyclylalkyl, heterocyclylalkoxyalkyl, arylalkyl or arylalkoxyalkyl, or A and B together with the oxygen atoms to which they are attached form

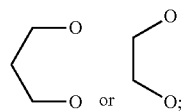

D is O, S, NH, or C=O;

E is H, alkyl, substituted alkyl, alkenyl, substituted alkenyl, alkynyl, substituted alkynyl, cycloalkyl, aryl, substituted aryl, heteroaryl, heterocyclyl, substituted heteroaryl, or heteroarylalkyl, where the heteroaryl group of heteroarylalkyl may be substituted or unsubstituted;

G is H, aryl, substituted aryl, heteroaryl, substituted heteroaryl, heterocyclyl, alkyl or cycloalkyl, cycloalkylalkyl, alkenyl or alkynyl, where alkyl, alkenyl or cycloalkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, carboxyl, oxo, carbamoyl, alkylcarbamoyl, dialkylcarbamoyl, where the alkyl groups of dialkylcarbamoyl may be the same or different, and heterocycyclylcarbonyl;

X is C—$R_4$ or N, where $R_4$ is H or alkyl;

Y is N, CH or C where C may be substituted with one of the groups $R_1$ or $R_2$; and $R_1$ and $R_2$ are, independently, H, alkyl, halo, alkoxy, trihaloalkyl, amino, alkylamino, dialkylamino, where the alkyl groups on dialkylamino may be the same or different; or a pharmaceutically acceptable salt thereof.

5. A compound according to preferred Embodiment 4 wherein A and B are, independently, alkyl, heterocyclylalkyl or heterocyclylalkoxyalkyl.

6. A compound according to preferred Embodiment 4 wherein A and B are, independently, alkyl.

7. A compound according to preferred Embodiment 4 wherein D is O, S or NH.

8. A compound according to preferred Embodiment 4 wherein D is O.

9. A compound according to preferred Embodiment 4 wherein $R_1$ and $R_2$ are, independently, halo, alkoxy, alkyl or H.

10. A compound according to preferred Embodiment 4 wherein $R_1$ and $R_2$ are, independently, halo or alkoxy.

11. A compound according to preferred Embodiment 4 wherein $R_1$ and $R_2$ are, independently, methoxy or fluoro.

12. A compound according to preferred Embodiment 4 wherein X is N or CH.

13. A compound according to preferred Embodiment 4 wherein X is CH.

14. A compound according to preferred Embodiment 4 wherein G is alkyl where alkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, carboxyl, oxo, carbamoyl, alkylcarbamoyl, dialkylcarbamoyl, where the alkyl groups of dialkylcarbamoyl may be the same or different, and heterocycyclylcarbonyl.

15. A compound according to preferred Embodiment 4 wherein E is aryl, substituted aryl or cycloalkyl.

16. A compound according to preferred Embodiment 4 wherein E is substituted aryl.

17. A compound according to preferred Embodiment 4 wherein A and B are, independently, alkyl; D is O, S or NH; $R_1$ and $R_2$ are, independently, halo, alkoxy, alkyl or H; X is N or CH; G is alkyl where alkyl may be substituted by one, two or three groups selected from the group consisting of alkanoyl, cycloalkyl, alkenyl, alkynyl, halo, hydroxyl, alkoxy, alkoxycarbonyl, heterocyclyl, aryl, substituted aryl, aryloxy, arylalkoxy, amino, alkylamino, dialkylamino, where the alkyl groups of dialkylamino may be the same or different, heteroaryl, carboxyl, oxo, carbamoyl, alkylcarbamoyl, dialkylcarbamoyl, where the alkyl groups of dialkylcarbamoyl may be the same or different, and heterocycyclylcarbonyl; and E is aryl, substituted aryl or cycloalkyl.

18. A compound which is
1-Ethyl-3-(4-fluorophenyl)-2,4-dioxo-1,2,3,4-tetrahydropyrimidine-5-carboxylicacid [4-(6,7-dimethoxyquinolin-4-yloxy)-3-fluorophenyl]amide;
3-(4-Fluorophenyl)-1-methyl-2,4-dioxo-1,2,3,4-tetrahydropyrimidine-5-carboxylic acid [4-(6,7-dimethoxyquinolin-4-yloxy)-3-fluoro-phenyl]-amide;
3-(4-Fluorophenyl)-1-(2-methoxyethyl)-2,4-dioxo-1,2,3,4-tetrahydropyrimidine-5-carboxylic acid [4-(6,7-dimethoxyquinolin-4-yloxy)-3-fluorophenyl]-amide;
1-(2-Ethoxyethyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-1-isopropyl-2,4-dioxo-1,2,3,4-tetrahydropyrimidine-5-carboxylic acid [4-(6,7-dimethoxyquinolin-4-yloxy)-3-fluorophenyl]-amide;
1-Cyclopropylmethyl-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-1-(3-methoxypropyl)-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-1-isobutyl-2,4-dioxo-1,2,3,4-tetrahydropyrimidine-5-carboxylic acid [4-(6,7-dimethoxyquinolin-4-yloxy)-3-fluorophenyl]-amide;
1-Allyl-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide;
1-(2-Benzyloxyethyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-2,4-dioxo-1-propyl-1,2,3,4-tetrahydropyrimidine-5-carboxylic acid [4-(6,7-dimethoxyquinolin-4-yloxy)-3-fluorophenyl]-amide;
3-(4-Fluorophenyl)-1-(2-isopropoxyethyl)-2,4-dioxo-1,2,3,4-tetrahydropyrimidine-5-carboxylic acid [4-(6,7-dimethoxyquinolin-4-yloxy)-3-fluorophenyl]-amide;
1-(3-Benzyloxypropyl)-3-(4-fluorophenyl)-2,4-dioxo-1,2,3,4-tetrahydropyrimidine-5-carboxylic acid [4-(6,7-dimethoxyquinolin-4-yloxy)-3-fluoro phenyl]-amide;
1-(3,3-Difluoro-allyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-1-(3-methyl-but-2-enyl)-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-1-(2-morpholin-4-yl-ethyl)-2,4-dioxo-1,2,3,4-tetrahydropyrimidine-5-carboxylic acid [4-(6,7-dimethoxyquinolin-4-yloxy)-3-fluoro phenyl]-amide;
3-(4-Fluorophenyl)-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-1-methyl-2,4-dioxo-1,2,3,4-tetrahydropyrimidine-5-carboxylic acid [4-(6,7-dimethoxyquinolin-4-yloxy)-phenyl]-amide;
1-(2-Benzyloxyethyl)-3-(4-fluoro-phenyl)-2,4-dioxo-1,2,3,4-tetrahydropyrimidine-5-carboxylic acid [4-(6,7-dimethoxyquinolin-4-yloxy)-phenyl]-amide;
1-(2-Dimethylaminoethyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide;
1-(3-Benzyloxypropyl)-3-(4-fluorophenyl)-2,4-dioxo-1,2,3,4-tetrahydropyrimidine-5-carboxylic acid [4-(6,7-dimethoxyquinolin-4-yloxy)phenyl]-amide;
1-(3-Benzyloxypropyl)-3-(4-fluorophenyl)-2,4-dioxo-1,2,3,4-tetrahydropyrimidine-5-carboxylic acid [4-(6,7-dimethoxyquinolin-4-yloxy)-2-fluorophenyl]-amide;
3-(4-Fluorophenyl)-1-isopropyl-2,4-dioxo-1,2,3,4-tetrahydropyrimidine-5-carboxylic acid [4-(6,7-dimethoxyquinolin-4-yloxy)phenyl]-amide;
3-(4-Fluorophenyl)-2,4-dioxo-1,2,3,4-tetrahydropyrimidine-5-carboxylic acid [4-(6,7-dimethoxyquinolin-4-yloxy)phenyl]-amide;
3-Cyclohexyl-1-ethyl-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-2,4-dioxo-1-(2-pyrrolidin-1-yl-ethyl)-1,2,3,4-tetrahydropyrimidine-5-carboxylic acid [4-(6,7-dimethoxyquinolin-4-yloxy)-3-fluoro phenyl]-amide;
3-(4-Fluorophenyl)-2,4-dioxo-1-(2-piperidin-1-yl-ethyl)-1,2,3,4-tetrahydropyrimidine-5-carboxylic acid [4-(6,7-dimethoxyquinolin-4-yloxy)-3-fluorophenyl]-amide;
1-Ethyl-3-(4-fluorophenyl)-2,4-dioxo-1,2,3,4-tetrahydropyrimidine-5-carboxylic acid [4-(6,7-dimethoxyquinolin-4-yloxy)-phenyl]-amide;
1-Cyclobutyl-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide;
3-(4-Fluorophenyl)-2,4-dioxo-1-(tetrahydropyran-4-yl)-1,2,3,4-tetrahydropyrimidine-5-carboxylic acid [4-(6,7-dimethoxyquinolin-4-yloxy)-3-fluoro phenyl]-amide;
1-Ethyl-3-(4-fluorophenyl)-2,4-dioxo-1,2,3,4-tetrahydropyrimidine-5-carboxylic acid [5-(6,7-dimethoxyquinolin-4-yloxy)-pyridin-2-yl]-amide was synthesized starting with 5-(6,7-dimethoxyquinolin-4-yloxy)-pyridin-2-ylamine;
1-Ethyl-3-(4-fluorophenyl)-6-methyl-2,4-dioxo-1,2,3,4-tetrahydropyrimidine-5-carboxylic acid [4-(6,7-dimethoxyquinolin-4-yloxy)-3-fluorophenyl]-amide;
1-Ethyl-3-(4-fluorophenyl)-2,4-dioxo-1,2,3,4-tetrahydropyrimidine-5-carboxylic acid [4-(6,7-diethoxyquinolin-4-yloxy)-3-fluorophenyl]-amide;
3-(4-Fluorophenyl)-1-isopropyl-2,4-dioxo-1,2,3,4-tetrahydropyrimidine-5-carboxylic acid [5-(6,7-dimethoxyquinolin-4-yloxy)-pyridin-2-yl]-amide;
1-Cyclopropylmethyl-3-(4-fluorophenyl)-2,4-dioxo-1,2,3,4-tetrahydropyrimidine-5-carboxylic acid [5-(6,7-dimethoxyquinolin-4-yloxy)pyridin-2-yl]-amide;
3-(4-Fluorophenyl)-2,4-dioxo-1-pentyl-1,2,3,4-tetrahydropyrimidine-5-carboxylic acid [4-(6,7-dimethoxyquinolin-4-yloxy)-3-fluorophenyl]-amide;
3-(4-Fluorophenyl)-1-isopropyl-2,4-dioxo-1,2,3,4-tetrahydropyrimidine-5-carboxylic acid [4-(6,7-diethoxyquinolin-4-yloxy)-3-fluoro-phenyl]-amide;
3-(4-Fluorophenyl)-1-isopropyl-2,4-dioxo-1,2,3,4-tetrahydropyrimidine-5-carboxylic acid [4-(5,7-dimethoxyquinolin-4-yloxy)phenyl]-amide;
1-Ethyl-3-(4-fluorophenyl)-2,4-dioxo-1,2,3,4-tetrahydropyrimidine-5-carboxylic acid [4-(5,7-dimethoxyquinolin-4-yloxy)-phenyl]-amide;
1-Ethyl-3-(4-fluorophenyl)-2,4-dioxo-1,2,3,4-tetrahydropyrimidine-5-carboxylic acid [4-(7-benzyloxy-6-methoxyquinolin-4-yloxy)-3-fluorophenyl]-amide;
3-(4-Fluorophenyl)-1-isopropyl-2,4-dioxo-1,2,3,4-tetrahydropyrimidine-5-carboxylic acid [4-(7-benzyloxy-6-methoxyquinolin-4-yloxy)-3-fluorophenyl]-amide;
1-Ethyl-3-(4-fluorophenyl)-2,4-dioxo-1,2,3,4-tetrahydropyrimidine-5-carboxylic acid [3-fluoro-4-(7-hydroxy-6-methoxyquinolin-4-yloxy)phenyl]-amide;
1-Ethyl-3-(4-fluorophenyl)-2,4-dioxo-1,2,3,4-tetrahydropyrimidine-5-carboxylic acid {3-fluoro-4-[6-methoxy-7-(3-morpholin-4-yl-propoxy)quinolin-4-yloxy]phenyl}-amide;

1-Ethyl-3-(4-fluorophenyl)-2,4-dioxo-1,2,3,4-tetrahydropyrimidine-5-carboxylic acid {3-fluoro-4-[6-methoxy-7-(2-methoxyethoxy)quinolin-4-yloxy]-phenyl}-amide;

1-Ethyl-3-(4-fluorophenyl)-2,4-dioxo-1,2,3,4-tetrahydropyrimidine-5-carboxylic acid {3-fluoro-4-[6-methoxy-7-(2-morpholin-4-yl-ethoxy)-quinolin-4-yloxy]phenyl}-amide;

3-(4-Fluorophenyl)-1-isopropyl-2,4-dioxo-1,2,3,4-tetrahydropyrimidine-5-carboxylic acid [3-fluoro-4-(7-hydroxy-6-methoxyquinolin-4-yloxy)-phenyl]-amide;

3-(4-Fluorophenyl)-1-isopropyl-2,4-dioxo-1,2,3,4-tetrahydropyrimidine-5-carboxylic acid {3-fluoro-4-[6-methoxy-7-(3-morpholin-4-yl-propoxy)-quinolin-4-yloxy]phenyl}-amide;

3-(4-Fluorophenyl)-1-(2-hydroxyethyl)-2,4-dioxo-1,2,3,4-tetrahydropyrimidine-5-carboxylic acid [4-(6,7-dimethoxyquinolin-4-yloxy)-3-fluorophenyl]-amide;

3-(4-Fluorophenyl)-1-(3-hydroxypropyl)-2,4-dioxo-1,2,3,4-tetrahydropyrimidine-5-carboxylic acid [4-(6,7-dimethoxyquinolin-4-yloxy)-3-fluorophenyl]-amide;

3-(4-Fluorophenyl)-1-(3-hydroxypropyl)-2,4-dioxo-1,2,3,4-tetrahydropyrimidine-5-carboxylic acid [4-(6,7-dimethoxy-quinolin-4-yloxy)-2-fluoro-phenyl]-amide;

3-(4-Fluorophenyl)-1-(3-hydroxypropyl)-2,4-dioxo-1,2,3,4-tetrahydropyrimidine-5-carboxylic acid [4-(6,7-dimethoxyquinolin-4-yloxy)phenyl]-amide;

3-(4-Fluorophenyl)-1-(2-hydroxyethyl)-2,4-dioxo-1,2,3,4-tetrahydropyrimidine-5-carboxylic acid [4-(6,7-dimethoxyquinolin-4-yloxy)phenyl]-amide;

1-((S)-2,3-Dihydroxypropyl)-3-(4-fluorophenyl)-2,4-dioxo-1,2,3,4-tetrahydropyrimidine-5-carboxylic acid [4-(6,7-dimethoxyquinolin-4-yloxy)-3-fluorophenyl]-amide;

3-(4-Fluorophenyl)-1-(4-hydroxybutyl)-2,4-dioxo-1,2,3,4-tetrahydropyrimidine-5-carboxylic acid [4-(6,7-dimethoxyquinolin-4-yloxy)-3-fluorophenyl]-amide;

3-(4-Fluorophenyl)-1-isopropyl-2,4-dioxo-1,2,3,4-tetrahydropyrimidine-5-carboxylic acid [4-(6-cyano-7-methoxyquinolin-4-yloxy)-phenyl]-amide;

3-(4-fluoro-phenyl)-1-methyl-2,4-dioxo-1,2,3,4-tetrahydropyrimidine-5-carboxylic acid {4-[(6,7-dimethoxy-quinolin-4-yl)-hydroxy-methyl]-3-fluoro-phenyl}-amide;

3-(4-fluoro-phenyl)-1-methyl-2,4-dioxo-1,2,3,4-tetrahydropyrimidine-5-carboxylic acid [4-(6,7-dimethoxy-quinolin-4-ylmethyl)-3-fluoro-phenyl]-amide;

1-Ethyl-3-(4-fluoro-phenyl)-2,4-dioxo-1,2,3,4-tetrahydro-pyrimidine-5-carboxylic acid [3-cyclopropyl-4-(6,7-dimethoxy-quinolin-4-yloxy)-phenyl]-amide;

3-(4-Fluoro-phenyl)-1-isopropyl-2,4-dioxo-1,2,3,4-tetrahydro-pyrimidine-5-carboxylic acid [3-cyclopropyl-4-(6,7-dimethoxy-quinolin-4-yloxy)-phenyl]-amide;

3-(4-Fluoro-phenyl)-2,4-dioxo-1-prop-2-ynyl-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-1-(2-imidazol-1-yl-ethyl)-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-2,4-dioxo-1-(2-pyrazol-1-yl-ethyl)-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-2,4-dioxo-1-phenethyl-1,2,3,4-tetrahydro-pyrimidine-5-carboxylic acid [4-(6,7-dimethoxy-quinolin-4-yloxy)-3-fluoro-phenyl]-amide;

1-[2-(1,3-Dioxolan-2-yl-ethyl)]-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

1-Diethylcarbamoylmethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-1-(2-morpholin-4-yl-2-oxo-ethyl)-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-2,4-dioxo-1-[2-(2-oxo-pyrrolidin-1-yl)-ethyl]-1,2,3,4-tetrahydro-pyrimidine-5-carboxylic acid [4-(6,7-dimethoxy-quinolin-4-yloxy)-3-fluoro-phenyl]-amide;

1-(2-Fluoro-ethyl)-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

[5-[4-(6,7-Dimethoxy-quinolin-4-yloxy)-3-fluoro-phenylcarbamoyl]-3-(4-fluoro-phenyl)-2,4-dioxo-3,4-dihydro-2H-pyrimidin-1-yl]-acetic acid tert-butyl ester;

[5-[4-(6,7-Dimethoxyquinolin-4-yloxy)-3-fluorophenylcarbamoyl]-3-(4-fluorophenyl)-2,4-dioxo-3,4-dihydro-2H-pyrimidin-1-yl]-acetic acid;

3-(4-Fluoro-phenyl)-1-oxazol-2-ylmethyl-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-2,4-dioxo-1-(tetrahydro-furan-2-ylmethyl)-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-2,4-dioxo-1-(tetrahydro-pyran-4-ylmethyl)-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-1-(2-methyl-thiazol-4-ylmethyl)-2,4-dioxo-1,2,3,4-tetrahydro-pyrimidine-5-carboxylic acid [4-(6,7-dimethoxy-quinolin-4-yloxy)-3-fluoro-phenyl]-amide;

1-Cyclopentyl-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

1-Benzyl-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-1-[2-(2-fluoro-phenyl)-ethyl]-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-1-[2-(4-fluoro-phenyl)-ethyl]-2,4-dioxo-1,2,3,4-tetrahydro-pyrimidine-5-carboxylic acid [4-(6,7-dimethoxy-quinolin-4-yloxy)-3-fluoro-phenyl]-amide;

1-(2-Cyclohexyl-ethyl)-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-2,4-dioxo-1-(3-phenyl-propyl)-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-2,4-dioxo-1-(2-oxo-2-pyrrolidin-1-yl-ethyl)-1,2,3,4-tetrahydro-pyrimidine-5-carboxylic acid [4-(6,7-dimethoxy-quinolin-4-yloxy)-3-fluoro-phenyl]-amide;

1-Dimethylcarbamoylmethyl-3-(4-fluorophenyl)-2,4-dioxo-1,2,3,4-tetrahydro-pyrimidine-5-carboxylic acid [4-(6,7-dimethoxy-quinolin-4-yloxy)-3-fluorophenyl]-amide;

1-(1-Dimethylcarbamoyl-2-oxo-propyl)-3-(4-fluoro-phenyl)-2,4-dioxo-1,2,3,4-tetrahydro-pyrimidine-5-carboxylic acid [4-(6,7-dimethoxy-quinolin-4-yloxy)-3-fluorophenyl]-amide;

3-(4-Fluoro-phenyl)-2,4-dioxo-1,2,3,4-tetrahydro-pyrimidine-5-carboxylic acid [4-(6,7-dimethoxy-quinolin-4-yloxy)-2-fluoro-phenyl]-amide;

3-(4-Fluoro-phenyl)-1-methyl-2,4-dioxo-1,2,3,4-tetrahydro-pyrimidine-5-carboxylic acid [4-(6,7-dimethoxy-quinolin-4-yloxy)-2-fluoro-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-2-fluoro-phenyl]-amide;

1-Allyl-3-(4-fluoro-phenyl)-2,4-dioxo-1,2,3,4-tetrahydro-pyrimidine-5-carboxylic acid [4-(6,7-dimethoxy-quinolin-4-yloxy)-2-fluoro-phenyl]-amide;

3-(4-Fluoro-phenyl)-2,4-dioxo-1,2,3,4-tetrahydropyrimidine-5-carboxylic acid [4-(6,7-dimethoxy-quinolin-4-yloxy)-3,5-difluoro-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3,5-difluoro-phenyl]-amide;

3-Ethyl-1-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

1,3-Dimethyl-2,4-dioxo-1,2,3,4-tetrahydropyrimidine-5-carboxylic acid [4-(6,7-dimethoxy-quinolin-4-yloxy)-3-fluorophenyl]-amide;

1,3-Diethyl-2,4-dioxo-1,2,3,4-tetrahydro-pyrimidine-5-carboxylic acid [4-(6,7-dimethoxy-quinolin-4-yloxy)-3-fluoro-phenyl]-amide;

1,3-Diisopropyl-2,4-dioxo-1,2,3,4-tetrahydro-pyrimidine-5-carboxylic acid [4-(6,7-dimethoxy-quinolin-4-yloxy)-3-fluoro-phenyl]-amide;

1,3-Bis-cyclopropylmethyl-2,4-dioxo-1,2,3,4-tetrahydro-pyrimidine-5-carboxylic acid [4-(6,7-dimethoxy-quinolin-4-yloxy)-3-fluoro-phenyl]-amide;

1,3-Diallyl-2,4-dioxo-1,2,3,4-tetrahydro-pyrimidine-5-carboxylic acid [4-(6,7-dimethoxy-quinolin-4-yloxy)-3-fluoro-phenyl]-amide;

1,3-Bis-(3-methyl-but-2-enyl)-2,4-dioxo-1,2,3,4-tetrahydro-pyrimidine-5-carboxylic acid [4-(6,7-dimethoxy-quinolin-4-yloxy)-3-fluoro-phenyl]-amide;

2,4-Dioxo-1,3-di-prop-2-ynyl-1,2,3,4-tetrahydro-pyrimidine-5-carboxylic acid [4-(6,7-dimethoxy-quinolin-4-yloxy)-3-fluoro-phenyl]-amide;

2,4-Dioxo-1,2,3,4-tetrahydro-pyrimidine-5-carboxylic acid [4-(6,7-dimethoxy-quinolin-4-yloxy)-3-fluoro-phenyl]-amide;

1-Ethyl-2,4-dioxo-3-phenyl-1,2,3,4-tetrahydro-pyrimidine-5-carboxylic acid [4-(6,7-dimethoxy-quinolin-4-yloxy)-3-fluoro-phenyl]-amide;

1-Isopropyl-2,4-dioxo-3-phenyl-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-2,4-dioxo-1-propyl-1,2,3,4-tetrahydro-pyrimidine-5-carboxylic acid [4-(6,7-dimethoxy-quinoline-4-carbonyl)-3-fluoro-phenyl]-amide;

4-(4-Fluoro-phenyl)-2-isopropyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-(4-Fluorophenyl)-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

2-Ethyl-4-(4-fluoro-phenyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-(4-Fluorophenyl)-2-isopropyl-3,5-dioxo-2,3,4,5-tetrahydro-[1,2,4]triazine-6-carboxylic acid [4-(2,3-dihydro-[1,4]dioxino[2,3-g]quinolin-9-yloxy)-3-fluorophenyl]-amide;

4-(4-Fluoro-phenyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-(4-Fluorophenyl)-2-(2-hydroxyethyl)-3,5-dioxo-2,3,4,5-tetrahydro-[1,2,4]triazine-6-carboxylic acid [4-(6,7-dimethoxyquinolin-4-yloxy)-3-fluorophenyl]-amide;

2-Ethyl-4-(4-fluorophenyl)-3,5-dioxo-2,3,4,5-tetrahydro[1,2,4]triazine-6-carboxylic acid [4-(6,7-diethoxy-quinolin-4-yloxy)-3-fluoro-phenyl]-amide;

4-(4-Fluoro-phenyl)-2-isopropyl-3,5-dioxo-2,3,4,5-tetrahydro-[1,2,4]triazine-6-carboxylic acid [5-(6,7-dimethoxy-quinolin-4-yloxy)-pyridin-2-yl]-amide;

4-(4-Fluorophenyl)-2-isopropyl-3,5-dioxo-2,3,4,5-tetrahydro-[1,2,4]triazine-6-carboxylic acid [3-fluoro-4-(7-methoxyquinolin-4-yloxy)-phenyl]-amide;

4-(4-Fluorophenyl)-3,5-dioxo-2-(2-oxo-propyl)-2,3,4,5-tetrahydro-[1,2,4]triazine-6-carboxylic acid [4-(6,7-dimethoxyquinolin-4-yloxy)-3-fluorophenyl]-amide;

4-(4-Fluoro-phenyl)-3,5-dioxo-2-prop-2-ynyl-2,3,4,5-tetrahydro-[1,2,4]triazine-6-carboxylic acid [4-(6,7-dimethoxy-quinolin-4-yloxy)-3-fluoro-phenyl]-amide;

2-Methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

2-Methyl-3,5-dioxo-4-prop-2-ynyl-2,3,4,5-tetrahydro-[1,2,4]triazine-6-carboxylic acid [4-(6,7-dimethoxy-uinolin-4-yloxy)-3-fluoro-phenyl]-amide;

2-Methyl-4-(5-methyl-isoxazol-3-ylmethyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

2-Methyl-3,5-dioxo-4-pent-2-ynyl-2,3,4,5-tetrahydro-[1,2,4]triazine-6-carboxylic acid [4-(6,7-dimethoxy-uinolin-4-yloxy)-3-fluoro-phenyl]-amide;

4-(4-Hydroxy-but-2-ynyl)-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-(1,5-Dimethyl-1H-pyrazol-3-ylmethyl)-2-methyl-3,5-dioxo-2,3,4,5-tetrahydro-[1,2,4]triazine-6-carboxylic acid [4-(6,7-dimethoxyquinolin-4-yloxy)-3-fluorophenyl]-amide;

2-Methyl-3,5-dioxo-4-(2-pyrazol-1-yl-ethyl)-2,3,4,5-tetrahydro-[1,2,4]triazine-6-carboxylic acid [4-(6,7-dimethoxyquinolin-4-yloxy)-3-fluorophenyl]-amide;

2-Methyl-4-(1-methyl-1H-[1,2,4]triazol-3-ylmethyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-Cyanomethyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-Ethyl-2-methyl-3,5-dioxo-2,3,4,5-tetrahydro-[1,2,4]triazine-6-carboxylic acid [4-(6,7-dimethoxyquinolin-4-yloxy)-3-fluoro-phenyl]-amide;

4-Allyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-Cyclopropylmethyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

2-Methyl-3,5-dioxo-4-(tetrahydro-pyran-4-ylmethyl)-2,3,4,5-tetrahydro-[1,2,4]triazine-6-carboxylic acid [4-(6,7-dimethoxy-quinolin-4-yloxy)-3-fluoro-phenyl]-amide;

4-Isobutyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-Cyclobutylmethyl-2-methyl-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

4-(2,2-Dimethylpropyl)-2-methyl-3,5-dioxo-2,3,4,5-tetrahydro-[1,2,4]triazine-6-carboxylic acid [4-(6,7-dimethoxyquinolin-4-yloxy)-3-fluorophenyl]-amide;

±2-Methyl-4-(2-methyl-butyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

3-(4-Fluoro-phenyl)-1-methyl-2,4-dioxo-1,2,3,4-tetrahydro-pyrimidine-5-carboxylic acid [4-([1,3]dioxolo[4,5-g]quinolin-8-yloxy)-3-fluoro-phenyl]-amide;

1-Ethyl-3-(4-fluorophenyl)-2,4-dioxo-1,2,3,4-tetrahydropyrimidine-5-carboxylic acid [4-(2,3-dihydro-[1,4]dioxino[2,3-g]quinolin-9-yloxy)-3-fluoro-phenyl]-amide;

2-Cyclopropylmethyl-4-(4-fluorophenyl)-3,5-dioxo-2,3,4,5-tetrahydro-[1,2,4]triazine-6-carboxylic acid [4-(6,7-dimethoxy-quinolin-4-yloxy)-3-fluoro-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-ylamino)-phenyl]-amide;

3-(4-Fluorophenyl)-1-isopropyl-2,4-dioxo-1,2,3,4-tetrahydropyrimidine-5-carboxylic acid [4-(6,7-dimethoxyquinolin-4-ylamino)-phenyl]-amide;

4-(4-Fluoro-phenyl)-2-isopropyl-3,5-dioxo-2,3,4,5-tetrahydro-[1,2,4]triazine-6-carboxylic acid [4-(6,7-dimethoxy-quinolin-4-ylamino)-phenyl]-amide;

1-ethyl-3-(4-fluoro-phenyl)-2,4-dioxo-1,2,3,4-tetrahydropyrimidine-5-carboxylic acid [4-(6,7-dimethoxy-quinolin-4-ylsulfanyl)-phenyl]-amide;

3-(4-Fluoro-phenyl)-1-isopropyl-2,4-dioxo-1,2,3,4-tetrahydro-pyrimidine-5-carboxylic acid [4-(6,7-dimethoxy-quinolin-4-ylsulfanyl)-phenyl]-amide;

3-(4-Fluorophenyl)-1-isopropyl-2,4-dioxo-1,2,3,4-tetrahydropyrimidine-5-carboxylic acid {4-[(6,7-dimethoxy-quinolin-4-yl)-methyl-amino]-phenyl}-amide;

1-Ethyl-3-(4-fluorophenyl)-2,4-dioxo-1,2,3,4-tetrahydropyrimidine-5-carboxylic acid {4-[(6,7-dimethoxy-quinolin-4-yl)-methylamino]-phenyl}-amide;

3-(4-Fluoro-phenyl)-1-isopropyl-2,4-dioxo-1,2,3,4-tetrahydro-pyrimidine-5-carboxylic acid [4-(6,7-dimethoxy-quinazolin-4-yloxy)-phenyl]-amide;

1-Ethyl-3-(4-fluorophenyl)-2,4-dioxo-1,2,3,4-tetrahydropyrimidine-5-carboxylic acid [4-(6,7-dimethoxy-quinazolin-4-yloxy)-phenyl]-amide;

1-Ethyl-3-(4-fluorophenyl)-2,4-dioxo-1,2,3,4-tetrahydropyrimidine-5-carboxylic acid [4-(6,7-dimethoxy-quinolin-4-yloxy)-2-methoxyphenyl]-amide;

1-Methyl-3-(4-fluoro-phenyl)-2,4-dioxo-1,2,3,4-tetrahydropyrimidine-5-carboxylic acid [4-(6,7-dimethoxy-quinolin-4-yloxy)-2-methoxy-phenyl]-amide;

1-Isopropyl-3-(4-fluoro-phenyl)-2,4-dioxo-1,2,3,4-tetrahydro-pyrimidine-5-carboxylic acid [4-(6,7-dimethoxy-quinolin-4-yloxy)-2-methoxy-phenyl]-amide;

1-Methyl-3-(4-fluorophenyl)-2,4-dioxo-1,2,3,4-tetrahydropyrimidine-5-carboxylic acid [4-(6,7-dimethoxy-quinolin-4-yloxy)-2,3-difluoro-phenyl]-amide;

1-Ethyl-3-(4-fluoro-phenyl)-2,4-dioxo-1,2,3,4-tetrahydropyrimidine-5-carboxylic acid [4-(6,7-dimethoxy-quinolin-4-yloxy)-2,3-difluoro-phenyl]-amide;

1-Ethyl-3-(4-fluoro-phenyl)-2,4-dioxo-1,2,3,4-tetrahydropyrimidine-5-carboxylic acid [4-(6,7-dimethoxy-quinolin-4-yloxy)-3-methyl-phenyl]-amide;

3-(4-Fluoro-phenyl)-2,4-dioxo-1,2,3,4-tetrahydro-pyrimidine-5-carboxylic acid [4-(6,7-dimethoxy-quinolin-4-yloxy)-3-methyl-phenyl]-amide;

3-(4-Fluoro-phenyl)-2,4-dioxo-1,2,3,4-tetrahydro-pyrimidine-5-carboxylic acid [4-(6,7-dimethoxy-quinolin-4-yloxy)-3-methoxy-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-methoxy-phenyl]-amide;

1-Ethyl-3-(4-fluoro-phenyl)-2,4-dioxo-1,2,3,4-tetrahydro-pyrimidine-5-carboxylic acid [3-chloro-4-(6,7-dimethoxy-quinolin-4-yloxy)-3-methoxy-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-2-dimethylamino-phenyl]-amide;

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-2-dimethylamino-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-isopropyl-phenyl]-amide;

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-3-isopropyl-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-2,3-dimethyl-phenyl]-amide;

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-2,3-dimethyl-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-trifluoromethyl-phenyl]-amide;

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-3-trifluoromethyl-phenyl]-amide;

1-Ethyl-3-(4-fluoro-phenyl)-2,4-dioxo-1,2,3,4-tetrahydro-pyrimidine-5-carboxylic acid [4-(6,7-dimethoxy-quinolin-4-yloxy)-3,5-dimethyl-phenyl]-amide;

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-3,5-dimethyl-phenyl]-amide;

3-(4-Fluoro-phenyl)-1-isopropyl-2,4-dioxo-1,2,3,4-tetrahydro-pyrimidine-5-carboxylic acid [4-(6,7-dimethoxy-quinolin-4-yloxy)-3-methyl-phenyl]-amide;

2-Ethyl-4-(4-fluoro-phenyl)-3,5-dioxo-2,3,4,5-tetrahydro-1,2,4-triazine-6-carboxylic acid [5-(6,7-dimethoxy-quinolin-4-yloxy)-pyridin-2-yl]-amide;

2-Ethyl-4-(4-fluoro-phenyl)-3,5-dioxo-2,3,4,5-tetrahydro-1,2,4-triazine-6-carboxylic acid [4-(6,7-dimethoxy-quinolin-4-yloxy)-3-isopropyl-phenyl]-amide; or 4-(4-Fluoro-phenyl)-2-isopropyl-3,5-dioxo-2,3,4,5-tetrahydro-1,2,4-triazine-6-carboxylic acid [4-(6,7-dimethoxy-quinolin-4-yloxy)-2-methoxy-phenyl]-amide; or a pharmaceutically acceptable salt thereof.

19. A method of treating a subject suffering from an AXL- or c-MET-mediated disorder or condition comprising administering to the subject a therapeutically effective amount of a compound according to any one of preferred Embodiments 1 to 18.

20. A method according to preferred Embodiment 19 wherein the AXL- or c-MET-mediated disorder or condition is the development of resistance to cancer therapies.

21. A compound according to any one of preferred Embodiments 1 to 18 for use in the treatment of a subject suffering from an AXL- or c-MET-mediated disorder or condition.

22. The method of preferred Embodiment 19 wherein the AXL- or c-MET-mediated disorder or condition is cancer.

23. A compound according to preferred Embodiment 21 wherein the AXL- or c-MET-mediated disorder or condition is cancer.

24. The method of preferred Embodiment 19 wherein the AXL- or c-MET-mediated disorder is selected from chronic myelogenous leukemia, chronic myeloproliferative disorder, lung cancer, prostate cancer, esophageal cancer, ovarian cancer, pancreatic cancer, gastric cancer, liver cancer, thyroid cancer, renal cell carcinoma, glioblastoma, breast cancer, acute myeloid leukemia, colorectal cancer, uterine cancer, malignant glioma, uveal melanoma, osteosarcoma and soft tissue sarcoma.

25. A compound according to preferred Embodiment 21 wherein the AXL- or c-MET-mediated disorder is selected from chronic myelogenous leukemia, chronic myeloproliferative disorder, lung cancer, prostate cancer, esophageal cancer, ovarian cancer, pancreatic cancer, gastric cancer, liver cancer, thyroid cancer, renal cell carcinoma, glioblastoma, breast cancer, acute myeloid leukemia, colorectal cancer, uterine cancer, malignant glioma, uveal melanoma, osteosarcoma and soft tissue sarcoma.

26. A method of treating a proliferative disorder in a subject in need thereof, comprising administering to the subject a therapeutically effective amount of a compound according to any one of preferred Embodiments 1 to 18.

27. A compound according to any one of preferred Embodiments 1 to 18 for use in the treatment of a subject suffering from a proliferative disorder.

28. A method according to preferred Embodiment 26 wherein the proliferative disorder is cancer.

29. A compound according to preferred Embodiment 27 wherein the proliferative disorder is cancer.

30. A method according to preferred Embodiment 26 wherein the proliferative disorder is selected from chronic myelogenous leukemia, chronic myeloproliferative disorder, lung cancer, prostate cancer, esophageal cancer, ovarian cancer, pancreatic cancer, gastric cancer, liver cancer, thyroid cancer, renal cell carcinoma, glioblastoma, breast cancer, acute myeloid leukemia, colorectal cancer, uterine cancer, malignant glioma, uveal melanoma, osteosarcoma and soft tissue sarcoma.

31. A compound according to preferred Embodiment 29 wherein the proliferative disorder is selected from chronic myelogenous leukemia, chronic myeloproliferative disorder, lung cancer, prostate cancer, esophageal cancer, ovarian cancer, pancreatic cancer, gastric cancer, liver cancer, thyroid cancer, renal cell carcinoma, glioblastoma, breast cancer, acute myeloid leukemia, colorectal cancer, uterine cancer, malignant glioma, uveal melanoma, osteosarcoma and soft tissue sarcoma.

32. A pharmaceutical composition comprising a compound according to any one of preferred Embodiments 1 to 18 and a pharmaceutically acceptable carrier, diluents or excipient therefor.

33. A compound of Formula I or a salt thereof,

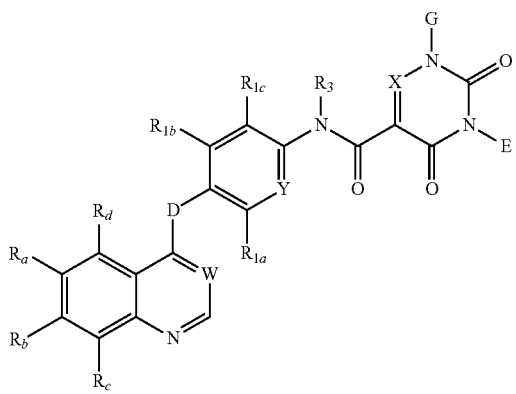

Formula I wherein:
E is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, phenyl optionally substituted by 1-6 $R^{19}$, and $C_{3-6}$cycloalkyl optionally substituted by 1-6 $R^{19}$;
G is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$ phenyl optionally substituted by 1-3 $R^{19}$, $C_{3-6}$cycloalkyl optionally substituted by 1-3 $R^{19}$, and 3-6 membered heterocyclyl optionally substituted by 1-3 $R^{19}$;
X is N or C—$R_4$;
Y is N or C—$R_{1d}$;
$R_3$ is H or $C_{1-6}$alkyl;
D is —O—, —S—, —C(=O)—, —CHOH—, —CH$_2$—, —NH— or —N$C_{1-6}$alkyl-;
W is CH or N;
$R_a$, $R_b$, $R_c$, and $R_d$ are independently chosen from H, $C_{1-6}$alkyl optionally substituted by 1-6 $R^{119}$, —CN, and —OR$^{110}$; or $R_a$ and $R_b$ can, together with the atoms linking them, form a 3-6 membered heterocyclyl optionally substituted by 1-6 $R^{119}$
$R_{1a}$, $R_{1b}$, $R_{1c}$, and $R_{1d}$ are independently chosen from H, $C_{1-6}$alkyl optionally substituted by 1-6 $R^{119}$, $C_{3-6}$cycloalkyl optionally substituted by 1-6 $R^{119}$, 3-6 membered heterocyclyl optionally substituted by 1-6 $R^{119}$, halogen, —CN, —NR$^{112}$R$^{113}$, and —OR$^{110}$;
$R_4$ is chosen from H and $C_{1-6}$alkyl;
$R^{19}$ at each occurrence is independently chosen from $C_{1-6}$alkyl optionally substituted by 1-6 $R^{39}$, phenyl optionally substituted by 1-6 $R^{39}$, $C_{3-6}$cycloalkyl optionally substituted by 1-6 $R^{39}$, 3-6 membered heterocyclyl optionally substituted by 1-6 $R^{39}$, 5-6 membered heteroaryl optionally substituted by 1-6 $R^{39}$, halogen, —CN, —C(=O)OR$^{30}$, —C(=O)NR$^{32}$R$^{33}$, —NR$^{32}$R$^{33}$, —OR$^{30}$, and =O;
$R^{30}$, $R^{32}$ and $R^{33}$ at each occurrence is independently chosen from H, $C_{1-6}$alkyl, $C_{1-6}$halolkyl, phenyl, benzyl, $C_{5-6}$cycloalkyl, 5-6 membered heterocyclyl, and 5-6 membered heteroaryl; or $R^{32}$ and $R^{33}$ may form, together with the nitrogen atom to which they are attached, a 5-6 membered heterocyclyl or a 5-6 membered heteroaryl;
$R^{39}$ at each occurrence is independently chosen from $C_{1-6}$alkyl, $C_{1-6}$haloalkyl, and benzyl;
$R^{110}$, $R^{112}$, and $R^{113}$ at each occurrence is independently chosen from H and $C_{1-6}$alkyl optionally substituted by 1-3 $R^{129}$;

$R^{119}$ at each occurrence is independently chosen from $C_{1-6}$alkyl optionally substituted by 1-3 $R^{159}$, 5-6 membered heterocyclyl optionally substituted by 1-3 $R^{159}$, and halogen;

$R^{129}$ and $R^{159}$ at each occurrence is independently chosen from $C_{1-6}$alkyl, $C_{1-6}$-haloalkyl, benzyl, and halogen; and n at each occurrence is independently chosen from 0, 1, and 2.

34. A compound according to preferred Embodiment 33, wherein E is chosen from H, $C_1$-6alkyl optionally substituted by 1-3 $R^{19}$, $C_{2-6}$alkenyl, $C_{2-6}$alkynyl optionally substituted by —OH, phenyl optionally substituted by halogen, and $C_{3-6}$cycloalkyl.

34. A compound according to preferred Embodiment 33, wherein E is chosen from H, $C_{1-6}$alkyl optionally substituted by 1-3 $R^{19}$, $C_{2-6}$alkenyl, $C_{2-6}$alkynyl optionally substituted by —OH, phenyl optionally substituted by halogen, and cyclohexyl.

35. A compound according to preferred Embodiment 33, wherein E is chosen from $C_{1-6}$alkyl optionally substituted by $R^{19}$, phenyl, and p-fluorophenyl.

36. A compound according to preferred Embodiment 33, wherein E is p-fluorophenyl.

37. A compound according to any of preferred Embodiments 33-36, wherein G is chosen from H, $C_{1-6}$alkyl optionally substituted by 1-3 $R^{19}$, $C_{2-6}$alkenyl optionally substituted by 1-3 halogen, $C_{2-6}$alkynyl, phenyl optionally substituted by 1-3 halogen, $C_{3-6}$cycloalkyl, and 3-6 membered heterocyclyl.

38. A compound according to any of preferred Embodiments 33-36, wherein G is chosen from H, $C_{1-6}$alkyl optionally substituted by 1-3 $R^{19}$, $C_{3-6}$alkenyl optionally substituted by 1-3 fluoro, $C_{3-6}$alkynyl, phenyl optionally substituted by 1-3 fluoro, $C_{3-6}$cycloalkyl, and 6 membered heterocyclyl.

39. A compound according to any of preferred Embodiments 33-36, wherein G is chosen from H, $C_{1-6}$alkyl optionally substituted by $R^{19}$, $C_{3-6}$alkenyl optionally substituted by 2 fluoro, $C_{3-6}$alkynyl, phenyl optionally substituted by fluoro, $C_{3-6}$cycloalkyl, and tetrahydropyranyl.

40. A compound according to any of preferred Embodiments 33-36, wherein G is $C_{1-6}$alkyl optionally substituted by cyclopropyl or —OH.

41. A compound according to any of preferred Embodiments 33-40, wherein X is N.

42. A compound according to any of preferred Embodiments 33-40, wherein X is C—$R_4$.

43. A compound according to any of preferred Embodiments 33-42, wherein Y is N.

44. A compound according to any of preferred Embodiments 33-42, wherein Y is CH.

45. A compound according to any of preferred Embodiments 33-42, wherein Y is C—$R_{1d}$.

46. A compound according to any of preferred Embodiments 33-45, wherein $R_3$ is H.

47. A compound according to any of preferred Embodiments 33-46, wherein D is —O—, —S—, —C(=O)—, —CHOH—, or —CH$_2$—.

48. A compound according to any of preferred Embodiments 33-46, wherein D is —O—, —C(=O)—, —CHOH—, or —CH$_2$—.

49. A compound according to any of preferred Embodiments 33-46, wherein D is —O—.

50. A compound according to any of preferred Embodiments 33-49, wherein W is CH.

51. A compound according to any of preferred Embodiments 33-50, wherein $R_a$, $R_b$, $R_c$, and $R_d$ are independently chosen from H, $C_{1-6}$alkyl optionally substituted by 1-6 $R^{119}$—CN, and —$OR^{110}$; or $R_a$ and $R_b$ can, together with the atoms linking them, form a 5-6 membered heterocyclyl.

52. A compound according to any of preferred Embodiments 33-50, wherein $R_a$ is chosen from H, —CN, and —$OC_{1-6}$alkyl; $R_b$ is chosen from H, $C_{1-6}$alkyl optionally substituted by 1-6 $R^{119}$, and —$OR^{110}$; Re is chosen from H and —$OC_{1-6}$alkyl; and $R_d$ is chosen from H and —$OC_{1-6}$alkyl; or $R_a$ and $R_b$ can, together with the atoms linking them, form a 5-6 membered heterocyclyl.

53. A compound according to any of preferred Embodiments 33-50, wherein $R_a$ is chosen from H, —CN, and —$OC_{1-6}$alkyl; $R_b$ is chosen from H, $C_{1-6}$alkyl optionally substituted by 6-membered heterocyclyl, —OH, —$OC_{1-6}$alkyl, —$OCH_2$phenyl, —$OC_{1-6}$alkyl-O—$C_{1-6}$alkyl; $R_c$ is chosen from H and —$OC_{1-6}$alkyl; and $R_d$ is chosen from H and —$OC_{1-6}$alkyl; or $R_a$ and $R_b$ can, together with the atoms linking them, form a 5-6 membered heterocyclyl.

54. A compound according to any of preferred Embodiments 33-50, wherein $R_a$ is chosen from H, —CN, and —$OC_{1-6}$alkyl; $R_b$ is chosen from H, $C_{1-6}$alkyl optionally substituted by morpholinyl, —OH, —$OC_{1-6}$alkyl, —$OCH_2$phenyl, —$OC_{1-6}$alkyl-O—$C_{1-6}$alkyl; $R_c$ is chosen from H and —$OC_{1-6}$alkyl; and $R_d$ is chosen from H and —$OC_{1-6}$alkyl; or $R_a$ and $R_b$ together form

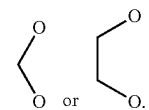

55. A compound according to any of preferred Embodiments 33-50, wherein $R_a$ is chosen from H and —$OC_{1-6}$alkyl; $R_b$ is chosen from H and —$OC_{1-6}$alkyl; $R_c$ is H; and $R_d$ is chosen from H and —$OC_{1-6}$alkyl; or $R_a$ and $R_b$ together form

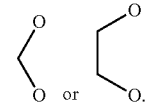

56. A compound according to any of preferred Embodiments 33-50, wherein $R_a$ is chosen from H and —$OC_{1-6}$alkyl; $R_b$ is chosen from H and —$OC_{1-6}$alkyl; $R_c$ is H; and $R_d$ is H; or $R_a$ and $R_b$ together form

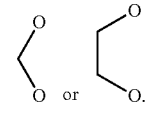

57. A compound according to any of preferred Embodiments 33-50, wherein $R_c$ and $R_d$ are H, and $R_a$ and $R_b$ are —$OC_{1-6}$alkyl; or $R_a$ and $R_b$ together form

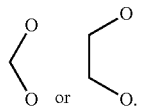

58. A compound according to any of preferred Embodiments 33-50, wherein $R_a$ is —$OC_{1-6}$alkyl; $R_b$ is —$OC_{1-6}$alkyl; $R_c$ is H; and $R_d$ is H.
59. A compound according to any of preferred Embodiments 33-40 or 42-58, wherein $R_4$ is H.
60. A compound according to any of preferred Embodiments 33-59, wherein $R_{1a}$, $R_{1b}$, $R_{1c}$, and $R_{1d}$ are independently chosen from H, $C_{1-6}$alkyl, $C_{1-6}$haloalkyl, $C_{3-6}$cycloalkyl, halogen, —$NH_2$, —$NHC_{1-6}$alkyl$_2$, —$N(C_{1-6}$alkyl$)_2$, —OH, and —$OC_{1-6}$alkyl.
61. A compound according to any of preferred Embodiments 33-59, wherein $R_{1a}$, $R_{1b}$, $R_{1c}$, and $R_{1d}$ are independently chosen from H, $C_{1-3}$alkyl, $C_{1-3}$haloalkyl, cyclopropyl, halogen, and —$OC_{1-3}$alkyl.
62. A compound according to any of preferred Embodiments 33-59, wherein $R_{1a}$, $R_{1b}$, $R_{1c}$, and $R_{1d}$ are independently chosen from H, halogen, and —$OC_{1-3}$alkyl.
63. A compound according to any of preferred Embodiments 33-59, wherein $R_{1a}$, $R_{1b}$, $R_{1c}$, and $R_{1d}$ are independently chosen from H and halogen.
64. A compound according to any of preferred Embodiments 33-59, wherein $R_{1a}$, $R_{1c}$, and $R_{1d}$ are H and $R_{1b}$ is chosen from H, $C_{1-3}$alkyl, $C_{1-3}$haloalkyl, cyclopropyl, halogen, and —$OC_{1-3}$alkyl.
65. A compound according to any of preferred Embodiments 33-59, wherein $R_{1a}$, $R_{1c}$, and $R_{1d}$ are H and $R_{1b}$ is chosen from H, halogen, and —$OC_{1-3}$alkyl.
66. A compound according to any of preferred Embodiments 33-59, wherein $R_{1a}$, $R_{1c}$, and $R_{1d}$ are H and $R_{1b}$ is fluoro.
67. A compound according to any of preferred Embodiments 33-66, wherein $R^{19}$ at each occurrence is independently chosen from $C_{1-6}$alkyl, phenyl optionally substituted by 1-3 halogen, $C_{3-6}$cycloalkyl, 5-6 membered heterocyclyl, 5-6 membered heteroaryl optionally substituted by 1-3 $C_{1-6}$alkyl, halogen, —CN, —C(=O)OH, —C(=O)OC$_{1-6}$alkyl, —C(=O)N(C$_{1-6}$alkyl)$_2$, —C(=O)pyrrolidinyl, —C(=O)morpholinyl, —N(C$_{1-6}$alkyl)$_2$, —OH, —OC$_{1-6}$alkyl, —Obenzyl, and =O.
68. A compound according to any of preferred Embodiments 33-67, wherein $R^{30}$, $R^{32}$ and $R^{33}$ at each occurrence is independently chosen from H and $C_{1-6}$alkyl.
69. A compound according to any of preferred Embodiments 33-68, wherein $R^{39}$ at each occurrence is $C_{1-6}$alkyl.
70. A compound according to any of preferred Embodiments 33-69, wherein $R^{110}$, $R^{112}$, and $R^{113}$ at each occurrence is independently chosen from H and $C_{1-6}$alkyl.
71. A compound according to any of preferred Embodiments 33-70, wherein $R^{119}$ at each occurrence is independently chosen from 6 membered heterocyclyl and halogen.
72. A compound according to any of preferred Embodiments 33-70, wherein $R^{119}$ at each occurrence is independently chosen from morpholinyl and fluoro.
73. A compound according to any of preferred Embodiments 33-72, wherein $R^{129}$ and $R^{159}$ at each occurrence is independently chosen from $C_{1-6}$alkyl and halogen.

74. A compound according to any of preferred Embodiments 33-73, wherein n at each occurrence is 2.
75. A compound according to preferred Embodiment 33, wherein E is p-fluorophenyl; G is $C_{1-4}$ alkyl optionally substituted by cyclopropyl, —OH, or —$OC_{1-3}$ alkyl; X, Y, and W are CH; $R_3$, $R_c$, $R_d$, $R_{1b}$ and $R_{1c}$ are H; D is —O—; $R_a$ and $R_b$ are —$OCH_3$ or together form

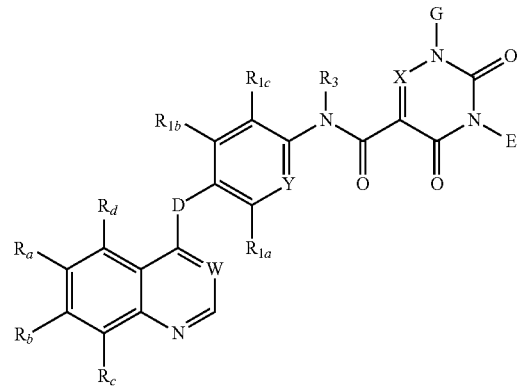

and $R_{1a}$ is fluoro.

What is claimed is:
1. A compound of Formula I or a salt form thereof,

Formula I wherein:
E and G are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{3-11}$cycloalkyl optionally substituted by 1-6 $R^{19}$, 3-15 membered heterocyclyl optionally substituted by 1-6 $R^{19}$, 5-15 membered heteroaryl optionally substituted by 1-6 $R^{19}$, —C(=O)$R^{20}$, —C(=O)O$R^{20}$, —C(=O)N$R^{22}R^{23}$, —S(=O)$_2R^{20}$, and —S(=O)$_2$N$R^{22}R^{23}$;
X is C—$R_4$;
Y is N or C—$R_{1d}$;
$R_3$ is H or $C_{1-6}$alkyl;
D is —O—, —S—, —SO—, —SO$_2$—, —C(=O)—, —CHOH—, —CH$_2$—, —NH— or —NC$_{1-6}$alkyl-;
W is CH or N;
$R_a$, $R_b$, $R_c$, $R_d$, $R_{1a}$, $R_{1b}$, $R_{1c}$, $R_{1d}$, and $R_4$ are independently chosen from H, $C_{1-6}$alkyl optionally substituted by 1-6 $R^{119}$, $C_{2-6}$alkenyl optionally substituted by 1-6 $R^{119}$, $C_{2-6}$alkynyl optionally substituted by 1-6 $R^{119}$, $C_{6-11}$aryl optionally substituted by 1-6 $R^{119}$, $C_{3-11}$cycloalkyl optionally substituted by 1-6 $R^{119}$, 3-15 membered heterocyclyl optionally substituted by 1-6 $R^{119}$, 5-15 membered heteroaryl optionally substituted by 1-6 $R^{119}$, halogen, —CN, —C(=O)$R^{110}$, —C(=O)O$R^{110}$, —C(=O)N$R^{112}R^{113}$, —NC, —NO$_2$, —N$R^{112}R^{113}$, —N$R^{114}$C(=O)O$R^{111}$, —N$R^{114}$C(=O)N$R^{112}$, $R^{113}$, —C(=O)N$R^{112}R^{113}$, —N$R^{114}$S(=O)$_2R^{111}$, —N$R^{114}$S(=O)$_2$N$R^{112}R^{113}$, —O$R^{110}$, —OCN, —OC(=O)R$^{110}$, —OC(=O)NR$^{112}$R$^{113}$, —OC(=O)OR$^{110}$, —S(=O)$_n$R$^{110}$, and —S(=O)$_2$NR$^{112}$R$^{113}$;

or any of R$_a$ and R$_b$, R$_a$ and R$_d$, and R$_b$ and R$_c$ can, together with the atoms linking them, form a C$_{6-11}$aryl optionally substituted by 1-6 R$^{119}$, C$_{3-11}$cycloalkyl optionally substituted by 1-6 R$^{119}$, 3-15 membered heterocyclyl optionally substituted by 1-6 R$^{119}$ or a 5-15 membered heteroaryl optionally substituted by 1-6 R$^{119}$;

R$^{19}$ at each occurrence is independently chosen from C$_{1-6}$alkyl optionally substituted by 1-6 R$^{39}$, C$_{2-6}$alkenyl optionally substituted by 1-6 R$^{39}$, C$_{2-6}$alkynyl optionally substituted by 1-6 R$^{39}$, C$_{6-11}$aryl optionally substituted by 1-6 R$^{39}$, C$_{3-11}$cycloalkyl optionally substituted by 1-6 R$^{39}$, 3-15 membered heterocyclyl optionally substituted by 1-6 R$^{39}$, 5-15 membered heteroaryl optionally substituted by 1-6 R$^{39}$, halogen, —CN, —C(=O)R$^{30}$, —C(=O)OR$^{30}$, —C(=O)NR$^{32}$R$^{33}$, —NO$_2$, —NR$^{32}$R$^{33}$, —NR$^{34}$C(=O)R$^{30}$, —NR$^{34}$C(=O)OR$^{31}$, —NR$^{34}$C(=O)NR$^{32}$R$^{33}$, —NR$^{34}$S(=O)$_2$R$^{31}$, —NR$^{34}$S(=O)$_2$NR$^{32}$R$^{33}$, —OR$^{30}$, =O, —OC(=O)R$^{30}$, —OC(=O)NR$^{32}$R$^{33}$, —OC(=O)OR$^{30}$, —S(=O)$_n$R$^{30}$, and —S(=O)$_2$NR$^{32}$R$^{33}$;

R$^{20}$, R$^{30}$, R$^{31}$, and R$^{34}$ at each occurrence is independently chosen from H, C$_{1-6}$alkyl optionally substituted by 1-6 R$^{49}$, C$_{2-6}$alkenyl optionally substituted by 1-6 R$^{49}$, C$_{2-6}$alkynyl optionally substituted by 1-6 R$^{49}$, C$_{6-11}$aryl optionally substituted by 1-6 R$^{49}$, C$_{3-11}$cycloalkyl optionally substituted by 1-6 R$^{49}$, 3-15 membered heterocyclyl optionally substituted by 1-6 R$^{49}$, and 5-15 membered heteroaryl optionally substituted by 1-6 R$^{49}$;

R$^{22}$, R$^{23}$, R$^{32}$ and R$^{33}$ at each occurrence is independently chosen from H, C$_{1-6}$alkyl optionally substituted by 1-6 R$^{59}$, C$_{2-6}$alkenyl optionally substituted by 1-6 R$^{59}$, C$_{2-6}$alkynyl optionally substituted by 1-6 R$^{59}$, C$_{6-11}$aryl optionally substituted by 1-6 R$^{59}$, C$_{3-11}$cycloalkyl optionally substituted by 1-6 R$^{59}$, 3-15 membered Heterocyclyl optionally substituted by 1-6 R$^{59}$, and 5-15 membered heteroaryl optionally substituted by 1-6 R$^{59}$; or any R$^{22}$ and R$^{23}$ and/or R$^{32}$ and R$^{33}$ may form, together with the nitrogen atom to which they are attached, a 3-15 membered heterocyclyl optionally substituted by 1-6 R$^{69}$ or a 5-15 membered heteroaryl optionally substituted by 1-6 R$^{69}$;

R$^{39}$, R$^{49}$, R$^{59}$ and R$^{69}$ at each occurrence is independently chosen from C$_{1-6}$alkyl optionally substituted by 1-6 R$^{79}$, C$_{2-6}$alkenyl optionally substituted by 1-6 R$^{79}$, C$_{2-6}$alkynyl optionally substituted by 1-6 R$^{79}$, C$_{6-11}$aryl optionally substituted by 1-6 R$^{79}$, C$_{3-11}$cycloalkyl optionally substituted by 1-6 R$^{79}$, 3-15 membered heterocyclyl optionally substituted by 1-6 R$^{79}$, 5-15 membered heteroaryl optionally substituted by 1-6 R$^{79}$, halogen, —CN, —C(=O)R$^{70}$, —C(=O)OR$^{70}$, —C(=O)NR$^{72}$R$^{73}$, —NO$_2$, —NR$^{72}$R$^{73}$, —NR$^{74}$C(=O)R$^{70}$, —NR$^{74}$C(=O)OR$^{71}$, —NR$^{74}$C(=O)NR$^{72}$R$^{73}$, —NR$^{74}$S(=O)$_2$R$^{71}$, —NR$^{74}$S(=O)$_2$NR$^{72}$R$^{73}$, —OR$^{70}$, =O, —OC(=O)R$^{70}$, —OC(=O)NR$^{72}$R$^{73}$, —S(=O)$_n$R$^{70}$, and —S(=O)$_2$NR$^{72}$R$^{73}$;

R$^{70}$, R$^{71}$, R$^{72}$, R$^{73}$, and R$^{74}$ at each occurrence is independently chosen from H, C$_{1-6}$alkyl and C$_{1-6}$-haloalkyl;

R$^{79}$ at each occurrence is independently chosen from C$_{1-6}$alkyl, C$_{1-6}$-haloalkyl, benzyl, halogen, —CN, —C(=O)(C$_{1-6}$alkyl), —C(=O)O(C$_{1-6}$alkyl), —C(=O)N(C$_{1-6}$alkyl)$_2$, —C(=O)OH, —C(=O)NH$_2$, —C(=O)NHC$_{1-6}$alkyl, —NO$_2$, —NH$_2$, —NHC$_{1-6}$alkyl, —N(C$_{1-6}$alkyl)$_2$, —NHC(=O)C$_{1-6}$alkyl, —NHS(=O)$_2$C$_{1-6}$alkyl, —OH, —OC$_{1-6}$alkyl, =O, —OC(=O)C$_{1-6}$alkyl, —OS(=O)$_2$C$_{1-6}$alkyl, —S(=O)$_2$C$_{1-6}$alkyl, and —S(=O)$_2$N(C$_{1-6}$alkyl)$_2$;

R$^{110}$, R$^{111}$, and R$^{114}$ at each occurrence is independently chosen from H, C$_{1-6}$alkyl optionally substituted by 1-6 R$^{129}$, C$_{2-6}$alkenyl optionally substituted by 1-6 R$^{129}$, C$_{2-6}$alkynyl optionally substituted by 1-6 R$^{129}$, C$_{6-11}$aryl optionally substituted by 1-6 R$^{129}$, C$_{3-11}$cycloalkyl optionally substituted by 1-6 R$^{129}$, 3-15 membered heterocyclyl optionally substituted by 1-6 R$^{129}$, and 5-15 membered heteroaryl optionally substituted by 1-6 R$^{129}$;

R$^{112}$ and R$^{113}$ at each occurrence is independently chosen from H, C$_{1-6}$ alkyl optionally substituted by 1-6 R$^{139}$, C$_{2-6}$alkenyl optionally substituted by 1-6 R$^{139}$, C$_{2-6}$alkynyl optionally substituted by 1-6 R$^{139}$, C$_{6-11}$aryl optionally substituted by 1-6 R$^{139}$, C$_{3-11}$cycloalkyl optionally substituted by 1-6 R$^{139}$, 3-15 membered heterocyclyl optionally substituted by 1-6 R$^{139}$, and -15 membered heteroaryl optionally substituted by 1-6 R$^{139}$;

or any R$^{112}$ and R$^{113}$ may form, together with the nitrogen atom to which they are attached, a 3-15 membered heterocyclyl optionally substituted by 1-6 R$^{149}$ or a 5-15 membered heteroaryl optionally substituted by 1-6 R$^{149}$;

R$^{119}$ at each occurrence is independently chosen from C$_{1-6}$alkyl optionally substituted by 1-6 R$^{159}$, C$_{2-6}$alkenyl optionally substituted by 1-6 R$^{159}$, C$_{2-6}$alkynyl optionally substituted by 1-6 R$^{159}$, C$_{6-11}$aryl optionally substituted by 1-6 R$^{159}$, C$_{3-11}$cycloalkyl optionally substituted by 1-6 R$^{159}$, 3-15 membered heterocyclyl optionally substituted by 1-6 R$^{159}$, 5-15 membered heteroaryl optionally substituted by 1-6 R$^{159}$, halogen, —CN, —C(=O)R$^{150}$, —C(=O)OR$^{150}$, —C(=O)NR$^{152}$R$^{153}$, —NC, —NO$_2$, —NR$^{152}$R$^{153}$, —NR$^{154}$C(=O)R$^{150}$, —NR$^{154}$C(=O)OR$^{151}$, —NR$^{154}$C(=O)NR$^{152}$R$^{153}$, —NR$^{154}$S(=O)$_2$R$^{151}$, —NR$^{154}$S(=O)$_2$NR$^{152}$R$^{153}$, —OR$^{150}$, =O, —OC(=O)R$^{150}$, —OC(=O)NR$^{152}$R$^{153}$, —S(=O)$_n$R$^{150}$, and —S(=O)$_2$NR$^{152}$R$^{153}$;

R$^{150}$, R$^{151}$, R$^{152}$, R$^{153}$ and R$^{154}$ at each occurrence is independently chosen from H, C$_{1-6}$alkyl, benzyl, and C$_{1-6}$-haloalkyl;

R$^{129}$, R$^{139}$, R$^{149}$, and R$^{159}$ at each occurrence is independently chosen from C$_{1-6}$alkyl, C$_{1-6}$-haloalkyl, benzyl, halogen, —CN, —C(=O)(C$_{1-6}$alkyl), —C(=O)O(C$_{1-6}$alkyl), —C(=O)N(C$_{1-6}$alkyl)$_2$, —C(=O)OH, —C(=O)NH$_2$, —C(=O)NHC$_{1-6}$alkyl, —NO$_2$, —NH$_2$, —NHC$_{1-6}$alkyl, —N(C$_{1-6}$alkyl)$_2$, —NHC(=O)C$_{1-6}$alkyl, —NHS(=O)$_2$C$_{1-6}$alkyl, —OH, —OC$_{1-6}$alkyl, =O, —OC(=O)C$_{1-6}$alkyl, —OS(=O)$_2$C$_{1-6}$alkyl, —S(=O)$_2$C$_{1-6}$alkyl, and —S(=O)$_2$N(C$_{1-6}$alkyl)$_2$; and n at each occurrence is independently chosen from 0, 1, and 2.

2. A compound according to claim 1, wherein E and G are independently chosen from H, C$_{1-6}$alkyl optionally substituted by 1-6 R$^{19}$, C$_{2-6}$alkenyl optionally substituted by 1-6 R$^{19}$, C$_{2-6}$alkynyl optionally substituted by 1-6 R$^{19}$, phenyl optionally substituted by 1-5 R$^{19}$, C$_{3-6}$cycloalkyl optionally substituted by 1-6 R$^{19}$, 3-6 membered heterocyclyl optionally substituted by 1-5 R$^{19}$, 5-6 membered heteroaryl optionally substituted by 1-3 R$^{19}$, —C(=O)R$^{20}$, —C(=O)OR$^{20}$, —C(=O)NR$^{22}$R$^{23}$, —S(=O)$_2$R$^{20}$, and —S(=O)$_2$NR$^{22}$R$^{23}$.

3. A compound according to claim 1, wherein E is chosen from H, $C_{1-6}$ alkyl optionally substituted by 1-3 $R^{19}$, $C_{2-6}$alkenyl, $C_{2-6}$alkynyl optionally substituted by —OH, phenyl optionally substituted by halogen, and cyclohexyl.

4. A compound according to claim 1, wherein G is chosen from H, $C_{1-6}$alkyl optionally substituted by 1-3 $R^{19}$, $C_{3-6}$alkenyl optionally substituted by 1-3 fluoro, $C_{3-6}$alkynyl, phenyl optionally substituted by 1-3 fluoro, $C_{3-6}$cycloalkyl, and 6 membered heterocyclyl.

5. A compound according to claim 1, wherein $R_3$ is H.

6. A compound according to claim 1, wherein D is —O—, —S—, —C(=O)—, —CHOH—, or —CH$_2$—.

7. A compound according to claim 1, wherein W is CH.

8. A compound according to claim 1, wherein $R_a$, $R_b$, $R_c$, and $R_d$ are independently chosen from H, $C_{1-6}$alkyl optionally substituted by 1-6 $R^{119}$, —CN, and —OR$^{110}$; or $R_a$ and $R_b$ can, together with the atoms linking them, form a 5-6 membered heterocyclyl optionally substituted by 1-6 $R^{119}$.

9. A compound according to claim 1, wherein $R_a$ is chosen from H and —OC$_{1-6}$alkyl; $R_b$ is chosen from H and —OC$_{1-6}$alkyl; $R_c$ is H; and $R_d$ is chosen from H and —OC$_{1-6}$alkyl; or $R_a$ and $R_b$ together form

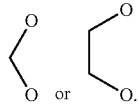

10. A compound according to claim 1, wherein $R_4$ is chosen from H and $C_{1-6}$alkyl.

11. A compound according to claim 1, wherein $R_{1a}$, $R_{1b}$, $R_{1c}$, and $R_{1d}$ are independently chosen from H, $C_{1-6}$alkyl optionally substituted by 1-6 $R^{119}$, $C_{3-6}$cycloalkyl optionally substituted by 1-6 $R^{119}$, 3-6 membered heterocyclyl optionally substituted by 1-6 $R^{119}$, halogen, —CN, —NR$^{112}$R$^{113}$, and —OR$^{110}$.

12. A compound according to claim 1, wherein $R_{1a}$, $R_{1b}$, $R_{1c}$, and $R_{1d}$ are independently chosen from H, $C_{1-6}$alkyl, $C_{1-6}$haloalkyl, $C_{3-6}$cycloalkyl, halogen, —N(C$_{1-6}$alkyl)$_2$, —OC$_{1-6}$alkyl.

13. A compound according to claim 1, wherein $R_{1a}$, $R_{1b}$, $R_{1c}$, and $R_{1d}$ are independently chosen from H and fluoro.

14. A compound according to claim 1, wherein $R_{1a}$ and $R_{1b}$ are independently chosen from H, $C_{1-3}$alkyl, $C_{1-3}$haloalkyl, $C_{3-6}$cycloalkyl, halogen, and —OC$_{1-3}$alkyl; and $R_{1c}$ and $R_{1d}$ are independently chosen from H, $C_{1-3}$alkyl, halogen, —N(C$_{1-3}$alkyl)$_2$, and —OC$_{1-3}$alkyl.

15. A compound according to claim 1, wherein $R_{1a}$, $R_{1c}$, and $R_{1d}$ are H and $R_{1b}$ is chosen from H, halogen, and —OC$_{1-3}$alkyl.

16. A compound according to claim 1, wherein $R^{19}$ at each occurrence is independently chosen from $C_{1-6}$alkyl, phenyl optionally substituted by 1-3 halogen, $C_{3-6}$cycloalkyl, 5-6 membered heterocyclyl, 5-6 membered heteroaryl optionally substituted by 1-3 $C_{1-6}$alkyl, halogen, —CN, —C(=O)OH, —C(=O)OC$_{1-6}$alkyl, —C(=O)N(C$_{1-6}$alkyl)$_2$, —C(=O) pyrrolidinyl, —C(=O)morpholinyl, —N(C$_{1-6}$alkyl)$_2$, —OH, —OC$_{1-6}$alkyl, —Obenzyl, and =O; R$^{20}$, R$^{22}$, and R$^{23}$ at each occurrence is independently chosen from H, $C_{1-6}$alkyl, $C_{1-6}$halolkyl, phenyl, benzyl, $C_{5-6}$cycloalkyl, 5-6 membered heterocyclyl, and 5-6 membered heteroaryl; R$^{110}$, R$^{112}$, R$^{113}$, and R$^{114}$ at each occurrence is independently chosen from H, benzyl, and $C_{1-6}$alkyl optionally substituted by —OC$_{1-3}$ alkyl; and R$^{119}$ at each occurrence is independently chosen from $C_{1-6}$alkyl, $C_{1-6}$haloalkyl, 5-6 membered heterocyclyl, and halogen.

17. A compound that is chosen from:
1-Ethyl-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]amide;
3-(4-Fluorophenyl)-1-methyl-2,4-dioxo-1,2,3,4-tetrahydropyrimidine-5-carboxylic acid[4-(6,7-dimethoxyquinolin-4-yloxy)-3-fluoro-phenyl]-amide;
3-(4-Fluorophenyl)-1-(2-methoxyethyl)-2,4-dioxo-1,2,3,4-tetrahydropyrimidine-5-carboxylic acid[4-(6,7-dimethoxyquinolin-4-yloxy)-3-fluorophenyl]-amide;
1-(2-Ethoxyethyl)-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]-amide;
3-(4-Fluorophenyl)-1-isopropyl-2,4-dioxo-1,2,3,4-tetrahydropyrimidine-5-carboxylic acid[4-(6,7-dimethoxyquinolin-4-yloxy)-3-fluorophenyl]-amide;
1-Cyclopropylmethyl-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]-amide;
3-(4-Fluorophenyl)-1-(3-methoxypropyl)-2,4-dioxo-1,2,3,4-tetrahydropyrimidine-5-carboxylic acid[4-(6,7-dimethoxyquinolin-4-yloxy)-3-fluorophenyl]-amide;
3-(4-Fluorophenyl)-1-isobutyl-2,4-dioxo-1,2,3,4-tetrahydropyrimidine-5-carboxylic acid[4-(6,7-dimethoxyquinolin-4-yloxy)-3-fluorophenyl]-amide;
1-Allyl-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]-amide;
1-(2-Benzyloxyethyl)-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]-amide;
3-(4-Fluorophenyl)-2,4-dioxo-1-propyl-1,2,3,4-tetrahydropyrimidine-5-carboxylic acid[4-(6,7-dimethoxyquinolin-4-yloxy)-3-fluorophenyl]-amide;
3-(4-Fluorophenyl)-1-(2-isopropoxyethyl)-2,4-dioxo-1,2,3,4-tetrahydropyrimidine-5-carboxylic acid[4-(6,7-dimethoxyquinolin-4-yloxy)-3-fluorophenyl]-amide;
1-(3-Benzyloxypropyl)-3-(4-fluorophenyl)-2,4-dioxo-1,2,3,4-tetrahydropyrimidine-5-carboxylic acid[4-(6,7-dimethoxyquinolin-4-yloxy)-3-fluoro phenyl]-amide;
1-(3,3-Difluoro-allyl)-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]-amide;
3-(4-Fluorophenyl)-1-(3-methyl-but-2-enyl)-2,4-dioxo-1,2,3,4-tetrahydropyrimidine-5-carboxylic acid[4-(6,7-dimethoxyquinolin-4-yloxy)-3-fluorophenyl]-amide;
3-(4-Fluorophenyl)-1-(2-morpholin-4-yl-ethyl)-2,4-dioxo-1,2,3,4-tetrahydropyrimidine-5-carboxylic acid[4-(6,7-dimethoxyquinolin-4-yloxy)-3-fluoro phenyl]-amide;
3-(4-Fluorophenyl)-2,4-dioxo-1,2,3,4-tetrahydropyrimidine-5-carboxylic acid[4-(6,7-dimethoxyquinolin-4-yloxy)-3-fluorophenyl]-amide;
3-(4-Fluorophenyl)-1-methyl-2,4-dioxo-1,2,3,4-tetrahydropyrimidine-5-carboxylic acid[4-(6,7-dimethoxyquinolin-4-yloxy)-phenyl]-amide;
1-(2-Benzyloxyethyl)-3-(4-fluoro-phenyl)-2,4-dioxo-1,2,3,4-tetrahydropyrimidine-5-carboxylic acid[4-(6,7-dimethoxyquinolin-4-yloxy)-phenyl]-amide;
1-(2-Dimethylaminoethyl)-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]-amide;

1-(3-Benzyloxypropyl)-3-(4-fluorophenyl)-2,4-dioxo-1,2,3,4-tetrahydropyrimidine-5-carboxylic acid[4-(6,7-dimethoxyquinolin-4-yloxy)phenyl]-amide;

1-(3-Benzyloxypropyl)-3-(4-fluorophenyl)-2,4-dioxo-1,2,3,4-tetrahydropyrimidine-5-carboxylic acid[4-(6,7-dimethoxyquinolin-4-yloxy)-2-fluorophenyl]-amide;

3-(4-Fluorophenyl)-1-isopropyl-2,4-dioxo-1,2,3,4-tetrahydropyrimidine-5-carboxylic acid[4-(6,7-dimethoxyquinolin-4-yloxy)phenyl]-amide;

3-(4-Fluorophenyl)-2,4-dioxo-1,2,3,4-tetrahydropyrimidine-5-carboxylic acid[4-(6,7-dimethoxyquinolin-4-yloxy)phenyl]-amide;

3-Cyclohexyl-1-ethyl-2,4-dioxo-1,2,3,4-tetrahydropyrimidine-5-carboxylic acid[4-(6,7-dimethoxyquinolin-4-yloxy)-3-fluorophenyl]-amide;

3-(4-Fluorophenyl)-2,4-dioxo-1-(2-pyrrolidin-1-yl-ethyl)-1,2,3,4-tetrahydropyrimidine-5-carboxylic acid [4-(6,7-dimethoxyquinolin-4-yloxy)-3-fluoro phenyl]-amide;

3-(4-Fluorophenyl)-2,4-dioxo-1-(2-piperidin-1-yl-ethyl)-1,2,3,4-tetrahydropyrimidine-5-carboxylic acid[4-(6,7-dimethoxyquinolin-4-yloxy)-3-fluorophenyl]-amide;

1-Ethyl-3-(4-fluorophenyl)-2,4-dioxo-1,2,3,4-tetrahydropyrimidine-5-carboxylic acid[4-(6,7-dimethoxyquinolin-4-yloxy)-phenyl]-amide;

1-Cyclobutyl-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]-amide;

3-(4-Fluorophenyl)-2,4-dioxo-1-(tetrahydropyran-4-yl)-1,2,3,4-tetrahydropyrimidine-5-carboxylic acid[4-(6,7-dimethoxyquinolin-4-yloxy)-3-fluoro phenyl]-amide;

1-Ethyl-3-(4-fluorophenyl)-2,4-dioxo-1,2,3,4-tetrahydropyrimidine-5-carboxylic acid[5-(6,7-dimethoxyquinolin-4-yloxy)-pyridin-2-yl]-amide was synthesized starting with 5-(6,7-dimethoxyquinolin-4-yloxy)-pyridin-2-ylamine;

1-Ethyl-3-(4-fluorophenyl)-6-methyl-2,4-dioxo-1,2,3,4-tetrahydropyrimidine-5-carboxylic acid[4-(6,7-dimethoxyquinolin-4-yloxy)-3-fluorophenyl]-amide;

1-Ethyl-3-(4-fluorophenyl)-2,4-dioxo-1,2,3,4-tetrahydropyrimidine-5-carboxylic acid[4-(6,7-diethoxyquinolin-4-yloxy)-3-fluorophenyl]-amide;

3-(4-Fluorophenyl)-1-isopropyl-2,4-dioxo-1,2,3,4-tetrahydropyrimidine-5-carboxylic acid[5-(6,7-dimethoxyquinolin-4-yloxy)-pyridin-2-yl]-amide;

1-Cyclopropylmethyl-3-(4-fluorophenyl)-2,4-dioxo-1,2,3,4-tetrahydropyrimidine-5-carboxylic acid[5-(6,7-dimethoxyquinolin-4-yloxy)pyridin-2-yl]-amide;

3-(4-Fluorophenyl)-2,4-dioxo-1-pentyl-1,2,3,4-tetrahydropyrimidine-5-carboxylic acid[4-(6,7-dimethoxyquinolin-4-yloxy)-3-fluorophenyl]-amide;

3-(4-Fluorophenyl)-1-isopropyl-2,4-dioxo-1,2,3,4-tetrahydropyrimidine-5-carboxylic acid[4-(6,7-diethoxyquinolin-4-yloxy)-3-fluoro-phenyl]-amide;

3-(4-Fluorophenyl)-1-isopropyl-2,4-dioxo-1,2,3,4-tetrahydropyrimidine-5-carboxylic acid[4-(5,7-dimethoxyquinolin-4-yloxy)phenyl]-amide;

1-Ethyl-3-(4-fluorophenyl)-2,4-dioxo-1,2,3,4-tetrahydropyrimidine-5-carboxylic acid[4-(5,7-dimethoxyquinolin-4-yloxy)-phenyl]-amide;

1-Ethyl-3-(4-fluorophenyl)-2,4-dioxo-1,2,3,4-tetrahydropyrimidine-5-carboxylic acid[4-(7-benzyloxy-6-methoxyquinolin-4-yloxy)-3-fluorophenyl]-amide;

3-(4-Fluorophenyl)-1-isopropyl-2,4-dioxo-1,2,3,4-tetrahydropyrimidine-5-carboxylic acid[4-(7-benzyloxy-6-methoxyquinolin-4-yloxy)-3-fluorophenyl]-amide;

1-Ethyl-3-(4-fluorophenyl)-2,4-dioxo-1,2,3,4-tetrahydropyrimidine-5-carboxylic acid[3-fluoro-4-(7-hydroxy-6-methoxyquinolin-4-yloxy)phenyl]-amide;

1-Ethyl-3-(4-fluorophenyl)-2,4-dioxo-1,2,3,4-tetrahydropyrimidine-5-carboxylic acid{3-fluoro-4-[6-methoxy-7-(3-morpholin-4-yl-propoxy)quinolin-4-yloxy]phenyl}-amide;

1-Ethyl-3-(4-fluorophenyl)-2,4-dioxo-1,2,3,4-tetrahydropyrimidine-5-carboxylic acid{3-fluoro-4-[6-methoxy-7-(2-methoxyethoxy)quinolin-4-yloxy]-phenyl}-amide;

1-Ethyl-3-(4-fluorophenyl)-2,4-dioxo-1,2,3,4-tetrahydropyrimidine-5-carboxylic acid{3-fluoro-4-[6-methoxy-7-(2-morpholin-4-yl-ethoxy)-quinolin-4-yloxy]phenyl}-amide;

3-(4-Fluorophenyl)-1-isopropyl-2,4-dioxo-1,2,3,4-tetrahydropyrimidine-5-carboxylic acid[3-fluoro-4-(7-hydroxy-6-methoxyquinolin-4-yloxy)-phenyl]-amide;

3-(4-Fluorophenyl)-1-isopropyl-2,4-dioxo-1,2,3,4-tetrahydropyrimidine-5-carboxylic acid{3-fluoro-4-[6-methoxy-7-(3-morpholin-4-yl-propoxy)-quinolin-4-yloxy]phenyl}-amide;

3-(4-Fluorophenyl)-1-(2-hydroxyethyl)-2,4-dioxo-1,2,3,4-tetrahydropyrimidine-5-carboxylic acid[4-(6,7-dimethoxyquinolin-4-yloxy)-3-fluorophenyl]-amide;

3-(4-Fluorophenyl)-1-(3-hydroxypropyl)-2,4-dioxo-1,2,3,4-tetrahydropyrimidine-5-carboxylic acid[4-(6,7-dimethoxyquinolin-4-yloxy)-3-fluorophenyl]-amide;

3-(4-Fluorophenyl)-1-(3-hydroxypropyl)-2,4-dioxo-1,2,3,4-tetrahydropyrimidine-5-carboxylic acid[4-(6,7-dimethoxy-quinolin-4-yloxy)-2-fluoro-phenyl]-amide;

3-(4-Fluorophenyl)-1-(3-hydroxypropyl)-2,4-dioxo-1,2,3,4-tetrahydropyrimidine-5-carboxylic acid[4-(6,7-dimethoxyquinolin-4-yloxy)phenyl]-amide;

3-(4-Fluorophenyl)-1-(2-hydroxyethyl)-2,4-dioxo-1,2,3,4-tetrahydropyrimidine-5-carboxylic acid[4-(6,7-dimethoxyquinolin-4-yloxy)phenyl]-amide;

1-((S)-2,3-Dihydroxypropyl)-3-(4-fluorophenyl)-2,4-dioxo-1,2,3,4-tetrahydropyrimidine-5-carboxylic acid[4-(6,7-dimethoxyquinolin-4-yloxy)-3-fluorophenyl]-amide;

3-(4-Fluorophenyl)-1-(4-hydroxybutyl)-2,4-dioxo-1,2,3,4-tetrahydropyrimidine-5-carboxylic acid[4-(6,7-dimethoxyquinolin-4-yloxy)-3-fluorophenyl]-amide;

3-(4-Fluorophenyl)-1-isopropyl-2,4-dioxo-1,2,3,4-tetrahydropyrimidine-5-carboxylic acid[4-(6-cyano-7-methoxy-quinolin-4-yloxy)-phenyl]-amide;

3-(4-fluoro-phenyl)-1-methyl-2,4-dioxo-1,2,3,4-tetrahydro-pyrimidine-5-carboxylic acid{4-[(6,7-dimethoxy-quinolin-4-yl)-hydroxy-methyl]-3-fluoro-phenyl}-amide;

3-(4-fluoro-phenyl)-1-methyl-2,4-dioxo-1,2,3,4-tetrahydro-pyrimidine-5-carboxylic acid[4-(6,7-dimethoxy-quinolin-4-ylmethyl)-3-fluoro-phenyl]-amide;

1-Ethyl-3-(4-fluoro-phenyl)-2,4-dioxo-1,2,3,4-tetrahydropyrimidine-5-carboxylic acid[3-cyclopropyl-4-(6,7-dimethoxy-quinolin-4-yloxy)-phenyl]-amide;

3-(4-Fluoro-phenyl)-1-isopropyl-2,4-dioxo-1,2,3,4-tetrahydro-pyrimidine-5-carboxylic acid[3-cyclopropyl-4-(6,7-dimethoxy-quinolin-4-yloxy)-phenyl]-amide;

3-(4-Fluoro-phenyl)-2,4-dioxo-1-prop-2-ynyl-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-1-(2-imidazol-1-yl-ethyl)-2,4-dioxo-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1-(2-pyrazol-1-yl-ethyl)-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1-phenethyl-1,2,3,4-tetrahydro-pyrimidine-5-carboxylic acid[4-(6,7-dimethoxy-quinolin-4-yloxy)-3-fluoro-phenyl]-amide;

1-[2-(1,3-Dioxolan-2-yl-ethyl)]-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

1-Diethylcarbamoylmethyl-3-(4-fluoro-phenyl)-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-1-(2-morpholin-4-yl-2-oxo-ethyl)-2,4-dioxo-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1-[2-(2-oxo-pyrrolidin-1-yl)-ethyl]-1,2,3,4-tetrahydro-pyrimidine-5-carboxylic acid[4-(6,7-dimethoxy-quinolin-4-yloxy)-3-fluoro-phenyl]-amide;

1-(2-Fluoro-ethyl)-3-(4-fluoro-phenyl)-2,4-dioxo-1,2,3,4-tetrahydro-pyrimidine-5-carboxylic acid[4-(6,7-dimethoxy-quinolin-4-yloxy)-3-fluoro-phenyl]-amide;

[5-[4-(6,7-Dimethoxy-quinolin-4-yloxy)-3-fluoro-phenylcarbamoyl]-3-(4-fluoro-phenyl)-2,4-dioxo-3,4-dihydro-2H-pyrimidin-1-yl]-acetic acid tert-butyl ester;

[5-[4-(6,7-Dimethoxyquinolin-4-yloxy)-3-fluorophenylcarbamoyl]-3-(4-fluorophenyl)-2,4-dioxo-3,4-dihydro-2H-pyrimidin-1-yl]-acetic acid;

3-(4-Fluoro-phenyl)-1-oxazol-2-ylmethyl-2,4-dioxo-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1-(tetrahydro-furan-2-yl-methyl)-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1-(tetrahydro-pyran-4-yl-methyl)-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-1-(2-methyl-thiazol-4-ylmethyl)-2,4-dioxo-1,2,3,4-tetrahydro-pyrimidine-5-carboxylic acid[4-(6,7-dimethoxy-quinolin-4-yloxy)-3-fluoro-phenyl]-amide;

1-Cyclopentyl-3-(4-fluoro-phenyl)-2,4-dioxo-1,2,3,4-tetrahydro-pyrimidine-5-carboxylic acid[4-(6,7-dimethoxy-quinolin-4-yloxy)-3-fluoro-phenyl]-amide;

1-Benzyl-3-(4-fluoro-phenyl)-2,4-dioxo-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-1-[2-(2-fluoro-phenyl)-ethyl]-2,4-dioxo-1,2,3,4-tetrahydro-pyrimidine-5-carboxylic acid [4-(6,7-dimethoxy-quinolin-4-yloxy)-3-fluoro-phenyl]-amide;

3-(4-Fluoro-phenyl)-1-[2-(4-fluoro-phenyl)-ethyl]-2,4-dioxo-1,2,3,4-tetrahydro-pyrimidine-5-carboxylic acid [4-(6,7-dimethoxy-quinolin-4-yloxy)-3-fluoro-phenyl]-amide;

1-(2-Cyclohexyl-ethyl)-3-(4-fluoro-phenyl)-2,4-dioxo-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1-(3-phenyl-propyl)-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1-(2-oxo-2-pyrrolidin-1-yl-ethyl)-1,2,3,4-tetrahydro-pyrimidine-5-carboxylic acid[4-(6,7-dimethoxy-quinolin-4-yloxy)-3-fluoro-phenyl]-amide;

1-Dimethylcarbamoylmethyl-3-(4-fluorophenyl)-2,4-dioxo-1,2,3,4-tetrahydro-pyrimidine-5-carboxylic acid [4-(6,7-dimethoxy-quinolin-4-yloxy)-3-fluorophenyl]-amide;

1-(1-Dimethylcarbamoyl-2-oxo-propyl)-3-(4-fluoro-phenyl)-2,4-dioxo-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1,2,3,4-tetrahydro-pyrimidine-5-carboxylic acid[4-(6,7-dimethoxy-quinolin-4-yloxy)-2-fluoro-phenyl]-amide;

3-(4-Fluoro-phenyl)-1-methyl-2,4-dioxo-1,2,3,4-tetrahydro-pyrimidine-5-carboxylic acid[4-(6,7-dimethoxy-quinolin-4-yloxy)-2-fluoro-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-2-fluoro-phenyl]-amide;

1-Allyl-3-(4-fluoro-phenyl)-2,4-dioxo-1,2,3,4-tetrahydro-pyrimidine-5-carboxylic acid[4-(6,7-dimethoxy-quinolin-4-yloxy)-2-fluoro-phenyl]-amide;

3-(4-Fluoro-phenyl)-2,4-dioxo-1,2,3,4-tetrahydropyrimidine-5-carboxylic acid[4-(6,7-dimethoxy-quinolin-4-yloxy)-3,5-difluoro-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-3,5-difluoro-phenyl]-amide;

3-Ethyl-1-(4-fluoro-phenyl)-2,4-dioxo-1,2,3,4-tetrahydro-pyrimidine-5-carboxylic acid[4-(6,7-dimethoxy-quinolin-4-yloxy)-3-fluoro-phenyl]-amide;

1,3-Dimethyl-2,4-dioxo-1,2,3,4-tetrahydropyrimidine-5-carboxylic acid[4-(6,7-dimethoxy-quinolin-4-yloxy)-3-fluorophenyl]-amide;

1,3-Diethyl-2,4-dioxo-1,2,3,4-tetrahydro-pyrimidine-5-carboxylic acid[4-(6,7-dimethoxy-quinolin-4-yloxy)-3-fluoro-phenyl]-amide;

1,3-Diisopropyl-2,4-dioxo-1,2,3,4-tetrahydro-pyrimidine-5-carboxylic acid[4-(6,7-dimethoxy-quinolin-4-yloxy)-3-fluoro-phenyl]-amide;

1,3-Bis-cyclopropylmethyl-2,4-dioxo-1,2,3,4-tetrahydro-pyrimidine-5-carboxylic acid[4-(6,7-dimethoxy-quinolin-4-yloxy)-3-fluoro-phenyl]-amide;

1,3-Diallyl-2,4-dioxo-1,2,3,4-tetrahydro-pyrimidine-5-carboxylic acid[4-(6,7-dimethoxy-quinolin-4-yloxy)-3-fluoro-phenyl]-amide;

1,3-Bis-(3-methyl-but-2-enyl)-2,4-dioxo-1,2,3,4-tetrahydro-pyrimidine-5-carboxylic acid[4-(6,7-dimethoxy-quinolin-4-yloxy)-3-fluoro-phenyl]-amide;

2,4-Dioxo-1,3-di-prop-2-ynyl-1,2,3,4-tetrahydro-pyrimidine-5-carboxylic acid[4-(6,7-dimethoxy-quinolin-4-yloxy)-3-fluoro-phenyl]-amide;

2,4-Dioxo-1,2,3,4-tetrahydro-pyrimidine-5-carboxylic acid[4-(6,7-dimethoxy-quinolin-4-yloxy)-3-fluoro-phenyl]-amide;

1-Ethyl-2,4-dioxo-3-phenyl-1,2,3,4-tetrahydro-pyrimidine-5-carboxylic acid[4-(6,7-dimethoxy-quinolin-4-yloxy)-3-fluoro-phenyl]-amide;

1-Isopropyl-2,4-dioxo-3-phenyl-1,2,3,4-tetrahydro-pyrimidine-5-carboxylic acid[4-(6,7-dimethoxy-quinolin-4-yloxy)-3-fluoro-phenyl]-amide;

3-(4-Fluoro-phenyl)-2,4-dioxo-1-propyl-1,2,3,4-tetrahydro-pyrimidine-5-carboxylic acid[4-(6,7-dimethoxy-quinoline-4-carbonyl)-3-fluoro-phenyl]-amide;

3-(4-Fluoro-phenyl)-1-methyl-2,4-dioxo-1,2,3,4-tetrahydro-pyrimidine-5-carboxylic acid[4-([1,3]dioxolo[4,5-g]quinolin-8-yloxy)-3-fluoro-phenyl]-amide;

1-Ethyl-3-(4-fluorophenyl)-2,4-dioxo-1,2,3,4-tetrahydropyrimidine-5-carboxylic acid[4-(2,3-dihydro-[1,4]dioxino[2,3-g]quinolin-9-yloxy)-3-fluoro-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-ylamino)-phenyl]-amide;

3-(4-Fluorophenyl)-1-isopropyl-2,4-dioxo-1,2,3,4-tetrahydropyrimidine-5-carboxylic acid[4-(6,7-dimethoxyquinolin-4-ylamino)-phenyl]-amide;

1-ethyl-3-(4-fluoro-phenyl)-2,4-dioxo-1,2,3,4-tetrahydro-pyrimidine-5-carboxylic acid[4-(6,7-dimethoxy-quinolin-4-ylsulfanyl)-phenyl]-amide;

3-(4-Fluoro-phenyl)-1-isopropyl-2,4-dioxo-1,2,3,4-tetrahydro-pyrimidine-5-carboxylic acid[4-(6,7-dimethoxy-quinolin-4-ylsulfanyl)-phenyl]-amide;

3-(4-Fluorophenyl)-1-isopropyl-2,4-dioxo-1,2,3,4-tetrahydropyrimidine-5-carboxylic acid{4-[(6,7-dimethoxy-quinolin-4-yl)-methyl-amino]-phenyl}-amide;

1-Ethyl-3-(4-fluorophenyl)-2,4-dioxo-1,2,3,4-tetrahydropyrimidine-5-carboxylic acid{4-[(6,7-dimethoxy-quinolin-4-yl)-methylamino]-phenyl}-amide;

3-(4-Fluoro-phenyl)-1-isopropyl-2,4-dioxo-1,2,3,4-tetrahydro-pyrimidine-5-carboxylic acid[4-(6,7-dimethoxy-quinazolin-4-yloxy)-phenyl]-amide;

1-Ethyl-3-(4-fluorophenyl)-2,4-dioxo-1,2,3,4-tetrahydro-pyrimidine-5-carboxylic acid[4-(6,7-dimethoxy-quinazolin-4-yloxy)-phenyl]-amide;

1-Ethyl-3-(4-fluorophenyl)-2,4-dioxo-1,2,3,4-tetrahydro-pyrimidine-5-carboxylic acid[4-(6,7-dimethoxy-quinolin-4-yloxy)-2-methoxyphenyl]-amide;

1-Methyl-3-(4-fluoro-phenyl)-2,4-dioxo-1,2,3,4-tetrahydro-pyrimidine-5-carboxylic acid[4-(6,7-dimethoxy-quinolin-4-yloxy)-2-methoxy-phenyl]-amide;

1-Isopropyl-3-(4-fluoro-phenyl)-2,4-dioxo-1,2,3,4-tetrahydro-pyrimidine-5-carboxylic acid[4-(6,7-dimethoxy-quinolin-4-yloxy)-2-methoxy-phenyl]-amide;

1-Methyl-3-(4-fluorophenyl)-2,4-dioxo-1,2,3,4-tetrahydro-pyrimidine-5-carboxylic acid[4-(6,7-dimethoxy-quinolin-4-yloxy)-2,3-difluoro-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-2,3-difluoro-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-3-methyl-phenyl]-amide;

3-(4-Fluoro-phenyl)-2,4-dioxo-1,2,3,4-tetrahydro-pyrimidine-5-carboxylic acid[4-(6,7-dimethoxy-quinolin-4-yloxy)-3-methyl-phenyl]-amide;

3-(4-Fluoro-phenyl)-2,4-dioxo-1,2,3,4-tetrahydro-pyrimidine-5-carboxylic acid[4-(6,7-dimethoxy-quinolin-4-yloxy)-3-methoxy-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-3-methoxy-phenyl]-amide;

1-Ethyl-3-(4-fluoro-phenyl)-2,4-dioxo-1,2,3,4-tetrahydro-pyrimidine-5-carboxylic acid[3-chloro-4-(6,7-dimethoxy-quinolin-4-yloxy)-3-methoxy-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-2-dimethylamino-phenyl]-amide;

3-(4-Fluoro-phenyl)-1-isopropyl-2,4-dioxo-1,2,3,4-tetrahydro-pyrimidine-5-carboxylic acid[4-(6,7-dimethoxy-quinolin-4-yloxy)-2-dimethylamino-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-3-isopropyl-phenyl]-amide;

3-(4-Fluoro-phenyl)-1-isopropyl-2,4-dioxo-1,2,3,4-tetrahydro-pyrimidine-5-carboxylic acid[4-(6,7-dimethoxy-quinolin-4-yloxy)-3-isopropyl-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-2,3-dimethyl-phenyl]-amide;

3-(4-Fluoro-phenyl)-1-isopropyl-2,4-dioxo-1,2,3,4-tetrahydro-pyrimidine-5-carboxylic acid[4-(6,7-dimethoxy-quinolin-4-yloxy)-2,3-dimethyl-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-3-trifluoromethyl-phenyl]-amide;

3-(4-Fluoro-phenyl)-1-isopropyl-2,4-dioxo-1,2,3,4-tetrahydro-pyrimidine-5-carboxylic acid[4-(6,7-dimethoxy-quinolin-4-yloxy)-3-trifluoromethyl-phenyl]-amide;

1-Ethyl-3-(4-fluoro-phenyl)-2,4-dioxo-1,2,3,4-tetrahydro-pyrimidine-5-carboxylic acid[4-(6,7-dimethoxy-quinolin-4-yloxy)-3,5-dimethyl-phenyl]-amide;

3-(4-Fluoro-phenyl)-1-isopropyl-2,4-dioxo-1,2,3,4-tetrahydro-pyrimidine-5-carboxylic acid[4-(6,7-dimethoxy-quinolin-4-yloxy)-3,5-dimethyl-phenyl]-amide; or 3-(4-Fluoro-phenyl)-1-isopropyl-2,4-dioxo-1,2,3,4-tetrahydro-pyrimidine-5-carboxylic acid[4-(6,7-dimethoxy-quinolin-4-yloxy)-3-methyl-phenyl]-amide;

or a pharmaceutically acceptable salt thereof.

18. A pharmaceutical composition comprising a compound according to claim 1 or a salt thereof and a pharmaceutically acceptable excipient.

19. A method of treating breast cancer in a subject in recognized need thereof, comprising administering to the subject a therapeutically effective amount of a compound according to claim 1.

\* \* \* \* \*

UNITED STATES PATENT AND TRADEMARK OFFICE
CERTIFICATE OF CORRECTION

PATENT NO. : 9,029,538 B2
APPLICATION NO. : 14/276138
DATED : May 12, 2015
INVENTOR(S) : Reddeppa Reddy Dandu It is certified that error appears in the above-identified patent and that said Letters Patent is hereby corrected as shown below:

In the Specification

In column 6 at line 28, Change "heterocycyl" to --heterocyclyl--.

In column 6 at line 57, Change "heterocylylalkyl" to --heterocyclylalkyl--.

In column 7 at lines 5-6, Change "benzthiazinyl," to --benzothiazinyl,--.

In column 7 at line 18, Change "furopyridinyl," to --fluoropyridinyl,--.

In column 10 at line 14, Change "$R^{49}$" to --$R^{49}$,--.

In column 10 at line 22, Change "$R^{59}$" to --$R^{59}$,--.

In column 11 at line 2, Change "$C_{1-6}$ alkyl" to --$C_{1-6}$alkyl--.

In column 12 at line 25, Change "$C_{1-6}$ alkyl" to --$C_{1-6}$alkyl--.

In column 12 at line 25, Change "$C_{3-11}$ cycloalkyl" to --$C_{3-11}$cycloalkyl--.

In column 12 at line 51, Change "$R^{19}C_{3-6}$alkenyl" to --$R^{19}$, $C_{3-6}$alkenyl--.

In column 13 at line 31, Change "—$NR^{114}C(=O)OR^{11}$," to --"—$NR^{114}C(=O)OR^{111}$,--.

In column 15 at line 42, Change "$C_{1-3}$ alkyl." to --$C_{1-3}$alkyl.--.

In column 15 at line 52, Change "$R^{119}$halogen," to --$R^{119}$, halogen,--.

In column 15 at line 61, Change "$C_{1-3}$ haloalkyl," to --$C_{1-3}$haloalkyl,--.

In column 15 at line 62, Change "—$OC_{1-3}$ alkyl." to -- —$OC_{1-3}$alkyl.--.

In column 15 at line 64, Change "$C_{1-3}$ haloalkyl," to --$C_{1-3}$haloalkyl,--.

In column 15 at line 65, Change "—$OC_{1-3}$ alkyl." to -- —$OC_{1-3}$alkyl.--.

In column 16 at line 9, Change "$R^{119}$" to --$R^{119}$,--.

In column 19 at lines 47-48, Change "heterocycyclylcarbonyl;" to --heterocyclylcarbonyl;--.

In column 20 at line 51, Change "heterocycyclylcarbonyl;" to --heterocyclylcarbonyl;--.

In column 21 at line 26, Change "heterocycyclylcarbonyl." to --heterocyclylcarbonyl.--.

In column 21 at line 45, Change "heterocycyclylcarbonyl." to --heterocyclylcarbonyl.--.

Signed and Sealed this
Eighth Day of March, 2016

Michelle K. Lee
*Director of the United States Patent and Trademark Office*

CERTIFICATE OF CORRECTION (continued)
U.S. Pat. No. 9,029,538 B2

In the Specification

In column 21 at line 63, Change "trifluoracetate," to --trifluoroacetate,--.

In column 30 at line 55, Change "alkyl" to --alkyl.--.

In column 38 at line 23, Change "carboxylicacid" to --carboxylic acid--.

In column 44 at line 58, Change "fluoro phenyl]" to --fluorophenyl]--.

In column 45 at line 63, Change "8.78 9 (s, H)," to --8.78 (s, 1H),--.

In column 45 at line 66, Change "2H," to --1H,--.

In column 46 at line 30, Change "fluoro phenyl]" to --fluorophenyl]--.

In column 51 at line 31, Change "fluoro phenyl]" to --fluorophenyl]--.

In column 53 at line 30, Change "fluoro phenyl]" to --fluorophenyl]--.

In column 61 at line 51, Change "(2 mL1)" to --(2 mL)--.

In column 62 at line 47, Change "3.76-" to --3.76--.

In column 67 at line 7, Change "7.8) d," to --7.8 (d,--.

In column 68 at line 26, Change "9 d," to --(d,--.

In column 79 at line 31, Change "trifuoroacetic" to --trifluoroacetic--.

In column 93 at line 62, Change "trifluoracetic" to --trifluoroacetic--.

In column 97 at line 50, Change "d4) a:" to --d4) δ:--.

In column 97 at line 64, Change "(s, 2H2.21" to --(s, 2H), 2.21--.

In column 103 at line 28, Change "Hydrochloride" to --hydrochloride--.

In column 105 at line 65, Change "dimethoxy-uinolin" to --dimethoxy-quinolin--.

In column 106 at line 64, Change "dimethoxy-uinolin" to --dimethoxy-quinolin--.

In column 115 at line 51, Change "amide 1" to --amide-1--.

In column 117 at line 9, Change "δ: δ" to --δ:--.

In column 127 at line 50, Change "(m, 1HO," to --(m, 1H),--.

In column 134 at line 36, Change "7.24-" to --7.24--.

In column 135 at line 30, Change "(M+1););" to --(M+1);--.

In column 135 at line 60, Change "(M+1););" to --(M+1);--.

In column 141 at lines 7-8, Change "heterocycyclylcarbonyl;" to --heterocyclylcarbonyl;--.

In column 142 at line 9, Change "heterocycyclylcarbonyl;" to --heterocyclylcarbonyl;--.

In column 142 at line 49, Change "heterocycyclylcarbonyl." to --heterocyclylcarbonyl.--.

In column 142 at line 66, Change "heterocycyclylcarbonyl;" to --heterocyclylcarbonyl;--.

In column 143 at line 40, Change "fluoro phenyl]" to --fluorophenyl]--.

In column 143 at line 49, Change "fluoro phenyl]" to --fluorophenyl]--.

In column 144 at line 13, Change "fluoro phenyl]" to --fluorophenyl]--.

In column 144 at line 25, Change "fluoro phenyl]" to --fluorophenyl]--.

CERTIFICATE OF CORRECTION (continued)
U.S. Pat. No. 9,029,538 B2

In the Specification

In column 148 at line 27, Change "dimethoxy-uinolin" to --dimethoxy-quinolin--.

In column 148 at line 34, Change "dimethoxy-uinolin" to --dimethoxy-quinolin--.

In column 152 at line 29, Change "$R^{19}$phenyl" to --$R^{19}$ phenyl--.

In column 152 at line 43, Change "$R^{119}$," to --$R^{119}$;--.

In column 154 at lines 10-11, Change "$R^{119}$—CN," to --$R^{119}$—CN--.

In column 154 at line 16, Change "Re" to --$R_c$--.

In column 155 at line 52, Change "$R^{32}$and" to --$R^{32}$ and--.

In column 156 at line 4, Change "$C_{1-4}$ alkyl" to --$C_{1-4}$alkyl--.

In the Claims

In column 156 at line 65, In Claim 1, after "—$NR^{112}R^{113}$," insert --$NR^{114}C(=O)R^{110}$,--.

In column 156 at lines 65-66, In Claim 1, change "—$NR^{114}C(=O)NR^{112}R^{113}$," to --$NR^{114}C(=O)NR^{112}R^{113}$,--.

In column 156 at lines 65-66, In Claim 1, after "—$NR^{114}C(=O)NR^{112}R^{113}$," delete "$C(=O)NR^{112}R^{113}$,".

In column 158 at line 15, In Claim 1, change "$C_{1-6}$ alkyl" to --$C_{1-6}$alkyl--.

In column 158 at line 21, Change "-15" to --5-15--.

In column 158 at line 25, In Claim 1, change "$R^{149}$or" to --$R^{149}$ or--.

In column 159 at line 2, In Claim 3, change "$C_{1-6}$ alkyl" to --$C_{1-6}$alkyl--.

In column 160 at line 45, In Claim 17, change "fluoro phenyl]" to --fluorophenyl]--.

In column 160 at line 54, In Claim 17, change "fluoro phenyl]" to --fluorophenyl]--.

In column 161 at line 19, In Claim 17, change "fluoro phenyl]" to --fluorophenyl]--.

In column 161 at line 32, In Claim 17, change "fluoro phenyl]" to --fluorophenyl]--.